(12) United States Patent
Iida et al.

(10) Patent No.: US 8,507,484 B2
(45) Date of Patent: Aug. 13, 2013

(54) PREVENTIVE AND/OR THERAPEUTIC AGENT FOR NEUTROPHILIC INFLAMMATORY DISEASES

(75) Inventors: Kyoichiro Iida, Naka-gun (JP); Nobumasa Otsubo, Sunto-gun (JP); Takeshi Kuboyama, Sunto-gun (JP); Hitoshi Arai, Nishinomiya (JP); Akihiko Watanabe, Mishima (JP); Mayumi Saki, Numazu (JP); Naoko Hiura, Tokyo (JP); Haruhiko Manabe, Sunto-gun (JP); Hidenori Takada, Sunto-gun (JP); Jun Saito, Sakai (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 1774 days.

(21) Appl. No.: 10/590,845

(22) PCT Filed: Feb. 25, 2005

(86) PCT No.: PCT/JP2005/003656
§ 371 (c)(1),
(2), (4) Date: Aug. 28, 2006

(87) PCT Pub. No.: WO2005/082904
PCT Pub. Date: Sep. 9, 2005

(65) Prior Publication Data
US 2007/0213361 A1    Sep. 13, 2007

(30) Foreign Application Priority Data

Feb. 26, 2004 (JP) ................... 2004-050934
Oct. 22, 2004 (JP) ................... 2004-307948

(51) Int. Cl.
*C07D 413/02* (2006.01)
*A61K 31/535* (2006.01)

(52) U.S. Cl.
USPC ........................ 514/234.2; 544/127

(58) Field of Classification Search
USPC ..................... 544/127; 514/234.2
See application file for complete search history.

(56) References Cited

U.S. PATENT DOCUMENTS

| | | |
|---|---|---|
| 5,151,435 A | 9/1992 | Bagley et al. |
| 5,242,939 A | 9/1993 | Sircar |
| 5,281,613 A | 1/1994 | Bradbury et al. |
| 5,317,023 A | 5/1994 | Ross et al. |
| 5,359,073 A | 10/1994 | Weier et al. |
| 5,374,638 A | 12/1994 | Dhanoa et al. |
| 5,387,592 A | 2/1995 | Bradbury et al. |
| 5,459,147 A | 10/1995 | Hauel et al. |
| 5,514,682 A | 5/1996 | Street |
| 5,554,624 A | 9/1996 | Almansa et al. |
| 5,789,415 A | 8/1998 | Carpino et al. |
| 5,861,403 A | 1/1999 | Khanna et al. |
| 6,235,770 B1 | 5/2001 | Connell et al. |
| 6,329,380 B1 | 12/2001 | Goulet et al. |
| 6,734,187 B1 | 5/2004 | Tanaka et al. |
| 2006/0252679 A1 | 11/2006 | Saki et al. |

FOREIGN PATENT DOCUMENTS

| | | |
|---|---|---|
| EP | 0 429 257 A2 | 5/1991 |
| JP | 04-360874 | 12/1992 |
| JP | 05-262768 | 10/1993 |
| JP | 06-073051 | 3/1994 |
| JP | 07-061983 | 3/1995 |
| JP | 09-176116 | 7/1997 |
| WO | WO 2004/093912 A1 | 11/2004 |

OTHER PUBLICATIONS

Simpson et al., Respiratory Medicine (2009), 103, 881-887.*
Science (1999), vol. 286, 531-537.*
Cancer and Metastasis Reviews (1998), 17(1), 91-106.*
Huff, Joel R., "HIV Protease: A Novel Chemotherapeutic Target for AIDS," Journal of Medicinal Chemistry, vol. 34, No. 8, Aug. 1991, pp. 2305-2314.*
Sircar et al., J. Med. Chem. 1993, 36, 1735-1745.*
Translation of the International Preliminary Report on Patentability mailed Mar. 29, 2007, for International Application No. PCT/JP2005/003656, filed Feb. 25, 2005.

* cited by examiner

*Primary Examiner* — Rebecca Anderson
(74) *Attorney, Agent, or Firm* — Antonelli, Terry, Stout & Kraus, LLP.

(57) ABSTRACT

The present invention provides a preventive and/or therapeutic agent for neutrophilic inflammatory diseases which comprises, as an active ingredient, a bicyclic heterocyclic compound represented by formula (I):

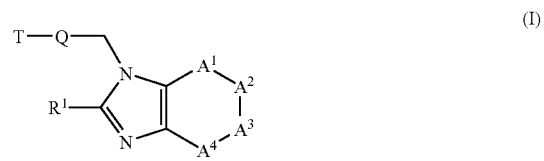

(I)

[wherein $R^1$ represents a hydrogen atom, substituted or unsubstituted alkyl, or the like, $A^1$-$A^2$-$A^3$-$A^4$ represents $N=CR^3-CR^4=CR^5$ (wherein $R^3$, $R^4$, and $R^5$ are the same or different and each represents a hydrogen atom, substituted or unsubstituted lower alkyl, and the like), Q represents substituted or unsubstituted phenylene, and the like, and T represents substituted or unsubstituted lower alkyl, substituted or unsubstituted aroyl, and the like].

19 Claims, 2 Drawing Sheets

PREVENTIVE AND/OR THERAPEUTIC AGENT FOR NEUTROPHILIC INFLAMMATORY DISEASES

TECHNICAL FIELD

The present invention relates to preventive and/or therapeutic agents for neutrophilic inflammatory diseases which comprises, as an active ingredient, bicyclic heterocyclic compounds or pharmaceutically acceptable salts thereof.

BACKGROUND ART

Neutrophils have the action of infiltrating inflammatory regions to produce superoxide anions, tumor necrosis factor (TNF)-α which is an inflammatory cytokine, and the like and exacerbate inflammation. It has been suggested that neutrophils are involved in various inflammatory diseases, such as chronic obstructive pulmonary disease (COPD), arthritis, sepsis, ischemic reperfusion injury, and pulmonary fibrosis (Laboratory Investigation, 2000, vol. 80, pp. 617-653). The infiltration of neutrophils is induced by a neutrophil chemotactic factor. In order to treat these diseases, it is thus thought to be important to suppress the production of a neutrophil chemotactic factor and the infiltration of neutrophils.

It has been reported that GPR4 is a G protein-coupled receptor protein (abbreviated to "GPCR" hereinafter) and binds to lipids such as sphingosylphosphorylcholine (SPC) and lysophosphatidylcholine (LPC) to transmit signals and induce the migration of GPR4 expressing cells (Journal of Biological Chemistry (J. Biol. Chem.), 2001, vol. 276, pp. 41325-41335).

On the other hand, known examples of bicyclic heterocyclic compounds include benzazole derivatives which have a hypotensive activity (Japanese Published Unexamined Patent Application No. 73051/1994 and EP520723), benzimidazole derivatives (EP560330 and Japanese Published Unexamined Patent Application No. 360874/1992), indole derivatives (U.S. Pat. No. 5,151,435, EP520724, and EP429257), benzofuran derivatives (EP546449, EP514197, and U.S. Pat. No. 5,789,415), indole or benzofuran derivatives which have an anticephalalgic function (WO93/23396), imidazopyridine derivatives (WO94/12500) and purine derivatives which have a platelet-activating factor inhibitory activity (U.S. Pat. No. 5,861,403), purine derivatives which have a phosphodiesterase IV inhibitory activity (WO99/24432), and benzimidazole derivatives, imidazopyridine derivatives, and imidazopyrimidine derivatives which have an anti-inflammatory activity (Japanese Published Unexamined Patent Application No. 176116/1997).

DISCLOSURE OF INVENTION

The present invention provides preventive and/or therapeutic agents for neutrophilic inflammatory diseases which comprises, as an active ingredient, bicyclic heterocyclic compounds or pharmaceutically acceptable salts.

The present invention relates to (1) to (76):

(1) A preventive and/or therapeutic agent for neutrophilic inflammatory diseases which comprises, as an active ingredient, a bicyclic heterocyclic compound represented by formula (I):

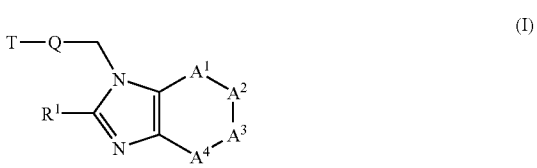

[wherein $R^1$ represents a hydrogen atom, halogen, cyano, substituted or unsubstituted lower alkyl, substituted or unsubstituted lower cycloalkyl, substituted or unsubstituted lower alkenyl, substituted or unsubstituted lower alkynyl, substituted or unsubstituted lower alkanoyl, substituted or unsubstituted lower cycloalkylcarbonyl, substituted or unsubstituted lower alkoxy, substituted or unsubstituted lower alkoxycarbonyl, substituted or unsubstituted aryl, substituted or unsubstituted aralkyl, substituted or unsubstituted aroyl, a substituted or unsubstituted aliphatic heterocyclic group, or a substituted or unsubstituted aromatic heterocyclic group (excluding tetrazolyl);

$A^1$-$A^2$-$A^3$-$A^4$ represents $CR^2$=$CR^3$—$CR^4CR^5$ (wherein $R^2$, $R^3$, $R^4$, and $R^5$ are the same or different and each has the same definition as $R^1$), N=$CR^3$—$CR^4$=$CR^5$ (wherein $R^3$, $R^4$, and $R^5$ have the same definitions as described above, respectively), $CR^2$=N—$CR^4$=$CR^5$ (wherein $R^2$, $R^4$, and $R^5$ each have the same definition as described above), $CR^2$=$CR^3$—N=$CR^5$ (wherein $R^2$, $R^3$, and $R^5$ have the same definitions as described above, respectively), $CR^2$=$CR^3$—$CR^4$=N (wherein $R^2$, $R^3$, and $R^4$ have the same definitions as described above, respectively), N=$CR^3$—N=$CR^5$ (wherein $R^3$ and $R^5$ have the same definitions as described above, respectively), $CR^2$=N—$CR^4$=N (wherein $R^2$ and $R^4$ have the same definitions as described above, respectively), or N=$CR^3$—$CR^4$=N (wherein $R^3$ and $R^4$ have the same definitions as described above, respectively);

Q represents substituted or unsubstituted phenylene, substituted or unsubstituted naphthylene, substituted or unsubstituted heteroarylene, or a divalent group formed by removing any one hydrogen atom from an aliphatic heterocycle of a substituted or unsubstituted aliphatic heterocyclic group;

T represents (i) formyl, (ii) substituted or unsubstituted lower alkyl, (iii) substituted or unsubstituted lower cycloalkyl, (iv) substituted or unsubstituted lower alkanoyl, (v) substituted or unsubstituted lower cycloalkylcarbonyl, (vi) substituted or unsubstituted aryl, (vii) substituted or unsubstituted aralkyl, (viii) substituted or unsubstituted aroyl, (ix) a substituted or unsubstituted aromatic heterocyclic group (excluding tetrazolyl), (x) substituted or unsubstituted aromatic heterocyclic carbonyl (wherein an aromatic heterocyclic moiety of the aromatic heterocyclic carbonyl is not tetrazolyl),
(xi) formula ($A^1$)

[wherein na represents an integer of 0 to 3,
nb represents an integer of 1 to 4,
$J^1$ represents a single bond or carbonyl,
X=Y represents $CR^7$—$CH_2$ (wherein $R^7$ represents a hydrogen atom, halogen, nitro, hydroxy, cyano, trifluoromethyl, formyl, lower alkyl, lower alkoxy, lower alkoxycarbonyl, lower alkanoyl, lower cycloalkylcarbonyl, or lower alkoxycarbonylamino) or C≡CH, and $R^6$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted aryl, substituted or unsubstituted aralkyl, substituted or unsubstituted aroyl, or a substituted or unsubstituted aromatic heterocyclic group (excluding tetrazolyl)], (xii) —$NR^{11a}R^{11b}$ [wherein $R^{11a}$ and $R^{11b}$ are the same or different and each represents a hydrogen atom, formyl, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, substituted or unsubstituted aryloxycarbonyl, a substituted or unsubstituted aliphatic heterocyclic group, a substituted or unsubstituted aromatic heterocyclic group (excluding tetrazolyl), or substituted or unsubstituted aromatic heterocyclic carbonyl (wherein an aromatic heterocyclic moiety of the aromatic heterocyclic carbonyl is not tetrazolyl), or $R^{11a}$ and $R^{11b}$ are combined together with the adjacent nitrogen atom thereto to form a substituted or unsubstituted heterocyclic group], (xiii) —$OR^{12}$ [wherein $R^{12}$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, substituted or unsubstituted aryloxycarbonyl, a substituted or unsubstituted aromatic heterocyclic group (excluding tetrazolyl), substituted or unsubstituted aromatic heterocyclic oxycarbonyl (wherein an aromatic heterocyclic moiety of the aromatic heterocyclic oxycarbonyl is not tetrazolyl), substituted or unsubstituted lower alkylsulfonyl, substituted or unsubstituted arylsulfonyl, substituted or unsubstituted aromatic heterocyclic sulfonyl (wherein an aromatic heterocyclic moiety of the aromatic heterocyclic sulfonyl is not tetrazolyl), or —C(=O)$NR^{13a}R^{13b}$ (wherein $R^{13a}$ and $R^{13b}$ have the same definitions as $R^{11a}$ and $R^{11b}$ described above, respectively)], (xiv) formula ($C^1$)

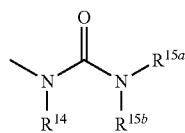

(wherein $R^{14}$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted aryl, substituted or unsubstituted aralkyl, or substituted or unsubstituted aroyl, and $R^{15a}$ and $R^{15b}$ have the same definitions as $R^{11a}$ and $R^{11b}$ described above, respectively), (xv) formula ($D^1$)

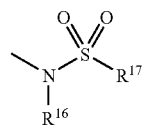

(wherein $R^{16}$ has the same definition as $R^{14}$ described above, and $R^{17}$ represents substituted or unsubstituted lower alkyl, substituted or unsubstituted lower cycloalkyl, substituted or unsubstituted aryl, or substituted or unsubstituted aralkyl), (xvi) formula ($E^1$)

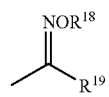

[wherein $R^{18}$ represents a hydrogen atom, substituted or unsubstituted lower alkyl, substituted or unsubstituted lower cycloalkyl, substituted or unsubstituted aryl, substituted or unsubstituted aralkyl, or a substituted or unsubstituted aromatic heterocyclic group (excluding tetrazolyl), and $R^{19}$ has the same definition as $R^{17}$ described above], (xvii) —C(=$X^1$)—$OR^{20}$ [wherein $X^1$ represents an oxygen atom or a sulfur atom, and $R^{20}$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted aryl, substituted or unsubstituted aralkyl, substituted or unsubstituted aroyl, or a substituted or unsubstituted aromatic heterocyclic group (excluding tetrazolyl), provided that $X^1$ represents an oxygen atom, $R^{20}$ is not a hydrogen atom], (xviii) —C(=$X^2$)—$NR^{21a}R^{21b}$ (wherein $X^2$ has the same definition as $X^1$, and $R^{21a}$ and $R^{21b}$ have the same definitions as $R^{11a}$ and $R^{11b}$ described above, respectively), or (xix) formula ($B^1$)

{wherein E═F represents $CR^9$=$CR^{10}$ [wherein $R^9$ and $R^{10}$ are the same or different and each represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl)] or C≡C, $R^8$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted aryl, substituted or unsubstituted aralkyl, substituted or unsubstituted aroyl, a substituted or unsubstituted aromatic heterocyclic group (excluding tetrazolyl), or —C($R^{A1}$)($R^{A2}$)$NR^{B1}R^{B2}$ [wherein $R^{A1}$ and $R^{A2}$ are the same or different and each represents a hydrogen atom, halogen, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl), $R^{A1}$ and $R^{A2}$ are combined together with the adjacent carbon atom thereto to form a saturated aliphatic ring, or $R^{A1}$ and $R^{A2}$ are combined together to represent an oxygen atom or a sulfur atom, and $R^{B1}$ and $R^{B2}$ have the same definitions as $R^{11a}$ and $R^{11b}$ described above, respectively]}] or a pharmaceutically acceptable salt thereof.

(2) The preventive and/or therapeutic agent for neutrophilic inflammatory diseases according to (1), wherein T is formula ($F^1$):

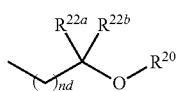

(F$^1$)

[wherein nd represents an integer of 0 to 3, $R^{22a}$ and $R^{22b}$ are the same or different and each represents a hydrogen atom, halogen, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl), $R^{22a}$ and $R^{22b}$ are combined together with the adjacent carbon atom thereto to form a saturated aliphatic ring, or $R^{22a}$ and $R^{22b}$ are combined together to represent an oxygen atom or a sulfur atom, and $R^{20}$ has the same definition as described above, provided that $R^{22a}$ and $R^{22b}$ are combined together to represent an oxygen atom, $R^{20}$ is not a hydrogen atom].

(3) The preventive and/or therapeutic agent for neutrophilic inflammatory diseases according to (1), wherein T is formula ($G^1$):

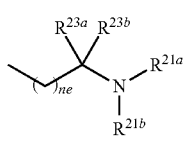

(G$^1$)

(wherein ne represents an integer of 0 to 3, $R^{21a}$ and $R^{21b}$ have the same definition as described above, respectively, and $R^{23a}$ and $R^{23b}$ have the same definitions as $R^{22a}$ and $R^{22b}$ described above, respectively).

(4) The preventive and/or therapeutic agent for neutrophilic inflammatory diseases according to (3), wherein $R^{21a}$ and $R^{21b}$ are the same or different and both or either of $R^{21a}$ and $R^{21b}$ is formula ($H^1$):

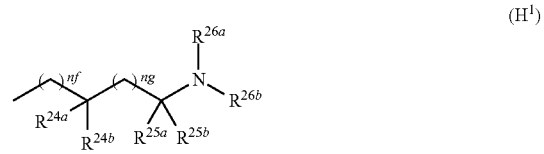

(H$^1$)

[wherein nf represents an integer of 0 to 5;

ng represents an integer of 0 to 3;

$R^{24a}$ and $R^{24b}$ are the same or different and each represents a hydrogen atom, formyl, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl), $R^{24a}$ and $R^{24b}$ are combined together with the adjacent carbon atom thereto to form a saturated aliphatic ring, or $R^{24a}$ and $R^{24b}$ are combined together to represent an oxygen atom or a sulfur atom;

$R^{25a}$ and $R^{25b}$ are the same or different and each represents a hydrogen atom, formyl, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl), $R^{25a}$ and $R^{25b}$ are combined together with the adjacent carbon atom thereto to form a saturated aliphatic ring, $R^{25a}$ and $R^{25b}$ are combined together to represent an oxygen atom or a sulfur atom, or $R^{25a}$ or $R^{25b}$ are combined together with $R^{26a}$ or $R^{26b}$ and the adjacent carbon atom and nitrogen atom thereto to form a substituted or unsubstituted heterocyclic group;

and $R^{26a}$ and $R^{26b}$ are the same or different and each represents a hydrogen atom, formyl, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted lower alkoxycarbonyl, substituted or unsubstituted aryl, substituted or unsubstituted aralkyl, substituted or unsubstituted aroyl, or a substituted or unsubstituted aromatic heterocyclic group (excluding tetrazolyl), $R^{26a}$ and $R^{26b}$ are combined together with the adjacent nitrogen atom thereto to form a substituted or unsubstituted heterocyclic group, or $R^{26a}$ or $R^{26b}$ are combined together with $R^{25a}$ or $R^{25b}$ and the adjacent nitrogen atom and carbon atom thereto to form a substituted or unsubstituted heterocyclic group].

(5) The preventive and/or therapeutic agent for neutrophilic inflammatory diseases according to (1), wherein T is formula ($B^2$):

(B$^2$)

[wherein E==F has the same definition as described above, and $R^{8a}$ is formula $(G^2)$:

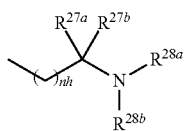

(wherein nh, $R^{27a}$, $R^{27b}$, $R^{28a}$, and $R^{28b}$ have the same definitions as nd, $R^{A1}$, $R^{A2}$, $R^{B1}$, and $R^{B2}$ described above, respectively)].

(6) The preventive and/or therapeutic agent for neutrophilic inflammatory diseases according to (1), wherein T is formula $(A^2)$:

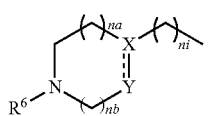

(wherein ni represents an integer of 0 to 2, and na, nb, X--Y and $R^6$ have the same definitions as described above, respectively).

(7) The preventive and/or therapeutic agent for neutrophilic inflammatory diseases according to (1), wherein T is formula $(E^2)$:

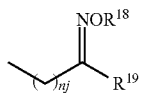

(wherein nj represents an integer of 0 to 3, and $R^{18}$ and $R^{19}$ have the same definitions as described above, respectively).

(8) A GPR4 antagonist which comprises, as an active ingredient, the bicyclic heterocyclic compound or pharmaceutically acceptable salt thereof described in any of (1) to (7).

(9) A preventive and/or therapeutic agent for neutrophilic inflammatory diseases which comprises, as an active ingredient, a bicyclic heterocyclic compound represented by formula (II):

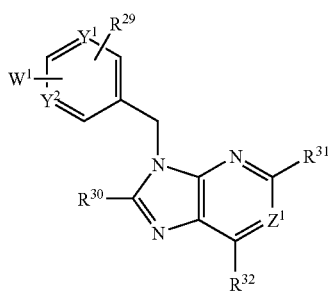

{wherein $Y^1$ and $Y^2$ are the same or different and each represents CH or a nitrogen atom;

$W^1$ has the same definition as T described above;

$Z^1$ represents a nitrogen atom or $CR^{33}$ [wherein $R^{33}$ represents a hydrogen atom, substituted or unsubstituted lower alkyl, substituted or unsubstituted lower cycloalkyl, substituted or unsubstituted lower alkanoyl, substituted or unsubstituted lower cycloalkylcarbonyl, substituted or unsubstituted aryl, substituted or unsubstituted aralkyl, substituted or unsubstituted aroyl, or a substituted or unsubstituted aromatic heterocyclic group (excluding tetrazolyl)];

$R^{29}$ represents a hydrogen atom, halogen, amino, nitro, cyano, carboxy, lower alkoxycarbonylamino, mono- or di-lower alkylamino, lower alkylsulfonyl, substituted or unsubstituted lower alkyl, substituted or unsubstituted lower cycloalkyl, substituted or unsubstituted lower alkenyl, substituted or unsubstituted lower alkynyl, substituted or unsubstituted lower alkoxy, substituted or unsubstituted aryl, substituted or unsubstituted aralkyl, or a substituted or unsubstituted aliphatic heterocyclic group;

and $R^{30}$, $R^{31}$, and $R^{32}$ are the same or different and each represent a hydrogen atom, halogen, cyano, substituted or unsubstituted lower alkyl, substituted or unsubstituted lower cycloalkyl, substituted or unsubstituted lower alkenyl, substituted or unsubstituted lower alkynyl, substituted or unsubstituted lower alkoxy, substituted or unsubstituted lower alkoxycarbonyl, substituted or unsubstituted aryl, substituted or unsubstituted aralkyl, substituted or unsubstituted aroyl, a substituted or unsubstituted aliphatic heterocyclic group, or a substituted or unsubstituted aromatic heterocyclic group (excluding tetrazolyl)} or a pharmaceutically acceptable salt thereof.

(10) The preventive and/or therapeutic agent for neutrophilic inflammatory diseases according to (9), wherein $W^1$ is formula $(G^1)$:

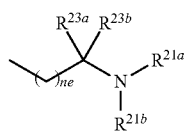

(wherein ne, $R^{21a}$, $R^{21b}$, $R^{23a}$, and $R^{23b}$ have the same definitions as described above, respectively).

(11) The preventive and/or therapeutic agent for neutrophilic inflammatory diseases according to (9), wherein $W^1$ is formula $(G^3)$:

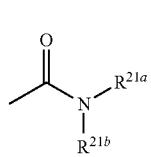

(wherein $R^{21a}$ and $R^{21b}$ have the same definitions described above, respectively).

(12) The preventive and/or therapeutic agent for neutrophilic inflammatory diseases according to (10) or (11), wherein $R^{21a}$ and $R^{21a}$ are the same or different and both or either of $R^{21a}$ and $R^{21a}$ is formula $(H^1)$:

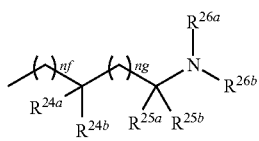

(wherein nf, ng, $R^{24a}$, $R^{24b}$, $R^{25a}$, $R^{25b}$, $R^{26a}$, and $R^{26b}$ have the same definitions as described above, respectively).

(13) The preventive and/or therapeutic agent for neutrophilic inflammatory diseases according to (9), wherein $W^1$ is formula ($G^4$):

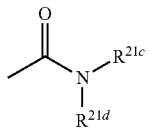

(wherein $R^{21c}$ and $R^{21d}$ are the same or different and each represents a hydrogen atom, substituted or unsubstituted lower alkyl, substituted or unsubstituted lower cycloalkyl, substituted or unsubstituted aryl, or substituted or unsubstituted aralkyl, or $R^{21c}$ and $R^{21d}$ are combined together with the adjacent nitrogen atom thereto to form a substituted or unsubstituted heterocyclic group).

(14) The preventive and/or therapeutic agent for neutrophilic inflammatory diseases according to (9), wherein $W^1$ is formula ($F^1$):

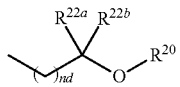

(wherein nd, $R^{20}$, $R^{22a}$, and $R^{22b}$ have the same definitions as described above, respectively).

(15) The preventive and/or therapeutic agent for neutrophilic inflammatory diseases according to (9), wherein $W^1$ is formula ($B^2$):

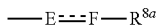

(wherein E==F and $R^{8a}$ have the same definitions as described above, respectively).

(16) The preventive and/or therapeutic agent for neutrophilic inflammatory diseases according to (9), wherein $W^1$ is —$NR^{11a}R^{11b}$ (wherein $R^{11a}$ and $R^{11b}$ have the same definitions as described above, respectively).

(17) The preventive and/or therapeutic agent for neutrophilic inflammatory diseases according to (9), wherein $W^1$ is —$NHR^{11a}$ (wherein $R^{11a}$ has the same definition as described above).

(18) The preventive and/or therapeutic agent for neutrophilic inflammatory diseases according to (9), wherein $W^1$ is —$NHR^{11c}$ [wherein $R^{11c}$ represents substituted or unsubstituted lower alkanoyl, substituted or unsubstituted lower cycloalkylcarbonyl, substituted or unsubstituted aroyl, or substituted or unsubstituted aromatic heterocyclic carbonyl (wherein an aromatic heterocyclic moiety of the aromatic heterocyclic carbonyl is not tetrazolyl)].

(19) The preventive and/or therapeutic agent for neutrophilic inflammatory diseases according to (9), wherein $W^1$ is formula ($C^1$):

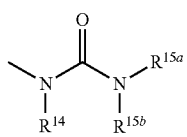

(wherein $R^{14}$, $R^{15a}$, and $R^{15b}$ have the same definitions as described above, respectively).

(20) The preventive and/or therapeutic agent for neutrophilic inflammatory diseases according to (9), wherein $W^1$ is formula ($C^2$):

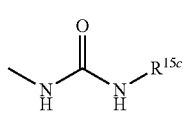

(wherein $R^{15c}$ represents substituted or unsubstituted lower alkyl, substituted or unsubstituted lower cycloalkyl, substituted or unsubstituted aryl, or substituted or unsubstituted aralkyl).

(21) The preventive and/or therapeutic agent for neutrophilic inflammatory diseases according to (9), wherein $W^1$ is formula ($D^1$):

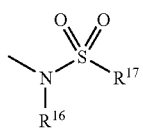

(wherein $R^{16}$ and $R^{17}$ have the same definitions as described above, respectively).

(22) The preventive and/or therapeutic agent for neutrophilic inflammatory diseases according to (9), wherein $W^1$ is formula ($D^2$):

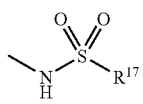

(wherein $R^{17}$ has the same definition as described above).

(23) The preventive and/or therapeutic agent for neutrophilic inflammatory diseases according to (9), wherein $W^1$ is formula ($A^2$):

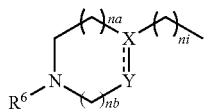

(wherein na, nb, ni, $X\text{-}\text{-}Y$ and $R^6$ have the same definitions as described above, respectively).

(24) The preventive and/or therapeutic agent for neutrophilic inflammatory diseases according to (9), wherein $W^1$ is formula ($E^2$):

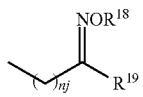

(wherein nj, $R^{18}$, and $R^{19}$ have the same definitions as described above, respectively).

(25) The preventive and/or therapeutic agent for neutrophilic inflammatory diseases according to any of (9) to (24), wherein $R^{29}$ is a hydrogen atom.

(26) The preventive and/or therapeutic agent for neutrophilic inflammatory diseases according to any of (9) to (25), wherein $R^{30}$, $R^{31}$, and $R^{32}$ are the same or different and each represents a hydrogen atom, halogen, or substituted or unsubstituted lower alkyl.

(27) The preventive and/or therapeutic agent for neutrophilic inflammatory diseases according to any of (9) to (26), wherein $Z^1$ is $CR^{33}$ (wherein $R^{33}$ has the same definition as described above).

(28) The preventive and/or therapeutic agent for neutrophilic inflammatory diseases according to any of (9) to (26), wherein $Z^1$ is CH.

(29) The preventive and/or therapeutic agent for neutrophilic inflammatory diseases according to any of (9) to (28), wherein $Y^1$ and $Y^2$ are CH.

(30) The preventive and/or therapeutic agent for neutrophilic inflammatory diseases according to any of (9) to (28), wherein $Y^1$ and $Y^2$ are a nitrogen atom.

(31) The preventive and/or therapeutic agent for neutrophilic inflammatory diseases according to any of (9) to (30), wherein $R^{30}$, $R^{31}$, and $R^{32}$ are the same or different and each represents a hydrogen atom or substituted or unsubstituted lower alkyl.

(32) The preventive and/or therapeutic agent for neutrophilic inflammatory diseases according to any of (9) to (30), wherein $R^{30}$ and $R^{32}$ are the same or different and each represents a hydrogen atom or substituted or unsubstituted lower alkyl, and $R^{31}$ represents halogen.

(33) A GPR4 antagonist which comprises, as an active ingredient, the bicyclic heterocyclic compound or pharmaceutically acceptable salt thereof described in any of (9) to (32).

(34) A bicyclic heterocyclic compound represented by formula (III):

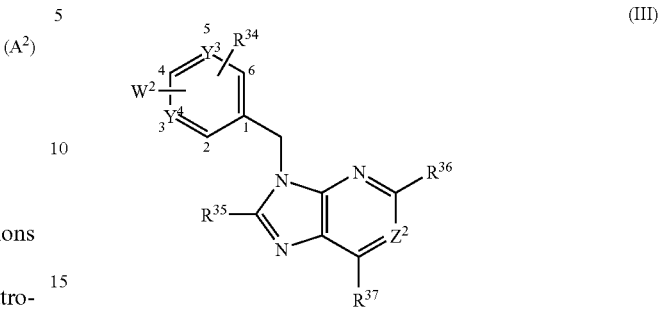

{wherein $Y^3$ and $Y^4$ have the same definitions as $Y^1$ and $Y^2$ described above, respectively;

$W^2$ is bonded at the 3-, 4-, or 5-position of a benzene ring and represents:

(i) formyl;

(ii) lower alkyl or lower alkyl substituted by 1 to 3 substitutents which are the same or different and selected from the following substitutent group A [substitutent group A: halogen, hydroxy, formyl, trifluoromethyl, vinyl, styryl, phenylethynyl, lower cycloalkyl, lower alkoxy, hydroxy-substituted lower alkoxy, lower alkoxy-substituted lower alkoxy, lower alkoxycarbonyl, lower alkanoyl, aryl-substituted lower alkanoyl, aryloxy, aralkyloxy, aroyl, a substituted or unsubstituted aliphatic heterocyclic group, a substituted or unsubstituted aromatic heterocyclic group (excluding tetrazolyl)];

(iii) substituted or unsubstituted lower cycloalkyl;

(iv) substituted or unsubstituted lower alkanoyl;

(v) substituted or unsubstituted lower cycloalkylcarbonyl;

(vi) substituted or unsubstituted aryl;

(vii) substituted or unsubstituted aralkyl;

(viii) substituted or unsubstituted aroyl;

(ix) a substituted or unsubstituted aromatic heterocyclic group (excluding tetrazolyl);

(x) substituted or unsubstituted aromatic heterocyclic carbonyl (wherein an aromatic heterocyclic moiety of the aromatic heterocyclic carbonyl is not tetrazolyl);

(xi) formula ($A^3$):

[wherein na, nb, $R^6$, and $X\text{-}\text{-}Y$ and $X\text{-}\text{-}Y$ have the same definitions as described above, respectively, and $J^2$ represents a single bond, carbonyl, $-CH_2-$, or $-(CH_2)_2-$];

(xii) $-NR^{11a}R^{11b}$ (wherein $R^{11a}$ and $R^{11b}$ have the same definitions as described above, respectively);

(xiii) —OR$^{12}$ (wherein R$^{12}$ has the same definition as described above);

(xiv) formula (C$^1$):

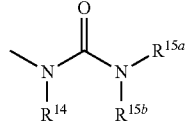

(C$^1$)

(wherein R$^{14}$, R$^{15a}$, and R$^{15b}$ have the same definitions as described above, respectively);

(xv) formula (D$^1$):

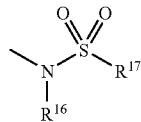

(D$^1$)

(wherein R$^{16}$ and R$^{17}$ have the same definitions as described above, respectively);

(xvi) formula (E$^2$):

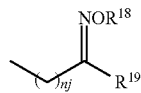

(E$^2$)

(wherein nj, R$^{18}$, and R$^{19}$ have the same definitions as described above, respectively);

(xvii) formula (F$^1$):

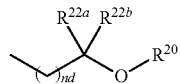

(F$^1$)

(wherein nd, R$^{20}$, R$^{22a}$, and R$^{22b}$ have the same definitions as described above, respectively);

(xviii) formula (G$^1$):

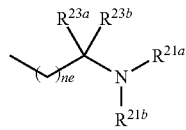

(G$^1$)

(wherein ne, R$^{21a}$, R$^{21b}$, R$^{23a}$, and R$^{23b}$ have the same definitions as described above, respectively); or (xix) formula (B$^1$):

(B$^1$)

(wherein E---F and R$^8$ have the same definitions as described above, respectively);

R$^{34}$, R$^{35}$, R$^{36}$, R$^{37}$, and Z$^2$ have the same definitions as R$^{29}$, R$^{30}$, R$^{31}$, R$^{32}$, and Z$^1$ described above, respectively;

Provided that Z$^2$ is a nitrogen atom, R$^{35}$ is a hydrogen atom or lower alkyl, R$^{36}$ and R$^{37}$ are each a hydrogen atom, lower alkyl, or an aliphatic heterocyclic group, and R$^{34}$ is lower alkoxy or halogen-substituted lower alkoxy, W$^2$ is not —OR$^{12a}$ (wherein R$^{12a}$ represents lower alkyl, halogen-substituted lower alkyl, or lower cycloalkyl);

Z$^2$ is a nitrogen atom or CH, R$^{35}$ is a hydrogen atom, one of R$^{36}$ and R$^{37}$ is a hydrogen atom, the other is a hydrogen atom, lower alkyl, or aryl, and R$^{34}$ is a hydrogen atom or amino, W$^2$ is neither amino nor hydroxy;

Z$^2$ is a nitrogen atom, R$^{35}$, R$^{36}$, and R$^{37}$ are each a hydrogen atom, and R$^{34}$ is a hydrogen atom, halogen, lower alkoxy, or substituted or unsubstituted lower alkyl, W$^2$ is not formula (G$^5$):

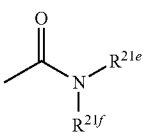

(G$^5$)

[wherein R$^{21e}$ an R$^{21f}$ are the same or different and each represents lower alkyl, (substituted or unsubstituted lower cycloalkyl)-substituted lower alkyl, lower cycloalkyl, or lower alkyl-substituted lower cycloalkyl]; and Z$^2$ is CR$^{33a}$ (wherein R$^{33a}$ represents a hydrogen atom, substituted or unsubstituted lower alkyl, substituted or unsubstituted cycloalkyl, substituted or unsubstituted lower alkanoyl, or substituted or unsubstituted aralkyl), W$^2$ is not formula (G$^6$):

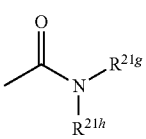

(G$^6$)

[wherein R$^{21g}$ and R$^{21h}$ are the same or different and each represents a hydrogen atom, lower alkyl, halogen-substituted lower alkyl, lower alkoxy-substituted lower alkyl, lower cycloalkyl, lower cycloalkyl substituted by 1 to 3 substitutents selected from the substitutent group B described below (substitutent group B: halogen, lower alkyl, halogen-substituted lower alkyl, and lower alkoxy), aryl, aryl substituted by 1 to 3 substitutents selected from the substitutent group B described above, aralkyl, or aralkyl substituted by 1 to 3 substitutents selected from the substitutent group B described above]} or a pharmaceutically acceptable salt thereof.

(35) The bicyclic heterocyclic compound or the pharmaceutically acceptable salt thereof according to (34), wherein W$^2$ is formula (B$^2$):

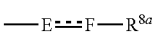

(B$^2$)

(wherein E=F and $R^{8a}$ have the same definitions as described above, respectively).

(36) The bicyclic heterocyclic compound or the pharmaceutically acceptable salt thereof according to (34), wherein $W^2$ is formula ($G^1$):

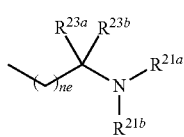

(G¹)

(wherein ne, $R^{21a}$, $R^{21b}$, $R^{23a}$, and $R^{23b}$ have the same definitions as described above, respectively).

(37) The bicyclic heterocyclic compound or the pharmaceutically acceptable salt thereof according to (34), wherein $W^2$ is formula ($G^3$):

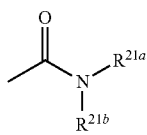

(G³)

(wherein $R^{21a}$ and $R^{21b}$ have the same definitions as described above, respectively).

(38) The bicyclic heterocyclic compound or the pharmaceutically acceptable salt thereof according to (36) or (37), wherein $R^{21a}$ and $R^{21b}$ are the same or different and both or either of $R^{21a}$ and $R^{21b}$ is formula ($H^1$):

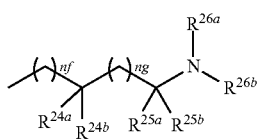

(H¹)

(wherein nf, ng, $R^{24a}$, $R^{24b}$, $R^{25a}$, $R^{25b}$, $R^{26a}$, and $R^{26b}$ have the same definitions as described above, respectively).

(39) The bicyclic heterocyclic compound or the pharmaceutically acceptable salt thereof according to (34), wherein $W^2$ is formula ($G^4$):

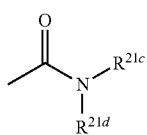

(G⁴)

(wherein $R^{21c}$ and $R^{21d}$ have the same definitions as described above, respectively).

(40) The bicyclic heterocyclic compound or the pharmaceutically acceptable salt thereof according to (34), wherein $W^2$ is —$NR^{11a}R^{11b}$ (wherein $R^{11a}$ and $R^{11b}$ have the same definitions as described above, respectively).

(41) The bicyclic heterocyclic compound or the pharmaceutically acceptable salt thereof according to (34), wherein $W^2$ is —$NHR^{11a}$ (wherein $R^{11a}$ has the same definition as described above).

(42) The bicyclic heterocyclic compound or the pharmaceutically acceptable salt thereof according to (34), wherein $W^2$ is —$NHR^{11c}$ (wherein $R^{11c}$ has the same definition as described above).

(43) The bicyclic heterocyclic compound or the pharmaceutically acceptable salt thereof according to (34), wherein $W^2$ is formula ($C^1$):

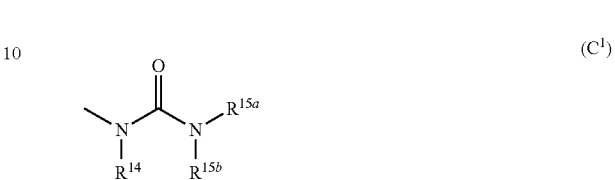

(C¹)

(wherein $R^{14}$, $R^{15a}$, and $R^{15b}$ have the same definitions as described above, respectively).

(44) The bicyclic heterocyclic compound or the pharmaceutically acceptable salt thereof according to (34), wherein $W^2$ is formula ($C^2$):

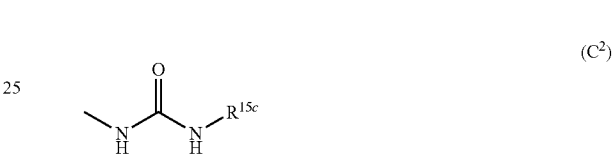

(C²)

(wherein $R^{15c}$ has the same definition as described above).

(45) The bicyclic heterocyclic compound or the pharmaceutically acceptable salt thereof according to (34), wherein $W^2$ is formula ($D^1$):

(D¹)

(wherein $R^{16}$ and $R^{17}$ have the same definitions as described above, respectively).

(46) The bicyclic heterocyclic compound or the pharmaceutically acceptable salt thereof according to (34), wherein $W^2$ is formula ($D^2$):

(D²)

(wherein $R^{17}$ has the same definition as described above).

(47) The bicyclic heterocyclic compound or the pharmaceutically acceptable salt thereof according to (34), wherein $W^2$ is —$NHR^{11d}$ (wherein $R^{11d}$ represents substituted or unsubstituted lower cycloalkylcarbonyl).

(48) The bicyclic heterocyclic compound or the pharmaceutically acceptable salt thereof according to any of (34) to (47), wherein $R^{34}$ is a hydrogen atom.

(49) The bicyclic heterocyclic compound or the pharmaceutically acceptable salt thereof according to any of (34) to (48), wherein $R^{35}$, $R^{36}$, and $R^{37}$ are the same or different and each is a hydrogen atom, halogen, or substituted or unsubstituted lower alkyl.

(50) The bicyclic heterocyclic compound or the pharmaceutically acceptable salt thereof according to any of (34) to (49), wherein $Z^2$ is $CR^{33}$ (wherein $R^{33}$ has the same definition as described above).

(51) The bicyclic heterocyclic compound or the pharmaceutically acceptable salt thereof according to any of (34) to (49), wherein $Z^2$ is CH.

(52) The bicyclic heterocyclic compound or the pharmaceutically acceptable salt thereof according to any of (34) to (51), wherein $Y^3$ and $Y^4$ are CH.

(53) The bicyclic heterocyclic compound or the pharmaceutically acceptable salt thereof according to any of (34) to (51), wherein $Y^3$ and $Y^4$ are a nitrogen atom.

(54) The bicyclic heterocyclic compound or the pharmaceutically acceptable salt thereof according to any of (34) to (53), wherein $R^{35}$, $R^{36}$, and $R^{37}$ are the same or different and each represents a hydrogen atom or substituted or unsubstituted lower alkyl.

(55) The bicyclic heterocyclic compound or the pharmaceutically acceptable salt thereof according to any of (34) to (53), wherein $R^{35}$ and $R^{37}$ are the same or different and each represents a hydrogen atom or substituted or unsubstituted lower alkyl, and $R^{36}$ represents halogen.

(56) A pharmaceutical composition which comprises, as an active ingredient, the bicyclic heterocyclic compound or the pharmaceutically acceptable salt thereof according to any of (34) to (55).

(57) A GPR4 antagonist which comprises, as an active ingredient, the bicyclic heterocyclic compound or the pharmaceutically acceptable salt thereof according to any of (34) to (55).

(58) A preventive and/or therapeutic agent for neutrophilic inflammatory diseases which comprises, as an active ingredient, the bicyclic heterocyclic compound or the pharmaceutically acceptable salt thereof according to any of (34) to (55).

(59) A preventive and/or therapeutic agent for diseases derived from hyperfunction of GPR4 which comprises, as an active ingredient, the bicyclic heterocyclic compound or the pharmaceutically acceptable salt thereof according to any of (1) to (7).

(60) A preventive and/or therapeutic agent for diseases derived from hyperfunction of GPR4 which comprises, as an active ingredient, the bicyclic heterocyclic compound or the pharmaceutically acceptable salt thereof according to any of (9) to (32).

(61) A preventive and/or therapeutic agent for diseases derived from hyperfunction of GPR4 which comprises, as an active ingredient, the bicyclic heterocyclic compound or the pharmaceutically acceptable salt thereof according to any of (34) to (55).

(62) A method for preventing and/or treating neutrophilic inflammatory diseases, which comprises a step of administering an effective amount of the bicyclic heterocyclic compound or the pharmaceutically acceptable salt thereof described in any of (1) to (7).

(63) A method for preventing and/or treating diseases derived from hyperfunction of GPR4, which comprises a step of administering an effective amount of the bicyclic heterocyclic compound or the pharmaceutically acceptable salt thereof described in any of (1) to (7).

(64) A method for preventing and/or treating neutrophilic inflammatory diseases, which comprises a step of administering an effective amount of the bicyclic heterocyclic compound or the pharmaceutically acceptable salt thereof described in any of (9) to (32).

(65) A method for preventing and/or treating diseases derived from hyperfunction of GPR4, which comprises a step of administering an effective amount of the bicyclic heterocyclic compound or the pharmaceutically acceptable salt thereof described in any of (9) to (32).

(66) A method for preventing and/or treating neutrophilic inflammatory diseases, which comprises a step of administering an effective amount of the bicyclic heterocyclic compound or the pharmaceutically acceptable salt thereof according to any of (34) to (55).

(67) A method for preventing and/or treating diseases derived from hyperfunction of GPR4, which comprises a step of administering an effective amount of the bicyclic heterocyclic compound or the pharmaceutically acceptable salt thereof according to any of (34) to (55).

(68) Use of the bicyclic heterocyclic compound or the pharmaceutically acceptable salt thereof described in any of (1) to (7) for the manufacture of a preventive and/or therapeutic agent for neutrophilic inflammatory diseases.

(69) Use of the bicyclic heterocyclic compound or the pharmaceutically acceptable salt thereof described in any of (1) to (7) for the manufacture of a GPR4 antagonist.

(70) Use of the bicyclic heterocyclic compound or the pharmaceutically acceptable salt thereof described in any of (1) to (7) for the manufacture of a preventive and/or therapeutic agent for diseases derived from hyperfunction of GPR4.

(71) Use of the bicyclic heterocyclic compound or the pharmaceutically acceptable salt thereof described in any of (9) to (33) for the manufacture of a preventive and/or therapeutic agent for neutrophilic inflammatory diseases.

(72) Use of the bicyclic heterocyclic compound or the pharmaceutically acceptable salt thereof described in any of (9) to (33) for the manufacture of a GPR4 antagonist.

(73) Use of the bicyclic heterocyclic compound or the pharmaceutically acceptable salt thereof described in any of (9) to (33) for the manufacture of a preventive and/or therapeutic agent for diseases derived from hyperfunction of GPR4.

(74) Use of the bicyclic heterocyclic compound or the pharmaceutically acceptable salt thereof according to any of (34) to (55) for the manufacture of a preventive and/or therapeutic agent for neutrophilic inflammatory diseases.

(75) Use of the bicyclic heterocyclic compound or the pharmaceutically acceptable salt thereof according to any of (34) to (55) for the manufacture of a GPR4 antagonist.

(76) Use of the bicyclic heterocyclic compound or the pharmaceutically acceptable salt thereof according to any of (34) to (55) for the manufacture of a preventive and/or therapeutic agent for diseases derived from hyperfunction of GPR4.

Hereinafter, compounds represented by formulae (I), (II), and (III) are referred to as "Compound (I)", "Compound (II)", and "Compound (III)", respectively. This applies to compounds of other formula numbers.

In the definition of each group in Compound (I), Compound (II), and Compound (III):

The halogen includes fluorine, chlorine, bromine, and iodine atoms.

The halogen in halogen-substituted lower alkyl and halogen-substituted lower alkoxy has the same definition as the halogen described above.

Examples of the lower alkyl include straight or branched alkyl having 1 to 10 carbon atoms and, more specifically, include methyl, ethyl, propyl, isopropyl, butyl, isobutyl, sec-butyl, tert-butyl, pentyl, neopentyl, hexyl, heptyl, octyl, nonyl, decyl, and the like.

The lower alkyl moieties of lower alkoxy, lower alkanoyl, lower alkoxycarbonyl, lower alkoxycarbonylamino, monoor di-lower alkylamino, lower alkylsulfonyl, lower alkoxy-substituted lower alkyl, lower alkoxy-substituted lower alkoxy, and lower alkyl-substituted lower cycloalkyl have the same definitions as the above-described lower alkyl. The two lower alkyl moieties of di-lower alkylamino may be the same or different.

The alkylene moieties of halogen-substituted lower alkyl, lower alkoxy-substituted lower alkyl, hydroxy-substituted lower alkoxy, lower alkoxy-substituted lower alkoxy, halogen-substituted lower alkoxy, and aryl-substituted lower alkanoyl have the same definitions as alkylene formed by removing one hydrogen atom from the lower alkyl described above.

Examples of lower cycloalkyl include monocyclic, bicyclic, or tricyclic cycloalkyl having 3 to 10 carbon atoms and, more specifically, include cyclopropyl, cyclobutyl, cyclopentyl, cyclohexyl, cycloheptyl, cyclooctyl, bicyclo[3.2.1]octanyl, adamantyl, and the like.

The lower cycloalkyl moiety of lower cycloalkylcarbonyl has the same definition as the lower cycloalkyl described above.

The cycloalkylene moieties of lower alkyl-substituted lower cycloalkyl and (lower alkyl-substituted lower cycloalkyl)-substituted lower alkyl have the same definitions as cycloalkylene formed by removing one hydrogen atom from the lower cycloalkyl described above.

Examples of lower alkenyl include straight or branched alkenyl having 2 to 10 carbon atoms and, more specifically, include vinyl, allyl, 2-butenyl, 3-butenyl, 4-pentenyl, 5-hexenyl, 6-heptenyl, 7-octenyl, 8-nonenyl, and 9-decenyl.

Examples of styryl include 1-phenylvinyl, 2-phenylvinyl, and the like.

Examples of lower alkynyl include straight or branched alkynyl having 2 to 10 carbon atoms and, more specifically, include ethynyl, propargyl, 3-butynyl, 3-hexynyl, 4-methyl-2-pentynyl, 6-heptynyl, 7-octynyl, 8-nonynyl, 9-decynyl, and the like.

Examples of a saturated aliphatic ring include saturated aliphatic rings having 3 to 8 carbon atoms and, more specifically, include a cyclopropane ring, a cyclobutane ring, a cyclopentane ring, a cyclohexane ring, a cycloheptane ring, a cyclooctane ring, and the like.

Examples of aryl include aryl having 6 to 14 carbon atoms and more specifically include phenyl, naphthyl, indenyl, anthryl, and the like.

The aryl moieties of aryloxy, aryloxycarbonyl, arylsulfonyl, and aroyl have the same definitions as the aryl described above.

The aryl moieties of aralkyl and aralkyloxy have the same definitions as the aryl described above, and the alkylene moieties thereof have the same definitions as alkylene formed by removing one hydrogen atom from the lower alkyl described above. In addition to the aryl moieties described above, examples of the aryl moieties of aralkyl and aralkyloxy include groups formed by removing one hydrogen atom from a fused ring of aryl and cycloalkyl and more specifically include indanyl, 1,2,3,4-tetrahydronaphthyl, 6,7,8,9-tetrahydro-5H-benzocycloheptyl, and the like.

Phenylene has the same definition as that formed by removing one hydrogen atom from phenyl.

Naphthylene has the same definition as that formed by removing one hydrogen atom from naphthyl.

Examples of an aromatic heterocyclic group include 5- or 6-membered monocyclic aromatic heterocyclic groups containing at least one atom selected from a nitrogen atom, an oxygen atom, and a sulfur atom; and bicyclic or tricyclic fused aromatic heterocyclic groups in which 3- to 8-membered rings are fused and which contain at least one atom selected from a nitrogen atom, an oxygen atom, and a sulfur atom. More specific examples include furyl, thienyl, pyrrolyl, pyridyl, isooxazolyl, oxazolyl, thiazolyl, imidazolyl, pyrazolyl, pyrimidinyl, triazinyl, indolyl, quinolyl, purinyl, benzoxazolyl, benzothiazolyl, thiadiazolyl, benzoimidazolyl, pyridonyl, oxadiazolyl, and pyrazinyl.

The aromatic heterocyclic moieties of aromatic heterocyclic carbonyl, aromatic heterocyclic oxycarbonyl, and aromatic heterocyclic sulfonyl have the same definitions as the aromatic heterocyclic group described above.

Heteroarylene has the same definition as that formed by removing one hydrogen atom from the above-described aromatic heterocyclic group described above.

Examples of an aliphatic heterocyclic group include 5- or 6-membered monocyclic aliphatic heterocyclic groups containing at least one atom selected from a nitrogen atom, an oxygen atom, and a sulfur atom; and bicyclic or tricyclic fused aliphatic heterocyclic groups in which 3 to 8-membered rings are fused and which contain at least one atom selected from a nitrogen atom, an oxygen atom, and a sulfur atom. More specific examples include pyrrolidinyl, piperidino, piperidyl, piperazinyl, morpholino, morpholinyl, thiomorpholino, thiomorpholinyl, homopiperidino, homopiperidyl, homopiperazinyl, tetrahydropyridyl, tetrahydroquinolyl, tetrahydroisoquinolyl, tetrahydrofuranyl, tetrahydropyranyl, dihydrobenzofuranyl, quinuclidinyl, indolinyl, isoindolinyl, and the like.

A divalent group formed by removing any one hydrogen atom from an aliphatic heterocycle of an aliphatic heterocyclic group has the same definition as that formed by removing one hydrogen atom from the aliphatic heterocyclic group described above.

Examples of a heterocyclic group formed together with the adjacent nitrogen atom include aliphatic heterocyclic groups formed together with the adjacent nitrogen atom, and aromatic heterocyclic groups formed together with the adjacent nitrogen atom. Examples of aliphatic heterocyclic groups formed together with the adjacent nitrogen atom include 5- or 6-member monocyclic aliphatic heterocyclic groups containing at least one nitrogen atom (which may contain other nitrogen atom(s), oxygen atom(s), or sulfur atom(s)); and bicyclic or tricyclic fused aliphatic heterocyclic groups in which fused 3- to 8-membered rings are fused and which contain at least one nitrogen atom (which may contain other nitrogen atom(s), oxygen atom(s), or sulfur atom(s)). More specific examples include pyrrolidinyl, piperidino, piperazinyl, morpholino, thiomorpholino, homopiperidino, homopiperazinyl, tetrahydropyridyl, tetrahydroquinolyl, tetrahydroisoquinolyl, indolinyl, isoindolinyl, and the like. Examples of an aromatic heterocyclic group formed together with the adjacent nitrogen atom include 5- or 6-membered monocyclic aromatic heterocyclic groups containing at least one nitrogen atom (which may contain other nitrogen atom(s), oxygen atom(s), or sulfur atom(s)); and bicyclic or tricyclic fused aromatic heterocyclic groups in which 3- to 8-membered rings are fused and which contain at least one nitrogen atom (which may contain other nitrogen atom(s), oxygen atom(s), or sulfur atom(s)). More specific examples include pyrrolyl, imidazolyl, indolyl, indazolyl, carbazolyl, and the like.

Examples of a heterocyclic group formed together with the adjacent carbon atom and nitrogen atom include aliphatic heterocyclic groups formed together with the adjacent carbon atom and nitrogen atom. Examples of an aliphatic heterocyclic group formed together with the adjacent carbon atom and nitrogen atom include 5- or 6-membered monocyclic aliphatic heterocyclic groups containing at least one nitrogen atom (which may contain other nitrogen atom(s), oxygen atom(s), or sulfur atom(s)); and bicyclic or tricyclic fused aliphatic heterocyclic groups in which 3- to 8-membered rings are fused and which contain at least one nitrogen atom (which may contain other nitrogen atom(s), oxygen atom(s), or sulfur atom(s)). More specific examples include pyrrolidinyl, piperidyl, piperazinyl, morpholinyl, thiomorpholinyl, homopiperidinyl, homopiperazinyl, tetrahydropyridyl, tetrahydroquinolyl, tetrahydroisoquinolyl, indolinyl, isoindolinyl, perhydroazepinyl, and the like.

Substituted lower alkyl, substituted lower alkoxy, substituted lower alkanoyl, substituted lower cycloalkyl, substituted lower cycloalkylcarbonyl, substituted lower alkoxycarbonyl, substituted lower alkylsulfonyl, substituted lower alkenyl, and substituted lower alkynyl have 1 to 3 substitutents which are the same or different. Examples of the substitutents (substitutent group C) include halogen, hydroxy, formyl, trifluoromethyl, vinyl, styryl, phenylethynyl, lower alkoxycarbonyl, aryloxy, aralkyloxy, aroyl, substituted or unsubstituted lower cycloalkyl [the substitutent(s) in the substituted lower cycloalkyl, which may be the same or different and is 1 to 3 in number, is for example, halogen, hydroxy, oxo, methylenedioxy, ethylenedioxy, aryl, a substituted or unsubstituted aliphatic heterocyclic group (the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), and the like], substituted or unsubstituted lower alkoxy (the substitutent(s) in the substituted lower alkoxy, which may be the same or different and is 1 to 3 in number, is for example, hydroxy, lower alkoxy, and the like), substituted or unsubstituted lower alkanoyl (the substitutent(s) in the substituted lower alkanoyl, which may be the same or different and is 1 to 3 in number, is for example, aryl and the like), substituted or unsubstituted lower cycloalkylcarbonyl (the substitutent(s) in the substituted lower cycloalkylcarbonyl, which may be the same or different and is 1 to 3 in number, is for example, aryl and the like), substituted or unsubstituted aralkyl (the substitutent(s) in the substituted aralkyl, which may be the same or different and is 1 to 3 in number, is for example, halogen, hydroxy, lower alkoxy, and the like), a substituted or unsubstituted aliphatic heterocyclic group (the substitutent(s) in the substituted aliphatic heterocyclic group has the same definition as the substitutent group D described below), a substituted or unsubstituted aromatic heterocyclic group (excluding tetrazolyl, the substitutent(s) in the substituted aromatic heterocyclic group has the same definition as the substitutent group D described below), mono or di(substituted or unsubstituted lower alkyl)aminocarbonyl [the substitutent(s) in the mono or di(substituted lower slkyl)aminocarbonyl, which may be the same or different and is 1 to 3 in number, is for example, halogen, hydroxy, substituted or unsubstituted aliphatic heterocyclic group (the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), and the like], substituted or unsubstituted aliphatic heterocyclic carbonyl [the substitutent(s) in the substituted aliphatic heterocyclic carbonyl, which may be the same or different and is 1 to 3 in number, is for example, halogen, hydroxy, lower alkyl, halogen-substituted alkyl, hydroxy-substituted lower alkyl, lower alkoxycarbonyl, a substituted or unsubstituted aliphatic heterocyclic group (the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), and the like], and —C(=NOR$^{45}$)R$^{46}$ [wherein R$^{45}$ represents a hydrogen atom, substituted or unsubstituted lower alkyl (the substitutent(s) in the substituted lower alkyl, which may be the same or different and is 1 to 3 in number, is for example, halogen, hydroxy, and the like), substituted or unsubstituted lower cycloalkyl (the substitutent(s) in the substituted lower cycloalkyl, which may be the same or different and is 1 to 3 in number, is for example, halogen, hydroxy, and the like), substituted or unsubstituted aryl (the substitutent(s) in the substituted aryl, which may be the same or different and is 1 to 3 in number, is for example, halogen, hydroxy, lower alkyl, and the like), substituted or unsubstituted aralkyl (the substitutent(s) in the substituted aralkyl, which may be the same or different and is 1 to 3 in number, is for example, halogen, hydroxy, lower alkyl, and the like), or a substituted or unsubstituted aromatic heterocyclic group (excluding tetrazolyl) (the substitutent(s) in the substituted aromatic heterocyclic group, which may be the same or different and is 1 to 3 in number, is for example, halogen, hydroxy, lower alkyl, and the like); and R$^{46}$ represents substituted or unsubstituted lower alkyl (the substitutent(s) in the substituted lower alkyl, which may be the same or different and is 1 to 3 in number, is for example, halogen, hydroxy, and the like), substituted or unsubstituted lower cycloalkyl (the substitutent(s) in the substituted lower cycloalkyl, which may be the same or different and is 1 to 3 in number, is for example, halogen, hydroxy, and the like), substituted or unsubstituted aryl (the substitutent(s) in the substituted aryl, which may be the same or different and is 1 to 3 in number, is for example, halogen, hydroxy, lower alkyl, or the like), substituted or unsubstituted aralkyl (the substitutent(s) in the substituted aralkyl, which may be the same or different and is 1 to 3 in number, is for example, halogen, hydroxy, lower alkyl, and the like)]. In addition to the substitutents described above, examples of substitutents in the substituted lower cycloalkyl and substituted lower cycloalkylcarbonyl include oxo, methylenedioxy, ethylenedioxy, substituted or unsubstituted lower alkyl [the substitutent(s) in the substituted lower alkyl, which may be the same or different and is 1 to 3 in number, is for example, halogen, hydroxy, a substituted or unsubstituted aliphatic heterocyclic group {the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, mono or di(substituted or unsubstituted lower alkyl)amino [the substitutent(s) in the mono or di(substituted lower alkyl)amino, which may be the same or different and is 1 to 3 in number, is for example, halogen, hydroxy, an aliphatic heterocyclic group, and the like], a substituted or unsubstituted aliphatic heterocyclic group (the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), and the like}, and mono or di(substituted or unsubstituted lower alkyl)amino [the substitutent(s) in the mono or di(substituted lower alkyl)amino, which may be the same or different and is 1 to 3 in number, is for example, halogen, hydroxy, an aliphatic heterocyclic group, and the like], and the like]. In addition to the substitutents described above, examples of substitutents in the substituted lower alkoxy, substituted lower alkanoyl, substituted lower cycloalkyl, substituted lower cycloalkylcarbonyl, substituted lower alkoxycarbonyl, substituted lower alkylsulfonyl, substituted lower alkenyl, and substituted lower alkynyl include substituted or unsubstituted aryl (the substitutent(s) in the substituted aryl, which may be the same or different and is 1 to 3 in number, is for example, halogen, hydroxy, lower alkoxy, and the like).

In the definitions of substitutents in the substituted lower alkyl, substituted lower alkoxy, substituted lower alkanoyl, substituted lower cycloalkyl, substituted lower cycloalkylcarbonyl, substituted lower alkoxycarbonyl, substituted lower alkylsulfonyl, substituted lower alkenyl, and substituted lower alkynyl described above, the halogen, the styryl, the lower alkoxy, the lower alkyl moieties of lower alkoxycarbonyl and lower alkanoyl, the lower cycloalkyl moieties of lower cycloalkyl and lower cycloalkylcarbonyl, the aryl, the aryl moieties of aryloxy and aroyl, the aryl moieties and alkylene moieties of aralkyl and aralkyloxy, the aliphatic heterocyclic group, and the aromatic heterocyclic group have the same definitions as described above, respectively. The lower alkyl moieties of mono or di(lower alkyl)amino and mono or di(lower alkyl)aminocarbonyl have the same definitions as the lower alkyl described above. The alkylene moieties of halogen-substituted lower alkyl and hydroxy-substituted lower alkyl have the same definitions as that formed by removing one hydrogen atom from the lower alkyl described above. The two lower alkyl moieties of di(lower alkyl)amino and di(lower alkyl)aminocarbonyl may be the same or different.

Substituted aryl, substituted aralkyl, substituted aroyl, substituted aryloxycarbonyl, substituted arylsulfonyl, a substituted aliphatic heterocyclic group, a substituted aromatic heterocyclic group, substituted aromatic heterocyclic carbonyl, substituted aromatic heterocyclic oxycarbonyl, substituted aromatic heterocyclic sulfonyl, substituted phenylene, substituted naphthylene, substituted heteroarylene, and a divalent group formed by removing any one hydrogen atom from an aliphatic heterocycle of a substituted aliphatic heterocyclic group have 1 to 3 substitutents which are the same or different. Examples of the substitutents (substitutent group D) include halogen, amino, nitro, hydroxy, cyano, formyl and equivalents thereof (for example, 1,3-dioxolan-2-yl), carbamoyl, trifluoromethoxy, methylenedioxy, ethylenedioxy, lower alkoxy, mono or di(lower alkyl)amino, (lower alkanoyl)amino, (lower alkoxycarbonyl)amino, substituted or unsubstituted lower alkyl {the substitutent(s) in the substituted lower alkyl, which may be the same or different and is 1 to 3 in number, is for example, halogen, hydroxy, a substituted or unsubstituted aliphatic heterocyclic group (the substitutent(s) in the substituted aliphatic heterocyclic group, which may be the same or different and is 1 to 3 in number, is for example, lower alkyl, lower alkoxycarbonyl, and the like), mono or di(substituted or unsubstituted lower alkyl)amino [the substitutent(s) in the mono or di(substituted lower alkyl)amino, which may be the same or different and is 1 to 3 in number, is for example, halogen, hydroxy, an aliphatic heterocyclic group, and the like], and the like}, substituted or unsubstituted lower cycloalkyl [the substitutent(s) in the substituted lower cycloalkyl, which may be the same or different and is 1 to 3 in number, is for example, halogen, hydroxy, a substituted or unsubstituted aliphatic heterocyclic group (the substitutent(s) in the aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), and the like], substituted or unsubstituted lower alkoxycarbonyl (the substitutent(s) in the substituted lower alkoxycarbonyl, which may be the same or different and is 1 to 3 in number, is for example, halogen, hydroxy, and the like), substituted or unsubstituted lower cycloalkyloxycarbonyl (the substitutent(s) in the substituted lower ayaloalkyloxycarbonyl, which may be the same or different and is 1 to 3 in number, is for example, halogen, hydroxy, or the like), substituted or unsubstituted lower alkanoyl (the substitutent(s) in the substituted lower alkanoyl, which may be the same or different and is 1 to 3 in number, is for example, halogen, hydroxy, and the like), substituted or unsubstituted lower cycloalkylcarbonyl (the substitutent(s) in the substituted lower cycloalkylcarbonyl, which may be the same or different and is 1 to 3 in number, is for example, halogen, hydroxy, and the like), substituted or unsubstituted aryl (the substitutent(s) in the substituted aryl, which may be the same or different and is 1 to 3 in number, is for example, halogen, hydroxy, and the like), substituted or unsubstituted aryloxy (the substitutent(s) in the substituted aryloxy, which may be the same or different and is 1 to 3 in number, is for example, halogen, hydroxy, and the like), substituted or unsubstituted aralkyl (the substitutent(s) in the substituted lower aralkyl, which may be the same or different and is 1 to 3 in number, is for example, halogen, hydroxy, and the like), substituted or unsubstituted aralkyloxy (the substitutent(s) in the substituted aralkyloxy, which may be the same or different and is 1 to 3 in number, is for example, halogen, hydroxy, and the like), substituted or unsubstituted aroyl (the substitutent(s) in the substituted aroyl, which may be the same or different and is 1 to 3 in number, is for example, halogen, hydroxy, and the like), a substituted or unsubstituted aromatic heterocyclic group (the substitutent(s) in the substituted aromatic heterocyclic group, which may be the same or different and is 1 to 3 in number, is for example, halogen, hydroxy, and the like), a substituted or unsubstituted aliphatic heterocyclic group (the substitutent(s) in the substituted aliphatic heterocyclic group, which may be the same or different and is 1 to 3 in number, is for example, lower alkyl, halogen-substituted lower alkyl, hydroxy-substituted lower alkyl, lower alkoxycarbonyl, and the like), substituted or unsubstituted aliphatic heterocyclic carbonyl (the substitutent(s) in the substituted aliphatic heterocyclic carbonyl, which may be the same or different and is 1 to 3 in number, is for example, lower alkyl, halogen-substituted lower alkyl, hydroxy-substituted lower alkyl, lower alkoxycarbonyl, and the like), and the like. In addition to the substitutents described above, substitutents in the substituted aliphatic heterocyclic group and the divalent group formed by removing any one hydrogen atom from the aliphatic heterocycle of a substituted aliphatic heterocyclic group may be oxo.

In the definitions of substitutents in the substituted aryl, the substituted aralkyl, the substituted aroyl, the substituted aryloxycarbonyl, the substituted arylsulfonyl, the substituted aliphatic heterocyclic group, the substituted aromatic heterocyclic group, the substituted aromatic heterocyclic carbonyl, substituted aromatic heterocyclic oxycarbonyl, substituted aromatic heterocyclic sulfonyl, substituted phenylene, substituted naphthylene, substituted heteroarylene, and divalent group formed by removing any one hydrogen atom in the aliphatic heterocycle of a substituted aliphatic heterocyclic group described above, the halogen, the lower alkyl, the lower alkoxy, the lower alkoxycarbonyl, the mono or di(lower alkyl)amino, the lower alkyl moieties of lower alkoxycarbonylamino and lower alkanoyl, the lower cycloalkyl, the lower cycloalkyl moieties of lower cycloalkylcarbonyl and lower cycloalkyloxycarbonyl, the aryl, the aryl moieties of aryloxy and aroyl, the aryl moieties and alkylene moieties of aralkyl and aralkyloxy, the aromatic heterocyclic group, and the aliphatic heterocyclic group have the same definitions as described above, respectively. The alkylene moieties of halogen-substituted lower alkyl and hydroxy-substituted lower alkyl have the same definition as that formed by removing one hydrogen atom from the lower alkyl described above. The lower alkyl moiety of lower alkanoylamino has the same definition as the lower alkyl described above. The aliphatic heterocyclic moiety of aliphatic heterocyclic carbonyl has the same definition as the aliphatic heterocyclic group described above.

Substituted heterocyclic group formed together with the adjacent nitrogen atom and a substituted heterocyclic group formed together with the adjacent carbon atom and nitrogen atom have 1 to 3 substitutents which are the same or different. Examples of the substitutents (substitutent group D) include halogen, hydroxy, oxo, carbamoyl, lower alkoxy, lower alkoxycarbonyl, lower alkanoyl, lower cycloalkylcarbonyl, lower alkylsulfonyl, aromatic heterocyclic carbonyl, substituted or unsubstituted lower alkyl (the substitutent(s) in the substituted lower alkyl has the same definition as the substitutent group C described above), substituted or unsubstituted lower cycloalkyl (the substitutent(s) in the substituted lower cycloalkyl has the same definition as the substitutent group C described above), substituted or unsubstituted aryl (the substitutent(s) in the substituted aryl has the same definition as the substitutent group D described above), substituted or unsubstituted aralkyl (the substitutent(s) in the substituted aralkyl has the same definition as the substitutent group D described above), a substituted or unsubstituted aliphatic heterocyclic group (the substitutent(s) in the substituted aliphatic heterocyclic group has the same definition as the substitutent group D described above), a substituted or unsubstituted aromatic heterocyclic group (excluding tetrazolyl, the substitutent(s) in the substituted aromatic heterocyclic group has the same definition as the substitutent group D described above), —NR$^{38a}$R$^{38b}$ [wherein R$^{38a}$ and R$^{38b}$ are the same or different and each represents lower alkanoyl, lower alkylsulfonyl, aromatic heterocyclic carbonyl, substituted or unsubstituted lower alkyl (the substitutent(s) in the substituted lower alkyl has the same definition as the substitutent group C described above), substituted or unsubstituted lower cycloalkyl (the substitutent(s) in the substituted lower cycloalkyl has the same definition as the substitutent group C described above), substituted or unsubstituted aryl (the substitutent(s) in the substituted aryl has the same definition as the substitutent group D described above), substituted or unsubstituted aralkyl (the substitutent(s) in the substituted aralkyl has the same definition as the substitutent group D described above), a substituted or unsubstituted aliphatic heterocyclic group (the substitutent(s) in the substituted aliphatic heterocyclic group has the same definition as the substitutent group D described above), or a substituted or unsubstituted aromatic heterocyclic group (the substitutent(s) in the substituted aromatic heterocyclic group has the same definition as the substitutent group D described above), or R$^{38a}$ and R$^{38b}$ are combined together with the adjacent nitrogen atom thereto to form a substituted or unsubstituted heterocyclic group (the substitutent(s) in the substituted heterocyclic group has the same definition as the substitutent group D described above)], or —CONR$^{38c}$R$^{38d}$ (wherein R$^{38c}$ and R$^{38d}$ have the same definitions as R$^{38a}$ and R$^{38b}$ described above, respectively), and the like.

In the definitions of substituents in the substituted heterocyclic group formed together with the adjacent nitrogen atom and a substituted heterocyclic group formed together with the adjacent carbon atom and nitrogen atom described above, the halogen, the lower alkyl, the lower alkoxy, the lower alkoxycarbonyl, the lower alkyl moieties of lower alkanoyl and lower alkylsulfonyl, the lower cycloalkyl and the lower cycloalkyl moiety of lower cycloalkylcarbonyl, the aryl and the aryl moiety of aralkyl, the alkylene moiety of aralkyl, the aromatic heterocyclic group and the aromatic heterocyclic moiety of an aromatic heterocyclic group and aromatic heterocyclic carbonyl, the aliphatic heterocyclic group, and the heterocyclic group formed together with the adjacent nitrogen atom have the same definitions as described above, respectively.

Examples of the pharmaceutically acceptable salts of Compounds (I), (II), and (III) include pharmaceutically acceptable metal salts, ammonium salts, organic amine addition salts, amino acid addition salts, acid addition salts, and the like. Examples of the pharmaceutically acceptable metal salts include alkali metal salt, such as sodium salts and potassium salts; alkaline earth metal salts, such as magnesium salts and calcium salts; aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of amino acids, such as lysine, glycine, phenylalanine, and the like. Examples of the pharmaceutically acceptable acid addition salts include inorganic acid salts, such as hydrochlorides, sulfates, and phosphates; and organic acid salts, such as acetates, maleates, fumarates, tartrates, and citrates.

Example of the neutrophilic inflammatory diseases include chronic obstructive pulmonary disease (COPD), pulmonary emphysema, chronic bronchitis, acute respiratory distress syndrome (ARDS), acute lung injury (ALI), rhinitis, sarcoidosis, interstitial pneumonia, pulmonary fibrosis, sepsis, articular rheumatism, Behçet's disease, Sjögrens's syndrome, scleroderma, psoriasis, atopic dermatitis, contact dermatitis, hives, angitis, erythema, conjunctivitis, eosinophilia, uveitis, alopecia areata, eczema, lichen planus, hydroa, pemphigus, proctitis, eosinophilic gastroenteritis, mastocytosis, Crohn's disease, ulcerative colitis, food allergy, multiple sclerosis, atherosclerosis, acquired immunodeficiency syndrome (AIDS), systemic lupus erythematodes, Hashimoto's disease, nephrotic syndrome, myasthenia gravis, 1-type diabetes, eosinophilic myofascitis, hyper IgE syndrome, leprosy, purpura, graft rejection, squamous cell carcinoma, lung cancer, cystic fibrosis, apoplexy, reperfusion injury of heart and extremities, gout, irritable bowel syndrome, and the like.

Compounds (I) and (II) or pharmaceutically acceptable salts thereof may include isomers such as regioisomers, geometrical isomers, optical isomers, or tautomers, however all possible isomers including these isomers and mixtures of these isomers at any ratio may be included in the preventive and/or therapeutic agents for neutrophilic inflammatory diseases of the present invention.

Also, Compound (III) or pharmaceutically acceptable salts thereof may include isomers such as regioisomers, geometrical isomers, optical isomers, or tautomers, but all possible isomers including these isomers and mixtures of these isomers at any ratio may be included in the bicyclic heterocyclic compounds of the present invention.

Compounds (I) and (II), or pharmaceutically acceptable salts thereof may be present in the form of an adduct with water or various solvents, however these adducts may be included in the preventive and/or therapeutic agents for neutrophilic inflammatory diseases of the present invention.

Also, Compound (III) or pharmaceutically acceptable salts thereof may be present in the form of an adduct with water or various solvents, however these adducts may be included in the bicyclic heterocyclic compounds of the present invention.

Next, production methods for Compound (II) will be described. Compound (III) can be produced by the same method as for Compound (II).

Some of the compounds obtained by the production methods below [for example, Compound (II-a), Compound (II-b), and the like] may not be included in the range of Compound (II), however such compounds are denoted by these compound numbers for convenience' sake.

When the defined groups are changed under reaction conditions or unsuitable for carrying out the production methods described below, the methods can be easily carried out by a method ordinarily used in synthetic organic chemistry, for example, by means of protection of functional groups and deprotection thereof, or the like (for example, Protective Groups in Organic Synthesis, the third edition, T. W. Greene, Peter G. M. Wuts, John W. & Sons Inc., 1999). If necessary, the order of reaction steps such as introduction of substitutent can be changed.

Compound (II) can be produced by, for example, any one of production methods 1 to 15 below.

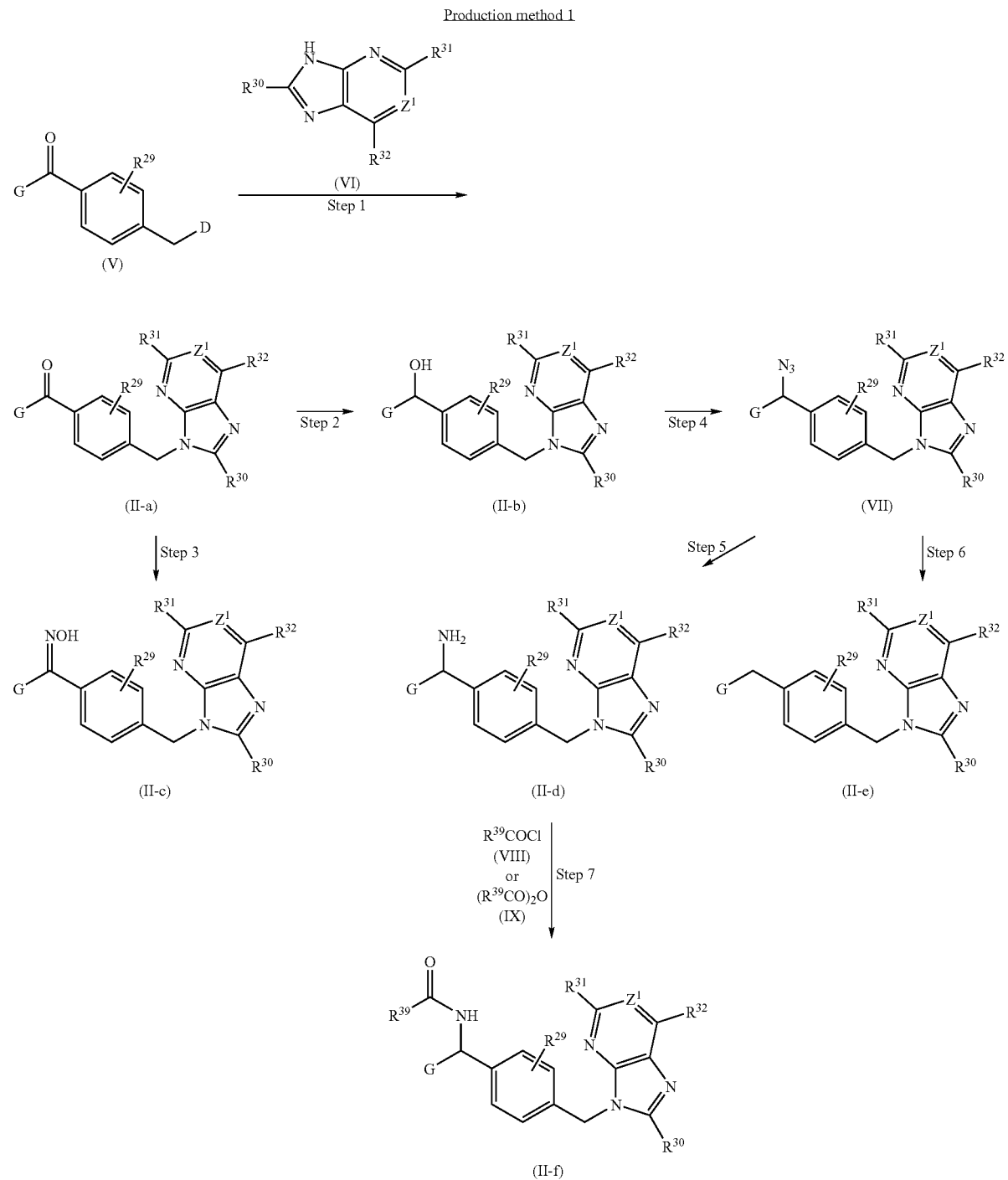

[wherein R$^{39}$ and G each represent substituted or unsubstituted lower alkyl, substituted or unsubstituted lower cycloalkyl, substituted or unsubstituted aryl, or a substituted or unsubstituted aromatic heterocyclic group (excluding tetrazolyl), D represents an iodine atom, a bromine atom, or a chlorine atom, and R$^{29}$, R$^{30}$, R$^{31}$, R$^{32}$, and Z$^{1}$ each have the same definitions as described above, respectively].

Step 1

Compound (II-a) can be synthesized by subjecting Compound (V) to the method described in U.S. Pat. No. 5,151,435 or a similar method thereto. Compound (VI) can be synthesized by the method descried in Japanese Unexamined Published Patent Application No. 95181/1991 or a similar method thereto.

Step 2

Compound (II-b) can be produced by reacting Compound (II-a) with 2 to 4 equivalents of a reducing agent in a solvent at −78 to 100° C. for 10 minutes to 24 hours, preferably 1 to 3 hours.

Examples of the reducing agent include lithium aluminum hydride, sodium borohydride, diisobutylaluminum hydride, and the like. Preferably, lithium aluminum hydride or sodium borohydride can be used.

Examples of the solvent include dichloromethane, chloroform, carbon tetrachloride, dichloroethane, benzene, toluene, xylene, diethyl ether, tetrahydrofuran (THF), 1,4-dioxane, N,N-dimethylformamide (DMF), N,N-dimethylacetamide (DMA), acetonitrile, methanol, ethanol, propanol, mixtures thereof, and the like. Preferably, methanol, THF, or toluene can be used.

Step 3

Compound (II-c) can be produced by reacting Compound (II-a) with 1 equivalent to a large excess amount of hydroxylamine hydrochloride or N,O-bis(trimethylsilyl)hydroxylamine in the presence of 1 equivalent to a large excess amount of a base in a solvent at a temperature between 0° C. and the boiling point of the solvent, preferably 0 to 80° C., for 1 to 48 hours.

Examples of the base include triethylamine, diisopropylethylamine, lithium diisopropylamide (LDA), potassium tert-butoxide, pyridine, N-methylmorpholine, potassium carbonate, 1,8-diazabicyclo[5.4.0]-7-undecene (DBU), sodium hydride, potassium hydride, and the like. Preferably, pyridine or potassium hydride can be used.

Examples of the solvent include pyridine, dichloromethane, chloroform, carbon tetrachloride, dichloroethane, benzene, toluene, xylene, diethyl ether, THF, 1,4-dioxane, DMF, DMA, acetonitrile, methanol, ethanol, propanol, mixtures thereof, and the like. Preferably, ethanol or pyridine can be used.

Step 4

Compound (VII) can be synthesized by reacting Compound (II-b) with 1 equivalent to a large excess amount, preferably 1 to 10 equivalents, of diphenylphosphoryl azide in the presence of 1 equivalent to a large excess amount of a base in a solvent at a temperature between 0° C. and the boiling point of the solvent, preferably 0 to 100° C., for 1 to 48 hours.

Examples of the base include triethylamine, diisopropylethylamine, LDA, potassium tert-butoxide, pyridine, N-methylmorpholine, potassium carbonate, DBU, sodium hydride, potassium hydride, and the like. Preferably, diisopropylethylamine or DBU can be used.

Examples of the solvent include pyridine, dichloromethane, chloroform, carbon tetrachloride, dichloroethane, benzene, toluene, xylene, diethyl ether, THF, 1,4-dioxane, DMF, DMA, acetonitrile, ethyl acetate, mixtures thereof, and the like. Preferably, dichloromethane or toluene can be used.

Step 5

Compound (II-d) can be synthesized by reacting Compound (VII) in the presence of a catalytic amount to 1 equivalent of a catalyst in a solvent under hydrogen atmosphere at 1 to 5 atm or in the presence of 1 equivalent to a large excess amount of formic acid, ammonium formate, or hydrazine at a temperature between 0° C. and the boiling point of the solvent, preferably room temperature to 120° C., for 10 minutes to 48 hours.

Examples of the catalyst include palladium-carbon, palladium hydroxide-carbon, palladium-aluminum, Raney nickel, platinum, platinum oxide, a Lindlar catalyst, rhodium, nickel, ruthenium, and the like. Preferably, the Lindlar catalyst can be used.

Examples of the solvent include methanol, ethanol, THF, 1,4-dioxane, dimethoxyethane, DMF, DMA, benzene, toluene, xylene, acetonitrile, mixtures thereof, and the like. Preferably, methanol or ethanol can be used.

Step 6

Compound (II-e) can be produced by reacting Compound (VII) in the presence of a catalytic amount to 1 equivalent of a catalyst in a solvent under hydrogen atmosphere at 1 to 5 atm or in the presence of 1 equivalent to a large excess amount of formic acid, ammonium formate, or hydrazine at a temperature between 0° C. and the boiling point of the solvent, preferably room temperature to 120° C., for 10 minutes to 48 hours.

Examples of the catalyst include palladium-carbon, palladium hydroxide-carbon, palladium-aluminum, Raney nickel, platinum, platinum oxide, a Lindlar catalyst, rhodium, nickel, ruthenium, and the like. Preferably, palladium-carbon or Raney nickel can be used.

Examples of the solvent include methanol, ethanol, THF, 1,4-dioxane, dimethoxyethane, DMF, DMA, benzene, toluene, xylene, acetonitrile, mixtures thereof, and the like. Preferably, methanol or ethanol can be used.

Step 7

Compound (II-f) can be synthesized by reacting Compound (II-d) with 1 equivalent to a large excess amount, preferably 1 to 10 equivalents, of Compound (VIII) or (IX) in a solvent in the presence of 1 equivalent to a large excess, preferably 1 to 10 equivalents, of a base at a temperature between 0° C. and the boiling point of the solvent used, preferably room temperature to 120° C., for 10 minutes to 48 hours.

Examples of the base include triethylamine, diisopropylethylamine, LDA, potassium tert-butoxide, pyridine, N-methylmorpholine, potassium carbonate, DBU, functional resins having basic functional groups which do not react with acid chlorides or acid anhydrides, and the like. Preferably, triethylamine, pyridine, or polyvinylpyridine can be used.

Examples of the solvent include dichloromethane, chloroform, THF, 1,4-dioxane, dimethoxyethane, DMF, DMA, benzene, toluene, xylene, acetonitrile, ethyl acetate, pyridine, tetralin, mixtures thereof, and the like. Preferably, chloroform or dichloromethane can be used.

Production Method 2

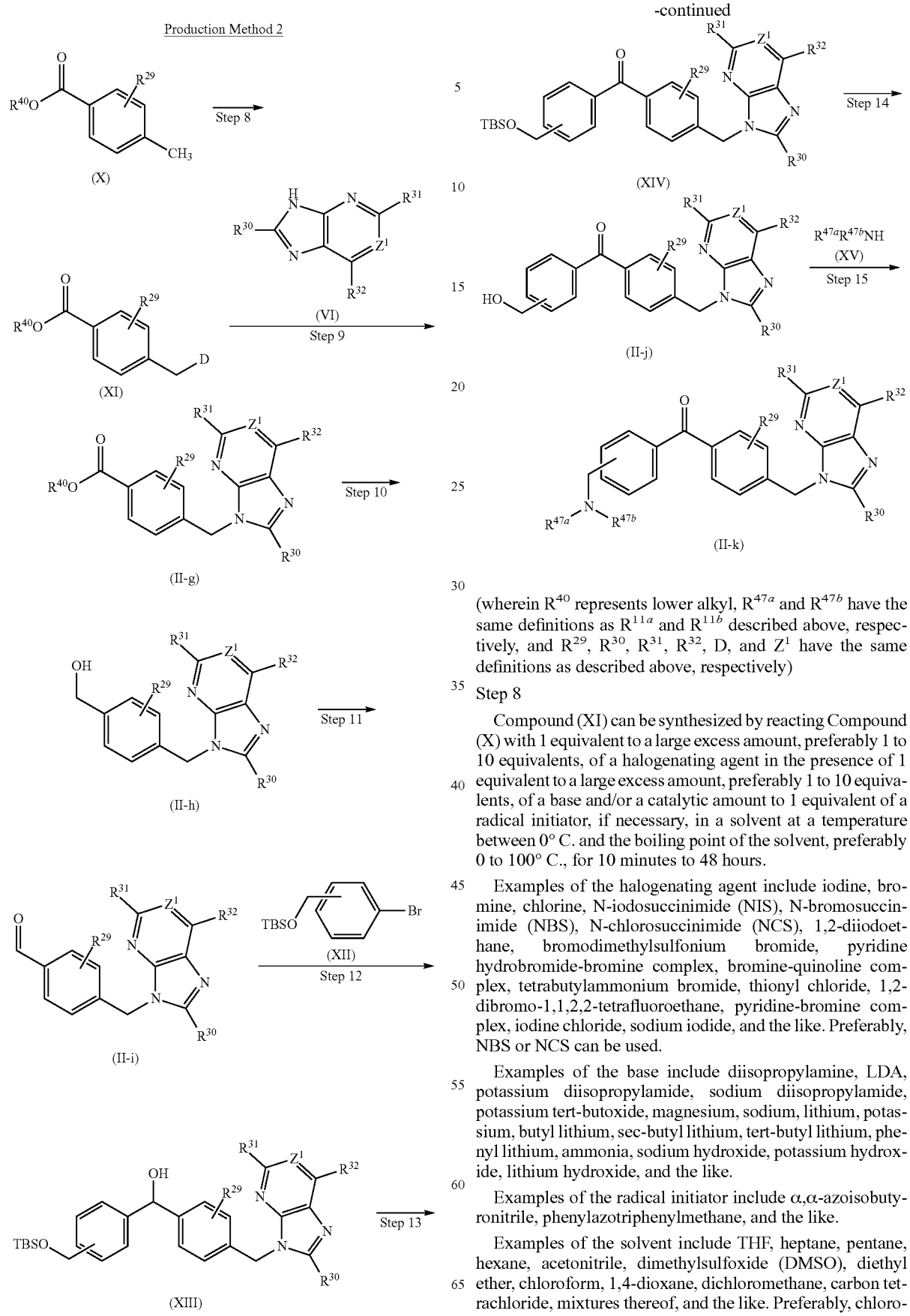

(wherein $R^{40}$ represents lower alkyl, $R^{47a}$ and $R^{47b}$ have the same definitions as $R^{11a}$ and $R^{11b}$ described above, respectively, and $R^{29}$, $R^{30}$, $R^{31}$, $R^{32}$, D, and $Z^1$ have the same definitions as described above, respectively)

Step 8

Compound (XI) can be synthesized by reacting Compound (X) with 1 equivalent to a large excess amount, preferably 1 to 10 equivalents, of a halogenating agent in the presence of 1 equivalent to a large excess amount, preferably 1 to 10 equivalents, of a base and/or a catalytic amount to 1 equivalent of a radical initiator, if necessary, in a solvent at a temperature between 0° C. and the boiling point of the solvent, preferably 0 to 100° C., for 10 minutes to 48 hours.

Examples of the halogenating agent include iodine, bromine, chlorine, N-iodosuccinimide (NIS), N-bromosuccinimide (NBS), N-chlorosuccinimide (NCS), 1,2-diiodoethane, bromodimethylsulfonium bromide, pyridine hydrobromide-bromine complex, bromine-quinoline complex, tetrabutylammonium bromide, thionyl chloride, 1,2-dibromo-1,1,2,2-tetrafluoroethane, pyridine-bromine complex, iodine chloride, sodium iodide, and the like. Preferably, NBS or NCS can be used.

Examples of the base include diisopropylamine, LDA, potassium diisopropylamide, sodium diisopropylamide, potassium tert-butoxide, magnesium, sodium, lithium, potassium, butyl lithium, sec-butyl lithium, tert-butyl lithium, phenyl lithium, ammonia, sodium hydroxide, potassium hydroxide, lithium hydroxide, and the like.

Examples of the radical initiator include α,α-azoisobutyronitrile, phenylazotriphenylmethane, and the like.

Examples of the solvent include THF, heptane, pentane, hexane, acetonitrile, dimethylsulfoxide (DMSO), diethyl ether, chloroform, 1,4-dioxane, dichloromethane, carbon tetrachloride, mixtures thereof, and the like. Preferably, chloroform or carbon tetrachloride can be used.

Step 9

Compound (II-g) can be synthesized by subjecting Compound (XI) to the method described in U.S. Pat. No. 5,151,435 or a similar method thereto.

Step 10

Compound (II-h) can be synthesized by subjecting Compound (II-g) to the same method as step 2 of Production Method 1.

Step 11

Compound (II-i) can be synthesized by reacting Compound (II-h) with 1 equivalent to a large excess amount of an oxidizing agent in a solvent at 0 to 100° C., preferably room temperature, for 10 minutes to 24 hours.

Examples of the oxidizing agent include manganese dioxide, chromic acid, pyridinium chlorochromate, pyridinium dichromate, potassium permanganate, sulfur trioxide-pyridine, DMSO-oxalyl dichloride, oxone, and the like. Preferably, manganese dioxide can be used.

Examples of the solvent include diethyl ether, THF, 1,4-dioxane, DMF, DMA, dichloromethane, chloroform, carbon tetrachloride, dichloroethane, benzene, toluene, xylene, ethyl acetate, acetic acid, propionic acid, butyric acid, trifluoroacetic acid, water, pyridine, mixtures thereof, and the like. Preferably, DMF can be used.

Step 12

Compound (XIII) can be synthesized by reacting Compound (II-i) with 1 equivalent to a large excess amount, preferably 1 to 3 equivalents, of Compound (XII) and 1 equivalent to a large excess amount, preferably 1 to 3 equivalents, of a base in a solvent at −100° C. to room temperature, preferably −100 to 0° C., for 1 minute to 48 hours, preferably 1 minute to 1 hour.

Examples of the base include magnesium, sodium, lithium, potassium, butyl lithium, sec-butyl lithium, tert-butyl lithium, phenyl lithium, and the like. Preferably, butyl lithium, sec-butyl lithium, or tert-butyl lithium can be used.

Examples of the solvent include THF, 1,4-dioxane, hexane, diethyl ether, ethylene glycol, glyme, diglyme, dichloromethane, benzene, toluene, and the like. Preferably, THF, diethyl ether, or hexane can be used.

Step 13

Compound (XIV) can be synthesized by subjecting Compound (XIII) to the same method as Step 11.

Step 14

Compound (II-j) can be synthesized by reacting Compound (XIV) with 1 to 10 equivalents, preferably 1 to 3 equivalents, of a deprotecting agent in a solvent at 0 to 100° C., preferably 0° C. to room temperature, for 1 minute to 24 hours, preferably 10 minutes to 2 hours.

Examples of the deprotecting agent include tetrabutylammonium fluoride (TBAF), hydrogen fluoride, hydrogen fluoride pyridine salt, cesium fluoride, potassium fluoride, boron trifluoride-ether complex, and the like. Preferably, TBAF or hydrogen fluoride can be used.

Examples of the solvent include benzene, toluene, xylene, THF, diethyl ether, diisopropyl ether, dimethoxyethane, dichloromethane, water, mixtures thereof, and the like. Preferably, THF can be used.

Step 15

Compound (II-k) can be produced as follows: Compound (II-j) is reacted with 1 equivalent to a large excess amount, preferably 1 to 3 equivalents, of a halogenating agent or sulfonylating agent in the presence of 1 equivalent to a large excess amount, preferably 1 to 3 equivalents, of a base in a solvent at a temperature between 0° C. and the boiling point of the solvent, preferably 0 to 60° C., for 10 minutes to 48 hours, preferably 10 minutes to 2 hours. Then, the product of above process is reacted with 1 to 10 equivalents, preferably 1 to 3 equivalents, of Compound (XV) at a temperature between 0° C. and the boiling point of the solvent, preferably 0 to 60° C., for 10 minutes to 48 hours, preferably 10 minutes to 24 hours.

Examples of the base include triethylamine, diisopropylethylamine, LDA, potassium tert-butoxide, pyridine, N-methylmorpholine, potassium carbonate, DBU, sodium hydride, potassium hydride, and the like. Preferably, pyridine or potassium hydride can be used.

Examples of the halogenating agent include iodine, bromine, chlorine, NIS, NBS, NCS, 1,2-diiodoethane, bromodimethylsulfonium bromide, pyridine hydrobromide-bromine complex, bromine-quinoline complex, tetrabutylammonium bromide, thionyl chloride, 1,2-dibromo-1,1,2,2-tetrafluoroethane, pyridine-bromine complex, iodine chloride, and sodium iodide.

Examples of the sulfonylating agent include methanesulfonyl chloride, methanesulfonic acid anhydride, trifluoromethanesulfonic acid anhydride, paratoluenesulfonyl chloride, and the like.

Examples of the solvent include pyridine, dichloromethane, chloroform, carbon tetrachloride, dichloroethane, benzene, toluene, xylene, diethyl ether, THF, 1,4-dioxane, DMF, DMA, acetonitrile, methanol, ethanol, propanol, mixtures thereof, and the like. Preferably, ethanol or pyridine can be used.

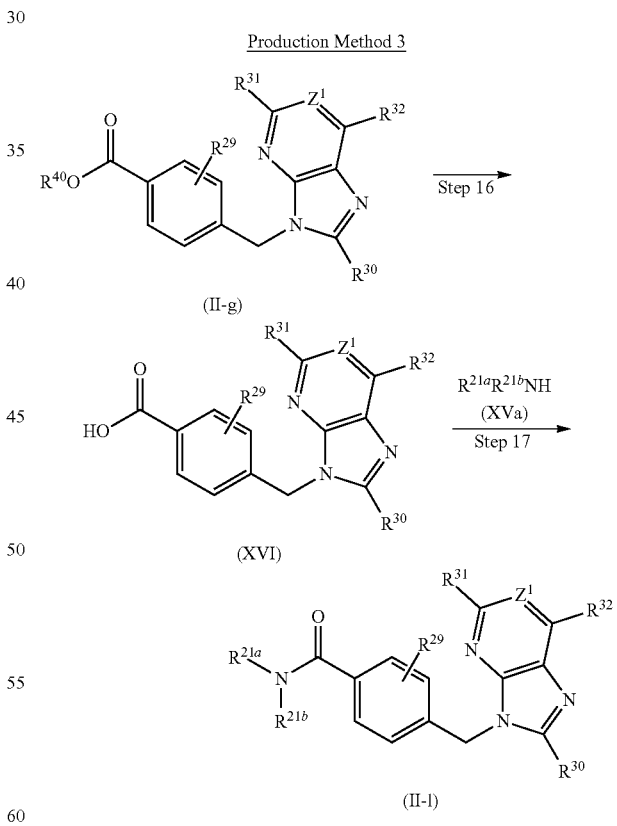

(wherein $R^{21a}$, $R^{21b}$, $R^{29}$, $R^{30}$, $R^{31}$, $R^{32}$, $R^{40}$, and $Z^1$ have the same definitions as described above, respectively).

Step 16

Compound (XVI) can be synthesized by reacting Compound (II-g) in the presence of 1 equivalent to a large excess amount of a base, in a solvent at a temperature between 0° C.

and the boiling point of the solvent, preferably room temperature to 100° C., for 1 to 48 hours, preferably 1 to 3 hours.

Examples of the base include sodium hydroxide, lithium hydroxide, potassium hydroxide, potassium carbonate, cesium carbonate, sodium methoxide, and the like. Preferably, sodium hydroxide can be used.

Examples of the solvent include water, THF, diethyl ether, methanol, ethanol, propanol, dichloromethane, dichloroethane, benzene, toluene, xylene, mixtures thereof, and the like. Preferably, THF, methanol, or a mixed solvent thereof with water can be used.

Step 17

Compound (XVI) is reacted with 1 equivalent to a large excess amount, preferably 1 to 20 equivalents, of a halogenating agent in a basic solvent at −10 to 100° C., preferably room temperature, for 10 minutes to 24 hours to synthesize a corresponding acid halide.

Examples of the basic solvent include pyridine, triethylamine, diisopropylethylamine, N-methylmorpholine, mixtures thereof, and the like; and mixtures of solvents such as dichloromethane, chloroform, ethyl acetate, THF, 1,4-dioxane, DMF, DMA, acetonitrile, benzene, toluene, or xylene with pyridine, triethylamine, diisopropylamine, N-methylmorpholine, and the like. Preferably, pyridine can be used.

Examples of the halogenating agent include thionyl chloride, oxalyl chloride, and phosphorus oxychloride. Preferably, thionyl chloride can be used.

Next, Compound (II-1) can be synthesized by reacting the resulting acid halide with 1 equivalent to a large excess amount, preferably 1 to 10 equivalents, of Compound (XVa), in the presence of 1 equivalent to a large excess amount, preferably 1 to 10 equivalents, of a base, if necessary, in a solvent at a temperature between −30° C. and the boiling point of the solvent, preferably 0° C. to room temperature, for 1 minute to 24 hours, preferably 30 minutes to 2 hours.

Examples of the base include pyridine, triethylamine, diisopropylethylamine, N-methylmorpholine, and the like. Preferably, pyridine or triethylamine can be used.

Examples of the solvent include diethyl ether, THF, 1,4-dioxane, DMF, DMA, DMSO, benzene, toluene, xylene, acetonitrile, ethyl acetate, pyridine, dichloromethane, chloroform, carbon tetrachloride, and the like.

Compound (II-1) can also be synthesized by a method generally used in peptide chemistry. Namely, Compound (II-1) can be synthesized by reacting Compound (XVI) with 1 to 10 equivalents of Compound (XVa) in the presence of 0.5 to 10 equivalents of a condensing agent in a solvent at 0 to 50° C. for 10 minutes to 70 hours.

Examples of the condensing agent include 1,3-dicyclohexylcarbodiimide, 1-[3-(dimethylamino)propyl]-3-ethylcarbodiimide hydrochloride (EDC), 1-[3-(dimethylamino) propyl]-3-ethylcarbodiimide polystyrene resin (EDC resin), and the like. The EDC resin can be produced by the method described in the document [Tetrahedron Letters, vol. 34, No. 48, p. 7685 (1993)].

Examples of the solvent include diethyl ether, THF, 1,4-dioxane, DMF, DMA, DMSO, benzene, toluene, xylene, acetonitrile, ethyl acetate, pyridine, dichloromethane, chloroform, carbon tetrachloride, and the like. Preferably, DMF or THF can be used.

In this step, an additive such as N-hydroxysuccinimide, 3,4-dihydro-3-hydroxy-4-oxo-1,2,3-benzotriazine, or 1-hydroxybenzotriazole, preferably 1-hydroxybenzotriazole, can also be used.

Production Method 4

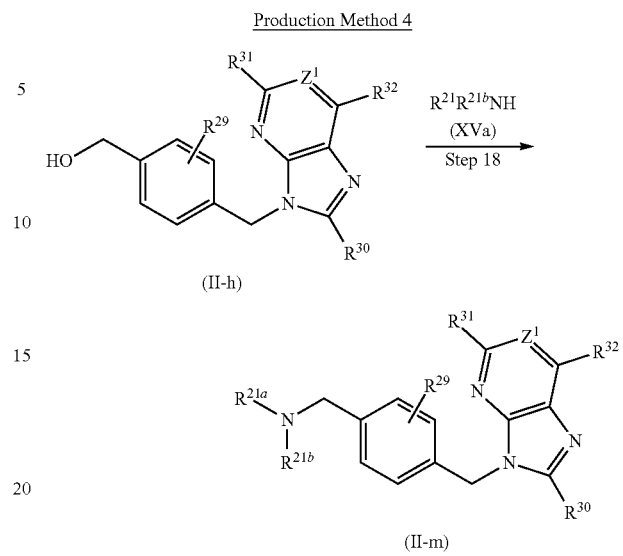

(wherein $R^{21a}$, $R^{21b}$, $R^{29}$, $R^{30}$, $R^{31}$, $R^{32}$, and $Z^1$ have the same definitions as described above, respectively).

Step 18

Compound (II-m) can be synthesized by subjecting Compound (II-h) to the same method as step 15 of Production Method 2.

Production Method 5

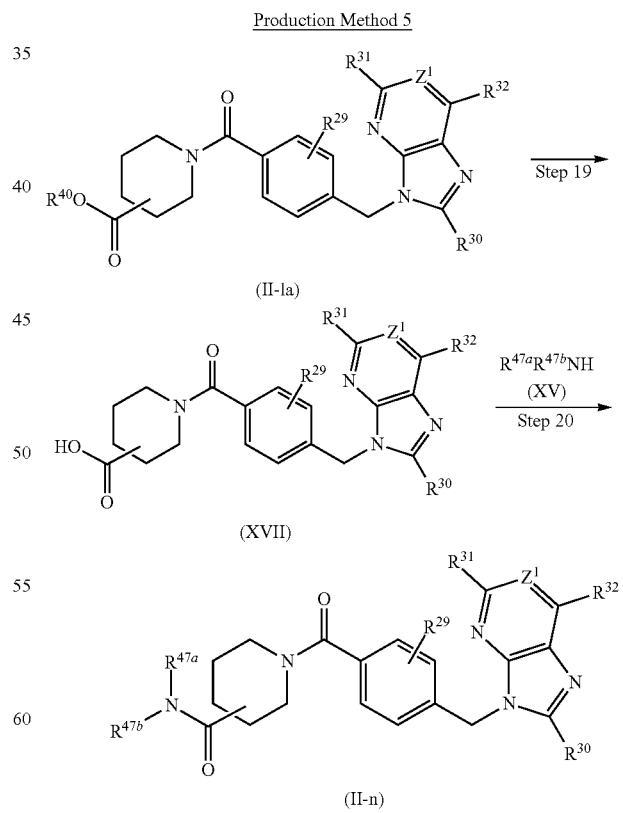

(wherein $R^{29}$, $R^{30}$, $R^{31}$, $R^{32}$, $R^{40}$, $R^{47a}$, $R^{47b}$, and $Z^1$ have the same definitions as described above, respectively).

Step 19

Compound (XVII) can be synthesized by subjecting Compound (II-Ia) obtained in a similar manner to Step 17 of Production Method 3, to the same method as step 16 of Production Method 3.

Step 20

Compound (II-n) can be synthesized by subjecting Compound (XVII) to the same method as step 17 of Production Method 3.

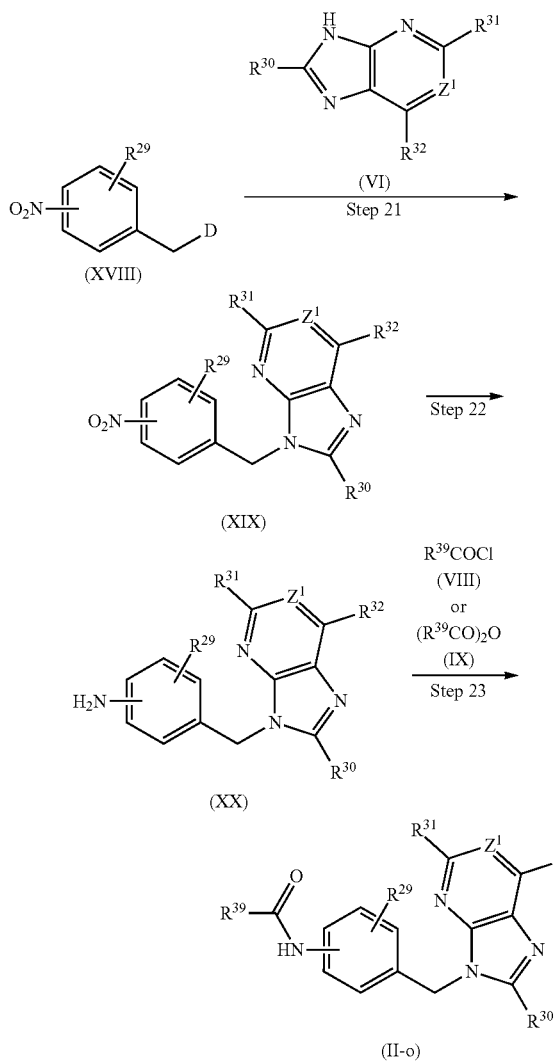

(wherein $R^{29}$, $R^{30}$, $R^{31}$, $R^{32}$, $R^{39}$, D, and $Z^1$ have the same definitions as described above, respectively)

Step 21

Compound (XIX) can be synthesized subjecting commercial Compound (XVIII) to the method described in U.S. Pat. No. 5,151,435 or a similar method thereto.

Step 22

Compound (XX) can be synthesized by reacting Compound (XIX) with 1 equivalent to a large excess amount, preferably 1 to 10 equivalents, of a reducing agent, in the presence of a catalytic amount to a large excess amount of an inorganic compound or an acid, in a solvent at a temperature between 0° C. and the boiling point of the solvent, preferably room temperature to 120° C., for 10 minutes to 48 hours.

Examples of the solvent include methanol, ethanol, THF, 1,4-dioxane, dimethoxyethane, DMF, DMA, benzene, toluene, xylene, acetonitrile, mixtures thereof, and the like. Preferably, methanol or ethanol can be used.

Examples of the reducing agent include tin(0), tin(II) chloride, titanium(III) chloride, chromium(II) chloride, zinc, iron, nickel, hydrazine, sodium borohydride, lithium aluminum hydride, and lithium borohydride. Preferably, tin(II) chloride or titanium(III) chloride can be used.

Examples of the inorganic compound include nickel(II) chloride, Raney nickel, cobalt(II) chloride, and the like.

Examples of the acid include hydrochloric acid, sulfuric acid, acetic acid, and the like. Preferably, hydrochloric acid can be used.

Compound (XX) can also be synthesized by subjecting Compound (XIX) to the similar method as step 5 of Production Method 1.

Step 23

Compound (II-o) can be synthesized by subjecting Compound (XX) to the same method as step 7 of Production Method 1.

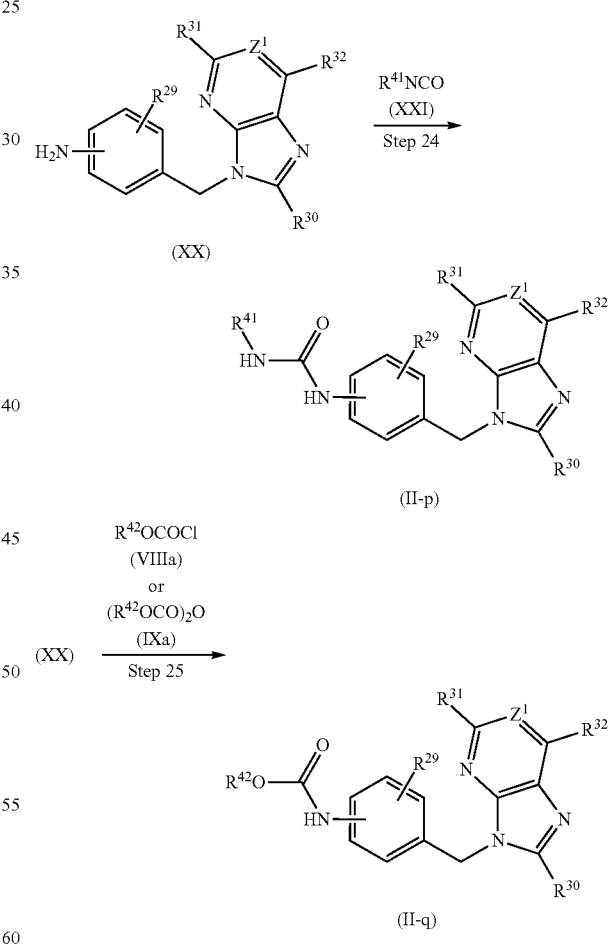

(wherein $R^{41}$ and $R^{42}$ each have the same definition as $R^{39}$, and $R^{29}$, $R^{30}$, $R^{31}$, $R^{32}$, and $Z^1$ have the same definitions as described above, respectively)

Step 24

Compound (II-p) can be synthesized by reacting Compound (XX) with 1 equivalent to a large excess amount, preferably 1 to 5 equivalents, of Compound (XXI), in the presence of 1 equivalent to a large excess amount, preferably 1 to 10 equivalents, of a base, if necessary, in a solvent at a temperature between 0° C. and the boiling point of the solvent, preferably room temperature to 120° C., for 10 minutes to 48 hours.

Examples of the base include triethylamine, diisopropylethylamine, LDA, potassium tert-butoxide, pyridine, N-methylmorpholine, potassium carbonate, DBU, functional resins having basic functional groups unreactive to isocyanate, and the like.

Examples of the solvent include dichloromethane, chloroform, THF, 1,4-dioxane, dimethoxyethane, DMF, DMA, benzene, toluene, xylene, acetonitrile, ethyl acetate, pyridine, tetralin, mixtures thereof, and the like. Preferably, chloroform or dichloromethane can be used.

Step 25

Compound (II-q) can be synthesized by subjecting Compound (XX) and Compound (VIIIa) or Compound (IXa) to the same method as step 7 of Production Method 1.

Production Method 8

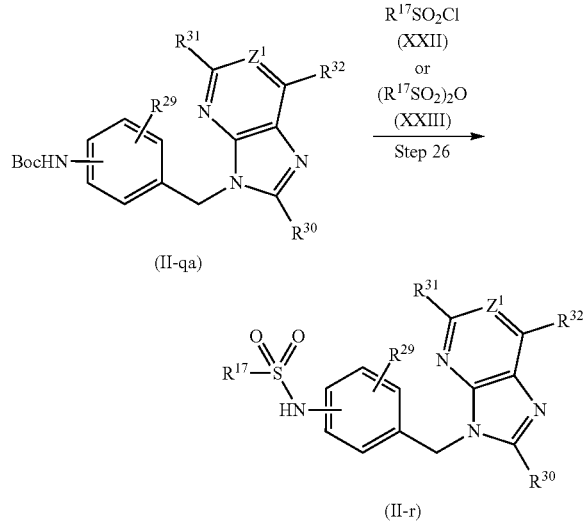

(wherein $R^{17}$, $R^{29}$, $R^{30}$, $R^{31}$, $R^{32}$, and $Z^1$ have the same definitions as described above, respectively)

Step 26

Compound (II-r) can be synthesized as follows: Compound (II-qa) obtained in a similar manner to step 25 of Production Method 7 is reacted with 1 equivalent to a large excess amount, preferably 1 to 10 equivalents, of Compound (XXII) or (XXIII) in the presence of 1 equivalent to a large excess amount, preferably 1 to 10 equivalents, of a base in a solvent at a temperature between 0° C. and the boiling point of the solvent used, preferably room temperature to 120° C., for 10 minutes to 48 hours. Then, the product of above process is reacted with a large excess amount of an acid in a solvent at a temperature between 0° C. and the boiling point of the solvent, preferably room temperature to 120° C., for 10 minutes to 48 hours.

Examples of the base include triethylamine, diisopropylethylamine, LDA, potassium tert-butoxide, pyridine, N-methylmorpholine, potassium carbonate, DBU, functional resins having basic functional groups unreactive to Compound (XXII) or Compound (XXIII), and the like. Preferably, triethylamine, potassium tert-butoxide, or diisopropylaminomethyl polystyrene can be used.

Examples of the acid include hydrochloric acid, sulfuric acid, nitric acid, acetic acid, TFA, methanesulfonic acid, trifluoromethanesulfonic acid, paratoluenesulfonic acid, aluminum chloride, titanium tetrachloride, boron trifluoride ether complex, tin tetrachloride, silica gel, zinc bromide, and the like. Preferably, hydrochloric acid, acetic acid, or TFA can be used.

Examples of the solvent include dichloromethane, chloroform, THF, 1,4-dioxane, dimethoxyethane, DMF, DMA, benzene, toluene, xylene, acetonitrile, pyridine, tetralin, mixtures thereof, and the like. Preferably, chloroform or dichloromethane can be used.

Production Method 9

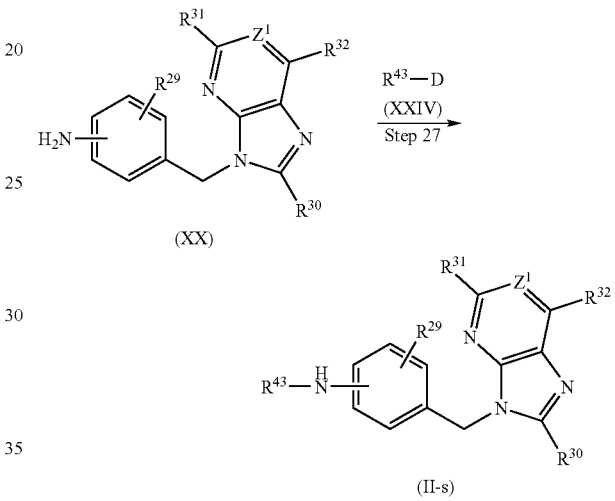

[wherein $R^{43}$ represents substituted or unsubstituted aryl or a substituted or unsubstituted aromatic heterocyclic group (excluding tetrazolyl), and $R^{29}$, $R^{30}$, $R^{31}$, $R^{32}$, D, and $Z^1$ have the same definitions as described above, respectively]

Step 27

Compound (II-s) can be synthesized by reacting Compound (XX) and 1 equivalent to a large excess amount, preferably 1 to 10 equivalents, of Compound (XXIV) in the presence of a catalytic amount to 3 equivalents of a palladium compound and 1 equivalent to a large excess amount, preferably 1 to 10 equivalents, of a base, and a catalytic amount to 1 equivalent of an organophosphorus compound, if necessary, in a solvent at a temperature between 0° C. and the boiling point of the solvent, preferably room temperature to 140° C., for 10 minutes to 48 hours. In this step, 0.2 to 5 equivalents, preferably 1 equivalent, of an inorganic compound, such as lithium chloride, potassium chloride, silver oxide, copper oxide, silver nitrate, or silver acetate, may be added.

Examples of the palladium compound include bis(triphenylphosphine)palladium(II) chloride, tetrakis(triphenylphosphine)palladium(0), [1,2-bis(diphenylphosphino) ethane]palladium(II) chloride, [1,1'-bis(diphenylphosphino) ferrocene]palladium(II) chloride, and the like. Preferably, bis (triphenylphosphine)palladium(II) chloride or tetrakis (triphenylphosphine)palladium(0) can be used.

Examples of the organophosphorus compound include triphenylphosphine, triorthotoluylphosphine, tributylphosphine, tri-tert-butylphosphine, tricyclohexylphosphine, trifurylphosphine, 2,2-bisdiphenylphosphino-1,1-binaphthyl, 1,1'-bisdiphenylphosphinoferrocene, trimethyl phosphate, and the like. Preferably, tri-tert-butylphosphine or trifurylphosphine can be used.

Examples of the base include triethylamine, sodium ethoxide, sodium tert-butoxide, potassium tert-butoxide, sodium hydroxide, sodium carbonate, lithium hydroxide, diisopropylethylamine, LDA, N-methylmorpholine, DBU, and the like. Preferably, sodium ethoxide, sodium tert-butoxide, potassium tert-butoxide can be used.

Examples of the solvent include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methanol, ethanol, propanol, 2-propanol, butanol, hexane, and the like. Preferably, THF, DMF, or toluene can be used.

Production Method 10

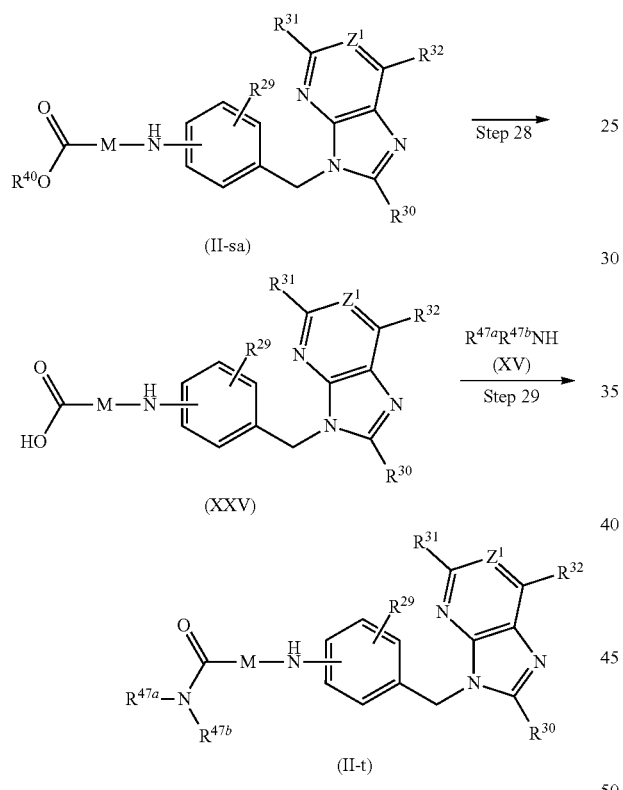

[wherein M represents substituted or unsubstituted aryl or a substituted or unsubstituted aromatic heterocyclic group (excluding tetrazolyl), and $R^{29}$, $R^{30}$, $R^{31}$, $R^{32}$, $R^{40}$, $R^{47a}$, $R^{47b}$, and $Z^1$ have the same definitions as described above, respectively]

Step 28

Compound (XXV) can be synthesized by subjecting Compound (II-sa) obtained in a similar manner to Step 27 of Production Method 9 to the same method as step 19 of Production Method 5.

Step 29

Compound (II-t) can be synthesized by subjecting Compound (XXV) to the same method as step 20 of Production Method 5.

Production Method 11

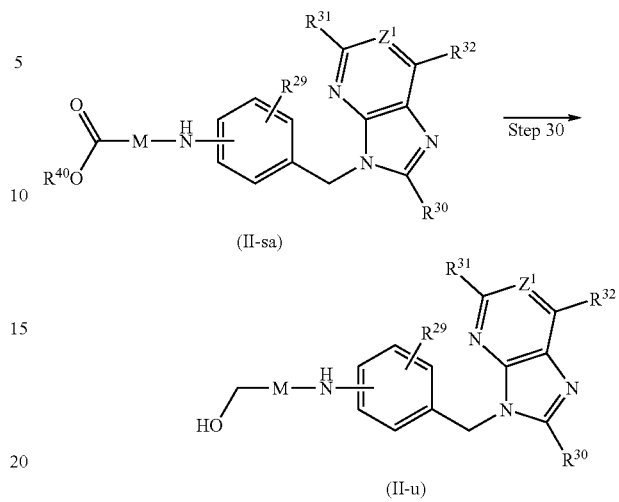

(wherein $R^{29}$, $R^{30}$, $R^{31}$, $R^{32}$, $R^{40}$, M, and $Z^1$ have the same definitions as described above, respectively)

Step 30

Compound (II-u) can be synthesized by subjecting Compound (II-sa) obtained in a similar manner to Step 27 of Production Method 9 to the same method as step 2 of Production Method 1.

Production Method 12

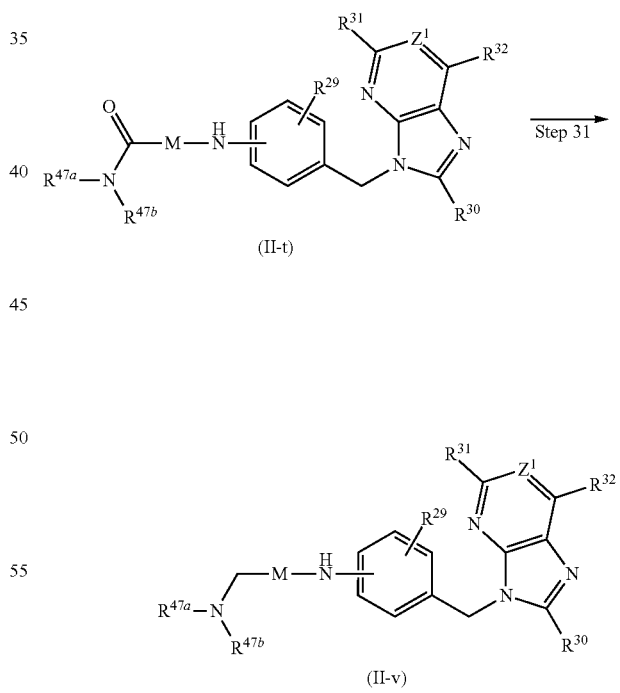

(wherein $R^{29}$, $R^{30}$, $R^{31}$, $R^{32}$, $R^{47a}$, $R^{47b}$, M, and $Z^1$ have the same definitions as described above, respectively).

Step 31

Compound (II-v) can be synthesized by subjecting Compound (II-t) to the same method as step 2 of Production Method 1.

Production Method 13

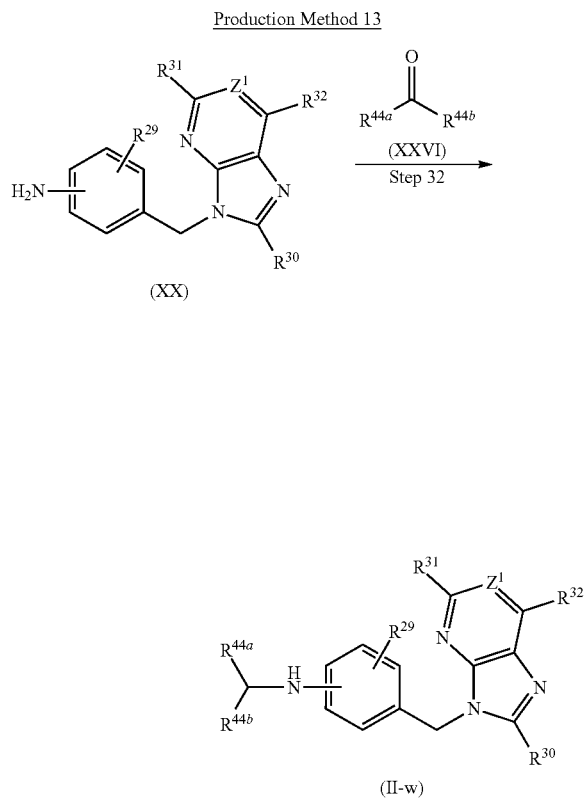

(wherein $R^{44a}$ and $R^{44b}$ are the same or different and each represents a hydrogen atom, substituted or unsubstituted lower alkyl, or substituted or unsubstituted lower cycloalkyl, or $R^{44a}$ and $R^{44b}$ are combined together to form substituted or unsubstituted lower cycloalkyl, and $R^{29}$, $R^{30}$, $R^{31}$, $R^{32}$, and $Z^1$ each have the same definitions as described above, respectively)

Step 32

Compound (II-w) can be synthesized by reacting Compound (XX) and 1 equivalent to a large excess amount, preferably 1 to 10 equivalents, of Compound (XXVI) in the presence of 1 equivalent to a large excess amount, preferably 1 to 3 equivalents, of a reducing agent, in a solvent at −78 to 100° C., preferably 0 to 50° C., for 10 minutes to 24 hours. In this step, a catalytic amount to a large excess amount, preferably 0.5 to 5 equivalents, of an acid may be added, if necessary.

Examples of the reducing agent include sodium borohydride, sodium triacetoxyborohydride, sodium cyanoborohydride, and the like. Preferably, sodium triacetoxyborohydride can be used.

Examples of the acid include formic acid, acetic acid, trifluoroacetic acid, propionic acid, hydrochloric acid, and the like. Preferably, acetic acid can be used.

Examples of the solvent include dichloromethane, chloroform, carbon tetrachloride, dichloroethane, benzene, toluene, xylene, diethyl ether, THF, 1,4-dioxane, DMF, DMA, acetonitrile, hexane, mixtures thereof, and the like. Preferably, THF or dichloromethane can be used.

Production Method 14

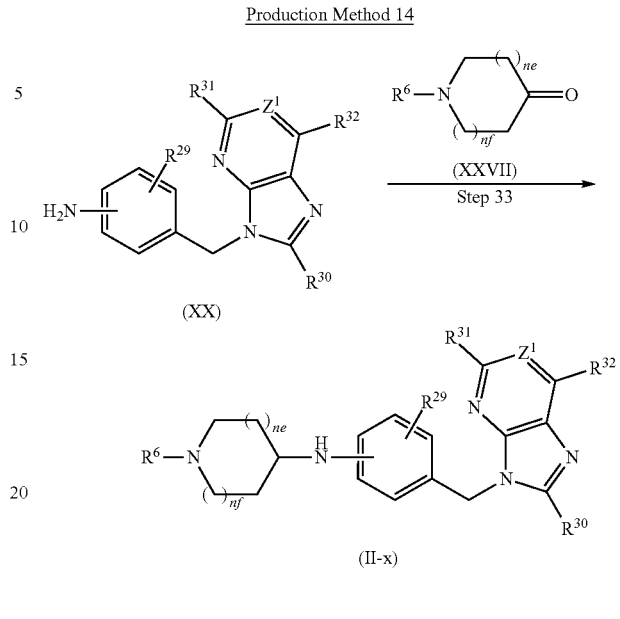

(wherein ne and nf have the same definitions as na and nb described above, respectively, and $R^6$, $R^{29}$, $R^{30}$, $R^{31}$, $R^{32}$, and $Z^1$ have the same definitions as described above, respectively)

Step 33

Compound (II-x) can be synthesized by subjecting Compound (XX) and Compound (XXVII) to the same method as step 32 of Production Method 13.

Production Method 15

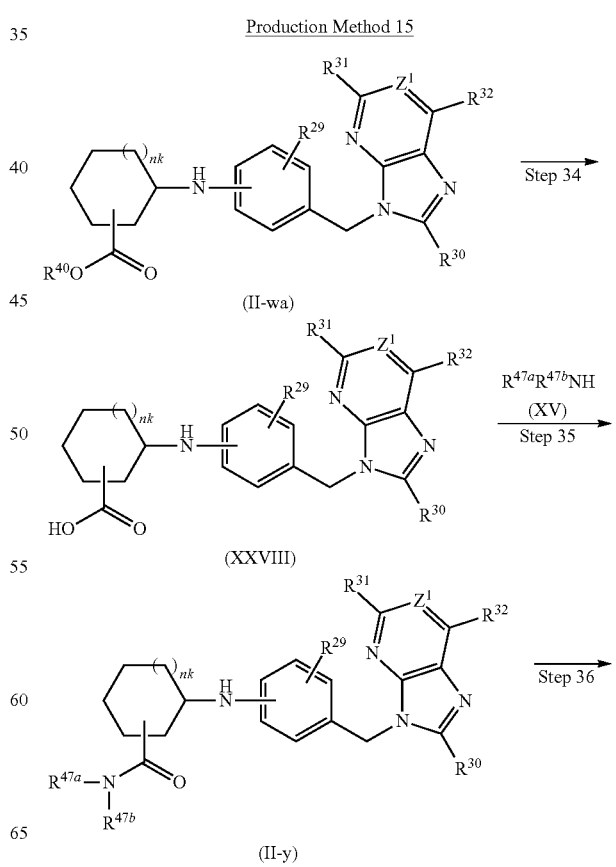

-continued

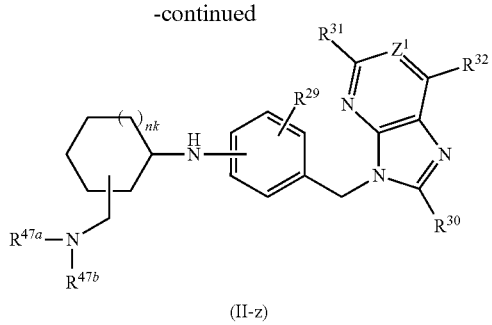

(II-z)

(wherein nk represents an integer of 0 to 3, and $R^{29}$, $R^{30}$, $R^{31}$, $R^{32}$, $R^{40}$, $R^{47a}$, $R^{47b}$, and $Z^1$ have the same definitions as described above, respectively)

Step 34

Compound (XXVIII) can be synthesized by subjecting Compound (II-wa) obtained in a similar manner to Step 32 of Production Method 13 to the same method as step 16 of Production Method 3.

Step 35

Compound (II-y) can be synthesized by subjecting Compound (XVIII) and Compound (XV) to the same method as step 17 of Production Method 3.

Step 36

Compound (II-z) can be synthesized by subjecting Compound (II-y) to the same method as step 2 of Production Method 1.

The products of the above-described production methods can be isolated and purified by a general method of organic synthesis, for example, filtration, extraction, washing, drying, concentration, crystallization, various chromatography, and appropriate combination thereof. Furthermore, a purification method generally used for general parallel synthesis, for example, purification with a scavenger resin or ion-exchange resin, can be used. Intermediates can be used in subsequent reactions without purification.

To obtain salts of Compound (II) and Compound (III), when Compound (II) and Compound (III) are obtained in the form of salts, the salts of Compound (II) and Compound (III) may be purified as it is. Further, when Compound (II) and Compound (III) are obtained in a free form, Compound (II) and Compound (III) may be dissolved or suspended in a suitable solvent, followed by addition of an acid or a base to form salts and the resulting salts may be isolated and purified.

Although specific examples of Compound (III) used in the present invention are given in Tables 1 to 18 below, the present invention is not limited to these compounds.

TABLE 1(1)

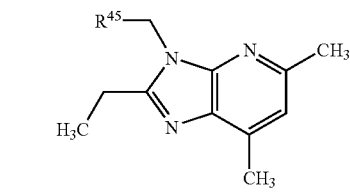

| Compound No. | $R^{45}$— |
|---|---|
| 1 | |
| 2 | |
| 3 | |
| 4 | |
| 5 | |
| 6 | |
| 7 | |
| 8 | |

TABLE 1(1)-continued
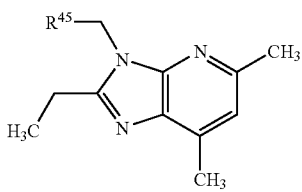
| Compound No. | R⁴⁵— |
|---|---|
| 9 | 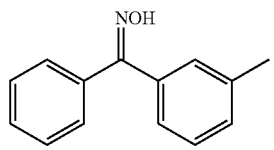 |
| 10 | 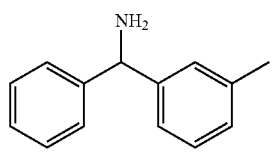 |
| 11 | 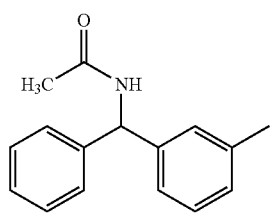 |
| 12 | 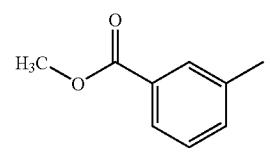 |
TABLE 1(2)
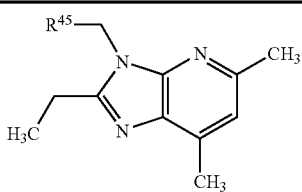
| Compound No. | R⁴⁵— |
|---|---|
| 13 | 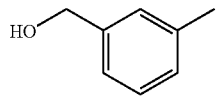 |
| 14 | 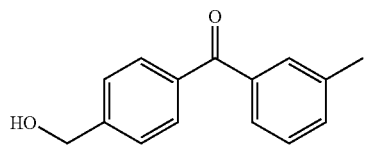 |
TABLE 1(2)-continued
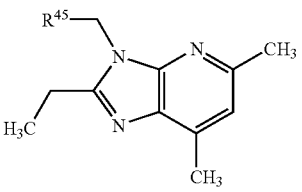
| Compound No. | R⁴⁵— |
|---|---|
| 15 | 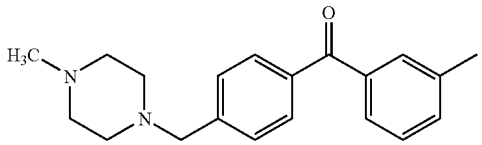 |
| 16 | 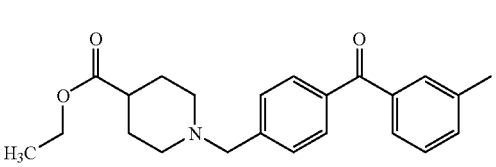 |
| 17 | 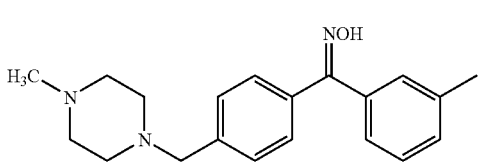 |
| 18 | 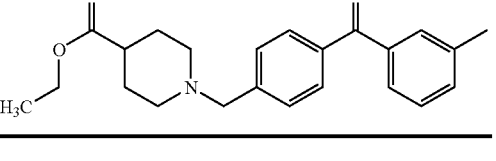 |
TABLE 1(3)
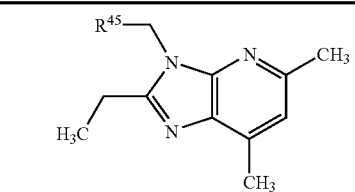
| Compound No. | R⁴⁵— |
|---|---|
| 19 | 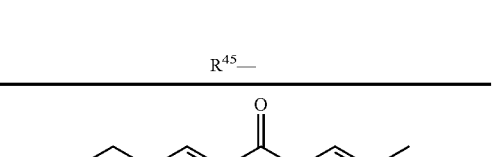 |
| 20 | 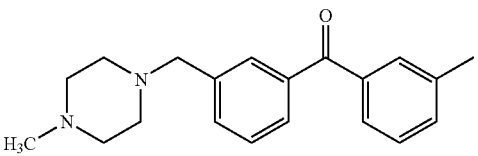 |

TABLE 1(3)-continued
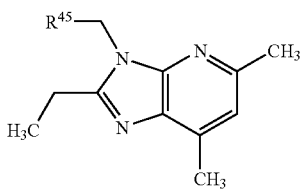
| Compound No. | R⁴⁵— |
|---|---|
| 21 | 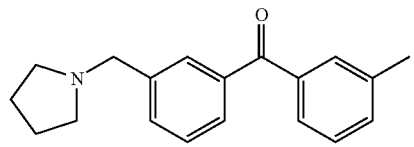 |
| 22 | 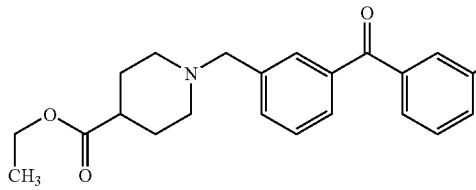 |
| 23 | 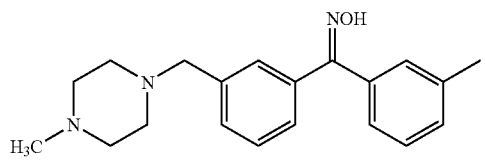 |
| 24 | 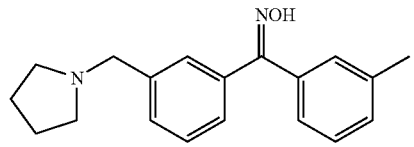 |
TABLE 1(4)
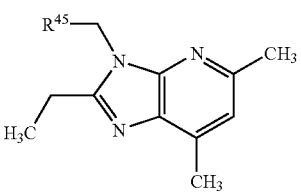
| Compound No. | R⁴⁵— |
|---|---|
| 25 | 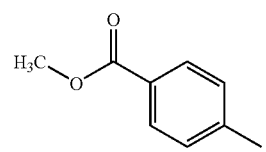 |
TABLE 1(4)-continued
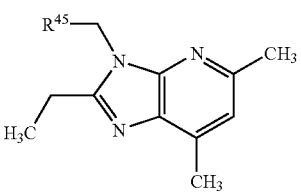
| Compound No. | R⁴⁵— |
|---|---|
| 26 | 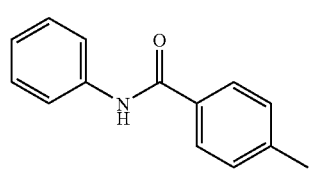 |
| 27 | 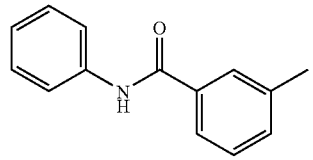 |
| 28 | 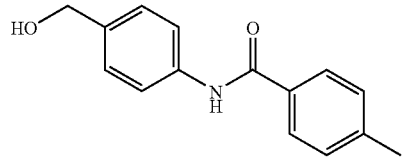 |
| 29 | 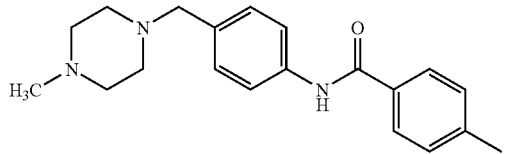 |
| 30 | 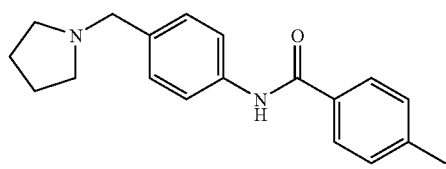 |

TABLE 1(5)

[Structure: imidazopyridine core with R45-CH2- substituent, ethyl, and two methyl groups]

| Compound No. | R45— |
|---|---|
| 31 | 4-(morpholinomethyl)phenyl-C(O)NH- (4-methylbenzamide with morpholinomethyl group) |
| 32 | Ethyl 1-(4-methylbenzoyl)piperidine-4-carboxylate group |
| 33 | 1-(4-methylbenzoyl)-4-(4-methylpiperazin-1-ylcarbonyl)piperidine group |
| 34 | 4-(hydroxymethyl)phenyl (HO-CH2-C6H4-CH3) |
| 35 | 4-methyl-N-phenylbenzylamine group |
| 36 | 3-methyl-N-phenylbenzylamine group |

TABLE 2(1)

[Structure: imidazopyridine core with R39-C(O)NH-C6H4-CH2- substituent, ethyl, and two methyl groups]

| Compound No. | •—R39 | Analytical value |
|---|---|---|
| 37 | 4-F-C6H4- | MS m/z 403 (M + H)+ |
| 38 | 2-Cl-C6H4- | MS m/z 419 (M + H)+ |
| 39 | C6H5- | MS m/z 385 (M + H)+ |
| 40 | 4-OCH3-C6H4- | MS m/z 415 (M + H)+ |
| 41 | 4-CH3-C6H4- | MS m/z 399 (M + H)+ |
| 42 | -CH2-O-C6H5 | MS m/z 415 (M + H)+ |
| 43 | 3-CF3-C6H4- | MS m/z 453 (M + H)+ |
| 44 | 4-(O-C3H7)-C6H4- (4-butoxyphenyl) | MS m/z 457 (M + H)+ |
| 45 | -CH2-C6H4-4-OCH3 | MS m/z 429 (M + H)+ |

TABLE 2(2)
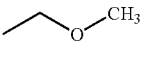
| Compound No. | —R³⁹ | Analytical value |
|---|---|---|
| 46 | 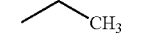 —CH₃ | MS m/z 323 (M + H)⁺ |
| 47 | 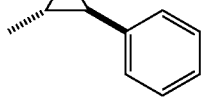 | MS m/z 353 (M + H)⁺ |
| 48 | 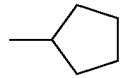 | MS m/z 337 (M + H)⁺ |
| 49 | 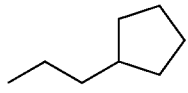 | MS m/z 425 (M + H)⁺ |
| 50 | 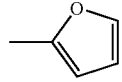 | MS m/z 377 (M + H)⁺ |
| 51 | 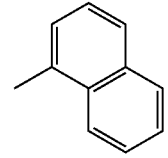 | MS m/z 405 (M + H)⁺ |
| 52 | 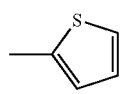 | MS m/z 375 (M + H)⁺ |
| 53 | 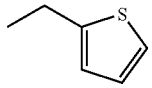 | MS m/z 435 (M + H)⁺ |
| 54 | 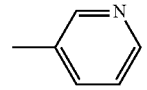 | MS m/z 391 (M + H)⁺ |
TABLE 2(3)
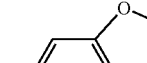
| Compound No. | —R³⁹ | Analytical value |
|---|---|---|
| 55 | 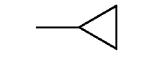 | MS m/z 405 (M + H)⁺ |
| 56 | 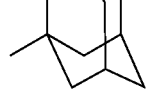 | MS m/z 386 (M + H)⁺ |
| 57 | 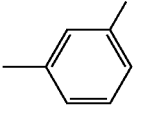 | MS m/z 429 (M + H)⁺ |
| 58 | 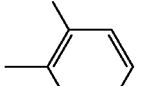 | MS m/z 349 (M + H)⁺ |
| 59 | 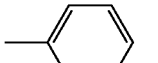 | MS m/z 443 (M + H)⁺ |
| 60 |  | MS m/z 410 (M + H)⁺ |
TABLE 3(1)
| Compound No. | —R⁴¹ | Analytical value |
|---|---|---|
| 61 |  | MS m/z 434 (M + H)⁺ |
| 62 |  | MS m/z 400 (M + H)⁺ |

TABLE 3(1)-continued
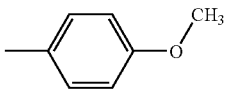
| Compound No. | —R41 | Analytical value |
|---|---|---|
| 63 | 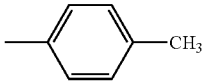 | MS m/z 430 (M + H)+ |
| 64 | 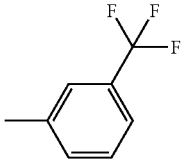 | MS m/z 414 (M + H)+ |
| 65 | 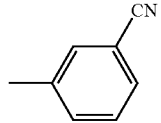 | MS m/z 468 (M + H)+ |
| 66 | 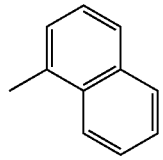 | MS m/z 425 (M + H)+ |
| 67 | 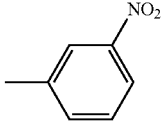 | MS m/z 450 (M + H)+ |
| 68 | 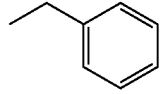 | MS m/z 445 (M + H)+ |
| 69 |  | MS m/z 414 (M + H)+ |
TABLE 3(2)
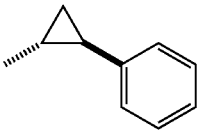
| Compound No. | —R41 | Analytical value |
|---|---|---|
| 70 | 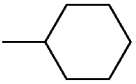 | MS m/z 352 (M + H)+ |
| 71 |  | MS m/z 440 (M + H)+ |
| 72 | 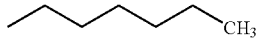 | MS m/z 406 (M + H)+ |
| 73 |  | MS m/z 366 (M + H)+ |
| 74 |  | MS m/z 408 (M + H)+ |
| 75 | 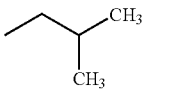 | MS m/z 418 (M + H)+ |
TABLE 4
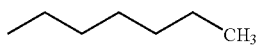
| Compound No. | —R42 | Analytical value |
|---|---|---|
| 76 | —CH3 | MS m/z 339 (M + H)+ |
| 77 | 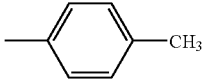 | MS m/z 353 (M + H)+ |
| 78 | | MS m/z 381 (M + H)+ |
| 79 | | MS m/z 409 (M + H)+ |
| 80 | | MS m/z 415 (M + H)+ |

TABLE 4-continued

[Structure: R$^{42}$-O-C(=O)-NH-phenyl-CH$_2$-N(imidazo[4,5-b]pyridine with H$_3$C, CH$_3$ substituents and ethyl group)]

| Compound No. | —R$^{42}$ | Analytical value |
|---|---|---|
| 81 | tert-butyl (C(CH$_3$)$_3$) | MS m/z 381 (M + H)$^+$ |

TABLE 5(1)

[Structure: R$^{17}$-S(=O)$_2$-NH-phenyl-CH$_2$-N(imidazo[4,5-b]pyridine with H$_3$C, CH$_3$ substituents and ethyl group)]

| Compound No. | —R$^{17}$ | Analytical value |
|---|---|---|
| 82 | n-butyl | MS m/z 401 (M + H)$^+$ |
| 83 | isopropyl-CH$_3$ (isobutyl) | MS m/z 387 (M + H)$^+$ |
| 84 | phenyl | MS m/z 421 (M + H)$^+$ |
| 85 | 4-methoxyphenyl | MS m/z 451 (M + H)$^+$ |
| 86 | 4-fluorophenyl | MS m/z 439 (M + H)$^+$ |
| 87 | 3-(trifluoromethyl)phenyl | MS m/z 489 (M + H)$^+$ |
| 88 | 1-methylnaphthyl | MS m/z 471 (M + H)$^+$ |
| 89 | 3-nitrophenyl | MS m/z 466 (M + H)$^+$ |
| 90 | 2,5-dichlorophenyl | MS m/z 490 (M + H)$^+$ |

TABLE 5(2)

[Structure: R$^{17}$-S(=O)$_2$-NH-phenyl-CH$_2$-N(imidazo[4,5-b]pyridine with H$_3$C, CH$_3$ substituents and ethyl group)]

| Compound Number | —R$^{17}$ | Analytical value |
|---|---|---|
| 91 | 4-(trifluoromethoxy)phenyl | MS m/z 505 (M + H)$^+$ |
| 92 | 5-methyl-1-(dimethylamino)naphthyl | MS m/z 514 (M + H)$^+$ |
| 93 | 2-naphthyl | MS m/z 471 (M + H)$^+$ |

TABLE 5(2)-continued

[Structure: N-(4-((5,7-dimethyl-2-ethyl-imidazo[4,5-b]pyridin-3-yl)methyl)phenyl)sulfonamide with R17 group]

| Compound Number | —R17 | Analytical value |
|---|---|---|
| 94 | 2,4,5-trimethylphenyl | MS m/z 463 (M + H)+ |
| 95 | ethyl (CH2CH3) | MS m/z 373 (M + H)+ |
| 96 | 4-methylphenyl | MS m/z 435 (M + H)+ |

TABLE 6

[Structure: 5,7-dimethyl-2-ethyl-3-((4-(R43-NH-)benzyl))imidazo[4,5-b]pyridine]

| Compound No. | R43—NH—(tolyl) |
|---|---|
| 97 | phenyl-NH-(4-methylphenyl) |
| 98 | phenyl-NH-(3-methylphenyl) |
| 99 | 4-(ethoxycarbonyl)phenyl-NH-(4-methylphenyl) |

TABLE 6-continued

| Compound No. | R43—NH—(tolyl) |
|---|---|
| 100 | 4-((4-methylpiperazin-1-yl)carbonyl)phenyl-NH-(4-methylphenyl) |
| 101 | 4-(hydroxymethyl)phenyl-NH-(4-methylphenyl) |
| 102 | 4-((4-methylpiperazin-1-yl)methyl)phenyl-NH-(4-methylphenyl) |
| 103 | 1-methylpiperidin-4-yl-NH-(4-methylphenyl) |

TABLE 7
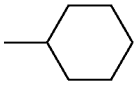
| Compound No. | —R⁴⁸ |
|---|---|
| 104 | 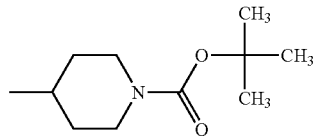 |
| 105 | 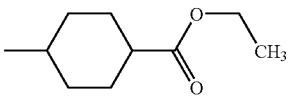 |
| 106 | 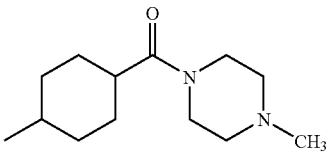 |
| 107 | 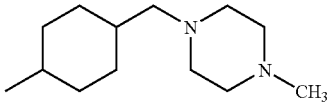 |
| 108 | 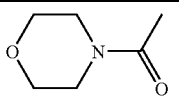 |
TABLE 8
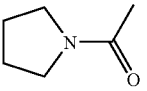
| Compound No. | R⁴⁹— |
|---|---|
| 109 | 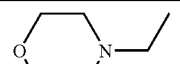 |
| 110 | 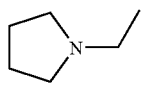 |
TABLE 8-continued
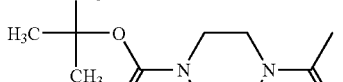
| Compound No. | R⁴⁹— |
|---|---|
| 111 | 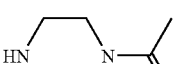 |
| 112 | 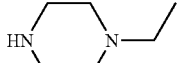 |
| 113 | 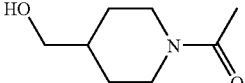 |
| 114 | 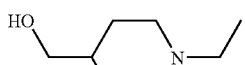 |
| 115 | 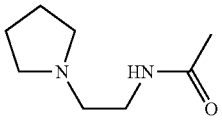 |
| 116 | 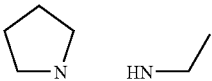 |
| 117 | 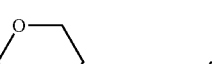 |
| 118 | 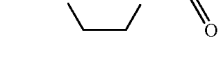 |
| 119 | |
| 121 | |
| 122 | |

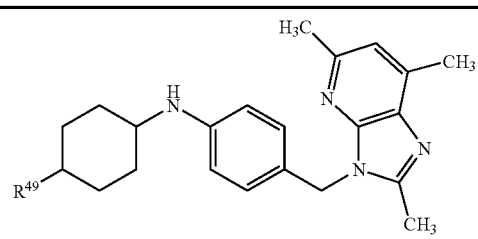

TABLE 10-continued

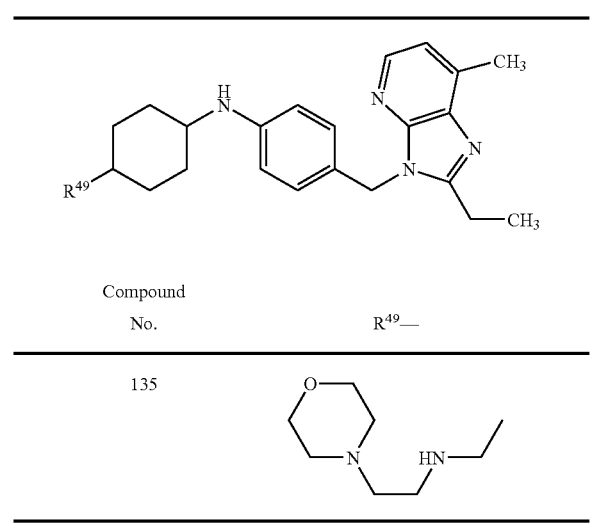

| Compound No. | R49— |
|---|---|
| 135 | (morpholinoethylamino) |

TABLE 11

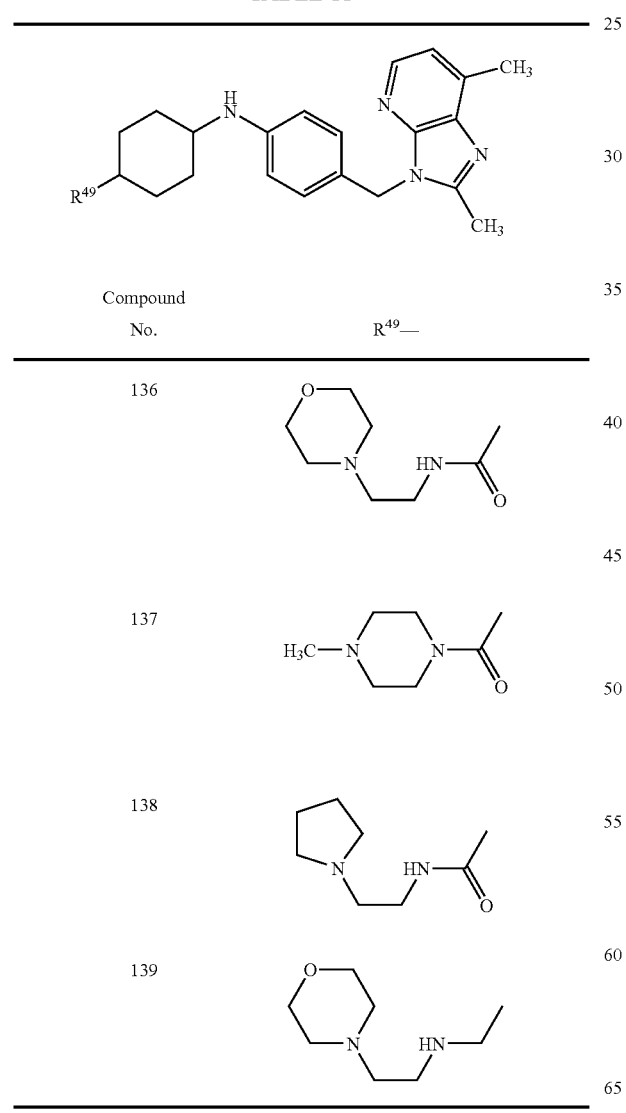

| Compound No. | R49— |
|---|---|
| 136 | (morpholinoethyl-acetamide) |
| 137 | (4-methylpiperazinyl-acetyl) |
| 138 | (pyrrolidinylethyl-acetamide) |
| 139 | (morpholinoethylamino) |

TABLE 12(1)

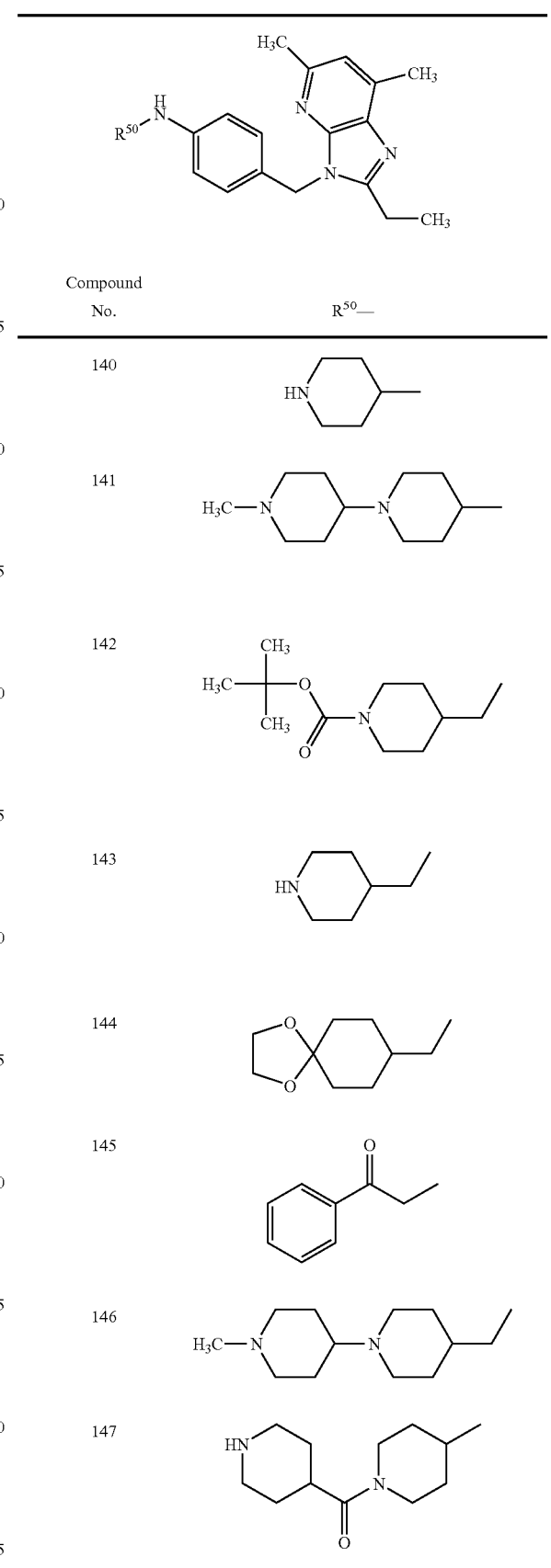

| Compound No. | R50— |
|---|---|
| 140 | (4-piperidinyl) |
| 141 | (1-methyl-4-(4-methylpiperidin-1-yl)piperidine) |
| 142 | (tert-butoxycarbonyl-4-ethylpiperidine) |
| 143 | (4-ethylpiperidine) |
| 144 | (1,4-dioxaspiro[4.5]decyl-ethyl) |
| 145 | (1-phenylpropan-1-one) |
| 146 | (1-methyl-4-(4-ethylpiperidin-1-yl)piperidine) |
| 147 | (4-(4-methylpiperidine-1-carbonyl)piperidine) |

TABLE 12(2)
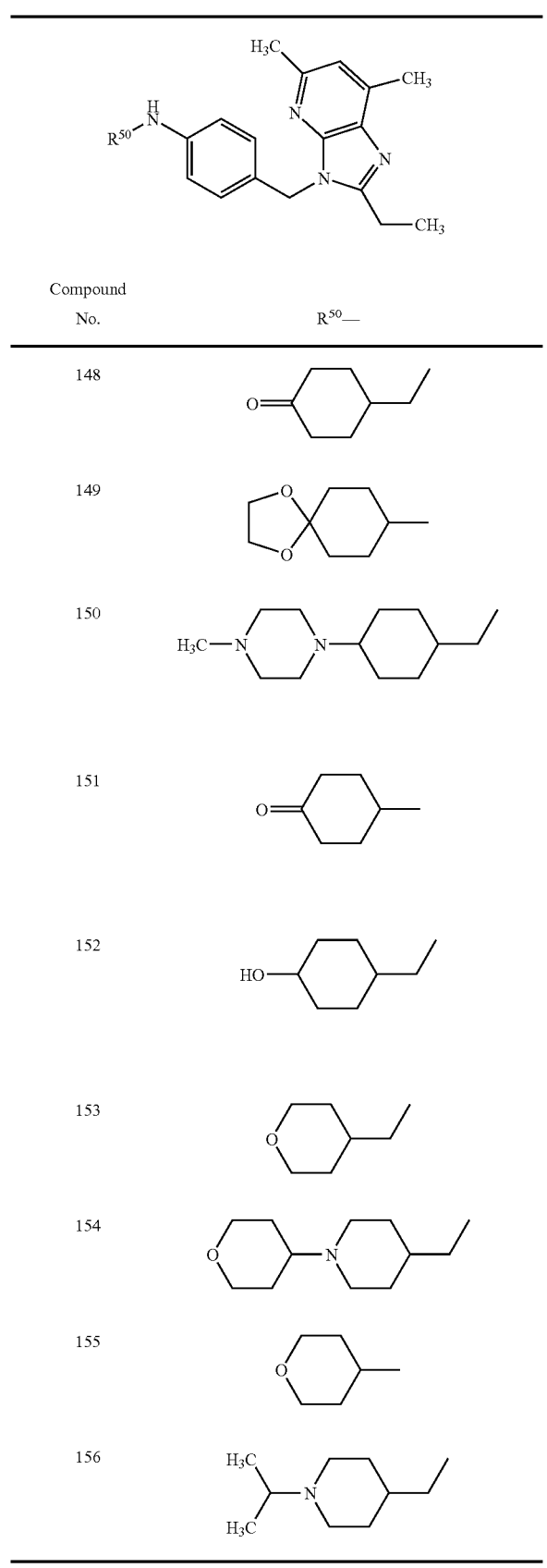
TABLE 13
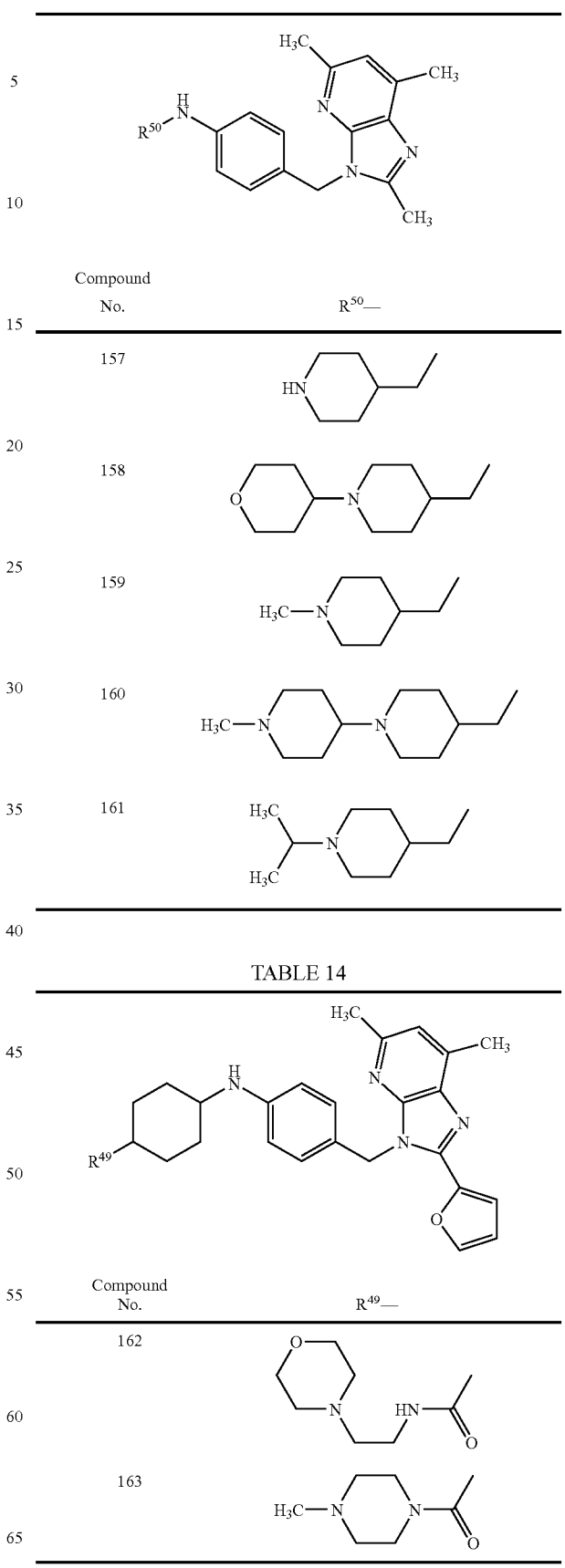

TABLE 15

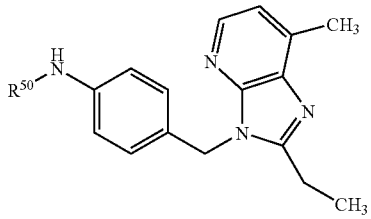

| Compound No. | R⁵⁰— |
|---|---|
| 164 | 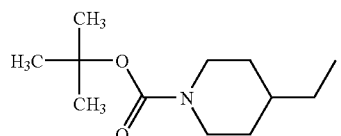 |
| 165 | 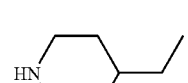 |
| 166 | 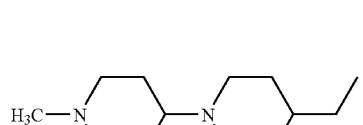 |

TABLE 16

| Compound No. | Structure |
|---|---|
| 167 | 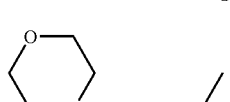 |
| 168 | 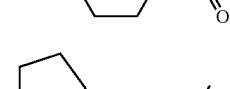 |

TABLE 17

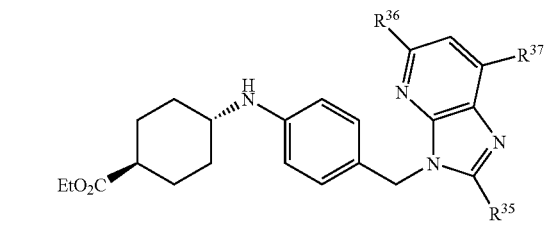

| Compound No. | —R³⁵ | —R³⁶ | —R³⁷ |
|---|---|---|---|
| 169 | —CH₃ | —CH₃ | —CH₃ |
| 170 | —CH₂CH₃ | —H | —CH₃ |
| 171 | —CH₃ | —H | —CH₃ |
| 172 |  | —CH₃ | —CH₃ |

TABLE 18

| Compound No. | R⁴⁹— |
|---|---|
| 173 | 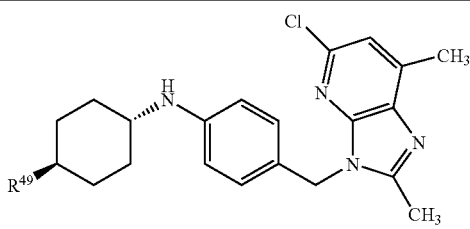 |
| 174 | 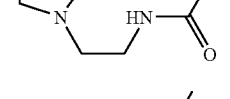 |
| 175 | |
| 176 | |

The pharmacollogical activity of Compound (I), (II), or (III) will be described with reference to test examples.

Although animals used in a screening method for therapeutic agents for neutrophilic inflammatory diseases are not particularly limited, for example, mammals excluding humans can be used. Although a substance which induces neutrophil infiltration in a bronchoalveolar lavage fluid (BALF) is not particularly limited, lysophosphatidylcholine (LPC) can be used.

TEST EXAMPLE 1

GPR4 Antagonism

Assay cells for human GPR4 were constructed according to the method descried in WO03/087366. By using the assay cells, the constitutive activity of human GPR4 can be detected by activity of a reporter (firefly luciferase).

Plasmid pAGal9-GPR4 for inducible expression of human GPR4 (2 μg: WO03/087366) and reporter plasmid pACREpluc (2 μg; WO03/087366) were co-transferred into $6\times10^6$ cells of KJMGER8 (WO03/087366) by electroporation. The resultant transformant was suspended in 8 mL of a RPMI1640-ITPSG medium [RPMI medium (Nissui Pharmaceutical Co., Ltd.) containing 6 mmol/L of L-glutamine (Invitrogen Corp.), 100 units/ml of penicillin (Invitrogen Corp.), 100 μg/ml of streptomycin (Invitrogen Corp.), 10 mmol/L of N-2-hydroxyethylpiperazine-N'-2-ethanesulfonic acid (HEPES) (Nacalai Tesque Inc.), 3 μg/ml of insulin (Sigma Co. Ltd.), 5 μg/ml of transferrin (Sigma Co. Ltd.), 5 mmol/L of sodium pyruvate (Wako Pure Chemical Industries, Ltd.), 125 nmol/L of selenious acid (Nacalai Tesque Inc.), and 1 mg/ml of galactose (Nacalai Tesque Inc.)], followed by culture in a $CO^2$ incubator at 37° C. for 24 hours. After the culture, blasticidin S (Funakoshi Co., Ltd., 2.0 μg/ml), hygromycin B (Wako Pure Chemical Industries, Ltd., 300 μg/ml), and geneticin (Nacalai Tesque Inc., 500 μg/ml) were added to the culture solution, followed by further culture for 14 days to prepare a stable transformant (referred to as "GPR4 assay cells"). The transformant was subcultured in a RPMI1640-ITPSG medium containing blastocidin S (Funakoshi Co., Ltd., 2.0 μg/ml), hygromycin B (manufactured by Wako Pure Chemical Industries, Ltd., 300 μg/ml), and geneticin (Nacalai Tesque Inc., 500 μg/ml).

Similarly, control plasmid pAGal9-nd (2 μg; WO03/087366) and reporter plasmid pACREpluc (2 μg; WO03/087366) were co-transferred in KJMGER8 to prepare a stable transformant (referred to as "control cells").

The resulting human GPR4 assay cells (expressing GPR4 by stimuli of 17β-estradiol) were seeded onto a white plate at a concentration of $10^5$ cells per well. Then, 17β-estradiol (Sigma Co. Ltd.), which was diluted with a medium so that the concentration in the reaction solution was 10 nmol/L, and 1 μmol/L of test compound were added to each well, followed by reaction in a 5% $CO_2$ incubator at 37° C. for 6 hours. Then, a Steady Glo Luciferase Assay System (Promega Co., Ltd.) solution was added to terminate the reaction, and the quantity of light emitted per second was measured by a TOP count (Packard, Meriden, Conn., USA).

The activity (GPR4 antagonism) of the test compound was shown by an inhibition rate calculated on the basis of counts (counts per second) in the presence or absence of 17β-estradiol according to the following equation:

$$\text{Inhinition rate (\%)} = \left\{1 - \left(\frac{A-B}{C-B}\right)\right\} \times 100$$

wherein A, B, and C represent the following values:
A: counts when 17β-estradiol and test compound were added
B: counts when neither 17β-estradiol nor test compound was added
C: counts when only 17β-estradiol was added The results are shown in Table 19.

TABLE 19

| Compound No. | Inhibition rate (%) |
|---|---|
| 1 | 31 |
| 24 | 34 |
| 53 | 74 |
| 81 | 77 |
| 97 | 45 |
| 98 | 37 |
| 118 | 97 |
| 143 | 97 |
| 158 | 83 |

These results indicate that the compounds of the present invention are useful as GPR4 antagonists.

TEST EXAMPLE 2

Inhibitory Activity on LPC-Induced Neutrophil Infiltration into Airway male BALB/c mice of 7-week old were intratracheally administered with 0.1 ml of a 1 mg/mL LPC solution prepared by dissolving in a 0.1% aqueous bovine serum albumin solution or a 0.1% aqueous bovine serum albumin solution (negative control group). Six hours after, bronchoalveola lavage was conducted, and the neutrophil infiltration in the recovered BALF was measured. In addition, Compound 53 or Compound 81 was suspended in a 0.5% aqueous methyl cellulose solution (solvent), and 100 mg/kg of the resultant suspension was orally administered to the mice 1 hour before LPC administration. In a positive control group, the solvent was administered instead of the test compound suspension. The infiltration of neutrophils was measured by measuring the number of cells in the recovered BALF with an automatic blood counter (Celltac α MEK-6158, Nihon Kohden Corporation, Tokyo) and then counting the number of neutrophils under a microscope using a smear prepared with Cytospin 3 (Shandon, Inc., Pittsburgh, Pa., USA). The number of neutrophils was calculated by multiplying the total number of cells by the percentage of the neutrophils. In this test, six mice per group were used for Compound 53, and six or seven mice per group were used for Compound 81.

The results are shown in FIGS. 1 and 2.

In the group administered with Compound 53 and the group administered with Compound 81, increases in the number of neutrophils were suppressed by 47% and 42%, respectively, as compared with the positive control group.

TEST EXAMPLE 3

Inhibitory Activity on LPC-Induced Neutrophil Infiltration into Airway

Male BALB/c mice of 7-week old were intratracheally administered with 0.1 mL of a 1 mg/mL LPC solution prepared by dissolving in a 0.1% aqueous bovine serum albumin solution or a 0.1% aqueous bovine serum albumin solution (negative control group). Six hours after, bronchoalveola lavage was conducted, and the neutrophil infiltration in the recovered BALF was measured. In addition, Compound 118 or Compound 160 was suspended in a 0.5% aqueous methyl cellulose solution (solvent), and 10 mg/kg of the resultant suspension was orally administered to the mice 1 hour before LPC administration. In a positive control group, the solvent was administered instead of the test compound suspension.

The infiltration of neutrophils was measured by measuring the number of cells in the recovered BALF with an automatic blood counter (Celltac α MEK-6158, Nihon Kohden Corporation, Tokyo) and then counting the number of neutrophils under a microscope using a smear prepared with Cytospin 3 (Shandon, Inc., Pittsburgh, Pa., USA). The number of neutrophils was calculated by multiplying the total number of cells by the percentage of the neutrophils. In this test, five mice per group were used for Compound 118, and six mice per group were used for Compound 160.

The results are shown in FIGS. 3 and 4.

In the group administered with Compound 118 and the group administered with Compound 160, increases in the number of neutrophils were suppressed by 60% and 74%, respectively, as compared with the positive control group.

Pharmaceutical formulations according to the present invention can contain as active ingredients Compound (I), (II), or (III) or a pharmaceutically acceptable salt thereof alone or as a mixture with any other effective ingredients for treatment. Furthermore, the pharmaceutical formulations are manufactured by mixing active ingredients with at least one pharmaceutically acceptable carrier according to any method well known in the technical field of pharmaceutics.

Compound (I), (II), or (III) or pharmaceutically acceptable salts thereof can be orally administered in the dosage form of a tablet, a capsule, granules, or the like or parenterally, for example, intravenously, administered in the dosage form of an injection or the like.

Examples of the carrier include sucrose, gelatin, lactose, mannitol, glucose, hydroxypropyl cellulose, microcrystalline cellulose, methyl cellulose, carboxymethyl cellulose, alginic acid, talc, sodium citrate, calcium carbonate, potassium hydrogen phosphate, starch, polyvinyl pyrrolidone, magnesium metasilicate aluminate, magnesium stearate, carmellose calcium, urea, silicone resin, sorbitan fatty acid esters, glycerin fatty acid esters, distilled water for injection, physiological saline, propylene glycol, polyethylene glycol, olive oil, ethanol, and the like.

The dosage and frequency of administration Compound (I), (II), or (III) or a pharmaceutically acceptable salt thereof vary depending on the ages, weights, symptoms, therapeutic effects, administration methods, and treatment times of patients. However, ordinary, the compound or a salt thereof is orally or parenterally administered once to several times per day in a dose in a range of 0.1 to 100 mg per adult.

: p<0.0001 (ratio of positive control group to negative control group; Aspin-welch test)

🟥🟥🟥: P=0.0005 (ratio of the group administered with Compound 53 to positive control group; Student's t-test)

Figure 1:
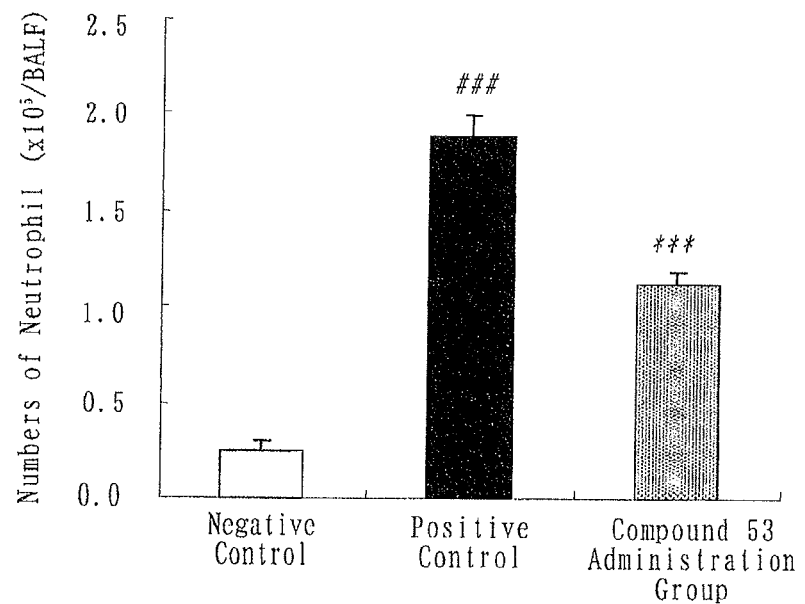
FIG. 1 is a diagram showing the inhibitory activity of Compound 53 on LPC-induced neutrophil infiltration in airway.
Figure 2:
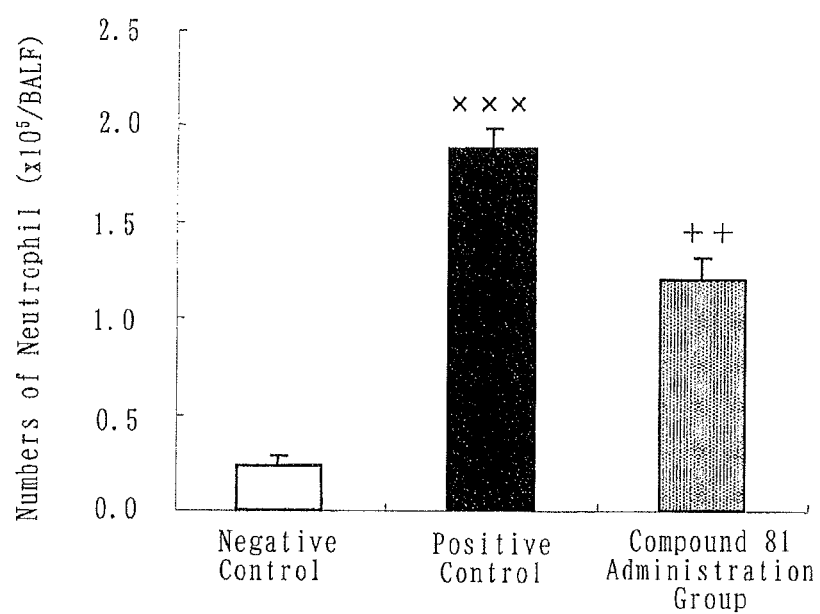

FIG. 2 is a diagram showing the inhibitory activity of Compound 81 on LPC-induced neutrophil infiltration in airway.

xxx: p<0.0001 (ratio of positive control group to negative control group; Aspin-welch test)

++: P=0.0024 (ratio of the group administered with Compound 81 to positive control group; Student's t-test)

Figure 3:
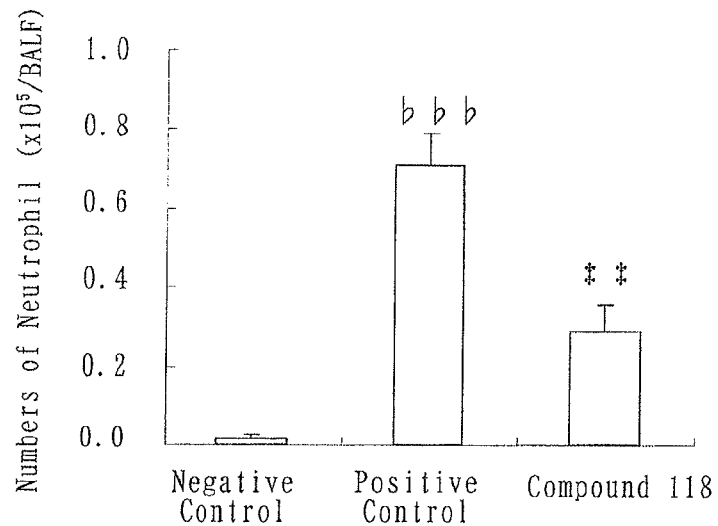

FIG. 3 is a diagram showing the inhibitory activity of Compound 118 on LPC-induced neutrophil infiltration in airway.

bbb: p=0.0009 (ratio of positive control group to negative control group; Aspin-welch test)

‡‡: P=0.0038 (ratio of the group administered with Compound 118 to positive control group; Student's t-test)

Figure 4:
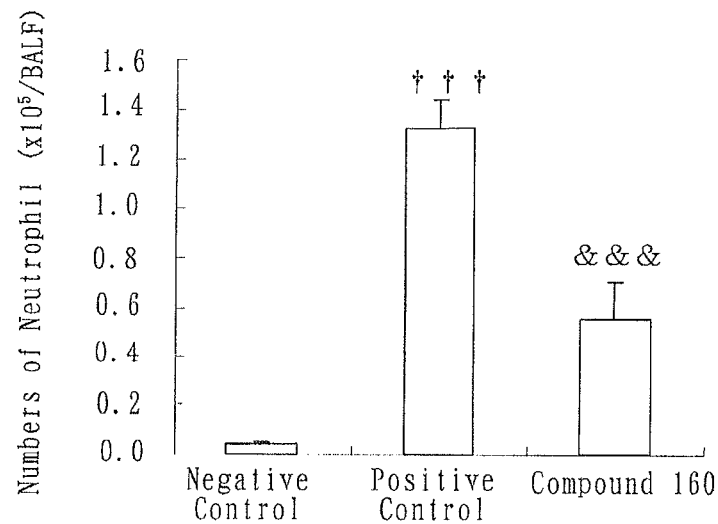

FIG. 4 is a diagram showing the inhibitory activity of Compound 160 on LPC-induced neutrophil infiltration in airway.

†††: p=0.0004 (ratio of positive control group to negative control group; Aspin-welch test)

&&&: P=0.0009 (ratio of the group administered with Compound 160 to positive control group; Aspin-welch test)

BEST MODE FOR CARRYING OUT THE INVENTION

The present invention will be described in further detail below with reference to reference examples and examples, but the present invention is not limited to these examples.

A proton nuclear magnetic resonance spectrum ($^1$H NMR) was measured with 270 MHz unless otherwise specified. In $^1$H NMR, exchangeable protons may not be clearly observed depending on the compound and measurement conditions used, and "br" means a broad signal. Mass spectrometry was performed by atmospheric pressure chemical ionization (APCI) or electrospray ionization (ESI). The results of mass spectrometry using these ionization methods are described as APCI-MS and ESI-MS, respectively.

Reference Example 1

1-{4-[3-(2-Ethyl-5,7-dimethylimidazo[4,5-b]pyridin-3-ylmethyl)benzoyl]benzyl}piperidine-4-carboxylic acid (Compound P1)

Compound 16 (0.180 g, 0.334 mmol) was dissolved in ethanol (3 mL), and a 1 mol/L aqueous sodium hydroxide solution (3 mL) was added to the solution, followed by stirring at room temperature for 3.5 hours. The reaction mixture was concentrated under reduced pressure, and water was added to the residue. Then, 1 mol/L hydrochloric acid was added to the mixture to control the pH to about 7. The mixture was extracted with chloroform twice, and the organic layer was dried over anhydrous magnesium sulfate and then concentrated under reduced pressure. The residue was crystallized with ethanol-diethyl ether to obtain Compound P1 (0.115 g, yield 68%).

ESI-MS: m/z 511 [M+H]$^+$ $^1$H NMR (CDCl$_3$) δ(ppm): 1.31 (t, J=7.5 Hz, 3H), 1.90-2.17 (m, 4H), 2.55 (s, 3H), 2.60 (s, 3H), 2.35-2.38 (m, 3H), 2.83 (q, J=7.5 Hz, 2H), 3.01-3.05 (m, 2H), 3.79 (s, 2H), 5.51 (s, 2H), 6.89 (s, 1H), 7.33 (brd, J=7.7 Hz, 1H), 7.40 (t, J=7.7 Hz, 1H), 7.46 (d, J=8.1 Hz, 2H), 7.59 (s, 1H), 7.67-7.70 (m, 3H).

Reference Example 2

1-[4-{[3-(2-Ethyl-5,7-dimethylimidazo[4,5-b]pyridin-3-ylmethyl)phenyl]hydroxyiminomethyl}benzyl]piperidine-4-carboxylic acid (Compound P2)

Compound 18 (0.195 g, 0.352 mmol) was dissolved in ethanol (3 mL), and a 1 mol/L aqueous sodium hydroxide solution (3 mL) was added to the solution, followed by stirring at room temperature for 3.5 hours. The reaction mixture was concentrated under reduced pressure, and water was added to the residue. Then, 1 mol/L hydrochloric acid was added to the mixture to control the pH to about 7. The precipitated crystals were collected by filtration, and then washed with diethyl ether to obtain Compound P2 (0.0500 g, yield 27%).

ESI-MS: m/z 526 [M+H]$^+$ $^1$H NMR (DMSO-d$_6$) δ(ppm): 1.20 (t, J=7.4 Hz, 3H), 1.62-1.83 (m, 6H), 2.21-2.25 (m, 1H), 2.46 (s, 3H), 2.49 (s, 3H), 2.74-2.89 (m, 2H), 2.76 (q, J=7.6 Hz, 2H), 3.39 (s, 0.65H), 3.42 (s, 0.35H), 5.43 (s, 0.35H), 5.49 (s, 0.65H), 6.91 (s, 1H), 7.05 (s, 1H), 7.17-7.43 (m, 8H), 11.3 (s, 1H).

Reference Example 3

1-{3-[3-(2-Ethyl-5,7-dimethylimidazo[4,5-b]pyridin-3-ylmethyl)benzoyl]benzyl}piperidine-4-carboxylic acid (Compound P3)

Compound P3 (0.0580 g, yield 38%) was obtained in a similar manner to Reference Example 1 using Compound 22 (0.160 g, 0.297 mmol).

ESI-MS: m/z 511 [M+H]$^+$ $^1$H NMR (CDCl$_3$) δ(ppm): 1.21 (t, J=7.4 Hz, 3H), 1.97-2.09 (m, 4H), 2.41-2.58 (m, 3H), 2.45 (s, 3H), 2.51 (s, 3H), 2.88-3.06 (m, 2H), 2.83 (q, J=7.4 Hz, 2H), 3.85 (s, 2H), 5.44 (s, 2H), 6.82 (s, 1H), 7.18-7.36 (m, 3H), 7.44 (s, 1H), 7.53 (d, J=7.8 Hz, 1H), 7.60 (d, J=8.7 Hz, 1H), 7.63 (s, 1H), 7.74 (d, J=5.9 Hz, 1H).

Reference Example 4

3-(2-Ethyl-5,7-dimethylimidazo[4,5-b]pyridin-3-ylmethyl)benzoic acid (Compound P4)

Compound P4 (1.04 g, yield 95%) was obtained in a similar manner to Reference Example 1 using Compound 12 (1.14 g, 3.53 mmol).

ESI-MS: m/z 310 [M+H]$^+$ $^1$H NMR (CDCl$_3$) δ(ppm): 1.22 (t, J=7.5 Hz, 3H), 2.50 (s, 3H), 2.52 (s, 3H), 2.76 (q, J=7.5 Hz, 2H), 5.53 (s, 2H), 6.96 (s, 1H), 7.37 (d, J=7.9 Hz, 1H), 7.46 (t, J=7.5 Hz, 1H), 7.70 (s, 1H), 7.84 (d, J=7.5 Hz, 1H).

Reference Example 5

4-(2-Ethyl-5,7-dimethylimidazo[4,5-b]pyridin-3-ylmethyl)benzoic acid (Compound P5)

Compound 25 (0.720 g, 2.23 mmol) was dissolved in ethanol (14 mL), and a 3 mol/L aqueous sodium hydroxide solution (7 mL) was added to the solution, followed by stirring at 90° C. for 3.5 hours. The reaction mixture was concentrated under reduced pressure, and water was added to the residue. Then, 1 mol/L hydrochloric acid was added to the mixture to control the pH to about 5 to 6. The precipitated crystals were collected by filtration and then washed with water to obtain Compound P5 (0.625 g, yield 91%).

ESI-MS: m/z 310 [M+H]$^+$ $^1$H NMR (CDCl$_3$) δ(ppm): 1.29 (t, J=7.5 Hz, 3H), 2.59 (s, 3H), 2.65 (s, 3H), 2.81 (q, J=7.5 Hz, 2H), 5.53 (s, 2H), 6.91 (s, 1H), 7.13 (d, J=8.4 Hz, 2H), 7.95 (d, J=8.2 Hz, 2H).

Reference Example 6

1-[4-(2-Ethyl-5,7-dimethylimidazo[4,5-b]pyridin-3-ylmethyl)benzoil]piperidine-4-carboxilic acid (Compound P6)

Compound P6 (2.39 g, yield 89%) was obtained in a similar manner to Reference Example 1 using Compound 32 (2.88 g, 6.42 mmol).

ESI-MS: m/z 421 [M+H]$^+$ $^1$H NMR (CDCl$_3$) δ(ppm): 1.30 (t, J=7.6 Hz, 3H), 1.64-1.78 (m, 2H), 1.88-1.95 (m, 2H), 2.53-2.59 (m, 2H), 2.56 (s, 3H), 2.61 (s, 3H), 2.75 (m, 1H), 2.79 (q, J=7.6 Hz, 2H), 3.07 (m, 2H), 5.46 (s, 2H), 6.87 (s, 1H), 7.15 (d, J=7.9 Hz, 2H), 7.30 (d, J=8.1 Hz, 2H).

Reference Example 7

3-(4-Aminobenzyl)-2-ethyl-5,7-dimethyl-3H-imidazo[4,5-b]pyridine (Compound P7)

Step 1

2-Ethyl-5,7-dimethyl-3H-imidazo[4,5-b]pyridine (U.S. Pat. No. 5,424,432) (3.50 g, 20.0 mmol) was dissolved in DMF (67 mL), and lithium hydroxide monohydrate (1.26 g, 30.0 mmol) was added thereto, followed by stirring at room temperature for 20 minutes. Then, p-nitorobenzylbromide (4.31 g, 20.0 mmol) was slowly added and stirred at room temperature for 30 minutes. Water (130 mL) was added to the reaction mixture and the precipitated crystals were collected by filtration, followed by washing with water. The crystals was dried under reduced pressure to obtain 2-ethyl-5,7-dimethyl-3-(4-nitrobenzyl)-3H-imidazo[4,5-b]pyridine (4.91 g, 15.8 mmol, yield 79.1%).

APCI-MS: m/z 311 [M+H]$^+$ $^1$H NMR (CDCl$_3$) δ(ppm): 1.32 (t, J=7.5 Hz, 3H), 2.57 (s, 3H), 2.64 (s, 3H), 2.77 (q, J=7.5 Hz, 2H), 5.45 (s, 2H), 6.92 (s, 1H), 7.28 (m, 2H), 8.16 (m, 1H).

Step 2

2-Ethyl-5,7-dimethyl-3-(4-nitrobenzyl)-3H-imidazo[4,5-b]pyridine (4.81 g, 15.5 mmol) obtained in Step 1 was dissolved in methanol (155 mL) and palladium/carbon (10%, wet, 1.65 g, 1.55 mmol) and ammonium formate (9.77 g, 155 mmol) were added to the solution, followed by stirring at room temperature for 40 minutes. The reaction mixture was filtered through Celite and the filtrate was concentrated under reduced pressure. Water was added to the residue and precipitated crystals were collected by filtration and washed with water. Ethyl acetate-hexane (2:3) was added to the obtained crude crystals and the mixture was stirred under reflux for 1 hour. After cooling to room temperature, the precipitated crystals were collected by filtration to obtain Compound P7 (3.53 g, 12.6 mmol, yield 81.2%).

APCI-MS: m/z 281 [M+H]$^+$ $^1$H NMR (CDCl$_3$) δ(ppm): 1.29 (t, J=7.5 Hz, 3H), 2.59 (s, 3H), 2.62 (s, 3H), 2.76 (q, J=7.5 Hz, 2H), 3.52 (brs, 2H), 5.33 (s, 2H), 6.56 (m, 2H), 6.87 (s, 1H), 6.93 (m, 2H).

Reference Example 8

3-(3-Aminobenzyl)-2-ethyl-5,7-dimethyl-3H-imidazo[4,5-b]pyridine (Compound P8)

Compound P8 (yield 65%) was obtained in a similar manner to Reference Example 7 using m-nitorobenzylbromide instead of p-nitorobenzylbromide.

APCI-MS: m/z 281 [M+H]$^+$ $^1$H NMR (CDCl$_3$) δ(ppm): 1.30 (t, J=7.6 Hz, 3H), 2.59 (s, 3H), 2.63 (s, 3H), 2.78 (q, J=7.5 Hz, 2H), 3.59 (brs, 2H), 5.37 (s, 2H), 6.33 (m, 1H), 6.53 (m, 2H), 6.8 (s, 1H), 7.06 (t, J=7.8 Hz, 1H).

Reference Example 9

4-{4-(2-Ethyl-5,7-dimethylimidazo[4,5-b]pyridin-3-ylmethyl)phenylamino)benzoic acid (Compound P9)

Compound 99 (0.393 g, 0.917 mmol) was suspended in ethanol (7.5 mL), and a 2 mol/L aqueous sodium hydroxide solution (7.5 mL) was added to the solution, followed by stirring at 60° C. for 7 hours. The reaction mixture was concentrated under reduced pressure, and 1 mol/L hydrochloride was added to the residue to control the pH to about 5. Precipitates were collected by filtration, and was washed with water and dried under reduced pressure. The crude crystals were recrystallized from ethanol-diethyl ether to obtain Compound P9 (0.340 g, 0.849 mmol, yield 93%).

APCI-MS: m/z 401 [M+H]$^+$
$^1$H NMR (DMSO-d$_6$) δ(ppm): 1.24 (t, J=7.4 Hz, 3H), 2.51 (6H, overlapping with the peak of DMSO), 2.80 (q, J=7.4 Hz, 2H), 5.39 (s, 2H), 6.95 (s, 1H), 6.98-7.03 (m, 2H), 7.11 (brs, 4H), 7.74 (brd, J=8.7 Hz, 2H), 8.72 (s, 1H), 12.30 (s, 1H).

Reference Example 11

2,5,7-Trimethyl-3H-imidazo[4,5-b]pyridine (Compound P11)

2,3-Diamino-4,6-dimethylpyridine (25.0 g, 0.182 mol) was suspended in polyphosphoric acid (465 g), and acetic acid (31.3 mL, 0.547 mol) was added to the suspension, followed by stirring at 100° C. for 3 hours. The reaction mixture was moved to ice water and sodium carbonate (345 g) was added in a little portion while stirring. Then, 28% aqueous ammonium solution was added to the residue to control the pH to 9 and the mixture was stirred for 1 hour. Precipitated crystals were collected by filtration, and was washed with water, and the obtained crystals were dried under reduced pressure at 40° C. overnight to obtain Compound P11 (26.2 g, 0.162 mol, 89%).

ESI-MS: m/z 162 [M+H]$^+$
$^1$H NMR (CDCl$_3$) δ(ppm): 2.68 (s, 3H), 2.70 (s, 3H), 6.95 (s, 1H), 8.15 (s, 1H), 13.8 (brs, 1H).

Reference Example 12

2,3-Diamino-4-methylpyridine (Compound P12)

Commercially available 2-amino-4-methyl-3nitropyridine (10.0 g, 65.3 mmol) was suspended in ethanol (450 mL) and the flask was filled with argon. 10% palladium carbon (13.9 g, 50% water-containing) was added to the mixture and stirred at room temperature overnight under the flow of hydrogen. Solids were filtered through Celite and this was washed with ethanol. The filtrate was concentrated under reduced pressure to obtain Compound P12 (7.81 g, 63.3 mmol, 97%).

ESI-MS: m/z 124 [M+H]$^+$
$^1$H NMR (CDCl$_3$) δ(ppm): 2.17 (s, 3H), 3.27 (brs, 2H), 4.16 (brs, 2H), 6.53 (d, J=5.3 Hz, 1H), 7.55 (d, J=5.0 Hz, 1H).

Reference Example 13

2-Ethyl-7-methyl-3H-imidazo[4,5-b]pyridine (Compound P13)

Compound P12 (1.80 g, 14.6 mmol) was suspended in polyphosphoric acid (38 g), and propionic acid (3.27 mL, 43.8 mmol) was added to the solution, followed by stirring at 100° C. for 3 hours. The reaction mixture was moved to ice water, and sodium carbonate was added in a little portion while stirring. Then, 28% aqueous ammonia solution was added to the mixture to control the pH to 9 and the mixture was stirred for 1 hour. The reaction mixture was extracted with chloroform twice, and the organic layer was washed with saturated brine and dried over anhydrous magnesium sulfate, then concentrated under reduced pressure. The residue was purified by silica gel column chromatography (chloroform:methanol=50:1) to obtain compound P13 (2.24 g, 14.0 mmol, 96%).

ESI-MS: m/z 162 [M+H]$^+$
$^1$H NMR (CDCl$_3$) δ(ppm): 1.53 (t, J=7.7 Hz, 3H), 2.68 (s, 3H), 3.08 (q, J=7.7 Hz, 2H), 7.02 (d, J=5.1 Hz, 1H), 8.17 (d, J=4.9 Hz, 1H), 14.1 (brs, 1H).

Reference Example 14

2,7-Dimethyl-3H-imidazo[4,5-b]pyridine (Compound P14)

Compound P12 (7.11 g, 57.7 mmol) was suspended in polyphosphoric acid (163 g), and acetic acid (9.90 mL, 0.172 mol) was added to the suspention, followed by stirring at 100° C. for 3 hours. The reaction mixture was moved to ice water and sodium carbonate (115 g) was added in a small portion while stirring. Then, aqueous ammonia solution was added to the mixture to control the pH to 9 and the mixture was stirred for 1 hour. The reaction mixture was extracted with chloroform 5 times, and the organic layer was dried over anhydrous magnesium sulfate and then concentrated under reduced pressure. The residue was purified by silica gel column chromatography (chloroform:methanol=15:1), dissolved in methanol (50 mL), added with active charcoal (0.284 g) and stirred at room temperature for 30 minutes. The solid was filtered out, and the filtrate was combined and concentrated under reduced pressure. The residue was recrystallized from ethanol to obtain Compound P14 (4.1 g, 27.7 mmol, 48%).

ESI-MS: m/z 148 [M+H]$^+$
$^1$H NMR (CDCl$_3$) δ(ppm): 2.68 (s, 3H), 2.74 (s, 3H), 7.02 (d, J=5.1 Hz, 1H), 8.17 (d, J=5.1 Hz, 1H).

Reference Example 15

5,7-Dimethyl-2-(furan-2-yl)-3H-imidazo[4,5-b]pyridine (Compound P15)

Step 1
2,3-Diamino-4,6-dimethylpyridine (2.74 g, 20.0 mmol) was dissolved in dichloromethane (50 mL), and triethylamine (6.70 mL, 48.0 mmol) and 2-froylchloride (4.73 mL, 48.0 mmol) was added to the solution, followed by stirring at room temperature for 3 hours. Then, the reaction mixture was concentrated under reduced pressure and the residue was triturated in dichloromethane to obtain 2,3-di(2-froylamino)-4,6-dimethylpyridine (3.40 g, 10.45 mmol, 52%).

Step 2
2,3-Di(2-froylamino)-4,6-dimethylpyridine (1.00 g, 3.07 mmol) obtained in Step 1 was dissolved in DMF (10 mL), and 28% Sodium methoxide-methanol solution (2.37 g, 12.30 mmol) was added to the solution, followed by stirring at 90° C. for 24 hours. Then, the reaction mixture was concentrated under reduced pressure, and the residue was extracted with ethyl acetate. The organic layer was dried over anhydrous potassium carbonate, concentrated under reduced pressure, and the residue was triturated in dichloromethane to obtain Compound P15 (425 mg, 1.99 mmol, 65%).

ESI-MS: m/z 214 [M+H]$^+$

Reference Example 16 cis-4-(Phenylamino)cyclohexane carboxylic acid ethyl ester (Compound P16c) and trans-4-(Phenylamino)cyclohexane carboxylic acid ethyl ester (Compound P16t)

Commercially available 4-cyclohexanone carboxylic acid ethyl (16.8 g, 98.7 mmol) and aniline (6.00 mL, 65.8 mmol)

was dissolved in acetonitrile (400 mL), followed by stirring at room temperature for 30 minutes. The mixture was added with Sodium triacetoxyborohydride (56.0 g, 0.264 mol) and further stirred for 6 hours. Saturated aqueous sodium hydrogencarbonate solution was added to the reaction mixture slowly and the mixture was stirred for a while. Then, the mixture was extracted with ethyl acetate twice. The organic layer was sequentially washed with water and saturated brine and dried over anhydrous magnesium sulfate, then concentrated under reduced pressure. The residue was purified by silica gel column chromatography (ethyl acetate:hexane=1:13) to obtain compound P16c (5.80 g, 36%) and compound P16t (6.51 g, 40%).

Compound P16c
ESI-MS: m/z 248 [M+H]$^+$
$^1$H NMR (CDCl$_3$) δ(ppm): 1.25 (t, J=7.3 Hz, 3H), 1.61-1.98 (m, 8H), 2.47 (m, 1H), 3.47 (m, 1H), 4.13 (q, J=7.3 Hz, 2H), 6.60 (dd, J=1.0, 8.6 Hz, 2H), 6.65 (tt, J=1.0, 8.2 Hz, 1H), 7.14 (t, J=8.6 Hz, 2H).

Compound P16t
ESI-MS: m/z 248 [M+H]$^+$
$^1$H NMR (CDCl$_3$) δ(ppm): 1.13 (dq, J=3.6, 13.2 Hz, 2H), 1.26 (t, J=7.3 Hz, 3H), 1.60 (dq, J=3.3, 13.2 Hz, 2H), 2.05 (m, 2H), 2.21 (m, 2H), 2.29 (tt, J=3.6, 12.2 Hz, 1H), 3.25 (tt, J=4.0, 11.2 Hz, 1H), 4.13 (q, J=7.3 Hz, 2H), 6.57 (dd, J=1.0, 8.6 Hz, 2H), 6.68 (tt, J=1.0, 7.6 Hz, 1H), 7.16 (dd, J=7.3, 7.6 Hz, 2H).

Reference Example 17 cis-4-[4-(Pyrrolidin-1-ylmethyl)phenylamino]cyclohexane carboxylic acid ethyl ester (Compound P17)

Compound P16c (0.500 g, 2.02 mmol) was dissolved in 1,4-dioxane (16 mL) and acetic acid (4 mL), and 37% formalin (0.452 mL, 6.07 mmol) and pyrrolidine (0.338 mL, 4.05 mmol) was added, followed by stirring at 60° C. for 4 hours. The reaction mixture was concentrated under reduced pressure and was extracted with chloroform. The organic layer was washed with saturated aqueous sodium hydrogen carbonate solution and saturated brine, dried over anhydrous magnesium sulfate, then concentrated under reduced pressure. The residue was purified by a silica gel column chromatography (chloroform:2 mol/L ammonia-methanol=30:1) to obtain Compound P17 (0.501 g, 75%).

ESI-MS: m/z 331 [M+H]$^+$
$^1$H NMR (CDCl$_3$) δ(ppm): 1.25 (t, J=7.2 Hz, 3H), 1.64-1.97 (m, 12H), 2.51 (m, 5H), 3.47 (m, 1H), 3.51 (s, 2H), 3.65 (brs, 1H), 4.13 (q, J=7.2 Hz, 2H), 6.53 (d, J=8.6 Hz, 2H), 7.10 (d, J=8.6 Hz, 2H).

Reference Example 19 cis-4-[4-(2,5,7-Trimethyl-3H-imidazo[4,5-b]pyridin-3-ylmethyl)phenylamino]cyclohexane carboxylic acid (Compound P19)

Compound 168 (0.402 g, 0.955 mmol) was dissolved in ethanol (7 mL), and 3 mol/L aqueous sodium hydroxide solution (3.20 mL, 9.60 mmol) was added, followed by stirring for 3 hours. The reaction mixture was concentrated under reduced pressure, and 1 mol/L hydrochloric acid was added to the residue to control the pH to 6.4. The precipitated crude crystals were washed with water to obtain Compound P19 (0.375 g, 91%).

ESI-MS: m/z 393 [M+H]$^+$
$^1$H NMR (DMSO-d$_6$) δ(ppm): 1.49-1.81 (m, 8H), 2.37 (m, 1H), 2.45 (s, 3H), 2.49 (s, 3H), 2.50 (s, 3H), 3.32 (m, 1H), 5.21 (s, 2H), 5.47 (brs, 1H), 6.49 (d, J=8.6 Hz, 2H), 6.89 (s, 1H), 6.91 (d, J=8.6 Hz, 1H).

Reference Example 20 trans-4-[4-(Pyrrolidin-1-ylmethyl)phenylamino]cyclohexane carboxylic acid ethyl ester (Compound P20)

Compound P20 (1.28 g, 96%) was obtained in a similar manner to Reference Example 17 using Compound P16t (1.00 g, 4.04 mmol).

ESI-MS: m/z 331 [M+H]$^+$
$^1$H NMR (CDCl$_3$) δ(ppm): 1.15 (dq, J=3.3, 13.0 Hz, 2H), 1.27 (t, J=7.2 Hz, 3H), 1.58 (dq, J=3.1, 13.4 Hz, 2H), 1.76-1.80 (m, 4H), 2.06 (m, 2H), 2.19 (m, 2H), 2.30 (tt, J=3.7, 12.1 Hz, 1H), 2.50 (m, 4H), 3.24 (brt, J=10.8 Hz, 1H), 3.51 (s, 2H), 4.14 (q, J=7.2 Hz, 2H), 6.54 (d, J=8.4 Hz, 2H), 7.12 (d, J=8.4 Hz, 2H).

Reference Example 22 trans-4-[4-(2,5,7-Trimethyl-3H-imidazo[4,5-b]pyridin-3-ylmethyl)phenylamino]cyclohexane carboxylic acid (Compound P22)

Compound P22 (0.589 g, 94%) was obtained in a similar manner to Reference Example 19 using Compound 169 (0.670 g, 1.59 mmol).

ESI-MS: m/z 393 [M+H]$^+$
$^1$H NMR (DMSO-d$_6$) δ(ppm): 1.11 (brq, J=12.4 Hz, 2H), 1.40 (brq, J=12.5 Hz, 2H), 1.86-1.97 (m, 4H), 2.15 (brt, J=12.2 Hz, 1H), 2.44 (s, 3H), 2.46 (s, 3H), 2.51 (s, 3H), 3.07 (m, 1H), 5.21 (s, 2H), 5.41 (brs, 1H), 6.47 (d, J=8.3 Hz, 2H), 6.85 (s, 1H), 6.90 (d, J=8.3 Hz, 1H).

Reference Example 23 trans-4-[4-(Piperidin-1-ylmethyl)phenylamino]cyclohexanecarboxilic acid ethyl ester (Compound P23)

Compound P16t (1.92 g, 7.76 mmol) was dissolved in 1,4-dioxane (40 mL) and acetic acid (10 mL), and 37% formalin (1.74 mL, 23.4 mmol) and piperidine (2.31 mL, 23.3 mmol) were added thereto followed by stirring at 60° C. for 3.5 hours. The reaction mixture was concentrated under reduced pressure, and was extracted with chloroform. The organic layer was washed with saturated aqueous sodium hydrogen carbonate solution and saturated brine, dried over anhydrous magnesium sulfate and concentrated under reduced pressure. The residue was purified by silica gel column chromatography (chloroform: 2 mol/L ammonia-methanol=20:1) to obtain compound P23 (2.01 g, 75%).

ESI-MS: m/z 345 [M+H]$^+$
$^1$H NMR (CDCl$_3$) δ(ppm): 1.12 (dq, J=3.1, 13.0 Hz, 2H), 1.26 (t, J=7.2 Hz, 3H), 1.41-1.64 (m, 8H), 2.05 (m, 2H), 2.19 (m 2H), 2.28 (tt, J=3.7, 12.1 Hz, 1H), 2.34 (m, 4H), 3.23 (tt, J=3.7, 11.2 Hz, 1H), 3.37 (s, 2H), 4.13 (q, J=7.2 Hz, 2H), 6.53 (d, J=8.4 Hz, 2H), 7.09 (d, J=8.4 Hz, 2H).

Reference Example 25 trans-4-[4-(2-Ethyl-7-methyl-3H-imidazo[4,5-b]pyridin-3-ylmethyl)phenylamino]cyclohexanecarboxilic acid (Compound P25)

Compound P25 (0.166 g, 91%) was obtained in a similar manner to Reference Example 19 using Compound 170 (0.220 g, 0.523 mmol).
ESI-MS: m/z 393 [M+H]$^+$
$^1$H NMR (DMSO-d$_6$) δ(ppm): 1.16 (brq, J=13.2 Hz, 2H), 1.22 (t, J=7.6 Hz, 3H), 1.37 (brq, J=12.7 Hz, 2H), 1.88 (m, 4H), 2.12 (brt, J=12.2 Hz, 1H), 2.48 (s, 3H), 2.81 (q, J=7.4 Hz, 2H), 3.05 (m, 1H), 5.24 (s, 2H), 5.36 (brs, 1H), 6.44 (d, J=8.4 Hz, 2H), 6.90 (d, J=8.4 Hz, 2H), 7.02 (d, J=5.0 Hz, 1H), 8.12 (d, J=5.0 Hz, 1H).

Reference Example 27 trans-4-[4-(2,7-Dimethyl-3H-imidazo[4,5-b]pyridin-3-ylmethyl)phenylamino]cyclohexanecarboxilic acid (Compound P27)

Compound P27 (0.278 g, 83%) was obtained in a similar manner to Reference Example 19 using Compound 171 (0.360 g, 0.885 mmol).
ESI-MS: m/z 379 [M+H]$^+$
$^1$H NMR (DMSO-d$_6$) δ(ppm): 1.06 (brq, J=12.7 Hz, 2H), 1.38 (brq, J=12.5 Hz, 2H), 1.84-1.93 (m, 4H), 2.12 (brt, J=12.1 Hz, 1H), 2.47 (s, 3H), 2.49 (s, 3H), 3.05 (m, 1H), 5.23 (s, 2H), 5.38 (brd, J=7.0 Hz, 1H), 6.45 (d, J=8.4 Hz, 2H), 6.93 (d, J=8.6 Hz, 2H), 7.02 (d, J=5.0 Hz, 1H), 8.12 (d, J=5.0 Hz, 1H).

Reference Example 29 trans-4-{4-[2-(Furan-2-yl)-5,7-dimethyl-3H-imidazo[4,5-b]pyridin-3-ylmethyl]phenylamino}cyclohexanecarboxilic acid (Compound P29)

Compound P29 (0.163 g, 83%) was obtained in a similar manner to Reference Example 19 using Compound 172 (0.210 g, 0.444 mmol).
ESI-MS: m/z 445 [M+H]$^+$
$^1$H NMR (DMSO-d$_6$) δ(ppm): 1.16 (brq, J=13.2 Hz, 2H), 1.38 (brq, J=11.9 Hz, 2H), 1.89 (m, 4H), 2.14 (brt, J=11.9 Hz, 1H), 2.50 (s, 3H), 2.54 (s, 3H), 3.05 (m, 1H), 5.38 (brs, 1H), 5.56 (s, 2H), 6.41 (d, J=8.3 Hz, 2H), 6.70 (dd, J=1.7, 3.3 Hz, 1H), 6.83 (d, J=8.6 Hz, 2H), 7.03 (d, J=3.6 Hz, 1H), 7.11 (d, J=3.6 Hz, 1H), 7.96 (d, J=1.7 Hz, 1H), 12.02 (s, 1H).

Reference Example 31 cis-4-[4-(2-Ethyl-5,7-dimethyl-3H-imidazo[4,5-b]pyridin-3-ylmethyl)phenylamino]cyclohexanecarboxilic acid (Compound P31)

Compound 106c (2.80 g, 6.44 mmol) was dissolved in ethanol (20 mL), and 2 mol/L aqueous sodium hydroxide solution (20 mL) was added, followed by stirring at room temperature for 1.5 hours. The reaction mixture was added with 1 mol/L hydrochloric acid to control the pH to about 6. The precipitated crude crystals were collected by filtration, dried under reduced pressure, and recrystallized twice from ethanol-DMF (3:1) to obtain Compound P31 (1.17 g, 2.88 mmol, 44.7%).
APCI-MS: m/z 407 [M+H]$^+$
$^1$H NMR (DMSO-d$_6$) δ(ppm): 1.22 (t, J=7.5 Hz, 3H), 1.39-1.67 (m, 6H), 1.79-1.92 (m, 2H), 2.38 (brs, 1H), 2.51 (6H, overlapping with the peak of DMSO), 2.78 (q, J=7.5 Hz, 2H), 3.31 (1H, overlapping with the peak of H$_2$O), 5.23 (s, 2H), 5.48 (brd, J=6.8 Hz, 1H), 6.49 (d, J=8.6 Hz, 2H), 6.88 (d, J=8.6 Hz, 2H), 6.91 (s, 1H), 12.09 (brs, 1H).

Reference Example 32 trans-4-[4-(2-Ethyl-5,7-dimethyl-3H-imidazo[4,5-b]pyridin-3-ylmethyl)phenylamino]cyclohexanecarboxilic acid (Com Compound P32)

Compound P32 (yield 84%) was obtained in a similar manner to Reference Example 31 using Compound 106t.
APCI-MS: m/z 407 [M+H]$^+$
$^1$H NMR (DMSO-d$_6$) δ(ppm): 1.09 (brq, J=12.7 Hz, 2H), 1.22 (t, J=7.5 Hz, 3H), 1.40 (brq, J=12.7 Hz, 2H), 1.91 (brt, J=13.4 Hz, 4H), 2.15 (brt, J=11.8 Hz, 1H), 2.51 (overlapping with the peak of 6H, DMSO), 2.78 (q, J=7.5 Hz, 2H), 3.08 (br s, 1H), 5.24 (s, 2H), 5.40 (brd, J=7.7 Hz, 1H), 6.47 (d, J=8.2 Hz, 2H), 6.88 (d, J=8.2 Hz, 2H), 6.92 (s, 1H), 12.07 (br s, 1H).

Reference Example 33

4-Formylpiperidine-1-carboxilic acid tert-butyl ester (Compound P33)

Dichloromethane solution of DMSO (2.4 mL, 33.4 mmol) was added to dichloromethane solution of oxalyl chloride (1.5 mL, 16.7 mmol) at −76° C. for 30 minutes. After stirring for 30 minutes at −78° C., dichloromethane solution (15 mL) of 4-(hydroxymethyl)piperidine-1-carboxilic acid tert-butyl ester (3.00 g, 13.9 mmol) was added at −76° C. for 30 minutes. After stirring for 30 minutes at −76° C., triethylamine (9.7 mL) was added at −76° C. for 10 minutes. The mixture was stirred at −76° C. for 15 minutes and was stirred for 45 minutes after increasing the temperature to room temperature. The reaction was terminated by adding water. The reaction mixture was extracted with dichloromethane three times. The organic layer was dried over anhydrous magnesium sulfate and concentrated under reduced pressure. The residue was purified by silica gel chromatography (hexane:ethyl acetate=3:1) to obtain compound P33 (2.41 g, 11.3 mmol, 81%).
$^1$H NMR (CDCl$_3$) δ(ppm): 1.41 (s, 9H), 1.48-1.54 (m, 2H), 1.82-1.88 (m, 2H), 2.34-2.41 (m, 1H), 2.84-2.93 (m, 2H), 3.90-3.97 (m, 2H), 9.62 (s, 1H).

Reference Example 34

2-Ethyl-7-methyl-3-(4-nitrobenzyl)-3H-imidazo[4,5-b]pyridine (Compound P34)

2-Ethyl-7-methyl-3H-imidazo[4,5-b]pyridine (1.00 g, 6.20 mmol) was dissolved in DMF (15 mL) and lithium hydroxide monohydrate (0.391 g, 9.31 mmol) was added at room temperature followed by stirring for 20 minutes. Then, 4-nitrobenzylbromide (1.34 g, 6.20 mmol) was slowly added to the mixture, and stirred at room temperature. After 30 minutes, water (20 mL) was added and precipitated crystals were collected by filtration, followed by washing with water. The crystals were dried under reduced pressure to obtain Compound P34 (0.819 g, 2.76 mmol, 45%).
APCI-MS: m/z 297 [M+H]$^+$ ¹H NMR (CDCl₃) δ(ppm): 1.36 (t, J=7.55 Hz, 3H), 2.70 (s, 3H), 2.83 (q, J=7.55 Hz, 2H), 5.57 (s, 2H), 7.06 (d, J=4.59 Hz, 1H), 7.28 (d, J=9.17 Hz, 2H), 8.16 (d, J=9.17 Hz, 1H), 8.19 (d, J=4.59 Hz, 1H).

Reference Example 35

3-(4-Aminobenzyl)-2-ethyl-7-methyl-3H-imidazo[4,5-b]pyridine (Compound P35)

Compound P34 (1.09 g, 3.67 mmol) was dissolved in methanl (25 mL) and palladium/carbon (10%, 0.392 g, 0.184 mmol) was added thereto. Methanol solution (15 mL) of ammonium formate (2.31 g, 36.7 mmol) was dropped to the reaction mixture for 15 minutes and the mixture was stirred at room temperature. After 15 minutes, the mixture was filtered through Celite and the filtrate was concentrated under reduced pressure. The residue was added with water (10 mL) and the precipitated crystals were collected by filtration. The crystals were washed with water and dried under reduced pressure to obtain Compound P35 (0.809 g, 3.04 mmol, 83%).
APCI-MS: m/z 267 [M+H]⁺
¹H NMR (CDCl₃) δ(ppm): 1.32 (t, J=7.51 Hz, 3H), 2.67 (s, 3H), 2.85 (q, J=7.51 Hz, 2H), 3.64 (s, 2H), 5.35 (s, 2H), 6.57 (d, J=8.59 Hz, 1H), 6.95 (d, J=8.59 Hz, 2H), 7.00 (d, J=4.95 Hz, 1H), 8.20 (d, J=4.95 Hz, 1H).

Reference Example 36

2,5,7-Trimethyl-3-(4-nitrobenzyl)-3H-imidazo[4,5-b]pyridine (Compound P36)

Compound P36 (8.26 g, 27.9 mmol, 90%) was obtained in a similar manner to Reference Example 34 using Compound P11 (5.00 g, 31.0 mmol).

Reference Example 37

3-(4-Aminobenzyl)-2,5,7-trimethyl-3H-imidazo[4,5-b]pyridine (Compound P37)

Compound P37 (5.98 g, 22.4 mmol, 81%) was obtained in a similar manner to Reference Example 35 using Compound P36 (8.26 g, 27.9 mmol).
APCI-MS: m/z 267 [M+H]⁺
¹H NMR (CDCl₃) δ(ppm): 2.49 (s, 3H), 2.60 (s, 6H), 3.64 (s, 2H), 5.31 (s, 2H), 6.58 (d, J=8.42 Hz, 1H), 6.87 (s, 1H), 6.97 (d, J=8.42 Hz, 2H).

Reference Example 38

5-Chloro-2,7-dimethylimidazo[4,5-b]pyridine (Compound P38)

2-Amino-6-chloro-4-methyl-3-nitropiridine (1.2 g, 6.40 mmol) synthesized according to the method described in WO98/02442 was dissolved in ethanol (65 mL), and tin(II) chloride dihydrate (4.33 g, 19.2 mmol) was added, followed by stirring at 75° C. for 2 hours. The reaction mixture was diluted with ethyl acetate and was added with 3 mol/L aqueous sodium hydroxide solution. The unsoluble material was filtered out through Celite, and washed with ethyl acetate. The filtrate was sequentially washed with water, saturated brine, dried over anhydrous magnesium sulfate and concentrated under reduced pressure. Next, polyphosphoric acid (15.3 g) and acetic acid (1.72 mL, 30.0 mmol) was added to the residue, and was stirred for 80° C. for 3 hours. The reaction mixture was moved to ice water and sodium carbonate (11.4 g, 0.108 mol) was added in a little portion while stirring. Then, 28% aqueous ammonia solution was added to the residue to control the pH to 9 and the mixture was stirred for 1 hour. Precipitated crude crystals were collected by filtration, and were washed with water, and the obtained crystals were dried in vacuo at 40° C. overnight to obtain Compound P38 (395 mg, 34%).
ESI-MS: m/z 182 [M+H]⁺
¹H NMR (DMSO-d₆) δ(ppm): 2.49 (s, 3H), 3.33 (s, 3H), 7.07 (s, 1H), 12.74 (brs, 0.5H), 12.76 (brs, 0.5H).

Reference Example 39 trans-4-[4-(5-Chloro-2,7-dimethyl-3H-imidazo[4,5-b]pyridin-3-ylmethyl)phenylamino]cyclohexane carboxilic acid (Compound P39)

Compound P39 (0.308 g, 89%) was obtained in a similar manner to Reference Example 19, using Compound 176 (0.370 g, 0.839 mmol).
ESI-MS: m/z 413 [M+H]⁺, 415 [M+2+H]⁺
¹H NMR (DMSO-d₆) δ(ppm): 1.10 (brq, J=12.9 Hz, 2H), 1.41 (brq, J=12.2 Hz, 2H), 1.92 (m, 4H), 2.16 (brtt, J=3.6, 12.2 Hz, 1H), 2.50 (s, 3H, overlapping with the peak of DMSO), 2.52 (s, 3H, overlapping with the peak of DMSO), 3.10 (brt, J=10.6 Hz, 1H), 5.22 (s, 2H), 5.48 (brs, 1H), 6.50 (d, J=8.6 Hz, 2H), 6.94 (d, J=8.6 Hz, 2H), 7.16 (s, 1H), 12.03 (brs, 1H).

Example 1

4-(2-Ethyl-5,7-dimethylimidazo[4,5-b]pyridin-3-ylmethyl)benzophenone (Compound 1)

Commercially available 4-bromomethylbenzophenone (5.00 g, 18.2 mmol) was dissolved in DMF (100 mL), and 2-ethyl-5,7-dimethylimidazo[4,5-b]pyridine (3.82 g, 21.8 mmol) and lithium hydroxide monohydrate (0.920 g, 21.9 mmol) was added to the solution, followed by stirring at room temperature for 3 hours. After the reaction mixture was concentrated under reduced pressure, the residue was dissolved in ethyl acetate, and washed with water and saturated brine. The organic layer was dried over anhydrous magnesium sulfate, and concentrated under reduced pressure. The residue was purified by silica gel column chromatography (ethyl acetate:hexane=2:1), and recrystallized from ethanol to obtain Compound 1 (5.33 g, yield 79%).
ESI-MS: m/z 370 [M+H]⁺
¹H NMR (CDCl₃) δ(ppm): 1.33 (t, J=7.5 Hz, 3H), 2.59 (s, 3H), 2.64 (s, 3H), 2.79 (q, J=7.5 Hz, 2H), 5.54 (s, 2H), 6.91 (s, 1H), 7.21 (d, J=8.1 Hz, 1H), 7.25 (d, J=10.6 Hz, 1H), 7.45 (t, J=7.3 Hz, 2H), 7.55 (dt, J=1.1, 7.3 Hz, 1H), 7.72 (d, J=5.1 Hz, 1H), 7.75 (dd, J=1.1, 6.8 Hz, 1H).
melting point: 98° C.

Example 2

4-(2-Ethyl-5,7-dimethylimidazo[4,5-b]pyridin-3-ylmethyl)benzhydrol (Compound 2)

Compound 1 (2.27 g, 6.14 mmol) was dissolved in ethanol (50 mL), and sodium borohydride (0.465 g, 12.3 mmol) was added to the solution, followed by stirring at room temperature for 2 hours. The reaction mixture was added with acetone and stirred for 30 minutes, then concentrated under reduced pressure. The residue was dissolved in ethyl acetate, and washed with water and saturated brine. The organic layer was dried over anhydrous magnesium sulfate, and concentrated under reduced pressure. The residue was purified by silica gel column chromatography (chloroform:methanol=40:1), and obtained crystals were triturated with diethyl ether-hexane to obtain Compound 2 (2.10 g, yield 92%).

ESI-MS: m/z 372 [M+H]+

$^1$H NMR (CDCl$_3$) δ(ppm): 1.23 (t, J=7.4 Hz, 3H), 2.56 (s, 3H), 2.61 (s, 3H), 2.72 (q, J=7.4 Hz, 2H), 5.41 (s, 2H), 5.78 (d, J=3.0 Hz, 1H), 6.87 (s, 1H), 7.05 (d, J=8.1 Hz, 2H), 7.23-7.34 (m, 7H).

Example 3

4-(2-Ethyl-5,7-dimethylimidazo[4,5-b]pyridin-3-ylmethyl)benzophenone oxime (Compound 3)

Compound 1 (0.300 g, 0.812 mmol) was dissolved in ethanol (10 mL), and hydroxylamine monohydrochloride (0.113 g, 1.63 mmol) and pyridine (0.145 mL, 1.79 mmol) was added to the solution, followed by stirring at 60° C. for 3.5 hours. The reaction mixture was diluted with chloroform, and sequentially washed with water, 0.5 mol/L hydrochloric acid, and saturated brine. The organic layer was dried over anhydrous magnesium sulfate, and concentrated under reduced pressure. The crude crystals were recrystallized from ethanol to obtain Compound 3 (0.213 g, yield 68%).

ESI-MS: m/z 385 [M+H]+

$^1$H NMR (CDCl$_3$) δ(ppm): 1.31 (t, J=7.6 Hz, 2.25H), 1.35 (t, J=7.6 Hz, 0.75H), 2.58 (s, 2.25H), 2.61 (s, 0.75H), 2.63 (s, 2.25H), 2.65 (s, 0.75H), 2.76 (q, J=7.6 Hz, 1.5H), 2.84 (q, J=7.6 Hz, 0.5H), 5.47 (s, 1.5H), 5.53 (s, 0.5H), 6.89 (s, 0.75H), 6.92 (s, 0.25H), 7.01 (d, J=8.4 Hz, 1.5H), 7.18 (d, J=8.4 Hz, 0.5H), 7.27-7.45 (m, 7H), 9.64 (brs, 0.25H), 9.87 (brs, 0.75H).

Example 4

3-(4-Benzylbenzyl)-2-ethyl-5,7-dimethylimidazo[4,5-b]pyridine (Compound 4)

Step 1

Compound 2 (0.600 g, 1.61 mmol) was dissolved in toluene (15 mL), and diphenylphosphoryl azide (0.696 mL, 3.23 mmol) and DBU (0.483 mL, 3.22 mmol) was added to the solution, followed by stirring at 60° C. for 4 hours. The reaction mixture was diluted with toluene, and washed with water and saturated brine. The organic layer was dried over anhydrous magnesium sulfate, and concentrated under reduced pressure. The residue was purified by silica gel column chromatography (ethyl acetate:hexane=1:1) to obtain [4-(2-ethyl-5,7-dimethylimidazo[4,5-b]pyridin-3-ylmethyl)phenyl]phenylmethylazide (0.590 g, yield 92%).

ESI-MS: m/z 397 [M+H]+

$^1$H NMR (CDCl$_3$) δ(ppm): 1.28 (t, J=7.7 Hz, 3H), 2.57 (s, 3H), 2.62 (s, 3H), 2.75 (q, J=7.6 Hz, 2H), 5.43 (s, 2H), 5.65 (s, 1H), 6.88 (s, 1H), 7.10 (d, J=8.1 Hz, 2H), 7.20-7.36 (m, 7H).

Step 2

[4-(2-Ethyl-5,7-dimethylimidazo[4,5-b]pyridin-3-ylmethyl)phenyl]phenylmethylazide (0.580 g, 1.46 mmol) obtained in Step 1 was dissolved in ethanol (30 mL), and the flask was filled with argon. 10% Palladium-carbon (50% wet, 0.311 g) was added to the solution, followed by stirring for 6 hours under hydrogen atmosphere. The unsoluble material was filtered out through Celite, and washed with ethanol. The filtrate was combined and concentrated under reduced pressure. The residue was crystallized from diisopropyl ether-hexane to obtain Compound 4 (0.510 g, yield 94%).

ESI-MS: m/z 356 [M+H]+

$^1$H NMR (CDCl$_3$) δ(ppm): 1.29 (t, J=7.6 Hz, 3H), 2.57 (s, 3H), 2.62 (s, 3H), 2.77 (q, J=7.6 Hz, 2H), 3.92 (s, 2H), 5.41 (s, 2H), 7.01-7.29 (m, 9H).

Example 5

4-(2-Athyl-5,7-dimethylimidazo[4,5-b]pyridin-3-ylmethyl)benzhydrylamine (Compound 5)

[4-(2-Ethyl-5,7-dimethylimidazo[4,5-b]pyridin-3-ylmethyl)phenyl]phenylmethylazide (0.450 g, 1.13 mmol) obtained in Step 1 of Example 4 was dissolved in ethanol (15 mL), and the flask was filled with argon. Lindlar catalyst (0.240 g) was added to the solution, followed by stirring for 2.5 hours under hydrogen atmosphere. The unsoluble material was filtered out through Celite, and washed with ethanol. The filtrate was combined and concentrated under reduced pressure. The residue was purified by silica gel column chromatography (chloroform:methanol=40:1) to obtain Compound 5 (0.510 g, quantitative yield).

ESI-MS: m/z 371 [M+H]+

$^1$H NMR (CDCl$_3$) δ(ppm): 1.28 (t, J=7.4 Hz, 3H), 2.56 (s, 3H), 2.61 (s, 3H), 2.77 (q, J=7.6 Hz, 2H), 5.13 (s, 1H), 5.39 (s, 2H), 6.86 (s, 1H), 7.05 (d, J=8.1 Hz, 2H), 7.15-7.32 (m, 7H).

Example 6

N-Acetyl-4-(2-ethyl-5,7-dimethylimidazo[4,5-b]pyridin-3-ylmethyl)benzhydrylamine (Compound 6)

Compound 5 (0.255 g, 0.688 mmol) was dissolved in dichloromethane (5 mL), and triethylamine (0.240 mL, 2.21 mmol) and acetyl chloride (0.980 mL, 1.38 mmol) was added to the solution at 0° C., followed by stirring at room temperature for 5.5 hours. The reaction mixture was added with water to decompose excess reagent, and extracted with chloroform. The organic layer was washed with water and saturated brine, and dried over anhydrous magnesium sulfate, then concentrated under reduced pressure. The residue was purified by silica gel column chromatography (chloroform:methanol=60:1), then crystallized from diethyl ether to obtain Compound 6 (0.191 g, yield 67%).

ESI-MS: m/z 413 [M+H]+

$^1$H NMR (CDCl$_3$) δ(ppm): 1.29 (t, J=7.4 Hz, 3H), 1.96 (s, 3H), 2.56 (s, 3H), 2.61 (s, 3H), 2.75 (q, J=7.4 Hz, 2H), 5.43 (s, 2H), 6.17 (d, J=7.9 Hz, 1H), 6.30 (d, J=8.0 Hz, 1H), 6.87 (s, 1H), 7.03-7.31 (m, 9H).

Example 7

3-(2-Ethyl-5,7-dimethylimidazo[4,5-b]pyridin-3-ylmethyl)benzophenone (Compound 7)

Step 1

Commercially available 3-methylbenzophenone (4.00 g, 20.4 mmol) was dissolved in carbon tetrachloride (100 mL), and N-bromosuccinimide (4.71 g, 26.5 mmol) and 2,2'-azobisisobutyronitrile (1.00 g, 6.09 mmol) was added to the solution, followed by stirring at 75° C. for 6.5 hours. After the reaction mixture was cooled, the precipitates were filterd out. The filtrate was combined and concentrated under reduced pressure. The residue was purified by silica gel column chromatography (ethyl acetate:hexane=1:20) to obtain 3-bromomethylbenzophenone (4.31 g, yield 77%).

Step 2

Compound 7 (1.91 g, yield 71%) was obtained in a similar manner to Example 1 using 3-bromomethylbenzophenone (2.00 g, 7.26 mmol) obtained in Step 1.

ESI-MS: m/z 370 [M+H]$^+$ $^1$H NMR (CDCl$_3$) δ(ppm): 1.29 (t, J=7.2 Hz, 3H), 2.52 (s, 3H), 2.60 (s, 3H), 2.78 (q, J=7.4 Hz, 2H), 5.48 (s, 2H), 6.86 (s, 1H), 7.27 (brd, J=6.4 Hz, 1H), 7.35 (t, J=7.4 Hz, 1H), 7.26 (t, J=7.9 Hz, 2H), 7.50-7.70 (m, 4H).

Example 8

3-(2-Ethyl-5,7-dimethylimidazo[4,5-b]pyridin-3-ylmethyl)benzhydrol (Compound 8)

Compound 8 (1.05 g, yield 85%) was obtained in a similar manner to Example 2 using Compound 7 (1.50 g, 4.06 mmol).

ESI-MS: m/z 372 [M+H]$^+$ $^1$H NMR (CDCl$_3$) δ(ppm): 1.24 (t, J=7.6 Hz, 3H), 2.56 (s, 3H), 2.62 (s, 3H), 2.72 (q, J=7.3 Hz, 2H), 5.41 (s, 2H), 5.77 (d, J=3.3 Hz, 1H), 6.87 (s, 1H), 6.93 (brd, J=6.9 Hz, 1H), 7.18-7.32 (m, 8H).

Example 9

3-(2-Ethyl-5,7-dimethylimidazo[4,5-b]pyridin-3-ylmethyl)benzophenone oxime (Compound 9)

Compound 9 (0.271 g, yield 70%) was obtained in a similar manner to Example 3 using Compound 7 (0.370 g, 1.00 mmol).

ESI-MS: m/z 385 [M+H]$^+$ $^1$H NMR (CDCl$_3$) δ(ppm): 1.33 (t, J=7.6 Hz, 3H), 2.59 (s, 1.5H), 2.60 (s, 1.5H), 2.74 (s, 3H), 3.02 (m, 2H), 5.51 (s, 1H), 5.58 (s, 1H), 7.02 (s, 0.5H), 7.03 (s, 0.5H), 7.22-7.43 (m, 9H).

Example 10

3-(2-Ethyl-5,7-dimethylimidazo[4,5-b]pyridin-3-ylmethyl)benzhydrylamine (Compound 10)

Step 1

[3-(2-Ethyl-5,7-dimethylimidazo[4,5-b]pyridin-3-ylmethyl)phenyl]phenylmethylazide (0.830 g, yield 86%) was obtained in a similar manner to Step 1 of Example 4 using Compound 8 (0.900 g, 2.42 mmol).

ESI-MS: m/z 397 [M+H]$^+$ $^1$H NMR (CDCl$_3$) δ(ppm): 1.25 (t, J=7.6 Hz, 3H), 2.57 (s, 3H), 2.63 (s, 3H), 2.73 (q, J=7.4 Hz, 2H), 5.43 (s, 2H), 5.64 (s, 1H), 6.88 (s, 1H), 6.99 (d, J=7.3 Hz, 1H), 7.14-7.34 (m, 8H).

Step 2

Compound 10 (0.560 g, yield 93%) was obtained in a similar manner to Example 5 using [3-(2-ethyl-5,7-dimethylimidazo[4,5-b]pyridin-3-ylmethyl)phenyl]phenylmethylazide (0.650 g, 1.64 mmol) obtained in Step 1.

ESI-MS: m/z 371 [M+H]$^+$ $^1$H NMR (CDCl$_3$) δ(ppm): 1.24 (t, J=7.4 Hz, 3H), 2.56 (s, 3H), 2.61 (s, 3H), 2.72 (q, J=7.5 Hz, 2H), 5.12 (s, 1H), 5.40 (s, 2H), 6.86 (s, 1H), 6.89 (d, J=5.7 Hz, 2H), 7.13-7.29 (m, 8H).

Example 11

N-Acetyl-3-(2-ethyl-5,7-dimethylimidazo[4,5-b]pyridin-3-ylmethyl)benzhydrylamine (Compound 11)

Compound 11 (0.212 g, yield 63%) was obtained in a similar manner to Example 6 using Compound 10 (0.300 g, 0.810 mmol).

ESI-MS: m/z 413 [M+H]$^+$ $^1$H NMR (CDCl$_3$) δ(ppm): 1.26 (t, J=7.6 Hz, 3H), 2.00 (s, 3H), 2.56 (s, 3H), 2.62 (s, 3H), 2.73 (q, J=7.4 Hz, 2H), 5.38 (s, 2H), 6.09 (d, J=7.8 Hz, 1H), 6.18 (d, J=7.9 Hz, 1H), 6.87 (s, 1H), 6.93 (d, J=7.4 Hz, 1H), 7.02 (s, 1H), 7.09-7.32 (m, 7H).

Example 12

Methyl 3-(2-ethyl-5,7-dimethylimidazo[4,5-b]pyridin-3-ylmethyl)benzoate (Compound 12)

Compound 12 (2.99 g, yield 71%) was obtained in a similar manner to Example 1 using commercially available methyl 3-bromomethylbenzoate (3.00 g, 13.1 mmol).

$^1$H NMR(CDCl$_3$) δ(ppm): 1.28 (t, J=7.5 Hz, 3H), 2.57 (s, 3H), 2.62 (s, 3H), 2.75 (q, J=7.5 Hz, 2H), 3.88 (s, 3H), 5.48 (s, 2H), 6.89 (s, 1H), 7.23 (brd, J=7.7 Hz, 1H), 7.33 (t, J=7.9 Hz, 1H), 7.90 (s, 1H), 7.93 (d, J=7.5 Hz, 1H).

Example 13

3-(2-Ethyl-5,7-dimethylimidazo[4,5-b]pyridin-3-ylmethyl)benzylalcohol (Compound 13)

Compound 12 (2.64 g, 8.16 mmol) was dissolved in toluene (40 mL), and diisobutylaluminum hydride (1.0 mol/L toluene solution, 24.5 mL) was added to the solution at 0° C. under argon atmosphere, followed by stirring at 0° C. for 1.5 hours. The reaction mixture was added with a saturated aqueous (+)-potassium sodium tartrate tetrahydrate solution to terminate the reaction, and diluted with ethyl acetate, followed by stirring vigorously for 30 minutes. The organic layer was separated from the aqueous layer, and washed with saturated brine, and dried over anhydrous magnesium sulfate, then concentrated under reduced pressure. The residue was purified by silica gel column chromatography (ethyl acetate:hexane=5:1) to obtain Compound 13 (2.32 g, yield 90%).

ESI-MS: m/z 296 [M+H]$^+$ $^1$H NMR (CDCl$_3$) δ(ppm): 1.24 (t, J=7.5 Hz, 3H), 2.56 (s, 3H), 2.60 (s, 3H), 2.71 (q, J=7.5 Hz, 2H), 2.93 (brs, 1H), 4.59 (d, J=4.0 Hz, 2H), 5.41 (s, 2H), 6.87 (s, 1H), 6.96 (m, 1H), 7.10 (s, 1H), 7.21-7.23 (m, 2H).

Example 14

4-[3-(2-Ethyl-5,7-dimethylimidazo[4,5-b]pyridin-3-ylmethyl)benzoyl]benzylalcohol (Compound 14)

Step 1

Commercially available 4-bromobenzylalcohol (4.00 g, 21.5 mmol) was dissolved in DMF (100 mL), and tert-butyldimethylsilyl chloride (4.86 g, 32.2 mmol) and imidazole (2.20 g, 32.3 mmol) were added to the solution, followed by stirring at room temperature for 1.5 hours. The reaction mixture was concentrated under reduced pressure, and the residue was dissolved in ethyl acetate. The solution was washed with a saturated aqueous sodium hydrogen carbonate solution and saturated brine, and dried over anhydrous magnesium sulfate, then concentrated under reduced pressure. The residue was purified by silica gel column chromatography (ethyl acetate:hexane=1:80) to obtain 4-bromobenzyloxy-tert-butyldimethylsilane (5.52 g, yield 85%).

$^1$H NMR (CDCl$_3$) δ(ppm): 0.11 (s, 6H), 0.96 (s, 9H), 4.70 (s, 2H), 7.20 (d, J=8.3 Hz, 2H), 7.45 (d, J=8.3 Hz, 2H).

Step 2

Compound 13 (2.08 g, 7.04 mmol) was dissolved in chloroform (100 mL), and Manganese(IV) oxide (9.20 g, 0.106 mol) was added to the solution, followed by stirring at room temperature overnight. The unsoluble material was filtered out through Celite, and the filtrate was combined and concentrated under reduced pressure. The residue was purified by silica gel column chromatography (ethyl acetate:hexane=3:1) to obtain 3-(2-ethyl-5,7-dimethylimidazo[4,5-b]pyridin-3-ylmethyl)benzaldehyde (2.04 g, quantitative yield).

$^1$H NMR (CDCl$_3$) δ(ppm): 1.24 (t, J=7.5 Hz, 3H), 2.52 (s, 3H), 2.57 (s, 3H), 2.71 (q, J=7.5 Hz, 2H), 5.46 (s, 2H), 6.84 (s, 1H), 7.31 (brdd, J=1.3, 7.7 Hz, 1H), 7.40 (t, J=7.5 Hz, 1H), 7.63 (brs, 1H), 7.71 (brdd, J=1.3, 7.5 Hz, 1H), 9.88 (s, 1H).

Step 3

4-Bromobenzyloxy-tert-butyldimethylsilane (1.23 g, 4.08 mmol) obtained in Step 1 was dissolved in THF (30 mL) and the flask was filled with argon. The reaction mixture was cooled to −78° C., and a 1.57 mol/L n-butyl lithium-hexane solution (2.60 mL, 4.09 mmol) was added thereto, followed by stirring at same temperature for 5 minutes. A solution of 3-(2-ethyl-5,7-dimethylimidazo[4,5-b]pyridin-3-ylmethyl)benzaldehyde (0.800 g, 2.72 mmol) obtained in Step 2 in THF (5 mL) was dropped into the mixture for 15 minutes, followed by stirring at −78° C. for 1 hour. The reaction mixture was added with a saturated aqueous ammonium chloride solution to terminate the reaction, and diluted with ethyl acetate. The organic layer was separated from the aqueous layer, and washed with water and saturated brine. The organic layer was dried over anhydrous magnesium sulfate, and concentrated under reduced pressure. The residue was purified by silica gel column chromatography (ethyl acetate:hexane=3:2) to obtain [4-(tert-butyldimethylsilyloxymethyl)phenyl][3-(2-ethyl-5,7-dimethylimidazo[4,5-b]pyridin-3-ylmethyl)phenyl]methanol (0.923 g, yield 66%).

ESI-MS: m/z 516 [M+H]$^+$ $^1$H NMR (CDCl$_3$) δ(ppm): 0.10 (s, 6H), 0.94 (s, 9H), 1.19 (t, J=7.4 Hz, 3H), 2.53 (s, 3H), 2.59 (s, 3H), 2.68 (q, J=7.6 Hz, 2H), 3.66 (brs, 1H), 4.71 (s, 2H), 5.38 (s, 2H), 5.71 (s, 1H), 6.86 (s, 1H), 6.87 (d, J=7.9 Hz, 1H), 7.13-7.29 (m, 7H).

Step 4

[4-(tert-Butyldimethylsilyloxymethyl)phenyl][3-(2-ethyl-5,7-dimethylimidazo[4,5-b]pyridin-3-ylmethyl)phenyl]methanol (0.923 g, 1.78 mmol) obtained in Step 3 was dissolved in chloroform (20 mL), and Manganese(IV) oxide (3.11 g, 35.8 mmol) was added to the solution, followed by stirring overnight. The unsoluble material was filtered out through Celite, and the filtrate was combined and concentrated under reduced pressure. The residue was purified by silica gel column chromatography (ethyl acetate:hexane=2:1) to obtain {4-[3-(2-ethyl-5,7-dimethylimidazo[4,5-b]pyridin-3-ylmethyl)benzoyl]benzyloxy}-tert-butyldimethylsilane (0.898 g, yield 98%).

ESI-MS: m/z 514 [M+H]$^+$ $^1$H NMR (CDCl$_3$) δ(ppm): 0.14 (s, 6H), 0.98 (s, 9H), 1.33 (t, J=7.6 Hz, 3H), 2.57 (s, 3H), 2.64 (s, 3H), 2.82 (q, J=7.6 Hz, 2H), 4.83 (s, 2H), 5.52 (s, 2H), 6.90 (s, 1H), 7.29 (brd, J=8.9 Hz, 1H), 7.39 (brt, J=7.4 Hz, 1H), 7.41 (d, J=7.9 Hz, 2H), 7.66-7.74 (m, 4H).

Step 5

{4-[3-(2-Ethyl-5,7-dimethylimidazo[4,5-b]pyridin-3-ylmethyl)benzoyl]benzyloxy)-tert-butyldimethylsilane (0.898 g, 1.75 mmol) obtained in Step 4 was dissolved in THF (15 mL), and a 1.0 mol/L TBAF-THF solution (5.24 mL, 5.24 mmol) was added to the solution, followed by stirring at room temperature for 2 hours. The reaction mixture was diluted with ethyl acetate, and washed with water and saturated brine. The organic layer was dried over anhydrous magnesium sulfate, and concentrated under reduced pressure. The residue was purified by silica gel column chromatography (ethyl acetate:hexane=2:1), followed by crystallization from ethanol to obtain Compound 14 (0.579 g, yield 83%).

ESI-MS: m/z 400 [M+H]$^+$ $^1$H NMR (CDCl$_3$) δ(ppm): 1.30 (t, J=7.6 Hz, 3H), 2.55 (s, 3H), 2.61 (s, 3H), 2.79 (q, J=7.6 Hz, 2H), 4.77 (s, 2H), 5.50 (s, 2H), 6.89 (s, 1H), 7.28 (brd, J=6.9 Hz, 1H), 7.35-7.42 (m, 3H), 7.65 (d, J=7.6 Hz, 2H), 7.67 (d, J=8.1 Hz, 2H).

Example 15

4-{4-[3-(2-Ethyl-5,7-dimethylimidazo[4,5-b]pyridin-3-ylmethyl)benzoyl]benzyl}-1-methylpiperazine (Compound 15)

Compound 14 (0.250 g, 0.625 mmol) was dissolved in dichloromethane (5 mL), and triethylamine (0.131 mL, 0.939 mmol) and methanesulfonyl chloride (0.730 mL, 0.943 mmol) was added to the solution at 0° C., followed by stirring for 1 hour. The reaction mixture was added with a saturated aqueous sodium hydrogen carbonate solution, and diluted with chloroform, then washed with water and saturated brine. The organic layer was dried over anhydrous magnesium sulfate, and concentrated under reduced pressure. The residue was dissolved in dichloromethane (5 mL), and 1-methylpiperazine (0.208 mL, 1.87 mmol) and triethylamine (0.870 mL, 0.623 mmol) was added to the solution, followed by stirring at room temperature overnight. The reaction mixture was diluted with chloroform, and washed with water and saturated brine. The organic layer was dried over anhydrous magnesium sulfate, and concentrated under reduced pressure. The residue was purified by silica gel column chromatography (chloroform:methanol=20:1) to obtain Compound 15 (0.0900 g, yield 30%).

ESI-MS: m/z 482 [M+H]$^+$ $^1$H NMR (CDCl$_3$) δ(ppm): 1.29 (t, J=7.6 Hz, 3H), 2.27 (s, 3H), 2.46-2.60 (m, 6H), 2.53 (s, 3H), 2.59 (s, 3H), 2.79 (q, J=7.6 Hz, 2H), 3.22 (t, J=5.1 Hz, 2H), 3.54 (s, 2H), 5.48 (s, 2H), 6.86 (s, 1H), 7.25 (brd, J=7.6 Hz, 1H), 7.32-7.38 (m, 3H), 7.64-7.67 (m, 4H).

Example 16

1-{4-[3-(2-Ethyl-5,7-dimethylimidazo[4,5-b]pyridin-3-ylmethyl)benzoyl]benzyl}piperidine-4-carboxylic acid ethyl ester (Compound 16)

Compound 16 (0.414 g, yield 95%) was obtained in a similar manner to Example 15 using Ethyl isonipecotate (0.621 mL, 4.03 mmol).

ESI-MS: m/z 539 [M+H]$^+$ $^1$H NMR (CDCl$_3$) δ(ppm): 1.25 (t, J=7.1 Hz, 3H), 1.31 (t, J=7.5 Hz, 3H), 1.71-2.15 (m, 6H), 2.24-2.33 (m, 1H), 2.79-2.86 (m, 2H), 2.55 (s, 3H), 2.61 (s, 3H), 2.80 (q, J=7.5 Hz, 2H), 3.54 (s, 2H), 4.13 (q, J=7.1 Hz, 2H), 5.51 (s, 2H), 6.88 (s, 1H), 7.25 (brd, J=7.5 Hz, 1H), 7.35-7.40 (m, 3H), 7.65-7.70 (m, 4H).

Example 17

4-(4-{[3-(2-Ethyl-5,7-dimethylimidazo[4,5-b]pyridin-3-ylmethyl)phenyl]hydroxyiminomethyl}benzyl)-1-methylpiperazine (Compound 17)

Compound 17 (0.0549 g, yield 67%) was obtained in a similar manner to Example 3 using Compound 15 (0.0800 g, 0.166 mmol).

ESI-MS: m/z 497 [M+H]$^+$

¹H NMR (CDCl₃) δ(ppm): 1.27 (t, J=7.5 Hz, 1.5H), 1.30 (t, J=7.5 Hz, 1.5H), 2.29 (s, 1.5H), 2.32 (s, 1.5H), 2.54 (s, 1.5H), 2.56 (s, 1.5H), 2.60 (s, 3H), 2.17-2.63 (m, 8H), 2.76 (q, J=7.5 Hz, 1H), 2.82 (q, J=7.5 Hz, 1H), 3.51 (s, 1H), 3.57 (s, 1H), 5.44 (s, 1H), 5.50 (s, 1H), 6.86 (s, 0.5H), 6.87 (s, 0.5H), 6.86 (brd, J=7.5 Hz, 0.5H), 7.09 (brd, J=7.5 Hz, 0.5H), 7.17 (t, J=7.7 Hz, 0.5H), 7.21-7.37 (m, 6.5H).

Example 18

1-(4-{[3-(2-Ethyl-5,7-dimethylimidazo[4,5-b]pyridin-3-ylmethyl)phenyl]hydroxyiminomethyl}benzyl)piperidine-4-carboxylic acid ethyl ester (Compound 18)

Compound 18 (0.243 g, yield 88%) was obtained in a similar manner to Example 3 using Compound 16 (0.270 g, 0.501 mmol).
ESI-MS: m/z 554 [M+H]⁺
¹H NMR (CDCl₃) δ(ppm): 1.18-1.30 (m, 6H), 1.75-2.17 (m, 6H), 2.24-2.31 (m, 1H), 2.55 (s, 1.5H), 2.57 (s, 1.5H), 2.60 (s, 1.5H), 2.61 (s, 1.5H), 2.76 (q, J=7.6 Hz, 2H), 2.81-2.92 (m, 2H), 3.47 (s, 1H), 3.52 (s, 1H), 4.13 (q, J=7.1 Hz, 1H), 4.15 (q, J=7.1 Hz, 1H), 5.46 (s, 1H), 5.50 (s, 1H), 6.86 (s, 1H), 6.94 (brd, J=7.4 Hz, 0.5H), 7.10 (brd, J=7.4 Hz, 0.5H), 7.16 (t, J=7.8 Hz, 0.5H), 7.22-7.42 (m, 6.5H), 10.1 (s, 0.5H), 10.4 (s, 0.5H).

Example 19

3-[3-(2-Ethyl-5,7-dimethylimidazo[4,5-b]pyridin-3-ylmethyl)benzoyl]benzylalcohol (Compound 19)

Step 1
(3-Bromobenzyloxy)-tert-butyldimethylsilane (5.23 g, yield 100%) was obtained in a similar manner to Step 1 of Example 14 using commercially available 3-bromobenzylalcohol (3.24 g, 17.4 mmol).
¹H NMR (CDCl₃) δ(ppm): 0.15 (s, 6H), 0.99 (s, 9H), 4.74 (s, 2H), 7.21 (t, J=7.7 Hz, 1H), 7.27 (dt, J=1.4, 7.7 Hz, 1H), 7.41 (dt, J=1.4, 7.7 Hz, 1H), 7.51 (s, 1H).
Step 2
[3-(tert-Butyldimethylsilyloxymethyl)phenyl][3-(2-ethyl-5,7-dimethylimidazo[4,5-b]pyridin-3-ylmethyl)phenyl]methanol (1.95 g, yield 74%) was obtained in a similar manner to Step 3 of Example 14 using (3-bromobenzyloxy)-tert-butyldimethylsilane (2.71 g, 8.99 mmol) obtained in Step 1.
ESI-MS: m/z 516 [M+H]⁺
¹H NMR (CDCl₃) δ(ppm): 0.07 (s, 6H), 0.92 (s, 9H), 1.19 (t, J=7.4 Hz, 3H), 2.53 (s, 3H), 2.59 (s, 3H), 2.67 (q, J=7.4 Hz, 2H), 4.68 (s, 2H), 5.38 (s, 2H), 5.71 (s, 1H), 6.85 (s, 1H), 6.87 (d, J=6.4 Hz, 1H), 7.13-7.28 (m, 7H).
Step 3
3-[3-(2-Ethyl-5,7-dimethylimidazo[4,5-b]pyridin-3-ylmethyl)benzoyl]benzyloxy-tert-butyldimethylsilane (1.88 g, yield 97%) was obtained in a similar manner to Step 4 of Example 14 using [3-(tert-butyldimethylsilyloxymethyl)phenyl][3-(2-ethyl-5,7-dimethylimidazo[4,5-b]pyridin-3-ylmethyl)phenyl]methanol (1.95 g, 3.78 mmol) obtained in Step 2.
ESI-MS: m/z 514 [M+H]⁺
¹H NMR (CDCl₃) δ(ppm): 0.10 (s, 6H), 0.93 (s, 9H), 1.32 (t, J=7.6 Hz, 3H), 2.56 (s, 3H), 2.62 (s, 3H), 2.79 (q, J=7.6 Hz, 2H), 4.77 (s, 2H), 5.51 (s, 2H), 6.89 (s, 1H), 7.27 (brd, J=7.8 Hz, 1H), 7.37 (t, J=7.6 Hz, 1H), 7.40 (t, J=7.6 Hz, 1H), 7.57 (brd, J=8.3 Hz, 1H), 7.59 (brd, J=7.6 Hz, 1H), 7.65 (brd, J=7.4 Hz, 1H), 7.70 (d, J=1.8 Hz, 1H), 7.72 (d, J=1.5 Hz, 1H).
Step 4
Compound 19 (1.18 g, yield 81%) was obtained in a similar manner to Step 5 of Example 14 using 3-[3-(2-ethyl-5,7-dimethylimidazo[4,5-b]pyridin-3-ylmethyl)benzoyl]benzyloxy-tert-butyldimethylsilane (1.88 g, 3.65 mmol) obtained in Step 3.
ESI-MS: m/z 400 [M+H]⁺
¹H NMR (CDCl₃) δ(ppm): 1.32 (t, J=7.6 Hz, 3H), 2.52 (s, 3H), 2.59 (s, 3H), 2.78 (q, J=7.4 Hz, 2H), 4.68 (s, 2H), 5.50 (s, 2H), 6.86 (s, 1H), 7.35-7.44 (m, 4H), 7.54-7.61 (m, 3H), 7.72 (dt, J=1.7, 7.3 Hz, 1H).

Example 20

4-{3-[3-(2-Ethyl-5,7-dimethylimidazo[4,5-b]pyridin-3-ylmethyl)benzoyl]benzyl}-1-methylpiperazine (Compound 20)

Compound 20 (0.189 g, yield 78%) was obtained in a similar manner to Example 15 using Compound 19 (0.200 g, 0.5501 mmol).
ESI-MS: m/z 482 [M+H]⁺
¹H NMR (CDCl₃) δ(ppm): 1.27 (t, J=7.4 Hz, 3H), 2.21 (s, 3H), 2.26-2.50 (m, 8H), 2.49 (s, 3H), 2.57 (s, 3H), 2.76 (q, J=7.6 Hz, 2H), 3.48 (s, 2H), 5.45 (s, 2H), 6.82 (s, 1H), 7.24 (brd, J=8.7 Hz, 1H), 7.31 (t, J=7.6 Hz, 1H), 7.32 (t, J=7.6 Hz, 1H), 7.48 (brd, J=7.8 Hz, 1H), 7.51 (brd, J=7.6 Hz, 1H), 7.61 (brd, J=7.4 Hz, 1H), 7.65 (s, 2H).

Example 21

1-{3-[3-(2-Ethyl-5,7-dimethylimidazo[4,5-b]pyridin-3-ylmethyl)benzoyl]benzyl}pyrrolidine (Compound 21)

Compound 21 (0.184 g, yield 82%) was obtained in a similar manner to Example 15 using Compound 19 (0.200 g, 0.501 mmol) and pyrrolidine (0.125 mL, 1.50 mmol).
ESI-MS: m/z 453 [M+H]⁺
¹H NMR (CDCl₃) δ(ppm): 1.29 (t, J=7.4 Hz, 3H), 1.72-1.77 (m, 4H), 2.48-2.59 (m, 2H), 2.51 (s, 3H), 2.58 (s, 3H), 2.77 (q, J=7.4 Hz, 2H), 3.61 (s, 2H), 5.47 (s, 2H), 6.84 (s, 1H), 7.25 (brd, J=7.8 Hz, 1H), 7.34 (t, J=7.6 Hz, 2H), 7.53 (d, J=7.6 Hz, 1H), 7.55 (d, J=7.6 Hz, 1H), 7.63 (d, J=7.6 Hz, 1H), 7.67 (s, 1H).

Example 22

1-{3-[3-(2-Ethyl-5,7-dimethylimidazo[4,5-b]pyridin-3-ylmethyl)benzoyl]benzyl}piperidine-4-carboxylic acid ethyl ester (Compound 22)

Compound 22 (0.311 g, yield 77%) was obtained in a similar manner to Example 16 using Compound 19 (0.300 g, 0.751 mmol).
ESI-MS: m/z 539 [M+H]⁺
¹H NMR (CDCl₃) δ(ppm): 1.17 (t, J=7.1 Hz, 3H), 1.26 (t, J=7.6 Hz, 3H), 1.62-1.85 (m, 4H), 1.99 (dt, J=2.3, 11.2 Hz, 2H), 2.17-2.28 (m, 1H), 2.48 (s, 3H), 2.56 (s, 3H), 2.75 (q, J=7.6 Hz, 2H), 2.71-2.80 (m, 2H), 3.44 (s, 2H), 4.06 (q, J=7.1 Hz, 2H), 5.45 (s, 2H), 6.82 (s, 1H), 7.25 (brd, J=8.2 Hz, 1H), 7.30 (t, J=7.6 Hz, 1H), 7.32 (t, J=7.6 Hz, 1H), 7.48-7.53 (m, 2H), 7.56-7.65 (m, 3H).

Example 23

4-(3-{[3-(2-Ethyl-5,7-dimethylimidazo[4,5-b]pyridin-3-ylmethyl)phenyl]hydroxyiminomethyl}benzyl)-1-methylpiperazine (Compound 23)

Compound 23 (0.185 g, yield 86%) was obtained in a similar manner to Example 3 using Compound 20 (0.180 g, 0.373 mmol).
ESI-MS: m/z 497 [M+H]$^+$
$^1$H NMR (CDCl$_3$) δ(ppm): 1.19 (t, J=7.4 Hz, 1.5H), 1.21 (t, J=7.4 Hz, 1.5H), 2.20 (s, 1.5H), 2.21 (s, 1.5H), 2.33-2.57 (m, 8H), 2.45 (s, 1.5H), 2.48 (s, 1.5H), 2.55 (s, 3H), 2.67 (q, J=7.4 Hz, 1H), 2.73 (q. J=7.4 Hz, 1H), 3.46 (s, 2H), 5.35 (s, 1H), 5.40 (s, 1H), 6.78 (s, 0.5H), 6.79 (s, 0.5H), 6.90-7.29 (m, 7.5H), 7.57 (s, 0.5H).

Example 24

1-(3-{[3-(2-Ethyl-5,7-dimethylimidazo[4,5-b]pyridin-3-ylmethyl)phenyl]hydroxyiminomethyl}benzyl)pyrrolidine (Compound 24)

Compound 24 was obtained in a similar manner to Example 3 using Compound 21 (0.115 g, 0.254 mmol). Compound 24 was recrystallized from ethanol-diethyl ether (0.103 g, yield 87%).
ESI-MS: m/z 468 [M+H]$^+$
$^1$H NMR (CDCl$_3$) δ(ppm): 1.18 (t, J=7.4 Hz, 1.5H), 1.19 (t, J=7.4 Hz, 1.5H), 1.92 (brs, 4H), 2.44 (s, 1.5H), 2.47 (s, 1.5H), 2.51 (s, 3H), 2.68 (q, J=7.4 Hz, 1H), 2.72 (q, J=7.4 Hz, 1H), 2.97 (brs, 4H), 3.93 (s, 1H), 3.97 (s, 1H), 5.36 (s, 1H), 5.42 (s, 1H), 6.79 (s, 1H), 6.90 (brd, J=6.9 Hz, 0.5H), 7.02-7.36 (m, 6H), 7.48 (s, 0.5H), 7.60 (brs, 1H).
melting point: 231-236° C.

Example 25

Methyl 4-(2-ethyl-5,7-dimethylimidazo[4,5-b]pyridin-3-ylmethyl)benzoate (Compound 25)

Compound 25 (0.720 g, yield 51%) was obtained in a similar manner to Example 1 using commercially available methyl 4-bromomethylbenzoate (1.00 g, 4.36 mmol).
ESI-MS: m/z 324 [M+H]$^+$
$^1$H NMR (CDCl$_3$) δ(ppm): 1.29 (t, J=7.6 Hz, 3H), 2.58 (s, 3H), 2.64 (s, 3H), 2.74 (q, J=7.6 Hz, 2H), 3.89 (s, 3H), 5.50 (s, 2H), 6.91 (s, 1H), 7.14 (d, J=7.9 Hz, 2H), 7.95 (d, J=8.2 Hz, 2H).

Example 26

4-(2-Ethyl-5,7-dimethylimidazo[4,5-b]pyridin-3-ylmethyl)-N-phenylbenzamide (Compound 26)

Compound P5 (0.200 g, 0.646 mmol) was dissolved in dichloromethane (6.5 mL), and aniline (0.117 mL, 1.28 mmol), EDC (0.248 g, 1.29 mmol) and 1-hydroxybenzotriazole hydrate (0.0873 g, 0.646 mmol) were added to the solution, followed by stirring at room temperature overnight. The reaction mixture was diluted with chloroform, and sequentially washed with water, a saturated aqueous sodium hydrogen carbonate solution, and saturated brine. The organic layer was dried over anhydrous magnesium sulfate, and concentrated under reduced pressure. The residue was crystallized from etanol to obtain Compound 26 (0.161 g, yield 65%).
ESI-MS: m/z 385 [M+H]$^+$
$^1$H NMR (CDCl$_3$) δ(ppm): 1.26 (t, J=7.4 Hz, 3H), 2.58 (s, 3H), 2.62 (s, 3H), 2.72 (q, J=7.6 Hz, 2H), 5.48 (s, 2H), 6.91 (s, 1H), 7.11 (t, J=7.4 Hz, 1H), 7.12 (d, J=8.3 Hz, 2H), 7.32 (t, J=7.6 Hz, 2H), 7.60 (d, J=7.8 Hz, 2H), 7.78 (d, J=8.1 Hz, 2H), 8.24 (brs, 1H).

Example 27

3-(2-Ethyl-5,7-dimethylimidazo[4,5-b]pyridin-3-ylmethyl)-N-phenylbenzamide (Compound 27)

Compound 27 (0.265 g, yield 71%) was obtained in a similar manner to Example 26 using Compound P4 (0.300 g, 0.970 mmol).
ESI-MS: m/z 385 [M+H]$^+$
$^1$H NMR (CDCl$_3$) δ(ppm): 1.32 (t, J=7.3 Hz, 3H), 2.59 (s, 3H), 2.63 (s, 3H), 2.79 (q, J=7.3 Hz, 2H), 5.51 (s, 2H), 6.91 (s, 1H), 7.15 (t, J=7.3 Hz, 1H), 7.24 (d, J=9.5 Hz, 1H), 7.37 (t, J=8.0 Hz, 2H), 7.39 (t, J=7.7 Hz, 1H), 7.60 (d, J=7.7 Hz, 2H), 7.75 (d, J=7.7 Hz, 1H), 7.80 (s, 1H), 7.83 (s, 1H).

Example 28

4-(2-Ethyl-5,7-dimethylimidazo[4,5-b]pyridin-3-ylmethyl)-N-(4-hydroxymethylphenyl)benzamide (Compound 28)

Compound 28 (1.78 g, yield 66%) was obtained in a similar manner to Example 26 using 4-aminobenzylalcohol (1.60 g, 12.9 mmol).
ESI-MS: m/z 415 [M+H]$^+$
$^1$H NMR (CDCl$_3$) δ(ppm): 1.28 (t, J=7.7 Hz, 3H), 2.58 (s, 3H), 2.64 (s, 3H), 2.73 (q, J=7.5 Hz, 2H), 4.66 (s, 2H), 5.50 (s, 2H), 6.91 (s, 1H), 7.15 (d, J=8.4 Hz, 2H), 7.29 (d, J=8.4 Hz, 2H), 7.56 (d, J=8.6 Hz, 2H), 7.78 (d, J=8.3 Hz, 2H), 8.05 (s, 1H).

Example 29

4-(2-Ethyl-5,7-dimethylimidazo[4,5-b]pyridin-3-ylmethyl)-N-[4-(4-methylpiperazin-1-ylmethyl)phenyl]benzamide (Compound 29)

Compound 29 (0.154 g, yield 43%) was obtained in a similar manner to Example 15 using Compound 28 (0.300 g, 0.724 mmol).
ESI-MS: m/z 497 [M+H]$^+$
$^1$H NMR (CDCl$_3$) δ(ppm): 1.25 (t, J=7.4 Hz, 3H), 2.25 (s, 3H), 2.43 (brs, 8H), 2.55 (s, 3H), 2.60 (s, 3H), 2.71 (q, J=7.4 Hz, 2H), 3.44 (s, 2H), 5.46 (s, 2H), 6.88 (s, 1H), 7.12 (d, J=8.3 Hz, 2H), 7.25 (d, J=8.4 Hz, 2H), 7.52 (d, J=8.4 Hz, 2H), 7.75 (d, J=8.3 Hz, 2H), 8.10 (s, 1H).

Example 30

4-(2-Ethyl-5,7-dimethylimidazo[4,5-b]pyridin-3-ylmethyl)-N-[4-(pyrrolidin-1-ylmethyl)phenyl]benzamide (Compound 30)

Compound 30 (0.205 g, yield 52%) was obtained in a similar manner to Example 15 using Compound 28 (0.350 g, 0.844 mmol) and pyrrolidine (0.290 mL, 3.38 mmol).
ESI-MS: m/z 468 [M+H]$^+$
$^1$H NMR (CDCl$_3$) δ(ppm): 1.29 (t, J=7.4 Hz, 3H), 1.79-1.85 (m, 4H), 2.54-2.57 (m, 4H), 2.59 (s, 3H), 2.64 (s, 3H), 2.75 (q, J=7.5 Hz, 2H), 3.63 (s, 2H), 5.51 (s, 2H), 6.92 (s, 1H), 7.17 (d, J=8.3 Hz, 2H), 7.32 (d, J=8.4 Hz, 2H), 7.57 (d, J=8.3 Hz, 2H), 7.81 (d, J=8.1 Hz, 2H), 8.15 (s, 1H).

Example 31

4-(2-Ethyl-5,7-dimethylimidazo[4,5-b]pyridin-3-ylmethyl)-N-[4-(morpholin-4-ylmethyl)phenyl]benzamide (Compound 31)

Compound 31 (0.252 g, yield 62%) was obtained in a similar manner to Example 15 using Compound 28 (0.350 g, 0.844 mmol) and morpholine (0.300 mL, 3.38 mmol).
ESI-MS: m/z 484 [M+H]$^+$
$^1$H NMR (CDCl$_3$) δ(ppm): 1.28 (t, J=7.6 Hz, 3H), 2.41-2.44 (m 4H), 2.58 (s, 3H), 2.63 (s, 3H), 2.74 (q, J=7.6 Hz, 2H), 3.46 (s, 2H), 3.67-3.71 (m, 4H), 5.49 (s, 2H), 6.91 (s, 1H), 7.17 (d, J=8.3 Hz, 2H), 7.30 (d, J=8.6 Hz, 2H), 7.56 (d, J=8.3 Hz, 2H), 7.78 (d, J=7.9 Hz, 2H), 8.07 (s, 1H).

Example 32

1-[4-(2-Ethyl-5,7-dimethylimidazo[4,5-b]pyridin-3-ylmethyl)benzoyl]piperidine-4-carboxylic acid ethyl ester (Compound 32)

Compound 32 (2.88 g, yield 99%) was obtained in a similar manner to Example 26 using Ethyl isonipecotate (2.00 mL, 12.9 mmol).
ESI-MS: m/z 449 [M+H]$^+$
$^1$H NMR (CDCl$_3$) δ(ppm): 1.25 (t, J=7.1 Hz, 3H), 1.31 (t, J=7.6 Hz, 3H), 1.71 (brs, 6H), 2.55 (m, 1H), 2.58 (s, 3H), 2.64 (s, 3H), 2.76 (q, J=7.6 Hz, 2H), 3.01 (brt, J=12.1 Hz, 2H), 4.15 (q, J=7.2 Hz, 2H), 5.47 (s, 2H), 6.91 (s, 1H), 7.13 (d, J=8.2 Hz, 2H), 7.31 (d, J=8.3 Hz, 2H).

Example 33

1-[4-(2-Ethyl-5,7-dimethylimidazo[4,5-b]pyridin-3-ylmethyl)benzoyl]piperidine-(4-methylpiperazine)carboxamide Compound P6 (0.200 g, 0.476 mmol) was dissolved in dichloromethane (5 mL), and 1-methylpiperazine (0.110 mL, 0.970 mmol), EDC (0.185 g, 0.970 mmol), and 1-hydroxybenzotriazole hydrate (0.0780 g, 0.580 mmol) was added to the solution, followed by stirring at room temperature overnight. The reaction mixture was diluted with chloroform, and sequentially washed with water, a saturated aqueous sodium hydrogen carbonate solution, and saturated brine. The organic layer was dried over anhydrous magnesium sulfate, and concentrated under reduced pressure. The residue was crystallized from diisopropyl ether to obtain Compound 33 (0.199 g, yield 83%).
ESI-MS: m/z 503 [M+H]$^+$
$^1$H NMR (CDCl$_3$) δ(ppm): 1.28 (t, J=7.4 Hz, 3H), 1.74-1.77 (m, 4H), 2.00 (brs, 4H), 2.28 (s, 3H), 2.36 (brs, 4H), 2.55 (s, 3H), 2.60 (s, 3H), 2.70 (m, 1H), 2.74 (q, J=7.6 Hz, 2H), 2.90 (brs, 2H), 3.49 (m 2H), 5.44 (s, 2H), 6.87 (s, 1H), 7.11 (d, J=8.1 Hz, 2H), 7.28 (d, J=8.1 Hz, 2H).

Example 34

4-(2-Ethyl-5,7-dimethylimidazo[4,5-b]pyridin-3-ylmethyl)benzylalcohol (Compound 34)

Compound 34 (1.52 g, yield 86%) was obtained in a similar manner to Example 13 using Compound 25 (2.00 g, 6.18 mmol).
ESI-MS: m/z 296 [M+H]$^+$
$^1$H NMR (CDCl$_3$) δ(ppm): 1.27 (t, J=7.4 Hz, 3H), 2.41 (brs, 1H), 2.58 (s, 3H), 2.62 (s, 3H), 2.73 (q, J=7.4 Hz, 2H), 4.64 (s, 2H), 5.43 (s, 2H), 6.89 (s, 1H), 7.06 (d, J=8.3 Hz, 2H), 7.25 (d, J=8.2 Hz, 2H).

Example 35

N-[4-(2-Ethyl-5,7-dimethylimidazo[4,5-b]pyridin-3-ylmethyl)benzyl]aniline (Compound 35)

Compound 34 (0.300 g, 1.01 mmol) was dissolved in dichloromethane (10 mL), and triethylamine (0.284 mL, 2.03 mmol) and methanesulfonyl chloride (0.118 mL, 1.52 mmol) was added to the solution at 0° C., followed by stirring for 1.5 hours. The reaction mixture was added with water to decompose excess reagent, and diluted with chloroform, then washed with water and saturated brine. The organic layer was dried over anhydrous magnesium sulfate, and concentrated under reduced pressure. Then, the residue was dissolved in dichloromethane (10 mL), triethylamine (0.283 mL, 2.03 mmol) and aniline (0.277 mL, 3.04 mmol) was added to the solution, followed by stirring at room temperature overnight. The reaction mixture was diluted with chloroform, and washed with water and saturated brine. The organic layer was dried over anhydrous magnesium sulfate, and concentrated under reduced pressure. The residue was purified by silica gel column chromatography (ethyl acetate:hexane=1:3). The desired compound was crystallized from diisopropyl ether to obtain Compound 35 (0.149 g, yield 40%).
ESI-MS: m/z 371 [M+H]$^+$
$^1$H NMR (CDCl$_3$) δ(ppm): 1.29 (t, J=7.4 Hz, 3H), 2.58 (s, 3H), 2.63 (s, 3H), 2.77 (q, J=7.4 Hz, 2H), 4.01 (brs, 1H), 4.28 (s, 2H), 5.43 (s, 2H), 6.59 (dd, J=1.0, 7.6 Hz, 2H), 6.70 (dt, J=1.0, 7.3 Hz, 1H), 6.89 (s, 1H), 7.08 (d, J=8.3 Hz, 2H), 7.15 (dt, J=1.3, 7.3 Hz, 2H), 7.27 (d, J=8.8 Hz, 1H).

Example 36

N-[3-(2-Ethyl-5,7-dimethylimidazo[4,5-b]pyridin-3-ylmethyl)benzyl]aniline (Compound 36)

Compound 36 (0.0400 g, yield 18%) was obtained in a similar manner to Example 35 using Compound 13 (0.180 g, 0.609 mmol).
ESI-MS: m/z 371 [M+H]$^+$
$^1$H NMR (CDCl$_3$) δ(ppm): 1.29 (t, J=7.6 Hz, 3H), 2.60 (s, 3H), 2.65 (s, 3H), 2.75 (q, J=7.6 Hz, 2H), 4.23 (s, 2H), 5.45 (s, 2H), 6.60 (d, J=7.6 Hz, 2H), 6.72 (t, J=7.4 Hz, 1H), 6.90 (s, 1H), 6.99-7.01 (m, 1H), 7.13-7.28 (m, 5H).

Example 37

Syntheses of Compound 37 to Compound 60

Compound P7 (0.0084 g, 0.030 mmol) was dissolved in chloroform (0.30 mL), and a solution of R$^{39}$COCl (wherein R$^{39}$ have the same definition as described above) in chloroform (1.0 mol/L, 0.050 mL) and poly(vinylpyridine) (2% copolymer, 0.029 g, Aldrich) was added to the solution, followed by stirring at room temperature for 3 hours. After confirming the termination of the reaction by thin-layer chromatography, the reaction mixture was added with chloroform (0.30 mL) and tris(2-aminoethyl)amine-polystylene (1% divinylbenzene copolymer, ca. 3.40 mmol/g, 0.044 g, NOVABIOCHEM), followed by stirring at room temperature overnight. The resin in the reaction mixture was filtered out, and the solvent of filtrate was evaporated. The residue was purified by chromatography (ethyl acetate:chloroform=1:4) to obtain Compound 37 to Compound 60.

The structures and data (APCI-MS) of the compounds were described in Table 2 (1) to (3).

Melting point (Compound 53): 215-218° C.

Example 38

Syntheses of Compound 61 to Compound 75

Compound P7 (0.0084 g, 0.030 mmol) was dissolved in chloroform (0.30 mL), and a solution of $R^{41}NCO$ (wherein $R^{41}$ have the same definition as described above) in chloroform (1.0 mol/L, 0.060 mL) was added to the solution, followed by stirring at room temperature overnight. After confirming the termination of the reaction by thin-layer chromatography, the reaction mixture was added with chloroform (0.60 mL) and tris(2-aminoethyl)amine-polystylene (1% divinylbenzene copolymer, ca. 3.40 mmol/g, 0.044 g, NOVABIOCHEM), followed by stirring at room temperature overnight. The resin in the reaction mixture was filtered out, and the solvent of filtrate was evaporated. The residue was added with chloroform (0.90 mL), polymer-bound benzoyl chloride (0.094 g), and morpholinomethyl-polystylene (2% divinylbenzene copolymer, ca. 3.20 mmol/g, 0.042 g, Fluka), followed by stirring at room temperature overnight. The resin in the reaction mixture was filtered out, and the solvent of filtrate was evaporated. The residue was purified by ion-exchange chromatography (BONDESIL SCX, VARIAN, the products were eluted by 2 mol/L ammonia-methanol solution) to obtain Compound 61 to Compound 75.

The structures and data (APCI-MS) of the compounds were described in Table 3 (1) to (2).

Example 39

Syntheses of Compound 76 to Compound 80

Compound P7 (0.084 g, 0.030 mmol) was dissolved in chloroform (0.40 mL), and triethylamine (0.014 mL, 0.100 mmol) and a solution of $R^{42}OCOCl$ (wherein $R^{42}$ has the same definition as described above) in chloroform (1.0 mol/L, 0.070 mL), followed by stirring at room temperature overnight. After confirming the termination of the reaction by thin-layer chromatography, the reaction mixture was added with chloroform (0.70 mL) and tris(2-aminoethyl)amine-polystylene (1% divinylbenzene copolymer, ca. 3.40 mmol/g, 0.088 g, NOVABIOCHEM), followed by stirring at room temperature overnight. The resin in the reaction mixture was filtered out, and the solvent of filtrate was evaporated. The residue was added with chloroform (0.90 mL), polymer-bound benzoyl chloride (0.045 g), and morpholinomethyl-polystylene (2% divinylbenzene copolymer, ca. 3.20 mmol/g, 0.042 g, Fluka), followed by stirring at room temperature overnight. The resin in the reaction mixture was filtered out, and the solvent of filtrate was evaporated. The residue was purified by preparative thin-layer chromatography (methanol:chloroform=1:20) to obtain Compound 76 to Compound 80.

The structures and data (APCI-MS) of the compounds were described in Table 4.

Example 40

4-(2-Ethyl-5,7-dimethylimidazo[4,5-b]pyridin-3-ylmethyl)phenyl}carbamic acid tert-butyl ester (compound 81)

Compound P7 (0.206 g, 0.735 mmol) was dissolved in THF (7.0 mL), and di-tert-butyl dicarbonate (0.192 g, 0.882 mmol) was added to the solution, followed by stirring under reflux overnight. The reaction mixture was concentrated under reduced pressure. The residue was recrystallized from ethyl acetate-hexane to obtain Compound 81 (0.281 g, 0.735 mmol, 100%).

The data of APCI-MS was described in Table 4.

$^1$H NMR (CDCl$_3$) δ(ppm): 1.29 (t, J=7.6 Hz, 3H), 1.50 (s, 9H), 2.59 (s, 3H), 2.62 (s, 3H), 2.77 (q, J=7.6 Hz, 2H), 5.39 (s, 2H), 6.43 (brs, 1H), 6.88 (s, 1H), 7.05 (brd, J=8.7 Hz, 2H), 7.26 (brd, J=8.7 Hz, 2H).

melting point: 151° C.

Example 41

Syntheses of Compound 82 to Compound 96

Compound 81 (0.011 g, 0.030 mmol) was dissolved in THF (0.40 mL), and potassium tert-butoxide (1 mol/L, 0.10 mL) and $R^{17}SO_2Cl$ (wherein, $R^{17}$ has the same definition as described above)(0.060 mmol) was added to the solution, followed by stirring at room temperature overnight. After confirming the termination of the reaction by thin-layer chromatography, the solvent was evaporated. The residue was added with a saturated aqueous sodium hydrogen carbonate solution, and the mixture was extracted with chloroform. The organic layer was washed with a saturated aqueous sodium hydrogen carbonate solution, and dried over anhydrous magnesium sulfate, then concentrated under reduced pressure. The residue was dissolved in dichloromethane (0.40 mL), and trifluoroacetic acid (0.10 mL) was added to the solution, followed by stirring at room temperature for 3 hours. The solvent was evaporated, and the residue was added with a saturated aqueous sodium hydrogen carbonate solution, then the mixture was extracted with chloroform. The organic layer was washed with a saturated aqueous sodium hydrogen carbonate solution, and dried over anhydrous magnesium sulfate, then concentrated under reduced pressure. The residue was added with chloroform (0.80 mL), polymer-bound benzoyl chloride (0.045 g), and morpholinomethyl-polystylene (2% divinylbenzene copolymer, ca. 3.20 mmol/g, 0.042 g, Fluka), followed by stirring at room temperature overnight. The resin in the reaction mixture was filtered out, and the solvent of filtrate was evaporated. The residue was purified by ion-exchange chromatography (BONDESIL SCX, VARIAN, the products were eluted by 2 mol/L ammonia-methanol solution) to obtain Compound 82 to Compound 96.

The structures and data (APCI-MS) of the compounds were described in Table 5 (1) to (2).

Example 42

{4-(2-Ethyl-5,7-dimethylimidazo[4,5-b]pyridin-3-ylmethyl)phenyl}phenylamine (Compound 97)

Compound P7 (0.100 g, 0.357 mmol) was dissolved in toluene (7.1 mL), and 1,1'-bis(diphenylphosphino)ferrocene (0.059 g, 0.107 mmol), tris(dibenzylideneacetone)dipalladium(0)(0.016 g, 0.0179 mmol), sodium tert-butoxide (0.0411 g, 0.428 mmol), and iodobenzene (0.0600 mL, 0.536 mmol) were added to the solution, followed by stirring at 100° C. for 2.5 hours under argon atmosphere. The reaction mixture was concentrated under reduced pressure, and the residue was purified by silica gel column chromatography (ethyl acetate:hexane=1:1). The obtained solid was recrystallized from ethyl acetate-hexane to obtain Compound 97 (0.0385 g, 0.108 mmol, yield 30%).

APCI-MS: m/z 357 [M+H]$^+$

¹H NMR (CDCl₃) δ(ppm): 1.31 (t, J=7.6 Hz, 3H), 2.60 (s, 3H), 2.62 (s, 3H), 2.81 (q, J=7.6 Hz, 2H), 5.38 (s, 2H), 5.70 (brs, 1H), 6.88-7.05 (m, 8H), 7.20-7.27 (m, 2H).
melting point: 151-152° C.

Example 43

13-(2-Ethyl-5,7-dimethylimidazo[4,5-b]pyridin-3-ylmethyl)phenyl}phenylamine (Compound 98)

Compound 98 (yield 13%) was obtained in a similar manner to Example 42 using Compound P8.
APCI-MS: m/z 357 [M+H]⁺
¹H NMR (CDCl₃) δ(ppm): 1.32 (t, J=7.6 Hz, 3H), 2.57 (s, 3H), 2.62 (s, 3H), 2.81 (q, J=7.6 Hz, 2H), 5.39 (s, 2H), 5.70 (brs, 1H), 6.65 (brd, J=7.4 Hz, 1H), 6.75 (brs, 1H), 6.87-7.00 (m, 5H), 7.12-7.25 (m, 3H).

Example 44

4-{4-(2-Ethyl-5,7-dimethylimidazo[4,5-b]pyridin-3-ylmethyl)phenylamino}benzoic acid ethyl ester (Compound 99)

Compound P7 (1.00 g, 3.57 mmol) was dissolved in toluene (36 mL), and 1,1'-bis(diphenylphosphino)ferrocene (0.396 g, 0.714 mmol), 1,1'-bis(diphenylphosphino) ferrocenedichloropalladium(II)(0.292 g, 0.357 mmol), and sodium tert-butoxide (0.515 g, 5.36 mmol) was added to the solution, and the mixture was degassed. Then, ethyl p-bromobenzoate (0.699 mL, 4.28 mmol) was added to the mixture, followed by stirring at 80° C. for 1.5 hours under argon atmosphere. The reaction mixture was added with a saturated aqueous sodium hydrogen carbonate solution, and extracted with chloroform. The organic layer was dried over anhydrous magnesium sulfate, and concentrated under reduced pressure. The residue was purified by silica gel column chromatography (ethyl acetate:hexane=75:35 to 35:75). The obtained solid was recrystallized from ethanol-diisopropyl ether to obtain Compound 99 (1.01 g, 2.36 mmol, yield 66%).
APCI-MS: m/z 429 [M+H]⁺
¹H NMR (CDCl₃) δ(ppm): 1.32 (t, J=7.6 Hz, 3H), 1.37 (t, J=7.0 Hz, 3H), 2.60 (s, 3H), 2.62 (s, 3H), 2.81 (q, J=7.6 Hz, 2H), 4.33 (q, J=7.0 Hz, 2H), 5.42 (s, 2H), 6.04 (brs, 1H), 6.88-6.97 (m, 3H), 7.03-7.13 (m, 4H), 7.88-7.93 (m, 2H).

Example 45

{4-(2-Ethyl-5,7-dimethylimidazo[4,5-b]pyridin-3-ylmethyl)phenyl}{4-(4-methylpiperazin-1-ylcarbonyl)phenyl}amine (Compound 100)

Compound P9 (0.259 g, 0.647 mmol) was dissolved in THF-DMF (3:1)(8.0 mL), and N-methylpiperazine (0.108 mL, 0.970 mmol), EDC (0.248 g, 1.29 mmol), and 1-hydroxybenzotriazole hydrate (0.099 g, 0.647 mmol) were added to the solution, followed by stirring at room temperature for 1.5 hours. The reaction mixture was concentrated under reduced pressure, and the residue was added with water and a saturated aqueous sodium hydrogen carbonate solution, then the mixture was extracted with ethyl acetate twice. The organic layer was washed with water and saturated brine, and dried over anhydrous magnesium sulfate, then concentrated under reduced pressure. The residue was recrystallized from diisopropyl ether to obtain Compound 100 (0.262 g, 0.543 mmol, yield 84%).
APCI-MS: m/z 483 [M+H]⁺
¹H NMR (CDCl₃) δ(ppm): 1.32 (t, J=7.6 Hz, 3H), 2.31 (s, 3H), 2.41 (brs, 4H), 2.60 (s, 3H), 2.63 (s, 3H), 2.81 (q, J=7.6 Hz, 2H), 3.64 (brs, 4H), 5.40 (s, 2H), 5.96 (s, 1H), 6.89 (s, 1H), 6.95-7.08 (m, 6H), 7.29-7.34 (m, 2H).

Example 46

{4-(2-Ethyl-5,7-dimethylimidazo[4,5-b]pyridin-3-ylmethyl)phenyl}{4-(hydroxymethyl)phenyl}amine (Compound 101)

Compound 99 (0.453 mg, 1.06 mmol) was dissolved in THF (10 mL), and a diisobutylaluminum hydride-toluene solution (1 mmol/L, 4.2 mL, 4.2 mmol) was added to the solution, followed by stirring at room temperature for 10 minutes. The reaction mixture was added with an aqueous potassium sodium tartrate solution and chloroform, followed by stirring at room temperature for 4 hours, then the mixture was extracted with chloroform three times. The organic layer was washed with saturated brine, and dried over anhydrous magnesium sulfate, then concentrated under reduced pressure. The residue was recrystallized from ethanol to obtain Compound 101 (0.384 g, 0.994 mmol, yield 94%).
APCI-MS: m/z 387 [M+H]⁺
¹H NMR (CDCl₃) δ(ppm): 1.32 (t, J=7.6 Hz, 3H), 2.60 (s, 3H), 2.62 (s, 3H), 2.81 (q, J=7.6 Hz, 2H), 4.60 (d, J=5.8 Hz, 2H), 5.39 (s, 2H), 5.72 (s, 1H), 6.88 (s, 1H), 6.93-7.08 (m, 6H), 7.22-7.26 (m, 2H).

Example 47

{4-(2-Ethyl-5,7-dimethylimidazo[4,5-b]pyridin-3-ylmethyl)phenyl}{4-(4-methylpiperazin-1-ylmethyl)phenyl}amine 2fumalate (Compound 102)

Lithium aluminum hydride (0.044 g, 1.16 mmol) was suspended in THF (5.0 mL), and a solution of aluminum chloride (0.0773 g, 0.580 mmol) in THF (7.0 mL) was added to the suspention at 0° C., followed by stirring at same temperature for 10 minutes. Then, a solution of Compound 100 (0.140 g, 0.290 mmol) in THF (6.0 mL) was slowly added to the mixture, followed by stirring at 0° C. for 15 minutes. The reaction mixture was added with a 2 mol/L aqueous sodium hydroxide solution, and extracted with dichloromethane three times. The organic layer was dried over anhydrous magnesium sulfate, and concentrated under reduced pressure. The residue was dissolved in THF, and a solution of fumaric acid (74 mg, 0.58 mmol) in THF (2 mL) was added to the solution. The precipitates were collected by filtration, and sequentially washed with THF and ethyl acetate to obtain Compound 102 (0.173 g, 0.247 mmol, yield 85%).
APCI-MS: m/z 469 [M+H]⁺
¹H NMR (DMSO-d₆) δ(ppm): 1.23 (t, J=7.4 Hz, 3H), 2.35 (s, 3H), 2.51 (10H, overlapping with the peak of DMSO), 2.61 (brs, 4H), 2.79 (q, J=7.4 Hz, 2H), 3.41 (s, 2H), 5.34 (s, 2H), 6.59 (s, 4H), 6.93-7.14 (m, 9H), 8.15 (s, 1H).

Example 48

{4-(2-Ethyl-5,7-dimethylimidazo[4,5-b]pyridin-3-ylmethyl)phenyl}(1-methylpiperidin-4-yl)amine (Compound 103)

Compound P7 (0.200 g, 0.713 mmol) was suspended in dichloroethane (3.0 mL), and acetic acid (0.50 mL), 1-methyl-4-piperidone (0.175 mL, 1.43 mmol), and sodium triacetoxyborohydride (0.303 g, 1.43 mmol) was added to the suspention, followed by stirring at room temperature for 1.5 hours. The reaction mixture was added with a 2 mol/L aqueous sodium hydroxide solution, and extracted with dichloromethane three times. The organic layer was washed with saturated brine, and dried over anhydrous magnesium sulfate, then concentrated under reduced pressure. The residue was recrystallized from ethanol-diisopropyl ether to obtain Compound 103 (0.192 g, 0.509 mmol, yield 71%).

APCI-MS: m/z 378 [M+H]$^+$
$^1$H NMR (CDCl$_3$) δ(ppm): 1.30 (t, J=7.5 Hz, 3H), 1.37-1.52 (m, 2H), 1.96-2.13 (m, 4H), 2.27 (s, 3H), 2.59 (s, 3H), 2.61 (s, 3H), 2.75-2.84 (m, 4H), 3.20 (m, 1H), 3.50 (brd, J=7.6 Hz, 1H), 5.32 (s, 2H), 6.48 (d, J=8.6 Hz, 2H), 6.87 (s, 1H), 6.96 (d, J=8.6 Hz, 2H).

Example 49

N-{4-(2-Ethyl-5,7-dimethylimidazo[4,5-b]pyridin-3-ylmethyl)phenyl}cyclohexylamine (Compound 104)

Compound 104 (yield 83%) was obtained in a similar manner to Example 48 using cyclohexanone.

APCI-MS: m/z 363 [M+H]$^+$
$^1$H NMR (CDCl$_3$) δ(ppm): 1.02-1.41 (m, 8H), 1.59-1.77 (m, 3H), 2.00 (m, 2H), 2.59 (s, 3H), 2.61 (s, 3H), 2.80 (q, J=7.5 Hz, 2H), 3.19 (m, 1H), 3.50 (m, 1H), 5.32 (s, 2H), 6.47 (d, J=8.6 Hz, 2H), 6.86 (s, 1H), 6.95 (d, J=8.6 Hz, 2H).

Example 50

4-{4-(2-Ethyl-5,7-dimethylimidazo[4,5-b]pyridin-3-ylmethyl)phenylamino}piperidine-1-carboxylic acid tert-butyl ester (Compound 105)

Compound 105 (yield 91%) was obtained in a similar manner to Example 48 using 4-oxopiperidine-1-carboxylic avid tert-butyl ester.

APCI-MS: m/z 464 [M+H]$^+$
$^1$H NMR (CDCl$_3$) δ(ppm): 1.23-1.34 (m, 5H), 1.45 (s, 9H), 1.99 (m, 2H), 2.59 (s, 3H), 2.61 (s, 3H), 2.75-2.94 (m, 4H), 3.37 (m, 1H), 3.48 (m, 1H), 4.02 (m, 2H), 5.32 (s, 2H), 6.49 (brd, J=8.6 Hz, 2H), 6.87 (s, 1H), 6.97 (d, J=8.6 Hz, 2H).

Example 51 cis-4-[4-(2-Ethyl-5,7-dimethyl-3H-imidazo[4,5-b]pyridin-3-ylmethyl)phenylamino]cylohexanecarboxylic acid ethyl ester (Compound 106c) and trans-4-[4-(2-Ethyl-5,7-dimethyl-3H-imidazo[4,5-b]pyridin-3-ylmethyl)phenylamino]cylohexanecarboxylic acid ethyl ester (Compound 106t)

Compound P7 (3.65 g, 13.0 mmol) was suspended in acetonitrile (52 mL), and ethyl 4-cyclohexanonecarboxylate (4.14 mL, 26.0 mmol) and sodium triacetoxyborohydride (5.51 g, 26.0 mmol) were added to the suspension, followed by stirring at room temperature overnight. The reaction mixture was added with a 2 mol/L aqueous sodium hydroxide solution, and extracted with ethyl acetate three times. The organic layer was washed with saturated brine, and dried over anhydrous magnesium sulfate, then concentrated under reduced pressure. The residue was purified by silica gel column chromatography (ethyl acetate:hexane=3:2). The obtained desired compound (mixture of cis-form and trans-form) was added with diisopropyl ether, and the crystals were collected by filtration. The filtrate was concentrated to obtain Compound 106c (cis:trans=90:10, 2.80 g, 6.44 mmol, 50%).

The crystals were recrystallized from ethanol-diisopropyl ether (1:1) to obtain Compound 106t (cis:trans=5:95, 1.84 g, 4.23 mmol, 32.5%).

Compound 106c
APCI-MS: m/z 435 [M+H]$^+$
$^1$H NMR (CDCl$_3$) δ(ppm): 1.25 (t, J=7.1 Hz, 3H), 1.30 (t, J=7.6 Hz, 3H), 1.52-1.96 (m, 8H), 2.46 (m, 1H), 2.59 (s, 3H), 2.61 (s, 3H), 2.80 (q, J=7.6 Hz, 2H), 3.42 (brs, 1H), 3.66 (brs, 1H), 4.13 (q, J=7.1 Hz, 2H), 5.32 (s, 2H), 6.47 (d, J=8.6 Hz, 2H), 6.86 (s, 1H), 6.96 (d, J=8.6 Hz, 2H).

Compound 106t
APCI-MS: m/z 435 [M+H]$^+$
$^1$H NMR (CDCl$_3$) δ(ppm): 1.11 (dq, J=12.0, 3.3 Hz, 2H), 1.25 (t, J=7.1 Hz, 3H), 1.30 (t, J=7.6 Hz, 3H), 1.54 (dq, J=12.8, 3.3 Hz, 2H), 2.03 (brd, J=13.3 Hz, 2H), 2.15 (brd, J=13.0 Hz, 2H), 2.26 (tt, J=12.2, 3.6 Hz, 1H), 2.59 (s, 3H), 2.61 (s, 3H), 2.80 (q, J=7.6 Hz, 2H), 3.19 (brs, 1H), 3.44 (brs, 1H), 4.12 (q, J=7.1 Hz, 2H), 5.32 (s, 2H), 6.47 (d, J=8.4 Hz, 2H), 6.87 (s, 1H), 6.96 (d, J=8.4 Hz, 2H).

Example 52 cis-{4-(2-Ethyl-5,7-dimethylimidazo[4,5-b]pyridin-3-ylmethyl)phenyl}{4-(4-methylpiperazin-1-ylcarbonyl)cyclohexyl}amine (Compound 107c) and trans-{4-(2-Ethyl-5,7-dimethylimidazo[4,5-b]pyridin-3-ylmethyl)phenyl}{4-(4-methylpiperazin-1-ylcarbonyl)cyclohexyl}amine (Compound 107t)

Compound P31 (1.25 g, 3.07 mmol) was dissolved in THF-DMF (5:1)(18.6 mL), and N-methylpiperazine (0.511 mL, 4.61 mmol), EDC (0.884 g, 4.61 mmol), 1-hydroxybenzotriazole hydrate (0.470 g, 3.07 mmol), followed by stirring at room temperature for 5 hours. The reaction mixture was concentrated under reduced pressure, and the residue was added with a saturated aqueous sodium hydrogen carbonate solution and extracted with ethyl acetate three times. The organic layer was washed with saturated brine, and dried over anhydrous magnesium sulfate, then concentrated under reduced pressure. The residue was purified by silica gel column chromatography (chloroform:methanol:triethylamine=95:2.5:2.5). The fraction containing the desired compound was concentrated, and the residue was dissolved in diethyl ether, then oxalic acid (0.276 g, 3.07 mmol) was added to the solution. The crystals were collected by filtration, and washed with diethyl ether to obtain Compound 107c (1.13 g, 1.95 mmol, yield 63.5%).

APCI-MS: m/z 489 [M+H]$^+$
$^1$H NMR (DMSO-d$_6$) δ(ppm): 1.23 (t, J=7.5 Hz, 3H), 1.43 (m, 2H), 1.50-1.77 (m, 6H), 2.50 (6H, overlapping with the peak of DMSO), 2.61 (s, 3H), 2.66 (m, 1H), 2.78 (q, J=7.5 Hz, 3H), 2.90 (brs, 4H), 3.43 (m, 1H), 3.64 (brs, 4H), 5.24 (s, 2H), 6.53 (d, J=8.6 Hz, 2H), 6.89 (d, J=8.6 Hz, 2H), 6.92 (s, 1H).

compound P32 (1.15 g, 2.83 mmol) was suspended in THF-DMF (5:1)(16.8 mL), and N-methylpiperazine (0.470 mL, 4.24 mmol), EDC (0.813 g, 4.24 mmol), and 1-hydroxybenzotriazole hydrate (0.433 g, 2.83 mmol) were added to the suspension, followed by stirring at room temperature for 4 hours. The reaction mixture was concentrated under reduced pressure, and the residue was added with a saturated aqueous sodium hydrogen carbonate solution and extracted with ethyl acetate three times. The residue was recrystallized from ethanol-diisopropyl ether (1:1) to obtain Compound 107t (1.20 g, 2.46 mmol, 86.8%).

APCI-MS: m/z 489 [M+H]$^+$

¹H NMR (DMSO-d₆) δ(ppm): 1.14 (m, 2H), 1.22 (t, J=7.5 Hz, 3H), 1.45 (m, 2H), 1.65 (m, 2H), 1.94 (m, 2H), 2.17 (s, 3H), 2.24 (m, 4H), 2.50 (7H, overlapping with the peak of DMSO), 2.78 (q, J=7.5 Hz, 2H), 3.07 (brs, 1H), 3.44 (m, 4H), 5.23 (s, 2H), 5.39 (d, J=7.7 Hz, 1H), 6.48 (d, J=8.4 Hz, 2H), 6.89 (d, J=7.7 Hz, 2H), 6.92 (s, 1H).

Example 53 cis-{4-(2-Ethyl-5,7-dimethylimidazo[4,5-b]pyridin-3-ylmethyl)phenyl}{4-(4-methylpiperazin-1-ylmethyl)cyclohexyl}amine (Compound 108c) and trans-{4-(2-Ethyl-5,7-dimethylimidazo[4,5-b]pyridin-3-ylmethyl)phenyl}{4-(4-methylpiperazin-1-ylmethyl)cyclohexyl}amine (Compound 108t)

Compound 107c (0.200 g, 0.346 mmol) was suspended in a saturated aqueous sodium hydrogen carbonate solution, and the suspention was extracted with chloroform twice, then the organic layer was dried over anhydrous magnesium sulfate and concentrated under reduced pressure. The residue was dissolved in THF (2.5 mL), and a solution of lithium aluminum hydride (0.105 g, 2.76 mmol) and aluminum chloride (0.092 g, 0.691 mmol) in THF (8 mL) was added to the solution, followed by stirring at 0° C. for 15 minutes. The reaction mixture was added with a 2 mol/L aqueous sodium hydroxide solution, and extracted with chloroform three times. The organic layer was dried over anhydrous magnesium sulfate, and concentrated under reduced pressure. The residue was recrystallized from diisopropyl ether to obtain Compound 108c (0.125 g, 0.263 mmol, yield 76%).

APCI-MS: m/z 475 [M+H]⁺

¹H NMR (CDCl₃) δ(ppm): 1.27 (m, 2H), 1.30 (t, J=7.6 Hz, 3H), 1.55-1.72 (m, 7H), 2.18 (d, J=6.8 Hz, 2H), 2.27 (s, 3H), 2.37-2.47 (m, 8H), 2.59 (s, 3H), 2.61 (s, 3H), 2.80 (q, J=7.6 Hz, 2H), 3.51 (m, 1H), 3.70 (brs, 1H), 5.32 (s, 2H), 6.48 (d, J=8.6 Hz, 2H), 6.86 (s, 1H), 6.95 (d, J=8.6 Hz, 2H).

melting point: 116-118° C.

Compound 107t (0.0572 g, 0.117 mmol) was dissolved in THF (1.1 mL), and a solution of lithium aluminum hydride (0.0178 g, 0.468 mmol) and aluminum chloride (0.0312 g, 0.234 mmol) in THF (3.0 mL) was added to the solution, followed by stirring at 0° C. for 15 minutes. The reaction mixture was added with a 2 mol/L aqueous sodium hydroxide solution, and extracted with chloroform three times. The organic layer was dried over anhydrous magnesium sulfate, and concentrated under reduced pressure. The residue was crystallized from diisopropyl ether to obtain Compound 108t (0.0426 g, 0.0897 mmol, yield 77%).

APCI-MS: m/z 475 [M+H]⁺

¹H NMR (CDCl₃) δ(ppm): 0.95-1.06 (m, 4H), 1.30 (t, J=7.6 Hz, 3H), 1.47 (m, 1H), 1.66 (m, 2H), 1.86 (m, 2H), 2.10 (m, 2H), 2.14 (d, J=7.1 Hz, 2H), 2.28 (s, 3H), 2.43 (brs, 6H), 2.59 (s, 3H), 2.61 (s, 3H), 2.80 (q, J=7.6 Hz, 2H), 3.13 (m, 1H), 3.46 (brs, 1H), 5.31 (s, 2H), 6.46 (d, J=8.6 Hz, 2H), 6.86 (s, 1H), 6.95 (d, J=8.6 Hz, 2H).

melting point: 177-180° C.

Example 54 cis-4-{4-[4-(2-Ethyl-5,7-dimethyl-3H-imidazo[4,5-b]pyridin-3-ylmethyl)phenylamino]cyclohexylcarbonyl}morpholine (Compound 109c) and trans-4-{4-[4-(2-Ethyl-5,7-dimethyl-3H-imidazo[4,5-b]pyridin-3-ylmethyl)phenylamino]cyclohexylcarbonyl}morpholine (Compound 109t)

Compound P31 (180 mg, 0.443 mmol) was suspended in THF-DMF (5:1)(2.6 mL), and morpholine (0.0579 mL, 0.664 mmol), EDC (127 mg, 0.664 mmol), 1-hydroxybenzotriazole hydrate (67.8 mg, 0.443 mmol) were added to the suspension, followed by stirring at room temperature for 5 hours. The reaction mixture was concentrated under reduced pressure, and a saturated aqueous sodium hydrogen carbonate solution was added to the residue, then extracted with ethyl acetate three times. The organic layer was washed with brine and dried over anhydrous magnesium sulfate, then dried under reduced pressure. The residue was recrystallized from DMF-ethanol (1:4) to obtain Compound 109c (183 mg, 0.384 mmol, 86.9%).

APCI-MS: m/z 476 [M+H]⁺

¹H NMR (CDCl₃) δ(ppm): 1.30 (t, J=7.5 Hz, 3H), 1.52-1.67 (m, 4H), 1.74-1.94 (m, 4H), 2.55 (m, 1H), 2.59 (s, 3H), 2.61 (s, 3H), 2.81 (q, J=7.5 Hz, 2H), 3.46-3.68 (m, 9H), 3.86 (br d, J=7.4 Hz, 1H), 5.32 (s, 2H), 6.48 (d, J=8.6 Hz, 2H), 6.87 (s, 1H), 6.96 (d, J=8.6 Hz, 2H).

Compound 109t (yield 95%) was obtained in a similar manner to the above method using Compound P32.

APCI-MS: m/z 476 [M+H]⁺

¹H NMR (CDCl₃) δ(ppm): 1.10 (dq, J=12.5, 3.8 Hz, 2H), 1.30 (t, J=7.6 Hz, 3H), 1.62-1.85 (m, 4H), 2.19 (brd, J=13.3 Hz, 2H), 2.44 (tt, J=11.2, 3.9 Hz, 1H), 2.59 (s, 3H), 2.61 (s, 3H), 2.80 (q, J=7.6 Hz, 2H), 3.24 (m, 1H), 3.43-3.76 (m, 9H), 5.32 (s, 2H), 6.47 (d, J=8.6 Hz, 2H), 6.87 (s, 1H), 6.97 (d, J=8.6 Hz, 2H).

Example 55 trans-1-{4-[4-(2-Ethyl-5,7-dimethyl-3H-imidazo[4,5-b]pyridin-3-ylmethyl)phenylamino]cyclohexylcarbonyl}pyrrolidine (Compound 110t) and cis-1-{4-[4-(2-Ethyl-5,7-dimethyl-3H-imidazo[4,5-b]pyridin-3-ylmethyl)phenylamino]cyclohexylcarbonyl}pyrrolidine (Compound 110c)

Compound 110t (yield 84%) was obtained in a similar manner to Example 54 using Compound P32 and pyrrolidine.

APCI-MS: m/z 460 [M+H]⁺

¹H NMR (CDCl₃) δ(ppm): 1.10 (dq, J=13.2, 3.5 Hz, 2H), 1.30 (t, J=7.6 Hz, 3H), 1.62-2.01 (m, 8H), 2.18 (brd, J=12.8 Hz, 2H), 2.34 (tt, J=11.7, 3.7 Hz, 1H), 2.59 (s, 3H), 2.61 (s, 3H), 2.80 (q, J=7.6 Hz, 2H), 3.24 (m, 1H), 3.43-3.50 (m, 5H), 5.32 (s, 2H), 6.47 (d, J=8.6 Hz, 2H), 6.86 (s, 1H), 6.95 (d, J=8.6 Hz, 2H).

Compound 110c (yield 73%) was obtained in a similar manner to Example 54 using Compound P31 and pyrrolidine.

APCI-MS: m/z 460 [M+H]⁺

¹H NMR (CDCl₃) δ(ppm): 1.30 (t, J=7.5 Hz, 3H), 1.55-2.00 (m, 12H), 2.43 (m, 1H), 2.60 (s, 3H), 2.61 (s, 3H), 2.81

(q, J=7.5 Hz, 2H), 3.45 (m, 4H), 3.60 (brs, 1H), 3.93 (brd, J=7.1 Hz, 1H), 5.32 (s, 2H), 6.49 (d, J=8.4 Hz, 2H), 6.86 (s, 1H), 6.96 (d, J=8.4 Hz, 2H).

Example 56 trans-[4-(2-Ethyl-5,7-dimethyl-3H-imidazo[4,5-b]pyridin-3-ylmethyl)phenyl][4-(morpholin-4-yl)methylcyclohexyl]amine (Compound 111t) and cis-[4-(2-Ethyl-5,7-dimethyl-3H-imidazo[4,5-b]pyridin-3-ylmethyl)phenyl][4-(morpholin-4-yl)methylcyclohexyl]amine 0.5oxalate (Compound 111c)

Lithium aluminum hydride (35.1 mg, 0.925 mmol) was suspended in THF (1 mL), and the suspention was cooled to 0° C., then a solution of aluminum trichloride (61.7 mg, 0.463 mmol) in THF (0.8 mL) was added to the suspension, followed by stirring for 10 minutes. Then, a solution of Compound 109t (0.170 g, 0.231 mmol) in THF (2.0 mL) was dropped slowly to the mixture, followed by stirring at 0° C. for 1 hour. A 2 mol/L aqueous sodium hydroxide solution was added to the reaction mixture, and the mixture was extracted with ethyl acetate twice. The organic layer was washed with saturated brine and dried over anhydrous magnesium sulfate, then concentrated under reduced pressure. The residue was recrystalized from DMF-ethanol (1:4) to obtain Compound 111t (88.7 mg, 0.192 mmol, 83.1%).

APCI-MS: m/z 462 [M+H]$^+$
$^1$H NMR (CDCl$_3$) δ(ppm): 0.91-1.13 (m, 4H), 1.30 (t, J=7.6 Hz, 3H), 1.48 (m, 1H), 1.87 (brd, J=11.7 Hz, 2H), 2.10 (brd, J=11.7 Hz, 2H), 2.14 (d, J=7.1 Hz, 2H), 2.38 (m, 4H), 2.59 (s, 3H), 2.61 (s, 3H), 2.80 (q, J=7.6 Hz, 2H), 3.14 (m, 1H), 3.46 (brs, 1H), 3.69 (m, 4H), 5.32 (s, 2H), 6.47 (d, J=8.6 Hz, 2H), 6.86 (s, 1H), 6.96 (d, J=8.6 Hz, 2H).

cis-[4-(2-Ethyl-5,7-dimethyl-3H-imidazo[4,5-b]pyridin-3-ylmethyl)phenyl][4-(morpholin-4-yl)methylcyclohexyl]amine was obtained in a similar manner to the above method using Compound 109c (0.100 g, 0.210 mmol). This compound was dissolved in diethylether and the solution was added with oxalic acid (18.9 mg, 0.210 mmol) dissolved in ethanol, then the mixture was concentrated. The residue was recrystallized from water to obtain Compound 111c (63.0 mg, 0.124 mmol, 59.1%).

APCI-MS: m/z 462 [M+H]$^+$
$^1$H NMR (DMSO-d$_6$) δ(ppm): 1.22 (t, J=7.4 Hz, 3H), 1.30-1.60 (m, 8H), 1.72 (brs, 1H), 2.44 (m, 2H), 2.51 (6H, overlapping with the peak of DMSO), 2.63 (m, 4H), 2.79 (q, J=7.4 Hz, 2H), 3.39 (brs, 1H), 3.65 (m, 4H), 5.24 (s, 2H), 6.52 (d, J=8.4 Hz, 2H), 6.90 (d, J=8.4 Hz, 2H), 6.92 (s, 1H).

Example 57 trans-[4-(2-Ethyl-5,7-dimethyl-3H-imidazo[4,5-b]pyridin-3-ylmethyl)phenyl](4-pyrrolidin-1-ylmethylcyclohexyl)amine (Compound 112t) and cis-[4-(2-Ethyl-5,7-dimethyl-3H-imidazo[4,5-b]pyridin-3-ylmethyl)phenyl](4-pyrrolidin-1-ylmethylcyclohexyl)amine (Compound 112c)

Compound 112t (yield 81%) was obtained in a similar manner to Example 56 using Compound 110t.

APCI-MS: m/z 446 [M+H]$^+$
$^1$H NMR (CDCl$_3$) δ(ppm): 0.92-1.14 (m, 4H), 1.29 (t, J=7.6 Hz, 3H), 1.45 (m, 1H), 1.76 (m, 4H), 1.89 (brd, J=10.3 Hz, 2H), 2.09 (brd, J=10.3 Hz, 2H), 2.27 (d, J=7.0 Hz, 2H), 2.45 (m, 4H), 2.59 (s, 3H), 2.61 (s, 3H), 2.80 (q, J=7.6 Hz, 2H), 3.14 (brs, 1H), 3.45 (brs, 1H), 5.31 (s, 2H), 6.47 (d, J=8.4 Hz, 2H), 6.86 (s, 1H), 6.95 (d, J=8.4 Hz, 2H).

Compound 112c (yield 78%) was obtained in a similar manner to Example 56 using Compound 110c.

APCI-MS: m/z 446 [M+H]$^+$
$^1$H NMR (CDCl$_3$) δ(ppm): 1.29 (t, J=7.6 Hz, 3H), 1.30 (m, 2H), 1.55-1.73 (m, 7H), 1.76 (m, 4H), 2.32 (d, J=6.8 Hz, 2H), 2.45 (m, 4H), 2.59 (s, 3H), 2.61 (s, 3H), 2.80 (q, J=7.6 Hz, 2H), 3.50 (brs, 1H), 3.71 (brs, 1H), 5.32 (s, 2H), 6.48 (d, J=8.4 Hz, 2H), 6.86 (s, 1H), 6.95 (d, J=8.4 Hz, 2H).

Example 58 trans-4-{4-[4-(2-Ethyl-5,7-dimethyl-3H-imidazo[4,5-b]pyridin-3-ylmethyl)phenylamino]cyclohexanecarbonyl}piperazin-1-carboxylic acid tert-butyl ester (Compound 113)

Compound 113 (yield 92%) was obtained in a similar manner to Example 54 using piperazin-1-carboxylic acid tert-butyl ester and Compound P32.

APCI-MS: m/z 575 [M+H]$^+$
$^1$H NMR (CDCl$_3$) δ(ppm): 1.11 (dq, J=12.2, 3.1 Hz, 2H), 1.30 (t, J=7.6 Hz, 3H), 1.47 (s, 9H), 1.62-1.85 (m, 4H), 2.19 (brd, J=12.7 Hz, 2H), 2.46 (tt, J=11.4, 3.8 Hz, 1H), 2.59 (s, 3H), 2.61 (s, 3H), 2.80 (q, J=7.6 Hz, 2H), 3.23 (m, 1H), 3.36-3.49 (m, 7H), 3.58 (m, 2H), 5.32 (s, 2H), 6.48 (d, J=8.4 Hz, 2H), 6.87 (s, 1H), 6.98 (d, J=8.4 Hz, 2H).

Example 59 trans-1-{4-[4-(2-Ethyl-5,7-dimethyl-3H-imidazo[4,5-b]pyridin-3-ylmethyl)phenylamino]cyclohexylcarbonyl}piperazine (Compound 114)

Compound 113 (261 mg, 0.454 mmol) was dissolved in chloroform (1.7 mL), and a 4 mol/L hydrogen chloride-ethyl acetate solution (4.5 mL) was added to the solution, followed by stirring at 0° C. for 1.5 hours. The reaction mixture was concentrated under reduced pressure, and the residue was added with a 2 mol/L aqueous sodium hydroxide solution, then extracted with ethyl acetate three times. The organic layer was washed with saturated brine and dried over anhydrous magnesium sulfate, then concentrated under reduced pressure. The residue was recrystallized from ethanol-diisopropyl ether (1:20) to obtain Compound 114 (201 mg, 0.423 mmol, 93.3%).

APCI-MS: m/z 475 [M+H]$^+$
$^1$H NMR (CDCl$_3$) δ(ppm): 1.10 (dq, J=12.2, 3.5 Hz, 2H), 1.30 (t, J=7.6 Hz, 3H), 1.63-1.85 (m, 4H), 2.19 (brd, J=12.4 Hz, 2H), 2.46 (tt, J=11.5, 3.8 Hz, 1H), 2.59 (s, 3H), 2.61 (s, 3H), 2.80 (q, J=7.6 Hz, 2H), 2.84 (m, 4H), 3.23 (m, 1H), 3.43-3.64 (m, 5H), 5.32 (s, 2H), 6.48 (d, J=8.6 Hz, 2H), 6.87 (s, 1H), 6.97 (d, J=8.6 Hz, 2H).

Example 60 trans-[4-(2-Ethyl-5,7-dimethyl-3-imidazo[4,5-b]pyridin-3-ylmethyl)phenyl](4-piperazin-1-ylmethylcyclohexyl)amine (Compound 115)

Compound 115 (yield 56%) was obtained in a similar manner to Example 56 using Compound 114.

APCI-MS: m/z 461 [M+H]$^+$
$^1$H NMR (CDCl$_3$) δ(ppm): 0.90-1.14 (m, 4H), 1.30 (t, J=7.6 Hz, 3H), 1.48 (m, 1H), 1.87 (brd, J=11.7 Hz, 2H), 2.09

(brd, J=11.7 Hz, 2H), 2.13 (d, J=7.1 Hz, 2H), 2.35 (m, 4H), 2.59 (s, 3H), 2.61 (s, 3H), 2.80 (q, J=7.6 Hz, 2H), 2.87 (m, 4H), 3.13 (m, 1H), 3.46 (brs, 1H), 5.31 (s, 2H), 6.47 (d, J=8.6 Hz, 2H), 6.86 (s, 1H), 6.95 (d, J=8.6 Hz, 2H).

Example 61 trans-1-{4-[4-(2-Ethyl-5,7-dimethyl-3H-imidazo[4,5-b]pyridin-3-ylmethyl)phenylamino]cyclohexylcarbonyl}-4-hydroxymethylpiperidine (Compound 116)

Compound 116 (yield 91%) was obtained in a similar manner to Example 54 using (piperidin-4-yl)methanol and compound P32.

APCI-MS: m/z 504 [M+H]$^+$ $^1$H NMR (CDCl$_3$) δ(ppm): 1.02-1.25 (m, 4H), 1.30 (t, J=7.6 Hz, 3H), 1.47 (t, J=5.3 Hz, 1H), 1.59-1.86 (m, 7H), 2.18 (brd, J=12.5 Hz, 2H), 2.42-2.56 (m, 2H), 2.59 (s, 3H), 2.61 (s, 3H), 2.80 (q, J=7.6 Hz, 2H), 3.02 (brt, J=11.6 Hz, 1H), 3.23 (m, 1H), 3.41-3.56 (m, 3H), 3.93 (brd, J=13.3 Hz, 1H), 4.66 (brd, J=13.0 Hz, 1H), 5.32 (s, 2H), 6.48 (d, J=8.4 Hz, 2H), 6.87 (s, 1H), 6.97 (d, J=8.4 Hz, 2H).

Example 62 trans-[4-(2-Ethyl-5,7-dimethyl-3H-imidazo[4,5-b]pyridin-3-ylmethyl)phenyl]{4-[4-(hydroxymethyl)piperidin-1-ylmethyl]cyclohexyl}amine (Compound 117)

Compound 117 was obtained in a similar manner to Example 56 using Compound 116. Compound 117 was recrystallized from diisopropyl ether-etanol (3:1)(yield 72%).

APCI-MS: m/z 490 [M+H]$^+$ $^1$H NMR (CDCl$_3$) δ(ppm): 0.90-1.14 (m, 4H), 1.18-1.73 (m, 6H), 1.29 (t, J=7.6 Hz, 3H), 1.80-1.92 (m, 4H), 2.05-2.14 (m, 4H), 2.59 (s, 3H), 2.61 (s, 3H), 2.80 (q, J=7.6 Hz, 2H), 2.83-2.90 (m, 2H), 3.13 (m, 1H), 3.40-3.51 (m, 3H), 5.31 (s, 2H), 6.46 (d, J=8.6 Hz, 2H), 6.86 (s, 1H), 6.95 (d, J=8.6 Hz, 2H).

melting point: 154-157° C.

Example 63 trans-4-[4-(2-Ethyl-5,7-dimethyl-3H-imidazo[4,5-b]pyridin-3-ylmethyl)phenylamino]cyclohexanecarboxylic acid [2-(pyrrolidin-1-yl)ethyl]amide (Compound 118)

Compound 118 was obtained in a similar manner to Example 54 using 1-(2-aminoethyl)pyrrolidine and Compound P32. Compound 118 was recrystallized from diisopropyl ether-etanol (2:1)(yield 63%).

APCI-MS: m/z 503 [M+H]$^+$ $^1$H NMR (CDCl$_3$) δ(ppm): 1.10 (dq, J=12.4, 3.5 Hz, 2H), 1.29 (t, J=7.6 Hz, 3H), 1.62 (dq, J=12.8, 2.8 Hz, 2H), 1.73-2.22 (m, 9H), 2.50 (m, 4H), 2.58 (m, 2H), 2.59 (s, 3H), 2.62 (s, 3H), 2.80 (q, J=7.6 Hz, 2H), 3.21 (m, 1H), 3.34 (q, J=5.7 Hz, 2H), 3.44 (m, 1H), 5.32 (s, 2H), 6.11 (brs, 1H), 6.47 (d, J=8.4 Hz, 2H), 6.86 (s, 1H), 6.96 (d, J=8.6 Hz, 2H).

melting point: 212-213° C.

Example 64 trans-[4-(2-Ethyl-5,7-dimethylimidazo[4,5-b]pyridin-3-ylmethyl)phenyl]{4-[(2-pyrrolidin-1-ylethylamino)methyl]cyclohexyl}amine oxalate (Compound 119)

Compound 119 (yield 21%) was obtained in a similar manner to Example 56 using Compound 118.

APCI-MS: m/z 489 [M+H]$^+$ $^1$H NMR (DMSO-d$_6$) δ(ppm): 0.97-1.13 (m, 4H), 1.22 (t, J=7.4 Hz, 3H), 1.56 (m, 1H), 1.70-1.82 (m, 6H), 1.92-2.00 (m, 2H), 2.51 (6H, overlapping with the peak of DMSO), 2.58 (m, 4H), 2.65-2.82 (m, 6H), 2.93 (t, J=6.1 Hz, 2H), 3.37 (brs, 1H), 5.24 (s, 2H), 6.46 (d, J=8.4 Hz, 2H), 6.89 (d, J=8.4 Hz, 2H), 6.92 (s, 1H).

Example 65 trans-4-[4-(2-Ethyl-5,7-dimethyl-3H-imidazo[4,5-b]pyridin-3-ylmethyl)phenylamino]cyclohexanecarboxylic acid (2-morpholinoethyl)amide (Compound 121)

Compound 121 (yield 74%) was obtained in a similar manner to Example 54 using Compound P32 and 4-(2-aminoethyl)morpholine.

APCI-MS: m/z 519 [M+H]$^+$ $^1$H NMR (DMSO-d$_6$) δ(ppm): 1.06 (brq, J=12.3 Hz, 2H), 1.22 (t, J=7.5 Hz, 3H), 1.43 (brq, J=12.8 Hz, 2H), 1.70 (brd, J=12.5 Hz, 2H), 1.94 (brd, J=11.7 Hz, 2H), 2.06 (m, 1H), 2.26-2.38 (m, 6H), 2.51 (6H, overlapping with the peak of DMSO), 2.78 (q, J=7.5 Hz, 2H), 3.07 (m, 1H), 3.13 (q, J=6.4 Hz, 2H), 3.54 (m, 4H), 5.23 (s, 2H), 5.38 (brd, J=7.9 Hz, 1H), 6.47 (d, J=8.2 Hz, 2H), 6.88 (d, J=8.2 Hz, 2H), 6.92 (s, 1H), 7.63 (brt, J=5.7 Hz, 1H).

Example 66 trans-[4-(2-Ethyl-5,7-dimethyl-3H-imidazo[4,5-b]pyridin-3-ylmethyl)phenyl]{4-[(2-morpholinoethylamino)methyl]cyclohexyl}amine (Compound 122)

Compound 122 (yield 46%) was obtained in a similar manner to Example 56 using Compound 121.

APCI-MS: m/z 505 [M+H]$^+$ $^1$H NMR (CDCl$_3$) δ(ppm): 0.95-1.15 (m, 4H), 1.30 (t, J=7.6 Hz, 3H), 1.47 (m, 1H), 1.84 (brd, J=10.2 Hz, 2H), 2.12 (brd, J=10.2 Hz, 2H), 2.41-2.52 (m, 8H), 2.59 (s, 3H), 2.61 (s, 3H), 2.69 (t, J=6.0 Hz, 2H), 2.80 (q, J=7.6 Hz, 2H), 3.14 (m, 1H), 3.46 (brs, 1H), 3.70 (m, 4H), 5.32 (s, 2H), 6.47 (d, J=8.6 Hz, 2H), 6.86 (s, 1H), 6.95 (d, J=8.6 Hz, 2H).

Example 67 trans-1-{4-[4-(2-Ethyl-5,7-dimethyl-3H-imidazo[4,5-b]pyridin-3-ylmethyl)phenylamino]cyclohexylcarbonyl}-4-morpholinopiperidine (Compound 123)

Compound 123 (yield 82%) was obtained in a similar manner to Example 54 using Compound P32.

APCI-MS: m/z 559 [M+H]$^+$ $^1$H NMR (CDCl$_3$) δ(ppm): 1.11 (brq, J=11.9 Hz, 2H), 1.30 (t, J=7.6 Hz, 3H), 1.38 (m, 2H), 1.60-1.97 (m, 6H), 2.18 (brd, J=12.4 Hz, 2H), 2.35-2.60 (m, 7H), 2.60 (s, 3H), 2.62 (s, 3H), 2.80 (q, J=7.6 Hz, 2H), 3.03 (brt, J=12.5 Hz, 1H), 3.22 (m, 1H), 3.44 (brs, 1H), 3.72 (m, 4H), 3.94 (brd, J=13.5 Hz, 1H), 4.64 (brd, J=13.5 Hz, 1H), 5.32 (s, 2H), 6.47 (d, J=8.6 Hz, 2H), 6.87 (s, 1H), 6.97 (d, J=8.6 Hz, 2H).

Example 68 trans-[4-(2-Ethyl-5,7-dimethyl-3H-imidazo[4,5-b]pyridin-3-ylmethyl)phenyl][4-(4-morpholinopiperidin-1-ylmethyl)cyclohexyl]amine (Compound 124)

Compound 124 (yield 82%) was obtained in a similar manner to Example 56 using Compound 123.

APCI-MS: m/z 545 [M+H]$^+$ $^1$H NMR (CDCl$_3$) δ(ppm): 0.89-1.15 (m, 4H), 1.29 (t, J=7.6 Hz, 3H), 1.40-1.92 (m, 9H), 2.05-2.20 (m, 5H), 2.54 (m, 4H), 2.59 (s, 3H), 2.61 (s, 3H), 2.80 (q, J=7.6 Hz, 2H), 2.88 (brd, J=11.2 Hz 2H), 3.13 (m, 1H), 3.45 (brs, 1H), 3.71 (m, 4H), 5.31 (s, 2H), 6.47 (d, J=8.6 Hz, 2H), 6.86 (s, 1H), 6.95 (d, J=8.6 Hz, 2H).

Example 69 cis-4-Methyl-1-{4-[4-(2,5,7-trimethyl-3H-imidazo[4,5-b]pyridin-3-ylmethyl)phenylamino]cyclohexylcarbonyl}piperazine (Compound 125c) and trans-4-Methyl-1-{4-[4-(2,5,7-trimethyl-3H-imidazo[4,5-b]pyridin-3-ylmethyl)phenylamino]cyclohexylcarbonyl}piperazine (Compound 125t)

Compound P19 (0.300 g, 0.764 mol) was dissolved in dichloromethane (10 mL), and 1-methylpiperazine (0.127 mL, 1.14 mmol), EDC (0.220 g, 1.14 mmol) and 1-hydroxybenzotriazole hydrate (0.176 g, 1.14 mmol) were added to the solution, followed by stirring at room temperature for 3 hours. The reaction mixture was diluted with chloroform and washed with water, a saturated aqueous sodium hydrogen carbonate solution, and saturated brine. The organic layer was dried over anhydrous magnesium sulfate and concentrated under reduced pressure. The residue was purified by silica gel column chromatography (chloroform:methanol=20:1) to obtain Compound 125c (0.345 g, 95%). Compound 125c was recrystallized from diethyl ether.

ESI-MS: m/z 475 [M+H]$^+$ $^1$H NMR (CDCl$_3$) δ(ppm): 1.53-1.66 (m, 4H), 1.74-1.92 (m, 4H), 2.30 (s, 3H), 2.38 (m, 4H), 2.50 (s, 3H), 2.59 (m, 1H), 2.60 (s, 6H), 3.50 (m, 2H), 3.62 (m, 2H), 5.29 (s, 2H), 6.48 (d, J=8.8 Hz, 2H), 6.87 (s, 1H), 6.98 (d, J=8.4 Hz, 2H)

melting point: 127-131° C.

Compound 125t (0.101 g, 94%) was obtained in a similar manner to the above method using Compound P22 (90.0 mg, 0.229 mmol). Compound 125t was recrystallized from ethanol-diethyl ether.

ESI-MS: m/z 475 [M+H]$^+$ $^1$H NMR (CDCl$_3$) δ(ppm): 1.11 (dq, J=3.7, 12.8 Hz, 2H), 1.66 (dq, J=3.2, 13.9 Hz, 2H), 2.16 (brd, J=10.6 Hz, 2H), 2.16 (brd, J=10.9 Hz, 2H), 2.28 (s, 3H), 2.34-2.45 (m, 5H), 2.48 (s, 3H), 2.48 (s, 3H), 3.22 (m, 2H), 3.48 (brs, 2H), 3.61 (brs, 2H), 5.27 (s, 2H), 6.45 (d, J=8.4 Hz, 1H), 6.84 (s, 1H), 6.96 (d, J=8.4 Hz, 2H)

melting point: 136-139° C. .

Example 70 cis-4-(4-Methylpiperazin-1-ylmethyl)cyclohexyl[4-(2,5,7-trimethyl-3H-imidazo[4,5-b]pyridin-3-ylmethyl)phenyl]amine (Compound 126c) and trans-4-(4-Methylpiperazin-1-ylmethyl)cyclohexyl[4-(2,5,7-trimethyl-3H-imidazo[4,5-b]pyridin-3-ylmethyl)phenyl]amine (Compound 126t)

Lithium aluminum hydride (96.0 mg, 1.45 mmol) was suspended in THF (5 mL). After cooling to 0° C., aluminum trichloride (96.0 mg, 0.720 mmol) was added to the suspension, followed by stirring for 10 minutes. Then, a solution of Compound 125c (0.170 g, 0.358 mmol) in THF was slowly dropped to the mixture, followed by stirring at room temperature for 2 hours. The reaction mixture was added with a 3 mol/L aqueous sodium hydroxide solution to decompose excess reagents, and the mixture was extracted with dichloromethane. The organic layer was washed with water and saturated brine, and dried over anhydrous magnesium sulfate, then concentrated under reduced pressure. The residue was purified by silica gel column chromatography (chloroform:methanol=20:1) to obtain compound 126c (0.134 g, 81%). Compound 126c was recrystallized from 2-propanol.

ESI-MS: m/z 461 [M+H]$^+$ $^1$H NMR (CDCl$_3$) δ(ppm): 1.24 (m, 2H), 1.60 (m, 7H), 2.16 (d, J=6.6 Hz, 2H), 2.26 (s, 3H), 2.42 (brs, 7H), 2.47 (s, 3H), 2.52 (s, 6H), 3.48 (brs, 1H), 3.77 (brs, 1H), 5.27 (s, 2H), 6.46 (d, J=8.4 Hz, 2H), 6.84 (s, 1H), 6.95 (d, J=8.4 Hz, 1H).

melting point: 161-165° C.

Compound 126t was obtained in a similar manner to the above method using Compound 125t (0.474 g, 0.999 mmol). Compound 126t was recrystallized from ethanol-diisopropyl ether (0.234 g, 51%).

ESI-MS: m/z 461 [M+H]$^+$ $^1$H NMR (CDCl$_3$) δ(ppm): 0.83-1.17 (m, 4H), 1.42 (m, 1H), 1.74 (brd, J=12.2 Hz, 2H), 1.91 (brd, J=11.6 Hz, 2H), 2.04 (d, J=7.3 Hz, 2H), 2.13 (s, 3H), 2.28 (m, 4H), 2.44 (s, 3H, overlapping with the peak of DMSO), 2.47 (s, 3H, overlapping with the peak of DMSO), 2.49 (s, 3H, overlapping with the peak of DMSO), 3.03 (m, 1H), 3.30 (m, 4H), 5.21 (s, 2H), 5.37 (d, J=7.8 Hz, 1H), 6.46 (d, J=8.4 Hz, 2H), 6.90 (s, 1H), 6.91 (d, J=8.4 Hz, 2H).

melting point: 178° C.

Example 71 trans-4-[4-(2,5,7-Trimethyl-3H-imidazo[4,5-b]pyridin-3-ylmethyl)phenylamino]cyclohexanecarboxylic acid (2-morpholinoethyl)amide (Compound 127t) and cis-4-[4-(2,5,7-Trimethyl-3H-imidazo[4,5-b]pyridin-3-ylmethyl)phenylamino]cyclohexanecarboxylic acid (2-morpholinoethyl)amide (Compound 127c)

Compound 127t (0.244 g, 90%) was obtained in a similar manner to Example 69 using Compound P22 (0.210 g, 0.535 mmol) and 1-(2-aminoethyl)morpholine (0.105 mL, 0.800 mmol). Compound 127t was recrystallized from ethanol-diethyl ether.

ESI-MS: m/z 505 [M+H]$^+$ $^1$H NMR (CDCl$_3$) δ(ppm): 1.10 (brq, J=11.2 Hz, 2H), 1.60 (brq, J=12.4 Hz, 2H), 1.93 (brd, J=13.4 Hz, 2H), 2.07 (tt, J=2.9 Hz, 12.1 Hz, 1H), 2.16 (brd, J=10.9 Hz, 2H), 2.41-2.46 (m, 6H), 2.49 (s, 3H), 2.59 (s, 6H), 3.19 (m, 1H), 3.30-3.37 (m, 2H), 3.68-3.71 (m, 4H), 5.28 (s, 2H), 6.06 (brs, 1H), 6.46 (d, J=8.6 Hz, 2H), 6.86 (s, 1H), 6.97 (d, J=8.6 Hz, 2H).

melting point: 224° C.

Compound 127c (yield 73%) was obtained in a similar manner to Example 69 using Compound P19. Compound 127c was recrystallized from diisopropyl ether-ethanol (10:1).

APCI-MS: m/z 505 [M+H]$^+$
$^1$H NMR (CDCl$_3$) δ(ppm): 1.62-1.88 (m, 8H), 2.21 (m, 1H), 2.41-2.50 (m, 6H), 2.51 (s, 3H), 2.60 (s, 6H), 3.35 (q, J=5.6 Hz, 2H), 3.55 (brs, 1H), 3.70 (m, 4H), 3.80 (brd, J=7.4 Hz, 1H), 5.30 (s, 2H), 6.02 (m, 1H), 6.49 (d, J=8.4 Hz, 2H), 6.87 (s, 1H), 6.99 (d, J=8.4 Hz, 2H).

melting point: 150-151° C.

Example 72 trans-4-[4-(2,5,7-Trimethyl-3H-imidazo[4,5-b]pyridin-3-ylmethyl)phenylamino]cyclohexanecarboxylic acid [2-(pyrrolidin-1-yl)ethyl]amide (Compound 128)

Compound 128 (0.100 g, 92%) was obtained in a similar manner to Example 69 using Compound P22 (80.0 mg, 0.204 mmol) and 1-(2-aminoethyl)pyrrolidine (0.0390 mL, 0.311 mmol). Compound 128 was triturated with ethyl acetate.

ESI-MS: m/z 489 [M+H]$^+$
$^1$H NMR (CDCl$_3$) δ(ppm): 1.10 (dq, J=2.9, 14.3 Hz, 2H), 1.61 (dq, J=2.9, 12.7 Hz, 2H), 1.75-1.80 (m, 4H), 1.93 (brd, J=14.3 Hz, 2H), 2.08 (tt, J=3.1, 11.9 Hz, 1H), 2.16 (brd, J=9.9 Hz, 2H), 2.50 (s, 3H), 2.49-2.58 (m, 6H), 2.59 (s, 6H), 3.20 (m, 1H), 3.33 (q, J=6.1 Hz, 2H), 3.44 (d, J=7.5 Hz, 1H), 5.29 (s, 2H), 6.08 (brs, 1H), 6.47 (d, J=8.6 Hz, 2H), 6.86 (s, 1H), 6.98 (d, J=8.6 Hz, 2H).

melting point: 218-220° C.

Example 73 trans-4-[2-(Morpholin-4-yl)ethylaminomethyl]cyclohexyl[4-(2,5,7-trimethyl-3H-imidazo[4,5-b]pyridin-3-ylmethyl)phenyl]amine (Compound 129t) and cis-4-[2-(Morpholin-4-yl)ethylaminomethyl]cyclohexyl[4-(2,5,7-trimethyl-3H-imidazo[4,5-b]pyridin-3-ylmethyl)phenyl]amine 2oxalate (Compound 129c)

Compound 129t (0.191 g, 94%) was obtained in a similar manner to Example 70 using Compound 127t (0.210 g, 0.416 mmol). Compound 129t was recrystallized from ethanol-diethyl ether.

ESI-MS: m/z 491 [M+H]$^+$
$^1$H NMR (CDCl$_3$) δ(ppm): 1.01-1.21 (m, 4H), 1.48 (m, 1H), 1.85 (brd, J=10.2 Hz, 2H), 2.12 (brd, J=9.5 Hz, 2H), 2.44-2.49 (m, 8H), 2.51 (s, 3H), 2.60 (s, 6H), 2.69 (t, J=6.2 Hz, 2H), 3.15 (m, 1H), 3.49 (brs, 1H), 3.71 (m, 4H), 5.30 (s, 2H), 6.47 (d, J=8.8 Hz, 2H), 6.87 (s, 1H), 6.98 (d, J=8.4 Hz, 2H).

melting point: 139° C.

Compound 129c was obtained in a similar manner to Example 56 using Compound 127c. Compound 129c (yield 38%) was reslurried with diisopropyl ether.

APCI-MS: m/z 491 [M+H]$^+$
$^1$H NMR (DMSO-d$_6$) δ(ppm): 1.35-1.62 (m, 8H), 1.79 (brs, 1H), 2.40-2.46 (m, 4H), 2.46 (s, 3H), 2.47 (s, 3H), 2.50 (3H, overlapping with the peak of DMSO), 2.57 (t, J=6.3 Hz, 2H), 2.84 (d, J=6.9 Hz, 2H), 3.05 (t, J=6.3 Hz, 2H), 3.40 (m, 1H), 3.58 (m, 4H), 5.23 (s, 2H), 6.52 (d, J=8.6 Hz, 2H), 6.92 (s, 1H), 6.93 (d, J=8.6 Hz, 2H).

melting point: 145-146° C.

Example 74 trans-4-Morpholino-1-{4-[4-(2,5,7-trimethyl-3H-imidazo[4,5-b]pyridin-3-ylmethyl)phenylamino]cyclohexylcarbonyl}piperidine (Compound 130t) and cis-4-Morpholino-1-{4-[4-(2,5,7-trimethyl-3H-imidazo[4,5-b]pyridin-3-ylmethyl)phenylamino]cyclohexylcarbonyl}piperidine (Compound 130c)

Compound 130t (0.174 g, 84%) was obtained in a similar manner to Example 69 using Compound P22 (0.150 g, 0.382 mmol) and 4-(morpholin-4-yl)piperidine (98.0 mg, 0.575 mmol). Compound 130t was recrystallized from ethanol-diethyl ether.

ESI-MS: m/z 545 [M+H]$^+$
$^1$H NMR (CDCl$_3$) δ(ppm): 1.08 (brq, J=11.4 Hz, 2H), 1.34 (brq, J=11.0 Hz, 2H), 1.63-1.88 (m, 6H), 2.15 (m, 2H), 2.37 (m, 1H), 2.48 (s, 3H), 2.50-2.53 (m, 6H), 2.57 (s, 6H), 3.00 (brt, J=12.1 Hz, 1H), 3.20 (m, 1H), 3.48 (brs, 1H), 3.69 (m, 4H), 3.91 (brd, J=13.2 Hz, 1H), 4.62 (brd, J=13.2 Hz, 1H), 5.27 (s, 2H), 6.45 (d, J=8.4 Hz, 2H), 6.84 (s, 1H), 6.96 (d, J=8.4 Hz, 2H)

melting point: 179° C.

Compound 130c (yield 97%) was obtained in a similar manner to Example 69 using Compound P19. Compound 130c was reslurried with diisopropyl ether-ethanol (4:3).

APCI-MS: m/z 545 [M+H]$^+$
$^1$H NMR (CDCl$_3$) δ(ppm): 1.38 (m, 2H), 1.53-1.96 (m, 10H), 2.39 (m, 1H), 2.51 (s, 3H), 2.51-2.57 (m, 6H), 2.60 (s, 6H), 3.02 (brt, J=12.3 Hz, 1H), 3.60 (brs, 1H), 3.71 (m, 4H), 3.85-3.97 (m, 2H), 4.63 (brd, J=13.3 Hz, 1H), 5.30 (s, 2H), 6.48 (d, J=8.4 Hz, 2H), 6.87 (s, 1H), 6.98 (d, J=8.4 Hz, 2H).

melting point: 216-217° C.

Example 75 trans-4-[4-(Morpholin-4-yl)piperidin-1-ylmethyl]cyclohexyl[4-(2-ethyl-7-methyl-3H-imidazo[4,5-b]pyridin-3-ylmethyl)phenyl]amine (Compound 131t) and cis-4-[4-(morpholin-4-yl)piperidin-1-ylmethyl]cyclohexyl[4-(2-ethyl-7-methyl-3H-imidazo[4,5-b]pyridin-3-ylmethyl)phenyl]amine (Compound 131c)

Compound 131t (84.4 mg, 79%) was obtained in a similar manner to Example 70 using Compound 130t (0.110 g, 0.201 mmol).

ESI-MS: m/z 531 [M+H]$^+$
$^1$H NMR (CDCl$_3$) δ(ppm): 0.91-1.07 (m, 4H), 1.47-1.56 (m, 3H), 1.73-1.89 (m, 6H), 2.07-2.15 (m, 5H), 2.47 (s, 3H), 2.49-2.15 (m, 4H), 2.57 (s, 6H), 2.87 (brd, J=11.6 Hz, 2H), 3.10 (m, 1H), 3.69 (m, 4H), 5.27 (s, 2H), 6.44 (d, J=8.4 Hz, 2H), 6.84 (s, 1H), 6.95 (d, J=8.4 Hz, 2H).

Compound 131c (yield 81%) was obtained in a similar manner to Example 70 using Compound 130c.

APCI-MS: m/z 531 [M+H]$^+$
$^1$H NMR (CDCl$_3$) δ(ppm): 1.18-1.30 (m, 2H), 1.43-1.93 (m, 13H), 2.10-2.21 (m, 3H), 2.51 (s, 3H), 2.53 (m, 4H), 2.60

(s, 6H), 2.88 (m, 2H), 3.51 (brs, 1H), 3.68-3.75 (m, 5H), 5.30 (s, 2H), 6.48 (d, J=8.6 Hz, 2H), 6.87 (s, 1H), 6.98 (d, J=8.6 Hz, 2H).

Example 76 cis-4-{4-[4-(2,5,7-Trimethyl-3H-imidazo[4,5-b]pyridine-3-ylmethyl)phenylamino]cyclohexylcarbonyl}morpholine (Compound 131-I)

Compound 131-I (yield 88%) was obtained in a similar manner to Example 54 using Compound P19.
APCI-MS: m/z 462 [M+H]$^+$
$^1$H NMR (CDCl$_3$) δ(ppm): 1.52-1.67 (m, 4H), 1.73-1.95 (m, 4H), 2.51 (s, 3H), 2.54 (m, 1H), 2.60 (s, 6H), 1.46-1.69 (m, 9H), 1.96 (brd, J=8.2 Hz, 1H), 5.30 (s, 2H), 6.48 (d, J=8.2 Hz, 2H), 6.87 (s, 1H), 6.98 (d, J=8.2 Hz, 2H).

Example 77 cis-[4-(Morpholin-4-ylmethyl)cyclohexyl][4-(2,5,7-trimethylimidazo[4,5-b]pyridin-3-ylmethyl)phenyl]amine (Compound 131-II)

Compound 131-II (yield 67%) was obtained in a similar manner to Example 56 using Compound 131-I.
APCI-MS: m/z 448 [M+H]$^+$
$^1$H NMR (CDCl$_3$) δ(ppm): 1.19-1.33 (m, 2H), 1.55-1.71 (m, 7H), 2.18 (d, J=6.9 Hz, 2H), 2.38 (m, 4H), 2.51 (s, 3H), 2.60 (S, 6H), 3.52 (brs, 1H), 3.69 (m, 4H), 5.30 (s, 2H), 6.48 (d, J=8.2 Hz, 2H), 6.87 (s, 1H), 6.98 (d, J=8.2 Hz, 2H).

Example 78 cis-4-Hydroxymethyl-1-{4-[4-(2,5,7-trimethyl-3H-[4,5-b]pyridin-3-ylmethyl)phenylamino]cyclohexylcarbonyl}piperidine (Compound 131-III)

Compound 131-III (yield 100%) was obtained in a similar manner to Example 54 using Compound P19 and piperidin-4-ylmethanol.
APCI-MS: m/z 490 [M+H]$^+$
$^1$H NMR (CDCl$_3$) δ(ppm): 1.05-1.25 (m, 2H), 1.49-1.95 (m, 11H), 2.50 (s, 3H), 2.53 (m, 2H), 2.60 (s, 6H), 3.02 (brt, J=12.3 Hz, 1H), 3.46-3.64 (m, 3H), 3.87-3.96 (m, 2H), 4.66 (brd, J=13.3 Hz, 1H), 5.30 (s, 2H), 6.48 (d, J=8.4 Hz, 2H), 6.87 (s, 1H), 6.98 (d, J=8.4 Hz, 2H).

Example 79 cis-{4-[4-(Hydroxymethyl)piperidin-1-ylmethyl]cyclohexyl}[4-(2,5,7-trimethyl-3H-imidazo[4,5-b]pyridin-3-ylmethyl)phenyl]amine (Compound 131-IV)

Compound 131-IV (yield 62%) was obtained in a similar manner to Example 56 using Compound 131-III.
APCI-MS: m/z 476 [M+H]$^+$
$^1$H NMR (CDCl$_3$) δ(ppm): 1.20-1.98 (m, 16H), 2.18 (m, 2H), 2.50 (s, 3H), 2.60 (s, 6H), 2.88 (m, 2H), 3.46-3.54 (m, 3H), 3.73 (m, 1H), 5.30 (s, 2H), 6.48 (d, J=8.6 Hz, 2H), 6.87 (s, 1H), 6.98 (d, J=8.6 Hz, 2H)
melting point: 81-84° C. (amorphous).

Example 80 trans-4-[4-(2-Ethyl-7-methyl-3H-imidazo[4,5-b]pyridin-3-ylmethyl)phenylamino]cyclohexanecarboxylic acid [2-(morpholin-4-yl)ethyl]amide (Compound 132)

Compound 132 (0.183 g, 95%) was obtained in a similar manner to Example 69 using Compound P25 (0.150 g, 0.382 mmol) and 1-(2-aminoethyl)morpholine (0.0760 mL, 0.579 mmol).
ESI-MS: m/z 505 [M+H]$^+$
$^1$H NMR (CDCl$_3$) δ(ppm): 1.08 (dq, J=2.4, 13.8 Hz, 2H), 1.31 (t, J=7.5 Hz, 3H), 1.58 (dq, J=2.6, 12.5 Hz, 2H), 1.91 (brd, J=13.0 Hz, 2H), 2.06 (tt, J=3.5, 11.9 Hz, 1H), 2.14 (m, 2H), 2.41-2.47 (m, 6H), 2.65 (s, 3H), 2.83 (q, J=7.7 Hz, 2H), 3.18 (m, 1H), 3.29-3.35 (m, 4H), 3.67-3.70 (m, 4H), 5.32 (s, 2H), 6.06 (brs, 1H), 6.45 (d, J=8.4 Hz, 2H), 6.95 (d, J=8.4 Hz, 2H), 6.97 (d, J=5.0 Hz, 1H), 8.18 (d, J=5.0 Hz, 1H).

Example 81 trans-1-{4-[4-(2-Ethyl-7-methyl-3H-imidazo[4,5-b]pyridine-3-ylmethyl)phenylamino]cyclohexylcarbonyl}-4-methylpiperazine (Compound 133)

Compound 133 (89.0 mg, 92%) was obtained in a similar manner to Example 69 using Compound P25 (80.0 mg, 0.204 mmol).
ESI-MS: m/z 475 [M+H]$^+$
$^1$H NMR (CDCl$_3$) δ(ppm): 1.08 (brq, J=11.4 Hz, 2H), 1.31 (t, J=7.7 Hz, 3H), 1.66 (brq, J=13.9 Hz, 2H), 1.78 (brd, J=11.2 Hz, 2H), 2.15 (brd, J=10.6 Hz, 2H), 2.28 (s, 3H), 2.34-2.48 (m, 5H), 2.65 (s, 3H), 2.83 (q, J=7.5 Hz, 2H), 3.20 (m, 1H), 3.48 (brs, 2H), 3.61 (brs, 2H), 5.32 (s, 2H), 6.45 (d, J=8.4 Hz, 2H), 6.95 (d, J=8.2 Hz, 2H), 6.98 (d, J=5.0 Hz, 1H), 8.18 (d, J=5.0 Hz, 1H).

Example 82 trans-4-[4-(2-Ethyl-7-methyl-3H-imidazo[4,5-b]pyridin-3-ylmethyl)phenylamino]cyclohexanecarboxylic acid [2-(pyrrolidin-1-yl)ethyl]amide (Compound 134)

Compound 134 (91.0 mg, 91%) was obtained in a similar manner to Example 69 using Compound P25 (80.0 mg, 0.204 mmol) and 1-(2-aminoethyl)pyrrolidine (0.0390 mL, 0.311 mmol).
ESI-MS: m/z 489 [M+H]$^+$
$^1$H NMR (CDCl$_3$) δ(ppm): 1.19 (dq, J=3.3, 12.7 Hz, 2H), 1.32 (t, J=7.5 Hz, 3H), 1.60 (dq, J=3.3, 13.0 Hz, 2H), 1.74-1.79 (m, 4H), 1.92 (brd, J=12.1 Hz, 2H), 2.07 (tt, J=3.5, 11.9 Hz, 1H), 2.15 (brd, J=10.5 Hz, 2H), 2.50 (brs, 4H), 2.57 (t, J=5.9 Hz, 2H), 2.66 (s, 3H), 2.85 (q, J=7.7 Hz, 2H), 3.19 (m, 1H), 3.33 (q, J=5.7 Hz, 2H), 3.44 (d, J=7.9 Hz, 1H), 5.34 (s, 2H), 6.07 (brs, 1H), 6.46 (d, J=8.6 Hz, 2H), 6.96 (d, J=8.6 Hz, 2H), 6.99 (d, J=5.0 Hz, 1H), 8.19 (d, J=5.0 Hz, 1H).

Example 83 trans-4-{[2-(Morpholin-4-yl)ethyl]aminomethyl}cyclohexyl[4-(2-ethyl-7-methyl-3H-imidazo[4,5-b]pyridin-3-ylmethyl)phenyl]amine (Compound 135)

Compound 135 (0.115 g, 82%) was obtained in a similar manner to Example 70 using Compound 132 (0.144 g, 0.285 mmol).
ESI-MS: m/z 491 [M+H]$^+$ ¹H NMR (CDCl₃) δ(ppm): 0.94-1.23 (m, 4H), 1.30 (t, J=7.7 Hz, 3H), 1.44 (m, 1H), 1.81 (brd, J=9.9 Hz, 2H), 2.08 (brd, J=9.1 Hz, 2H), 2.40-2.48 (m, 8H), 2.64 (s, 3H), 2.66 (t, J=6.2 Hz, 2H), 2.83 (q, J=7.7 Hz, 2H), 3.11 (m, 1H), 3.49 (brs, 1H), 3.67 (m, 4H), 5.32 (s, 2H), 6.44 (d, J=8.4 Hz, 2H), 6.94 (d, J=8.4 Hz, 2H), 6.97 (d, J=5.1 Hz, 1H), 8.18 (d, J=4.8 Hz, 1H).

Example 84 trans-4-[4-(2,7-Dimethyl-3H-imidazo[4,5-b]pyridin-3-ylmethyl)phenylamino]cyclohexanecarboxylic acid [2-(morpholin-4-yl)ethyl]amide (Compound 136)

Compound 136 (0.171 g, 88%) was obtained in a similar manner to Example 69 using Compound P27 (0.150 g, 0.396 mmol) and 1-(2-aminoethyl)morpholine 80.0780 mL, 0.594 mmol).
ESI-MS: m/z 491 [M+H]⁺
¹H NMR (CDCl₃) δ(ppm): 1.11 (dq, J=3.3, 11.4 Hz, 2H), 1.61 (dq, J=2.9, 12.1 Hz, 2H), 1.94 (brd, J=13.2 Hz, 2H), 2.09 (tt, J=3.7, 11.7 Hz, 1H), 2.18 (brd, J=13.9 Hz, 2H), 2.43-2.50 (m, 6H), 2.56 (s, 3H), 2.65 (s, 3H), 3.23 (m, 1H), 3.34 (q, J=5.9 Hz, 2H), 3.69-3.72 (m, 4H), 5.33 (s, 2H), 6.00 (brs, 1H), 6.48 (q, J=8.4 Hz, 2H), 7.00 (d, J=8.4 Hz, 2H), 7.01 (d, J=4.8 Hz, 1H), 8.21 (d, J=4.8 Hz, 1H).

Example 85 trans-1-{4-[4-(2,7-Dimethyl-3H-imidazo[4,5-b]pyridin-3-ylmethyl)phenylamino]cyclohexylcarbonyl}-4-methylpiperazine (Compound 137)

Compound 137 (70.7 mg, 97%) was obtained in a similar manner to Example 69 using Compound P27 (60.0 mg, 0.158 mmol).
ESI-MS: m/z 461 [M+H]⁺
¹H NMR (CDCl₃) δ(ppm): 1.08 (dq, J=3.3, 12.5 Hz, 2H), 1.65 (dq, J=2.2, 13.2 Hz, 2H), 1.77 (brd, J=11.0 Hz, 2H), 2.14 (brd, J=10.6 Hz, 2H), 2.27 (s, 3H), 2.32-2.41 (m, 4H), 2.44 (tt, J=4.6, 11.3 Hz, 1H), 2.52 (s, 3H), 2.62 (s, 3 h), 3.20 (tt, J=3.7, 11.4 Hz, 1H), 3.47 (brs, 2H), 3.59 (brs, 2H), 5.29 (s, 2H), 6.45 (d, J=8.8 Hz, 2H), 6.98 (d, J=8.8 Hz, 2H), 6.99 (d, J=5.8 Hz, 1H), 8.18 (d, J=4.8 Hz, 1H).

Example 86 trans-4-[4-(2,7-Dimethyl-3H-imidazo[4,5-b]pyridin-3-ylmethyl)phenylamino]cyclohexanecarboxylic acid [2-(pyrrolidin-1-yl)ethyl]amide (Compound 138)

Compound 138 (41.0 mg, 54%) was obtained in a similar manner to Example 69 using Compound P27 (60.0 mg, 0.158 mmol) and 1-(2-aminoethyl)pyrrolidine (0.0300 mL, 0.239 mmol).
ESI-MS: m/z 475 [M+H]⁺
¹H NMR (CDCl₃) δ(ppm): 1.08 (dq, J=3.3, 12.8 Hz, 2H), 1.60 (dq, J=2.9, 12.5 Hz, 2H), 1.72-1.82 (m, 4H), 1.92 (brd, J=13.2 Hz, 2H), 2.07 (tt, J=3.7, 12.1 Hz, 1H), 2.14 (brd, J=11.0 Hz, 2H), 2.56 (s, 3H), 2.49-2.60 (m, 6H), 2.64 (s, 3H), 3.20 (m, 1H), 3.33 (q, J=5.5 Hz, 2H), 3.48 (d, J=7.7 Hz, 1H), 5.31 (s, 2H), 6.17 (brs, 1H), 6.46 (d, J=8.4 Hz, 2H), 6.98 (d, J=6.6 Hz, 2H), 6.99 (d, J=8.1 Hz, 2H), 8.19 (d, J=4.8 Hz, 1H).

Example 87 trans-4-{[2-(Morpholin-4-yl)ethyl]aminomethyl}cyclohexyl[4-(2,7-dimethyl-3H-imidazo[4,5-b]pyridin-3-ylmethyl)phenyl]amine (Compound 139)

Compound 139 (78.9 mg, 68%) was obtained in a similar manner to Example 70 using Compound 136 (0.120 g, 0.244 mmol).
ESI-MS: m/z 477 [M+H]⁺
¹H NMR (CDCl₃) δ(ppm): 0.94-1.13 (m, 4H), 1.45 (m, 1H), 1.82 (brd, J=10.2 Hz, 2H), 2.08 (brd, J=9.9 Hz, 2H), 2.39-2.49 (m, 8H), 2.52 (s, 3H), 2.63 (s, 3H), 2.67 (t, J=5.9 Hz, 2H), 3.12 (m, 1H), 3.50 (brs, 1H), 3.67 (m, 4H), 5.29 (s, 2H), 6.44 (d, J=8.4 Hz, 2H), 6.96 (d, J=8.4 Hz, 2H), 6.97 (d, J=4.8 Hz, 1H), 8.18 (d, J=4.8 Hz, 1H).

Example 88

4-[4-(2-Ethyl-5,7-dimethyl-3H-imidazo[4,5-b]pyridin-3-ylmethyl)phenylamino]piperidine (Compound 140)

A solution of Compound 105 (1.44 g, 3.11 mmol) in chloroform (12 mL) was added with a 4 mol/L hydrogen chloride-ethyl acetate solution (9.0 mL), followed by stirring at room temperature for 1.5 hours. After the reaction mixture was concentrated under reduced pressure, the residue was added with a 2 mol/L aqueous sodium hydroxide solution to control the pH to 12, and the mixture was extracted with chloroform three times. The organic layer was dried over anhydrous magnesium sulfate and concentrated under reduced pressure. The obtained crystals were added with diisopropyl ether followed by stirring for 30 minutes, then the crystals were collected by filtration. The crystals were dried under reduced pressure to obtain Compound 140 (0.864 g, 2.38 mmol, 76%).
APCI-MS: m/z 363 [M+H]⁺
¹H NMR (CDCl₃) δ(ppm): 1.22-1.26 (m, 2H), 1.30 (t, J=7.48 Hz, 3H), 1.98-2.01 (m, 2H), 2.57 (s, 3H), 2.59 (s, 3H), 2.63-2.71 (m, 4H), 2.79 (q, J=7.48 Hz, 2H), 3.05-3.09 (m, 2H), 3.29 (s, 1H), 5.30 (s, 2H), 6.47 (d, J=8.35 Hz, 2H), 6.83 (s, 1H), 6.96 (d, J=8.35 Hz, 2H).

Example 89

4-[4-(2-Ethyl-5,7-dimethyl-3H-imidazo[4,5-b]pyridin-3-ylmethyl)phenylamino]-1-(1-methylpiperidin-4-yl)piperidine (Compound 141)

A solution of Compound 140 (0.100 g, 0.28 mmol) in dichloroethane was added with acetic acid (0.48 mL, 0.84 mmol) and 1-methyl-4-piperidone (0.84 mL, 0.68 mmol). After 20 minutes, the mixture was added with sodium triacetoxyborohydride (0.0827 g, 0.39 mmol) followed by stirring at room temperature overnight. The reaction mixture was added with a 2 mol/L aqueous sodium hydroxide solution, and extracted with chloroform three times. The organic layer was dried over anhydrous magnesium sulfate and concentrated under reduced pressure. The residue was recrystallized from diisopropyl ether-ethanol to obtain Compound 141 (0.0767 g, 0.17 mmol, 59%).
APCI-MS: m/z 461 [M+H]⁺
¹H NMR (CDCl₃) δ(ppm): 1.30 (t, J=7.48 Hz, 3H), 1:30-1.46 (m, 2H), 1.54-1.64 (m, 3H), 1.72-1.76 (m, 2H), 1.88-2.01 (m, 4H), 2.24 (s, 3H), 2.26-2.34 (m, 3H), 2.57 (s, 3H), 2.60 (s, 3H), 2.79 (q, J=7.48 Hz, 2H), 2.80-2.85 (m, 4H), 3.20 (s, 1H), 5.30 (s, 2H), 6.47 (d, J=8.44 Hz, 2H), 6.83 (s, 1H), 6.95 (d, J=8.44 Hz, 2H).

Example 90

{4-[4-(2-Ethyl-5,7-dimethyl-3H-imidazo[4,5-b]pyridin-3-ylmethyl)phenylamino]methyl}piperidine-1-carboxylic acid tert-butyl ester (Compound 142)

A solution of Compound P33 (0.277 g, 1.30 mmol) in dichloromethane was added with Compound P7 (0.241 g, 0.86 mmol) and acetic acid (0.345 mL, 6.02 mmol). After 15 minutes, the mixture was added with sodium triacetoxyborohydride (0.547 g, 2.58 mmol) followed by stirring at room temperature for 30 minutes. The reaction mixture was added with a 2 mol/L aqueous sodium hydroxide solution to terminate the reaction, and the mixture was extracted with dichloromethane three times. The organic layer was washed with saturated brine and dried over anhydrous magnesium sulfate, then concentrated under reduced pressure. The residue was purified by silica gel column chromatography (hexane:ethyl acetate=1:4). The obtained solid was recrystallized from ethanol-diisopropyl ether to obtain Compound 142 (0.243 g, 0.51 mmol, 59%).

APCI-MS: m/z 464 [M+H]$^+$
$^1$H NMR (CDCl$_3$) δ(ppm): 1.05-1.25 (m, 2H), 1.30 (t, J=7.49 Hz, 3H), 1.44 (s, 9H), 1.68-1.73 (m, 3H), 2.57 (s, 3H), 2.60 (s, 3H), 2.64-2.68 (m, 2H), 2.78 (q, J=7.49 Hz, 2H), 2.97-2.99 (m, 2H), 3.64 (s, 1H), 4.06-4.11 (m, 2H), 5.31 (s, 2H), 6.47 (d, J=8.44 Hz, 2H), 6.84 (s, 1H), 6.97 (d, J=8.44 Hz, 2H).

Example 91

4-[4-(2-Ethyl-5,7-dimethyl-3H-imidazo[4,5-b]pyridin-3-ylmethyl)phenylamino]methylpiperidine (Compound 143)

A solution of Compound 142 (0.338 g, 0.71 mmol) in chloroform (3.0 mL) was added with a 4 mol/L hydrogen chloride-ethyl acetate solution (2.0 mL) followed by stirring at room temperature for 30 minutes. The reaction mixture was concentrated under reduced pressure and added with a 2 mol/L aqueous sodium hydroxide solution to control the pH to 12. The reaction mixture was extracted with chloroform three times, and the organic layer was dried over anhydrous magnesium sulfate and concentrated under reduced pressure. The residue was purified by silica gel column chromatography (chloroform:2 mol/L ammonia-methanol solution=7:1), and the obtained crystals were recrystallized from ethanol-diisopropyl ether to obtain Compound 143 (43.2 mg, 0.11 mmol, 16%).

APCI-MS: m/z 364 [M+H]$^+$
$^1$H NMR (CDCl$_3$) δ(ppm): 1.12-1.24 (m, 2H), 1.30 (t, J=7.55 Hz, 3H), 1.63-1.76 (m, 3H), 2.55 (dd, J=2.57, 12.10 Hz, 2H), 2.60 (s, 3H), 2.62 (s, 3H), 2.80 (q, J=7.55 Hz, 2H), 2.95 (t, J=12.10 Hz, 2H), 3.06-3.10 (m, 2H), 3.71 (s, 1H), 5.32 (s, 2H), 6.48 (d, J=8.62 Hz, 2H), 6.87 (s, 1H), 6.97 (d, J=8.62 Hz, 2H).

melting point: 165-168° C.

Example 92

1,4-Dioxaspiro[4,5]dec-8-ylmethyl{4-(2-ethyl-5,7-dimethyl-3H-imidazo[4,5-b]pyridin-3-ylmethyl)phenyl}amine (Compound 144)

Compound P7 (500 mg, 1.78 mmol) was suspended in 1,2-dichloroethane (13 mL), and 1,4-dioxaspiro[4,5]decane-8-carboaldehyde (455 mg, 2.68 mmol) and sodium triacetoxyborohydride (755 mg, 3.56 mmol) was added to the suspention at 0° C., followed by stirring at 0° C. for 3 hours. The reaction mixture was added with a 2 mol/L aqueous sodium hydroxide solution and extracted with ethyl acetate twice. The organic layer was washed with saturated brine and dried over anhydrous magnesium sulfate, then concentrated under reduced pressure. The residue was purified by silica gel column chromatography (ethyl acetate:hexane=1:1 to 1:0). The desired compound was recrystallized from diethyl ether to obtain Compound 144 (546 mg, 1.26 mmol, 70.5%).

APCI-MS: m/z 471 [M+H]$^+$
$^1$H NMR (CDCl$_3$) δ(ppm): 1.30 (t, J=7.6 Hz, 3H), 1.32 (m, 2H), 1.47-1.59 (m, 3H), 1.73-1.83 (m, 4H), 2.59 (s, 3H), 2.61 (s, 3H), 2.80 (q, J=7.6 Hz, 2H), 2.97 (brd, J=6.6 Hz, 2H), 3.71 (brs, 1H), 3.94 (s, 4H), 5.32 (s, 2H), 6.47 (d, J=8.6 Hz, 2H), 6.86 (s, 1H), 6.97 (d, J=8.6 Hz, 2H).

Example 93

2-[4-(2-Ethyl-5,7-dimethyl-3-(4-aminobenzyl)-3H-imidazo[4,5-b]pyridin-3-ylmethyl)phenylamino]acetophenone (Compound 145)

Compound P7 (100 mg, 0.36 mmol) was dissolved in THF (3.0 mL), and 2-bromoacetophenone (86 mg, 0.43 mmol) and diisopropylethylamine (0.125 mL, 0.72 mmol) were added to the solution, then the mixture was stirred under reflux. After 8 hours, the reaction mixture was added with water to terminate the reaction, and extracted with ethyl acetate three times. The organic layer was washed with saturated brine and dried over anhydrous magnesium sulfate, then concentrated under reduced pressure. The residue was purified by silica gel column chromatography (hexane:ethyl acetate=1:3). The obtained crystals were recrystallized from ethanol to obtain Compound 145 (69.8 mg, 0.18 mmol, 49%).

APCI-MS: m/z 399 [M+H]$^+$
$^1$H NMR (CDCl$_3$) δ(ppm): 1.30 (t, J=7.6 Hz, 3H), 2.60 (s, 3H), 2.62 (s, 3H), 2.81 (q, J=7.55 Hz, 2H), 4.57 (d, J=8.5 Hz, 2H), 4.93 (s, 1H), 5.35 (s, 2H), 6.61 (d, J=8.53 Hz, 2H), 6.88 (s, 1H), 7.03 (d, J=8.5 Hz, 2H), 7.49-7.53 (m, 2H), 7.59-7.65 (m, 2H), 7.98-8.01 (m, 2H).

Example 94

4-[4-(2-Ethyl-5,7-dimethyl-3H-imidazo[4,5-b]pyridin-3-ylmethyl)phenylamino]methyl-1-(1-methylpiperidin-4-yl)piperidine (Compound 146)

A solution of compound 143 (100 mg, 0.28 mmol) in dichloroethane was added with acetic acid (0.842 mL, 1.47 mmol) and 1-methyl-4-piperidone (0.638 mL, 0.53 mmol). After 10 minutes, the mixture was added with sodium triacetoxyborohydride (0.134 g, 0.63 mmol) followed by stirring at room temperature overnight. The reaction mixture was added with a 2 mol/L aqueous sodium hydroxide solution and extracted with chloroform three times. The organic layer was dried over anhydrous magnesium sulfate and concentrated under reduced pressure. The residue was purified by silica gel column chromatography (chloroform:2 mol/L ammonia-methanol solution=7:1). The obtained crystals were recrystallized from ethanol-diisopropyl ether to obtain Compound 146 (44.2 mg, 0.093 mmol, 44%).

APCI-MS: m/z 475 [M+H]$^+$
$^1$H NMR (CDCl$_3$) δ(ppm): 1.27-1.38 (m, 2H), 1.30 (t, J=7.53 Hz, 3H), 1.53-1.75 (m, 6H), 1.90-1.98 (m, 3H), 2.13-2.25 (m, 3H), 2.25 (s, 3H), 2.57 (s, 3H), 2.60 (s, 3H), 2.79 (q, J=7.53 Hz, 2H), 2.90-2.98 (m, 6H), 5.30 (s, 2H), 6.46 (d, J=8.59 Hz, 2H), 6.81 (s, 1H), 6.96 (d, J=8.59 Hz, 2H).

Example 95

4-[4-(2-Ethyl-5,7-dimethyl-3H-imidazo[4,5-b]Pyridin-3-ylmethyl)phenylamino]-1-(piperidin-4-ylcarbonyl)piperidine (Compound 147)

Step 1

Compound 140 (0.200 g, 0.55 mmol) was dissolved in THF-DMF (1:4)(5.0 mL), and EDC (0.138 g, 0.72 mmol), 1-hydroxybenzotriazole hydrate (89.2 mg, 0.66 mmol) and 1-(tert-butoxycarbonyl)piperidine-4-carboxylic acid (151 mg, 0.66 mmol) were added to the solution, followed by stirring at room temperature overnight. The reaction mixture was added with water and extracted with ethyl acetate three times. The organic layer was washed with water and saturated brine, and dried over anhydrous magnesium sulfate, then concentrated under reduced pressure. The residue was purified by silica gel column chromatography (hexane:ethyl acetate=19:1) to obtain 4-[4-(2-ethyl-5,7-dimethyl-3H-imidazo[4,5-b]pyridin-3-ylmethyl)phenylamino]-1-[1-(tert-butoxycarbonyl)piperidin-4-ylcarbonyl]piperidine (0.311 g, 0.54 mmol, 98%).

APCI-MS: m/z 575 $[M+H]^+$ $^1$H NMR (CDCl$_3$) δ(ppm): 1.22 (t, J=7.70 Hz, 3H), 1.27-1.32 (m, 3H), 1.45 (s, 9H), 1.65-1.73 (m, 5H), 2.02-2.07 (m, 2H), 2.56 (s, 3H), 2.59 (s, 3H), 2.73-2.84 (m, 4H), 2.81 (q, J=7.70 Hz, 2H), 3.46 (m, 1H), 4.07-4.15 (m, 4H), 5.32 (s, 2H), 6.49 (d, J=8.44 Hz, 2H), 6.87 (s, 1H), 6.97 (d, J=8.44 Hz, 2H).

Step 2

A solution of 4-[4-(2-ethyl-5,7-dimethyl-3H-imidazo[4,5-b]pyridin-3-ylmethyl)phenylamino]-1-[1-(tert-butoxycarbonyl)piperidin-4-ylcarbonyl]piperidine (0.311 g, 0.54 mmol) obtained in Step 1 in chloroform (5.0 mL) was added with a 4 mol/L hydrogen chloride-ethyl acetate solution (2.0 mL) followed by stirring at room temperature for 1 hour. The reaction mixture was added with a 2 mol/L aqueous sodium hydroxide solution to control the pH to 12 and extracted with chloroform three times. The organic layer was dried over anhydrous magnesium sulfate and concentrated under reduced pressure. The obtained crystals were added with diisopropyl ether followed by stirring under reflux for 1 hour. The crystals were collected by filtration and dried under reduced pressure to obtain Compound 147 (0.153 g, 0.32 mmol, 60%).

APCI-MS: m/z 475 $[M+H]^+$ $^1$H NMR (CDCl$_3$) δ(ppm): 1.28-1.33 (m, 2H), 1.30 (t, J=7.48 Hz, 3H), 1.65-1.73 (m, 6H), 1.65-1.73 (m, 6H), 2.02-2.06 (m, 2H), 2.57 (s, 3H), 2.60 (s, 3H), 2.57-2.68 (m, 3H), 2.79 (q, J=7.48 Hz, 2H), 3.01-3.16 (m, 4H), 3.45 (s, 1H), 5.31 (s, 2H), 6.49 (d, J=8.44 Hz, 2H), 6.84 (s, 1H), 6.98 (d, J=8.44 Hz, 2H).

Example 96

4-{[4-(2-Ethyl-5,7-dimethyl-3H-imidazo[4,5-b]pyridin-3-ylmethyl)phenylamino]methyl}cyclohexanone (Compound 148)

Compound 144 (488 mg, 1.12 mmol) was dissolved in THF (7.4 mL), and 5% hydrochloric acid (3.7 mL) was added to the solution, followed by stirring at room temperature for 9 hours. The reaction mixture was added with a 2 mol/L aqueous sodium hydroxide solution and extracted with ethyl acetate three times. The organic layer was washed with saturated brine and dried over anhydrous magnesium sulfate, then concentrated under reduced pressure. The residue was purified by silica gel column chromatography (methanol:chloroform=1:19). The desired compound was recrystallized from diethyl ether to obtain Compound 148 (360 mg, 0.922 mmol, 82.1%).

APCI-MS: m/z 471 $[M+H]^+$ $^1$H NMR (CDCl$_3$) δ(ppm): 1.31 (t, J=7.6 Hz, 3H), 1.45 (m, 2H), 1.97-2.18 (m, 3H), 2.26-2.46 (m, 4H), 2.59 (s, 3H), 2.61 (s, 3H), 2.81 (q, J=7.6 Hz, 2H), 3.05 (brd, J=6.6 Hz, 2H), 3.76 (brs, 1H), 5.33 (s, 2H), 6.50 (d, J=8.4 Hz, 2H), 6.88 (s, 1H), 6.99 (d, J=8.6 Hz, 2H).

Example 97

(1,4-Dioxaspiro[4,5]dec-8-yl){4-(2-ethyl-5,7-dimethyl-3H-imidazo[4,5-b]pyridin-3-ylmethyl)phenyl}amine (Compound 149)

Compound 149 (yield 69%) was obtained in a similar manner to Example 92 using 1,4-dioxaspiro[4,5]decan-8-one.

APCI-MS: m/z 421 $[M+H]^+$ $^1$H NMR (DMSO-d$_6$) δ(ppm): 1.22 (t, J=7.4 Hz, 3H), 1.32-1.58 (m, 4H), 1.67 (m, 2H), 1.80 (m, 2H), 2.51 (6H, overlapping with the peak of DMSO), 2.78 (q, J=7.4 Hz, 2H), 3.24 (m, 1H), 3.84 (s, 4H), 5.23 (s, 2H), 5.48 (brd, J=8.1 Hz, 1H), 6.48 (d, J=8.4 Hz, 2H), 6.90 (d, J=8.4 Hz, 2H), 6.92 (s, 1H).

Example 98

[4-(2-Ethyl-5,7-dimethyl-3H-imidazo[4,5-b]pyridin-3-ylmethyl)phenyl][4-(4-methylpiperazin-1-yl)cyclohexylmethyl]amine 2fumalate (Compound 150)

Compound 148 (110 mg, 0.282 mmol) was dissolved in 1,2-dichloroethane (2.8 mL) and 1-methylpiperazine (0.625 mL, 0.563 mmol) and sodium triacetoxyborohydride (119 mg, 0.563 mmol) were added to the solution, followed by stirring at room temperature for 4 hours. The reaction mixture was added with a 2 mol/L aqueous sodium hydroxide solution and extracted with ethyl acetate three times. The organic layer was washed with saturated brine and dried over anhydrous magnesium sulfate, then concentrated under reduced pressure. The residue was purified by silica gel column chromatography (2 mol/L ammonia-methanol solution:chloroform=1:19). The obtained compound was dissolved in THF, and the solution was added with a solution of fumaric acid (68.7 mg, 0.592 mmol) in THF. The precipitates were collected by filtration to obtain Compound 150 (137 mg, 0.194 mmol, 68.8%).

APCI-MS: m/z 475 $[M+H]^+$ $^1$H NMR (DMSO-d$_6$) δ(ppm): 0.82-1.22 (m, 1H), 1.22 (t, J=7.4 Hz, 3H), 1.32-1.88 (m, 8H), 2.23-2.90 (m, 22H), 5.24 (s, 2H), 6.42-6.50 (m, 2H), 6.58 (s, 4H), 6.88-6.95 (m, 3H).

Example 99

4-[4-(2-Ethyl-5,7-dimethyl-3H-imidazo[4,5-b]pyridin-3-ylmethyl)phenylamino]cyclohexanone (Compound 151)

Compound 151 (yield 59%) was obtained in a similar manner to Example 148 using Compound 149.

APCI-MS: m/z 377 $[M+H]^+$

¹H NMR (CDCl₃) δ(ppm): 1.31 (t, J=7.5 Hz, 3H), 1.71 (m, 2H), 2.30 (m, 2H), 2.44 (m, 4H), 2.60 (s, 3H), 2.62 (s, 3H), 2.81 (q, J=7.5 Hz, 2H), 3.59 (brs, 1H), 3.70 (brs, 1H), 5.34 (s, 2H), 6.53 (d, J=8.6 Hz, 2H), 6.87 (s, 1H), 7.00 (d, J=8.6 Hz, 2H).

Example 100 trans-4-{[4-(2-Ethyl-5,7-dimethyl-3H-imidazo[4,5-b]pyridin-3-ylmethyl)phenylamino]methyl}cyclohexanol (Compound 152)

Lithium aluminum hydride (23.3 mg, 0.616 mmol) was suspended in THF (0.6 mL), and a solution of aluminum chloride (41.1 mg, 0.308 mmol) in THF (0.6 mL) was added to the suspension at 0° C., followed by stirring for 5 minutes. Then the mixture was added with a solution of Compound 148 (60.0 mg, 0.154 mmol) in THF (1.4 mL) followed by stirring at 0° C. for 0.5 hours. The reaction mixture was added with 2 mol/L aqueous sodium hydroxide solution and extracted with ethyl acetate twice. The organic layer was washed with saturated brine, and dried over anhydrous magnesium sulfate, then concentrated under reduced pressure. The residue was purified by silica gel column chromatography (methanol:chloroform=1:49). The obtained compound was crystallized from diethyl ether to obtain Compound 152 (cis:trans=15:85, 38.1 mg, 0.0971 mmol, 63.2%).

APCI-MS: m/z 393 [M+H]⁺

¹H NMR (CDCl₃) δ(ppm): 1.02 (dq, J=12.6, 2.6 Hz, 2×0.85H), 1.25 (m, 2×0.85H), 1.30 (t, J=7.6 Hz, 3H), 1.42-1.78 (m, 8×0.15H), 1.85 (brd, J=12.6 Hz, 2×0.85H), 2.00 (brd, J=12.6 Hz, 2×0.85H), 2.59 (s, 3H), 2.61 (s, 3H), 2.80 (q, J=7.6 Hz, 2H), 2.92 (d, J=6.6 Hz, 2×0.85H), 2.97 (d, J=6.1 Hz, 2×0.15H), 3.57 (m, 0.85H), 3.68 (m, 1H), 4.00 (m, 0.15H), 5.32 (s, 2H), 6.47 (d, J=8.4 Hz, 2H), 6.87 (s, 1H), 6.97 (d, J=8.4 Hz, 2H).

Example 101

4-{[4-(2-Ethyl-5,7-dimethyl-3H-imidazo[4,5-b]pyridin-3-ylmethyl)phenylamino]methyl}tetrahydropyran (Compound 153)

A solution of Compound P7 (0.150 g, 0.54 mmol) in dichloromethane was added with tetrahydropyran-4-carboaldehyde (98.2 mg, 0.86 mmol) and acetic acid (0.010 mL, 0.17 mmol) followed by stirring for 20 minutes. Then, the mixture was added with sodium triacetoxyborohydride (0.343 g, 1.62 mmol) followed by stirring at room temperature for 3.5 hours. The reaction mixture was added with a 2 mol/L aqueous sodium hydroxide solution to terminate the reaction and extracted with dichloromethane three times. The organic layer was dried over anhydrous magnesium sulfate and concentrated under reduced pressure. The residue was purified by silica gel column chromatography (hexane:ethyl acetate=1:1). The obtained crystals were recrystallized from ethanol-diisopropyl ether to obtain Compound 153 (82.8 mg, 0.22 mmol, 41%).

APCI-MS: m/z 379 [M+H]⁺

¹H NMR (CDCl₃) δ(ppm): 1.30 (t, J=7.57 Hz, 3H), 1.28-1.41 (m, 2H), 1.65-1.69 (m, 2H), 1.69-1.76 (m, 1H), 2.60 (s, 3H), 2.62 (s, 3H), 2.81 (q, J=7.57 Hz, 2H), 2.97-2.99 (m, 2H), 3.32-3.41 (m, 2H), 3.71 (s, 1H), 3.95-4.00 (m, 2H), 5.32 (s, 2H), 6.49 (d, J=8.51 Hz, 2H), 6.87 (s, 1H), 6.98 (d, J=8.51 Hz, 2H).

Example 102

4-[4-(2-Ethyl-5,7-dimethyl-3H-imidazo[4,5-b]pyridin-3-ylmethyl)phenylamino]methyl-1-(4-tetrahydropyranyl)piperidine (Compound 154)

A solution of Compound 143 (0.166 g, 0.44 mmol) in dichloroethane was added with acetic acid (0.176 mL, 3.08 mmol) and tetrahydro-4-pyranone (0.224 mL, 2.42 mmol) followed by stirring for 20 minutes. The mixture was added with sodium triacetoxyborohydride (0.345 g, 1.63 mmol) followed by stirring at room temperature overnight. The reaction mixture was added with a 2 mol/L aqueous sodium hydroxide solution and extracted with chloroform three times. The organic layer was dried over anhydrous magnesium sulfate and concentrated under reduced pressure. The residue was purified by silica gel column chromatography (chloroform:2 mol/L ammonia-methanol solution=7:1). The obtained crystals were recrystallized from ethanol-diisopropyl ether to obtain Compound 154 (44.2 mg, 0.093 mmol, 44%).

APCI-MS: m/z 462 [M+H]⁺

¹H NMR (CDCl₃) δ(ppm): 1.24-1.33 (m, 2H), 1.30 (t, J=7.52 Hz, 3H), 1.53-1.66 (m, 2H), 1.74-1.80 (m, 5H), 2.13-2.25 (m, 2H), 2.47 (s, 1H), 2.60 (s, 3H), 2.62 (s, 3H), 2.79 (q, J=7.52 Hz, 2H), 2.97-3.00 (m, 4H), 3.32-3.40 (m, 2H), 3.71 (s, 1H), 3.99-4.04 (m, 2H), 5.32 (s, 2H), 6.47 (d, J=8.62 Hz, 2H), 6.87 (s, 1H), 6.97 (d, J=8.62 Hz, 2H).

Example 103

4-[4-(2-Ethyl-5,7-dimethyl-3H-imidazo[4,5-b]pyridin-3-ylmethyl)phenylamino]tetrahydropyran (Compound 155)

A solution of Compound P7 (0.150 g, 0.54 mmol) in dichloromethane was added with tetrahydro-4-pyranone (0.075 mL, 0.81 mmol) and acetic acid (0.216 mL, 3.78 mmol) followed by stirring for 30 minutes. The mixture was added with sodium triacetoxyborohydride (0.343 g, 1.62 mmol) followed by stirring at room temperature overnight. The reaction mixture was added with a 2 mol/L aqueous sodium hydroxide solution to terminate the reaction and extracted with dichloromethane three times. The organic layer was dried over anhydrous magnesium sulfate and concentrated under reduced pressure. The residue was purified by silica gel column chromatography (hexane:ethyl acetate=1:1). The obtained crystals were recrystallized from ethanol-diisopropyl ether to obtain Compound 155 (53.0 mg, 0.15 mmol, 27%).

APCI-MS: m/z 365 [M+H]⁺

¹H NMR (CDCl₃) δ(ppm): 1.30 (t, J=7.49 Hz, 3H), 1.41-1.49 (m, 2H), 1.95-1.99 (m, 2H), 2.57 (s, 3H), 2.59 (s, 3H), 2.79 (q, J=7.49 Hz, 2H), 3.42-3.46 (m, 4H), 3.92-3.97 (m, 2H), 5.31 (s, 2H), 6.49 (d, J=8.62 Hz, 2H), 6.84 (s, 1H), 6.97 (d, J=8.62 Hz, 2H).

Example 104

4-[4-(2-Ethyl-5,7-dimethyl-3H-imidazo[4,5-b]pyridin-3-ylmethyl)phenylamino]methyl-1-(1-methylethyl)piperidine (Compound 156)

A solution of Compound 143 (0.150 g, 0.40 mmol) in ethanol was added with acetone (0.029 mL, 0.40 mmol) and titanium tetraisopropoxide (0.149 mL, 0.50 mmol). After 1 hour, the mixture was added with sodium cyanoborohydride (17 mg, 0.27 mmol) followed by stirring at room temperature overnight. The reaction mixture was added with water and extracted with chloroform three times. The organic layer was dried over anhydrous magnesium sulfate and concentrated under reduced pressure. The residue was purified by silica gel column chromatography (chloroform:2 mol/L ammonia-methanol solution=19:1). The obtained crystals were recrystallized from ethanol-diisopropyl ether to obtain Compound 156 (21.5 mg, 0.051 mmol, 13%).

APCI-MS: m/z 420 [M+H]$^+$ $^1$H NMR (CDCl$_3$) δ(ppm): 1.07 (d, J=6.61 Hz, 2H), 1.30 (t, J=7.53 Hz, 3H), 1.38-1.45 (m, 2H), 1.53-1.63 (m, 6H), 1.76-1.80 (m, 3H), 2.12-2.20 (m, 2H), 2.60 (s, 3H), 2.61 (s, 3H), 2.80 (q, J=7.53 Hz, 2H), 2.93-2.98 (m, 6H), 5.32 (s, 2H), 6.47 (d, J=8.59 Hz, 2H), 6.87 (s, 1H), 6.97 (d, J=8.59 Hz, 2H).

Example 105

4-[4-(2,5,7-Trimethyl-3H-imidazo[4,5-b]pyridin-3-ylmethyl)phenylamino]methylpiperidine (Compound 157)

Step 1

A solution of Compound P33 (1.44 g, 6.77 mmol) in dichloromethane was added with Compound P11 (1.20 g, 4.51 mmol) and acetic acid (0.074 mL, 1.35 mmol) followed by stirring for 15 minutes. The mixture was added with Sodium triacetoxyborohydride (2.86 g, 13.5 mmol) followed by stirring at room temperature for 1.5 hours. The reaction mixture was added with a 2 mol/L aqueous sodium hydroxide solution to terminate the reaction and extracted with dichloromethane three times. The organic layer was dried over anhydrous magnesium sulfate and concentrated under reduced pressure. The residue was purified by silica gel column chromatography (hexane:ethyl acetate=1:2) to obtain 4-[4-(2,5,7-trimethyl-3H-imidazo[4,5-b]pyridin-3-ylmethyl)phenylamino]methylpiperidine-1-carboxylic acid tert-butyl ester (1.60 g, 3.45 mmol, 77%).

APCI-MS: m/z 464 [M+H]$^+$ $^1$H NMR (CDCl$_3$) δ(ppm): 1.06-1.26 (m, 2H), 1.45 (s, 9H), 1.63-1.75 (m, 3H), 2.51 (s, 3H), 2.60 (s, 6H), 2.60-2.71 (m, 2H), 2.97-2.99 (m, 2H), 3.74 (s, 1H), 4.09-4.11 (m, 2H), 5.30 (s, 2H), 6.47 (d, J=8.59 Hz, 2H), 6.87 (s, 1H), 6.97 (d, J=8.59 Hz, 2H).

Step 2

A solution of 4-[4-(2,5,7-trimethyl-3H-imidazo[4,5-b]pyridin-3-ylmethyl)phenylamino]methylpiperidine-1-carboxylic acid tert-butyl ester (1.53 g, 3.31 mmol) obtained in Step 1 in chloroform (15 mL) was added with a 4 mol/L hydrogen chloride-ethyl acetate solution (7.0 mL) followed by stirring at room temperature for 2 hours. The reaction mixture was added with a 2 mol/L aqueous sodium hydroxide solution to control the pH to 12, and extracted with chloroform three times. The organic layer was dried over anhydrous magnesium sulfate and concentrated under reduced pressure to obtain Compound 157 (1.20 g, 3.3 mmol, 99%).

APCI-MS: m/z 364 [M+H]$^+$ $^1$H NMR (CDCl$_3$) δ(ppm): 1.12-1.24 (m, 2H), 1.60-1.76 (m, 3H), 1.86 (m, 2H), 2.50 (s, 3H), 2.58-2.62 (m, 2H), 2.60 (s, 6H), 2.93-2.98 (m, 2H), 3.06-3.11 (m, 2H), 5.30 (s, 2H), 6.49 (d, J=8.58 Hz, 2H), 6.87 (s, 1H), 7.02 (d, J=8.58 Hz).

Example 106

4-[4-(2,5,7-Trimethyl-3H-imidazo[4,5-b]pyridin-3-ylmethyl)phenylamino]methyl-1-(4-tetrahydropyranyl)piperidine (Compound 158)

A solution of Compound 157 (0.250 g, 0.69 mmol) in 1,2-dichloroethane was added with tetrahydro-4-pyranone (0.096 mL, 1.04 mmol) followed by stirring for 15 minutes. The mixture was added with sodium triacetoxyborohydride (0.439 g, 2.07 mmol) followed by stirring at room temperature for 5 hours. The reaction mixture was added with a 2 mol/L aqueous sodium hydroxide solution and extracted with dichloromethane three times. The organic layer was dried over anhydrous magnesium sulfate and concentrated under reduced pressure. The residue was purified by silica gel column chromatography (chloroform:2 mol/L ammonia-methanol solution=19:1). The obtained crystals were recrystallized from ethanol-diisopropyl ether to obtain Compound 158 (0.166 g, 0.37 mmol, 54%).

APCI-MS: m/z 448 [M+H]$^+$ $^1$H NMR (CDCl$_3$) δ(ppm): 1.24-1.36 (m, 2H), 1.62-1.65 (m, 3H), 1.72-1.76 (m, 4H), 2.08-2.16 (m, 2H), 2.41-2.50 (m, 1H), 2.50 (s, 3H), 2.60 (s, 6H), 2.95-2.99 (m, 4H), 3.32-3.40 (m, 2H), 3.72 (s, 1H), 3.99-4.04 (m, 2H), 5.30 (s, 2H), 6.48 (d, J=8.59 Hz, 2H), 6.87 (s, 1H), 6.99 (d, J=8.59 Hz, 2H).

melting point: 148-150° C.

Example 107

4-[4-(2,5,7-Trimethyl-3H-imidazo[4,5-b]pyridin-3-ylmethyl)phenylamino]methyl-1-methylpiperidine (Compound 159)

Step 1

A solution of Compound P37 (0.50 g, 1.88 mmol) in THF-DMF (1:1) (6.0 mL) was added with EDC (0.468 g, 2.44 mmol), 1-hydroxybenzotriazole hydrate (0.305 g, 2.26 mmol), and 1-methylpiperidine-4-carboxylic acid hydrate (0.406 g, 2.26 mmol) followed by stirring at room temperature for 12 hours. The reaction mixture was added with a 1 mol/L aqueous sodium hydroxide solution and extracted with chloroform three times. The organic layer was washed with a 1 mol/L aqueous sodium hydroxide solution, water, saturated brine, and dried over anhydrous magnesium sulfate, then concentrated under reduced pressure. The residue was purified by silica gel column chromatography (chloroform:2 mol/L ammonia-methanol solution=19:1) to obtain 1-methylpiperidine-4-carboxylic acid [4-(2,5,7-trimethyl-3H-imidazo[4,5-b]pyridin-3-ylmethyl)phenylamide] (0.596 g, 1.52 mmol, 81%).

APCI-MS: m/z 392 [M+H]$^+$ $^1$H NMR (CDCl$_3$) δ(ppm): 1.86-2.01 (m, 2H), 2.15-2.21 (m, 1H), 2.27 (s, 3H), 2.46 (s, 3H), 2.59 (s, 3H), 2.61 (s, 3H), 2.89-2.94 (m, 2H), 5.39 (s, 2H), 6.89 (s, 1H), 7.09 (d, J=8.59 Hz, 2H), 7.30 (s, 1H), 7.43 (d, J=8.59 Hz, 2H).

Step 2

Under argon atmosphere, a solution of aluminum trichloride (0.136 g, 1.02 mmol) in THF (2.5 mL) was dropped into a solution of lithium aluminum hydride (77.4 mg, 2.04 mmol) in THF (3.0 mL) at 0° C. Then, a solution of 1-methylpiperidine-4-carboxylic acid [4-(2,5,7-trimethyl-3H-imidazo[4,5-b]pyridin-3-ylmethyl)phenyl amide] (1.53 g, 3.31 mmol) obtained in Step 1 in THF (3.0 mL) was dropped into the mixture. The mixture was stirred at 0° C. for 15 minutes, then at room temperature for 1.5 hours. The reaction mixture was added with a 2 mol/L aqueous sodium hydroxide solution and extracted with ethyl acetate three times. The organic layer was washed with saturated brine and dried over anhydrous magnesium sulfate, then concentrated under reduced pressure. The obtained crystals were recrystallized from ethanol-diisopropyl ether to obtain Compound 159 (44.3 mg, 0.12 mmol, 23%).

APCI-MS: m/z 378 [M+H]$^+$

¹H NMR (CDCl₃) δ(ppm): 1.26-1.39 (m, 2H), 1.49-1.53 (m, 1H), 1.72-1.94 (m, 3H), 2.26 (s, 3H), 2.50 (s, 3H), 2.60 (s, 6H), 2.84-2.88 (m, 2H), 2.97 (s, 2H), 3.71 (s, 2H), 5.30 (s, 2H), 6.49 (d, J=8.34 Hz, 2H), 6.87 (s, 1H), 6.97 (d, J=8.34 Hz, 2H).

Example 108

4-[4-(2,5,7-Trimethyl-3H-imidazo[4,5-b]pyridin-3-ylmethyl)phenylamino]methyl-1-(1-methylpiperidin-4-yl)piperidine (Compound 160)

A solution of Compound 157 (0.250 g, 0.69 mmol) in 1,2-dichloroethane was added with 1-methyl-4-piperidone (0.128 mL, 1.04 mmol) followed by stirring for 20 minutes. The mixture was added with sodium triacetoxyborohydride (0.439 g, 2.07 mmol) followed by stirring at room temperature for 4 hours. The reaction mixture was added with a 2 mol/L aqueous sodium hydroxide solution and extracted with dichloromethane three times. The organic layer was dried over anhydrous magnesium sulfate and concentrated under reduced pressure. The residue was purified by silica gel column chromatography (chloroform:2 mol/L ammonia-methanol solution=19:1). The obtained crystals were recrystallized from ethanol-diisopropyl ether to obtain Compound 160 (0.139 g, 0.30 mmol, 44%).

APCI-MS: m/z 461 [M+H]⁺

¹H NMR (CDCl₃) δ(ppm): 1.22-1.37 (m, 2H), 1.55-1.68 (m, 4H), 1.74-1.79 (m, 8H), 1.88-1.96 (m, 2H), 2.13-2.22 (m, 2H), 2.28 (s, 3H), 2.50 (s, 3H), 2.60 (s, 3H), 2.90-2.96 (m, 6H), 3.72 (s, 1H), 5.30 (s, 2H), 6.47 (d, J=8.51 Hz, 2H), 6.87 (s, 1H), 6.99 (d, J=8.51 Hz, 2H).

melting point: 118-120° C.

Example 109

4-[4-(2,5,7-Trimethyl-3H-imidazo[4,5-b]pyridin-3-ylmethyl)phenylamino]methyl-1-(1-methylethyl)piperidine (Compound 161)

A solution of Compound 157 (0.350 g, 0.97 mmol) in 1,2-dichloroethane was added with acetone (0.106 mL, 1.46 mmol) followed by stirring for 20 minutes. The mixture was added with sodium triacetoxyborohydride (0.616 g, 2.91 mmol) followed by stirring at room temperature overnight. The reaction mixture was added with a 2 mol/L aqueous sodium hydroxide solution and extracted with dichloromethane three times. The organic layer was dried over anhydrous magnesium sulfate and concentrated under reduced pressure. The residue was purified by silica gel column chromatography (chloroform:2 mol/L ammonia-methanol solution=19:1). The obtained crystals were recrystallized from ethanol-diisopropyl ether to obtain Compound 161 (0.205 g, 0.51 mmol, 52%).

APCI-MS: m/z 406 [M+H]⁺

¹H NMR (CDCl₃) δ(ppm): 1.03 (d, J=6.60 Hz, 6H), 1.28-1.33 (m, 2H), 1.51-1.56 (m, 1H), 1.74-1.78 (m, 2H), 2.07-2.14 (m, 2H), 2.50 (s, 3H), 2.60 (s, 6H), 2.66-2.73 (m, 1H), 2.87-2.91 (m, 2H), 2.95-2.99 (m, 2H), 3.71-3.72 (m, 1H), 5.30 (s, 2H), 6.48 (d, J=8.53 Hz, 2H), 6.87 (s, 1H), 6.99 (d, J=8.53 Hz, 2H).

melting point: 134-136° C.

Example 110 trans-4-{4-[2-(Furan-2-yl)-5,7-dimethyl-3H-imidazo[4,5-b]pyridin-3-ylmethyl]phenylamino}cyclohexanecarboxylic acid (2-morpholinoethyl)amide (Compound 162)

Compound 162 (83.6 mg, 95%) was obtained in a similar manner to Example 69 using Compound P29 (75.0 mg, 0.158 mmol) and 1-(2-aminoethyl)morpholine (0.032 mL, 0.244 mmol).

ESI-MS: m/z 557 [M+H]⁺

¹H NMR (CDCl₃) δ(ppm): 1.08 (dq, J=2.4, 14.0 Hz, 2H), 1.58 (dq, J=2.6, 15.3 Hz, 2H), 1.91 (brd, J=12.9 Hz, 2H), 2.06 (tt, J=3.5, 12.0 Hz, 1H), 2.14 (brd, J=11.9 Hz, 2H), 2.42-2.48 (m, 6H), 2.61 (s, 3H), 2.66 (s, 3H), 3.18 (m, 1H), 3.33 (q, J=5.6 Hz, 2H), 3.67-3.81 (m, 4H), 5.63 (s, 2H), 6.02 (brs, 1H), 6.43 (d, J=8.6 Hz, 2H), 6.51 (dd, J=1.7, 3.5 Hz, 1H), 6.95 (d, J=8.6 Hz, 2H), 6.97 (d, J=3.5 Hz, 1H), 6.96 (s, 1H), 7.60 (d, J=1.3 Hz, 1H).

Example 111 trans-1-{4-{4-[2-(Furan-2-yl)-5,7-dimethyl-3H-imidazo[4,5-b]pyridin-3-ylmethyl]phenylamino}cyclohexylcarbonyl}-4-methylpiperazine (Compound 163)

Compound 163 (83.2 mg, 100%) was obtained in a similar manner to Example 69 using Compound P29 (75.0 mg, 0.158 mmol).

ESI-MS: m/z 527 [M+H]⁺

¹H NMR (CDCl₃) δ(ppm): 1.08 (brq, J=11.4 Hz, 2H), 1.65 (brq, J=13.2 Hz, 2H), 1.76 (brd, J=10.9 Hz, 2H), 2.14 (brd, J=10.7 Hz, 2H), 2.29 (s, 3H), 2.60 (s, 3H), 2.65 (s, 3H), 2.36-2.43 (m, 5H), 3.19 (m, 1H), 3.48 (brs, 2H), 3.61 (brs, 2H), 5.63 (s, 2H), 6.42 (d, J=8.4 Hz, 2H), 6.50 (dd, J=1.7, 3.3 Hz, 1H), 6.91 (s, 1H), 6.95 (d, J=3.1 Hz, 1H), 6.97 (d, J=8.3 Hz, 2H), 7.59 (d, J=1.5 Hz, 1H).

Example 112

4-[4-(2-Ethyl-7-methyl-3H-imidazo[4,5-b]pyridin-3-ylmethyl)phenylamino]methylpiperidine-1-carboxylic acid tert-butyl ester (Compound 164)

A solution of Compound P33 (0.810 g, 3.80 mmol) in dichloromethane was added with Compound P35 (0.809 g, 3.04 mmol) followed by stirring for 15 minutes. The mixture was added with Sodium triacetoxyborohydride (1.93 g, 9.12 mmol) followed by stirring at room temperature for 2 hours. The reaction mixture was added with a 2 mol/L aqueous sodium hydroxide solution to terminate the reaction and extracted with dichloromethane three times. The organic layer was dried over anhydrous magnesium sulfate and concentrated under reduced pressure. The residue was purified by silica gel column chromatography (hexane:ethyl acetate=1:2) to obtain Compound 164 (1.44 g, 3.04 mmol, 100%).

APCI-MS: m/z 464 [M+H]⁺

¹H NMR (CDCl₃) δ(ppm): 1.12-1.16 (m, 2H), 1.33 (t, J=7.49 Hz, 3H), 1.45 (s, 9H), 1.66-1.73 (m, 3H), 2.62-2.71 (m, 2H), 2.67 (s, 3H), 2.87 (q, J=7.49 Hz, 2H), 2.96-2.98 (m, 2H), 4.09 (s, 1H), 5.35 (s, 2H), 6.48 (d, J=8.44 Hz, 2H), 6.98 (d, J=8.44 Hz, 2H), 7.00 (d, J=5.14 Hz, 1H), 8.21 (d, J=5.14 Hz, 1H).

Example 113

4-[4-(2-Ethyl-7-methyl-3H-imidazo[4,5-b]pyridine-3-ylmethyl)phenylamino]methylpiperidine (Compound 165)

A solution of Compound 164 (1.44 g, 3.04 mmol) in chloroform (15 mL) was added with a 4 mol/L hydrogen chloride-ethyl acetate solution (7.0 mL) followed by stirring at room temperature for 2 hours. The reaction mixture was added with a 2 mol/L aqueous sodium hydroxide solution to control the pH to 12, and extracted with chloroform three times. The organic layer was dried over anhydrous magnesium sulfate and concentrated under reduced pressure to obtain Compound 165 (1.03 g, 2.84 mmol, 93%).

APCI-MS: m/z 364 [M+H]$^+$ $^1$H NMR (CDCl$_3$) δ(ppm): 1.12-1.23 (m, 2H), 1.33 (t, J=7.57 Hz, 3H), 1.62-1.71 (m, 4H), 2.53-2.62 (m, 2H), 2.67 (m, 3H), 2.86 (q, J=7.57 Hz, 2H), 2.95-2.97 (m, 2H), 3.06-3.10 (m, 2H), 3.72 (s, 1H), 5.35 (s, 2H), 6.73 (d, J=8.59 Hz, 2H), 6.97-7.00 (m, 3H), 8.20 (d, J=4.95 Hz, 1H).

Example 114

4-[4-(2-Ethyl-7-methyl-3H-imidazo[4,5-b]pyridin-3-ylmethyl)phenylamino]methyl-1-(1-methylpiperidin-4-yl)piperidine (Compound 166)

A solution of Compound 165 (0.250 g, 0.69 mmol) in 1,2-dichloroethane (3.5 mL) was added with 1-methyl-4-piperidone (0.128 mL, 1.04 mmol) followed by stirring for 20 minutes. The mixture was added with sodium triacetoxyborohydride (0.439 g, 2.07 mmol) followed by stirring at room temperature for 4 hours. The reaction mixture was added with a 2 mol/L aqueous sodium hydroxide solution, and extracted with dichloromethane three times. The organic layer was dried over anhydrous magnesium sulfate and concentrated under reduced pressure. The residue was purified by silica gel column chromatography (chloroform:2 mol/L ammonia-methanol solution=19:1). The obtained crystals were recrystallized from ethanol-diisopropyl ether to obtain Compound 166 (0.172 g, 0.37 mmol, 54%).

APCI-MS: m/z 461 [M+H]$^+$ $^1$H NMR (CDCl$_3$) δ(ppm): 1.25-1.29 (m, 2H), 1.33 (t, J=7.60 Hz, 3H), 1.57-1.62 (m, 3H), 1.73-1.77 (m, 4H), 2.12-2.20 (m, 3H), 2.25 (s, 3H), 2.67 (s, 6H), 2.86 (q, J=7.60 Hz, 2H), 2.87-2.98 (m, 6H), 3.69-3.73 (m, 1H), 5.35 (s, 2H), 6.47 (d, J=8.44 Hz, 2H), 7.00 (d, J=4.86 Hz, 1H), 8.20 (d, J=4.86 Hz, 1H).

Example 115

{5-(2-Ethyl-5,7-dimethylimidazo[4,5-b]pyridin-3-ylmethyl)pyrimidin-2-yl}phenylamine hydrochloride (Compound 167)

Step 1

Commercially available ethyl 4-chloro-2-(methylthio)pyrimidine-5-carboxylate (5.00 g, 21.5 mmol) was dissolved in ethanol (72 mL) and water (14 mL), and zinc powder (14.0 g, 214 mmol) was added to the solution. Then, the mixture was added with acetic acid (2.95 mL, 51.5 mmol) in three portions, followed by stirring at room temperature for 2 hours. After removing the insoluble material by filtration, the filtrate was concentrated under reduced pressure. The residue was dissolved in chloroform, and the organic layer was separated from the aqueous layer. The organic layer was sequentially washed with water and saturated brine, and dried over anhydrous magnesium sulfate, then concentrated under reduced pressure. The residue was purified by silica gel column chromatography (ethyl acetate:hexane=1:20) to obtain ethyl 2-(methylthio)pyrimidine-5-carboxylate (1.54 g, 36%).

ESI-MS: m/z 199 [M+H]$^+$ $^1$H NMR (CDCl$_3$) δ(ppm): 1.41 (t, J=7.1 Hz, 3H), 2.61 (s, 3H), 4.41 (q, J=7.1 Hz, 2H), 9.02 (s, 2H).

Step 2

Ethyl 2-(methylthio)pyrimidine-5-carboxylate (0.800 g, 4.03 mmol) obtained in Step 1 was dissolved in dichloromethane (40 mL), and m-chloroperbenzoic acid (1.61 g, 6.06 mmol) was added to the solution, followed by stirring at room temperature for 1 hour. After the reaction mixture was diluted with dichloromethane, the dilute solution was washed with a saturated aqueous sodium hydrogen carbonate solution and water, and dried over anhydrous magnesium sulfate and concentrated under reduced pressure. The residue was dissolved in dioxane (20 mL), and the solution was added with aniline (0.730 mL, 8.01 mmol) followed by stirring at 90° C. for 6 hours. After the reaction mixture was diluted with an aqueous (+)-potassium sodium tartrate solution and ethyl acetate, the organic layer was washed with water and saturated brine, and dried over anhydrous magnesium sulfate, then concentrated under reduced pressure. The residue was purified by silica gel column chromatography (ethyl acetate:hexane=1:3) to obtain ethyl 2-(phenylamino)pyrimidine-5-carboxylate (0.871 g, 89%).

ESI-MS: m/z 244 [M+H]$^+$ $^1$H NMR (CDCl$_3$) δ(ppm): 1.39 (t, J=7.1 Hz, 3H), 4.37 (q, J=7.1 Hz, 2H), 7.12 (tt, J=1.2, 7.4 Hz, 1H), 7.38 (t, J=1.2, 7.4 Hz, 2H), 7.63 (dt, J=1.0, 7.6 Hz, 2H), 7.72 (brs, 1H), 8.97 (s, 2H).

Step 3

Ethyl 2-(phenylamino)pyrimidine-5-carboxylate (0.590 g, 2.42 mmol) obtained in Step 2 was dissolved in toluene (25 mL). After cooling to −78° C., a 1 mol/L diisobutyl aluminum hydride-toluene solution (7.30 mL, 7.30 mmol) was added to the solution, followed by stirring at −78° C. for 3 hours. The reaction mixture was added with ethyl acetate followed by stirring vigorously at room temperature. The mixture was sequentially washed with water and saturated brine. The organic layer was dried over anhydrous magnesium sulfate and concentrated under reduced pressure. The residue was purified by silica gel column chromatography (chloroform:methanol=50:1) to obtain 5-hydroxymethyl-2-(phenylamino)pyrimidine (386 mg, 79%).

ESI-MS: m/z 202 [M+H]$^+$ $^1$H NMR (DMSO-d$_6$) δ(ppm): 4.39 (d, J=5.3 Hz, 2H), 5.18 (t, J=5.5 Hz, 1H), 6.92 (brt, J=7.4 Hz, 1H), 7.27 (brt, J=8.1 Hz, 2H), 7.7 (brd, J=8.2 Hz, 2H), 8.42 (s, 1H), 9.59 (s, 2H).

Step 4

5-Hydroxymethyl-2-(phenylamino)pyrimidine (280 mg, 1.39 mmol) obtained in Step 3 was dissolved in DMF (10 mL), and imidazole (190 mg, 2.76 mmol) and tert-butyldimethylsilylchloride (420 mg, 2.79 mmol) were added to the solution, followed by stirring at room temperature for 2 hours. The reaction mixture was diluted with ethyl acetate and washed with water and saturated brine. The organic layer was dried over anhydrous magnesium sulfate and concentrated under reduced pressure. The residue was purified by silica gel column chromatography (ethyl acetate:hexane=1:10) to obtain 5-(tert-butyldimethylsiloxymethyl)-2-(phenylamino)pyrimidine (423 mg, 82%).

ESI-MS: m/z 316 [M+H]$^+$

¹H NMR (CDCl₃) δ(ppm): 0.12 (s, 6H), 0.94 (s, 9H), 4.63 (s, 2H), 7.05 (brt, J=7.4 Hz, 1H), 7.35 (brt, J=8.3 Hz, 2H), 7.41 (brs, 1H), 7.62 (brd, J=7.8 Hz, 2H), 8.39 (s, 2H).

Step 5

5-(tert-Butyldimethylsiloxymethyl)-2-(phenylamino)pyrimidine (370 mg, 1.17 mmol) obtained in Step 4 was dissolved in THF (15 mL), and di-tert-butyl dicarbonate (770 mg, 3.52 mmol) and 4-dimethylaminopyridine (215 mg, 1.76 mmol) were added to the solution, followed by stirring at 70° C. for 2 hours. The reaction mixture was dissolved in ethyl acetate and washed with water and saturated brine. The organic layer was dried over anhydrous magnesium sulfate and concentrated under reduced pressure. The residue was purified by silica gel column chromatography (ethyl acetate: hexane=1:6) to obtain [5-(tert-butyldimethylsiloxymethyl) pyrimidin-2-yl]phenylcarbamic acid tert-butyl ester (564 mg, quantitative yield).

ESI-MS: m/z 416 [M+H]⁺

¹H NMR (CDCl₃) δ(ppm): 0.10 (s, 6H), 0.91 (s, 9H), 1.45 (s, 9H), 4.72 (s, 2H), 7.21 (dd, J=1.4, 8.8 Hz, 2H), 7.26 (brt, J=7.3 Hz, 1H), 7.37 (brt, J=7.7 Hz, 2H), 8.61 (s, 2H).

Step 6

[5-(tert-Butyldimethylsiloxymethyl)pyrimidin-2-yl]phenylcarbamic acid tert-butyl ester (560 mg, 1.34 mmol) obtained in Step 5 was dissolved in THF (10 mL), and a 1.0 mol/L tetrabutylammonium fluoride-THF solution (4.02 mL, 4.02 mmol) was added to the solution, followed by stirring at room temperature for 1.5 hours. The reaction mixture was diluted with ethyl acetate and washed with water and saturated brine. The organic layer was dried over anhydrous magnesium sulfate and concentrated under reduced pressure. The residue was purified by silica gel column chromatography (ethyl acetate:hexane=3:1) to obtain (5-hydroxymethylpyrimidin-2-yl)phenylcarbamic acid tert-butyl ester (336 mg, 83%).

ESI-MS: m/z 302 [M+H]⁺

¹H NMR (CDCl₃) δ(ppm): 1.47 (s, 9H), 4.65 (s, 2H), 7.23 (brd, J=7.3 Hz, 2H), 7.29 (brt, J=6.6 Hz, 1H), 7.39 (brt, J=7.9 Hz, 2H), 8.61 (s, 2H).

Step 7

(5-Hydroxymethylpyrimidin-2-yl)phenylcarbamic acid tert-butyl ester (286 mg, 0.949 mmol) obtained in Step 6 was dissolved in dichloromethane (10 mL), and triethylamine (0.265 mL, 1.90 mmol) and methanesulfonyl chloride (0.147 mL, 1.90 mmol) were added to the solution at 0° C., followed by stirring at room temperature for 2 hours. After the reaction was finished, the reaction mixture was added with methanol to decompose excess reagents, and the mixture was diluted with chloroform and washed with water and saturated brine. The organic layer was dried over anhydrous magnesium sulfate and concentrated under reduced pressure. Then the residue was dissolved in DMF (10 mL), and the solution was added with 2-ethyl-5,7-dimethylimidazo[4,5-b]pyridine (234 mg, 1.34 mmol) and lithium hydroxide monohydrate (56.0 mg, 1.34 mmol) followed by stirring at 60° C. for 3 hours. The reaction mixture was diluted with ethyl acetate and washed with water and saturated brine. The organic layer was dried over anhydrous magnesium sulfate and concentrated under reduced pressure. The residue was purified by silica gel column chromatography (ethyl acetate:hexane=3:1) to obtain [5-(2-ethyl-5,7-dimethylimidazo[4,5-b]pyridin-3-ylmethyl) pyrimidin-2-yl]phenylcarbamic acid tert-butyl ester (412 mg, 81%).

ESI-MS: m/z 459 [M+H]⁺

¹H NMR (CDCl₃) δ(ppm): 1.38 (t, J=7.52 Hz, 3H), 1.41 (s, 9H), 2.56 (s, 3H), 2.59 (s, 6H), 2.85 (q, J=7.5 Hz, 2H), 5.37 (s, 2H), 6.87 (s, 1H), 7.16 (dd, J=2.0, 7.0 Hz, 2H), 7.27 (tt, J=1.3, 7.3 Hz, 1H), 7.36 (tt, J=1.7, 7.7 Hz, 2H), 8.59 (s, 2H).

Step 8

[5-(2-Ethyl-5,7-dimethylimidazo[4,5-b]pyridin-3-ylmethyl)pyrimidin-2-yl]phenylcarbamic acid tert-butyl ester (310 mg, 0.676 mmol) obtained in Step 7 was dissolved in methanol (5 mL), and a 4 mol/L hydrogen chloride-1,4-dioxane solution (4 mL) was added to the solution, followed by stirring at room temperature for 1.5 hours. The reaction mixture was concentrated under reduced pressure, and the residue was recrystallized from diethyl ether to obtain Compound 167 (255 mg, 96%).

ESI-MS: m/z 359 [M+H]⁺

¹H NMR (DMSO-d₆) δ(ppm): 1.39 (t, J=7.7 Hz, 3H), 2.60 (s, 3H), 2.64 (s, 3H), 3.32 (q, J=7.7 Hz, 2H), 5.57 (s, 2H), 6.93 (t, J=7.3 Hz, 1H), 7.24 (t, J=8.1 Hz, 2H), 7.35 (s, 1H), 7.68 (d, J=7.7 Hz, 2H), 8.59 (s, 2H), 9.77 (brs, 1H)

melting point: 146-150° C.

Example 116 cis-4-[4-(2,5,7-Trimethyl-3H-imidazo[4,5-b]pyridin-3-ylmethyl)phenylamino]cyclohexanecarboxylic acid ethyl ester (Compound 168)

Compound P17 (0.500 g, 1.51 mmol) was dissolved in chloroform (15 mL), and iodomethane (0.377 mL, 6.06 mmol) was added to the solution, followed by stirring at room temperature overnight. The reaction mixture was concentrated under reduced pressure. The residue was dissolved in DMF (5 mL), and the solution was dropped into a solution of Compound P11 (0.476 g, 2.95 mmol) and 55% sodium hydride (0.129 g, 2.96 mmol) in DMF (10 mL) at 0° C., followed by stirring at room temperature for 5 hours. The reaction mixture was added with a saturated ammonium chloride solution followed by stirring for a while, then the mixture was extracted with ethyl acetate. The organic layer was washed with water and saturated brine, and dried over anhydrous magnesium sulfate, then concentrated under reduced pressure. The residue was purified by silica gel column chromatography (ethyl acetate:hexane=5:1) to obtain Compound 168 (0.636 g, 43%).

ESI-MS: m/z 421 [M+H]⁺

¹H NMR (CDCl₃) δ(ppm): 1.25 (t, J=7.1 Hz, 3H), 1.58-2.97 (m, 8H), 2.45 (m, 1H), 2.50 (s, 3H), 2.59 (s, 3H), 3.42 (m, 1H), 4.12 (q, J=7.1 Hz, 2H), 5.29 (s, 2H), 6.48 (d, J=8.4 Hz, 2H), 6.86 (s, 1H), 6.97 (d, J=8.4 Hz, 2H).

Example 117 trans-4-[4-(2,5,7-Trimethyl-3H-imidazo[4,5-b]pyridin-3-ylmethyl)phenylamino]cyclohexanecarboxylic acid ethyl ester (Compound 169)

Compound 169 (0.670 g, 49%) was obtained in a similar manner to Example 116 using Compound P20 (1.07 g, 3.23 mmol).

ESI-MS: m/z 421 [M+H]⁺

¹H NMR (CDCl₃) δ(ppm): 1.05 (dq, J=3.3, 13.2 Hz, 2H), 1.22 (t, J=6.9 Hz, 3H), 1.52 (dq, J=3.0, 13.2 Hz, 2H), 2.00 (m, 2H), 2.14 (m, 2H), 2.23 (tt, J=3.6, 12.2 Hz, 1H), 2.47 (s, 3H), 2.57 (s, 6H), 3.16 (brt, J=10.1 Hz, 1H), 4.09 (q, J=7.3 Hz, 2H), 5.26 (s, 2H), 6.45 (d, J=8.3 Hz, 2H), 6.84 (s, 1H), 6.96 (d, J=8.5 Hz, 2H).

Example 118 trans-4-[4-(2-Ethyl-7-methyl-3H-imidazo[4,5-b]pyridin-3-ylmethyl)phenylamino]cyclohexanecarboxylic acid ethyl ester (Compound 170)

Compound P23 (1.43 g, 4.15 mmol) was dissolved in chloroform (40 mL), and iodomethane (1.30 mL, 20.9 mol) was added to the solution, followed by stirring at room temperature overnight. The reaction mixture was concentrated under reduced pressure. The residue was dissolved in DMF (15 mL), and the solution was dropped into a solution of Compound P13 (1.20 g, 7.44 mmol) and 55% sodium hydride (0.325 g, 7.45 mmol) in DMF (30 mL) at 0° C. followed by stirring at room temperature for 5 hours. The reaction mixture was added with a saturated ammonium chloride solution followed by stirring for a while, then the mixture was extracted with ethyl acetate. The organic layer was washed with water and saturated brine, and dried over anhydrous magnesium sulfate, then concentrated under reduced pressure. The residue was purified by silica gel column chromatography (ethyl acetate:hexane=4:1) to obtain Compound 170 (0.340 g, 20%).

ESI-MS: m/z 421 [M+H]$^+$
$^1$H NMR (CDCl$_3$) δ(ppm): 1.15 (dq, J=3.3, 13.2 Hz, 2H), 1.23 (t, J=7.1 Hz, 3H), 1.32 (t, J=7.6 Hz, 3H), 1.53 (dq, J=3.1, 13.5 Hz, 2H), 2.03 (m, 2H), 2.15 (m, 2H), 2.23 (tt, J=3.6, 12.1 Hz, 1H), 2.66 (s, 3H), 3.17 (tt, J=3.8, 11.1 Hz, 1H), 4.11 (q, J=7.1 Hz, 2H), 5.33 (s, 2H), 6.46 (d, J=8.4 Hz, 2H), 6.95 (d, J=8.1 Hz, 2H), 6.98 (d, J=4.8 Hz, 1H), 8.19 (d, J=4.9 Hz, 1H).

Example 119 trans-4-[4-(2,7-Dimethyl-3H-imidazo[4,5-b]pyridin-3-ylmethyl)phenylamino]cyclohexanecarboxylic acid ethyl ester (Compound 171)

Compound 171 (0.370 g, 16%) was obtained in a similar manner to Example 118 using Compound P23 (2.00 g, 5.80 mmol) and Compound P14 (1.12 g, 6.95 mmol).

ESI-MS: m/z 407 [M+H]$^+$
$^1$H NMR (CDCl$_3$) δ(ppm): 1.09 (dq, J=3.0, 13.0 Hz, 2H), 1.24 (t, J=7.3 Hz, 3H), 1.54 (dq, J=3.1, 13.0 Hz, 2H), 2.04 (m, 2H), 2.12 (m, 2H), 2.26 (tt, J=3.6, 12.1 Hz, 1H), 2.55 (s, 3H), 2.65 (s, 3H), 3.19 (tt, J=3.6, 11.0 Hz, 1H), 4.12 (q, J=7.3 Hz, 2H), 5.32 (s, 2H), 6.47 (d, J=8.6 Hz, 2H), 6.99 (d, J=5.9 Hz, 1H), 7.01 (d, J=7.9 Hz, 2H), 8.20 (d, J=5.0 Hz, 1H).

Example 120 trans-4-{4-[2-(Furan-2-yl)-5,7-dimethyl-3H-imidazo[4,5-b]pyridin-3-ylmethyl]phenylamino}cyclohexanecarboxylic acid ethyl ester (Compound 172)

Compound 172 (0.218 g, 31%) was obtained in a similar manner to Example 118 using Compound P23 (0.509 g, 1.48 mmol) and Compound P15 (0.410 g, 1.92 mmol).

ESI-MS: m/z 473 [M+H]$^+$
$^1$H NMR (DMSO-d$_6$) δ(ppm): 1.06-1.20 (m, 5H), 1.38 (brq, 12.7 Hz, 2H), 1.89 (m, 4H), 2.23 (brt, J=12.5 Hz, 1H), 2.49 (s, 3H), 2.54 (s, 3H), 3.04 (m, 1H), 4.03 (q, J=7.1 Hz, 2H), 5.37 (d, J=8.2 Hz, 1H), 5.56 (s, 2H), 6.42 (d, J=8.4 Hz, 2H), 6.71 (dd, J=1.7, 3.3 Hz, 1H), 6.84 (d, J=8.4 Hz, 2H), 7.03 (s, 1H), 7.11 (d, J=3.4 Hz, 1H), 7.97 (d, J=1.7 Hz, 1H).

Example 121 trans-1-{4-[4-(5-Chloro-2,7-dimethyl-3H-imidazo[4,5-b]pyridin-3-ylmethyl)phenylamino]cyclohexylcarbonyl}-4-methylpiperazine (Compound 173)

Compound 173 (75.0 mg, 89%) was obtained in a similar manner to Example 69 using Compound P39 (70.0 mg, 0.170 mmol).

ESI-MS: m/z 495 [M+H]$^+$, 497 [M+2+H]$^+$
$^1$H NMR (CDCl$_3$) δ(ppm): 1.11 (dq, J=3.3, 11.7 Hz, 2H), 1.69 (dq, J=3.3, 12.4 Hz, 2H), 1.81 (brd, J=12.4 Hz, 2H), 2.12 (brd, J=13.9 Hz, 2H), 2.30 (s, 3H), 2.35-2.51 (m, 5H), 2.52 (s, 3H), 2.61 (s, 3H), 3.23 (brtt, 3.6, 11.4 Hz, 1H), 3.51 (m, 3H), 3.63 (m 2H), 5.27 (s, 2H), 6.48 (d, J=8.4 Hz, 2H), 7.00 (d, J=8.4 Hz, 2H), 7.03 (s, 1H).

Example 122 trans-4-[4-(5-Chloro-2,7-dimethyl-3H-imidazo[4,5-b]pyridin-3-ylmethyl)phenylamino]cyclohexanecarboxylic acid (2-morpholinoethyl)amide (Compound 174)

Compound 174 (0.157 g, 82%) was obtained in a similar manner to Example 69 using Compound P39 (0.150 g, 0.363 mmol) and 4-(2-aminoethyl)morpholine (0.0715 mL, 0.545 mmol).

ESI-MS: m/z 525 [M+H]$^+$, 527 [M+2+H]$^+$
$^1$H NMR (CDCl$_3$) δ(ppm): 1.12 (dq, J=3.7, 13.2 Hz, 2H), 1.61 (dq, J=3.7, 12.5 Hz, 2H), 1.95 (brd, J=13.2 Hz, 2H), 2.10 (tt, J=3.7, 12.1 Hz, 1H), 2.18 (brd, J=12.8 Hz, 2H), 2.43-2.50 (m, 6H), 2.52 (s, 3H), 2.62 (s, 3H), 3.22 (m, 1H), 3.35 (q, J=5.9 Hz, 2H), 3.51 (brs, 1H), 3.71 (m, 4H), 5.27 (s, 2H), 6.03 (brt, J=4.8 Hz, 1H), 6.49 (d, J=8.4 Hz, 2H), 7.00 (d, J=8.4, 2H), 7.03 (s, 1H).

Example 123 trans-4-[4-(5-Chloro-2,7-dimethyl-3H-imidazo[4,5-b]pyridin-3-ylmethyl)phenylamino]cyclohexanecarboxylic acid [2-(pyrrolidin-1-yl)ethyl]amide (Compound 175)

Compound 175 (78.4 mg, 91%) was obtained in a similar manner to Example 69 using Compound P38 (70.0 mg, 0.170 mmol) and 1-(2-aminoethyl)pyrrolidine (0.0319 mL, 0.254 mmol).

ESI-MS: m/z 509 [M+H]$^+$, 511 [M+2+H]$^+$
$^1$H NMR (CDCl$_3$) δ(ppm): 1.10 (dq, J=2.9, 11.7 Hz, 2H), 1.61 (dq, J=2.9, 12.5 Hz, 2H), 1.77 (m, 4H), 1.93 (brd, J=13.2 Hz, 2H), 2.08 (tt, J=3.3, 11.7 Hz, 1H), 2.16 (brd, J=13.9 Hz, 2H), 2.46-2.59 (m, 6H), 2.51 (s, 3H), 2.61 (s, 3H), 3.21 (m, 1H), 3.34 (q, J=5.50 Hz, 2H), 3.52 (d, J=8.1 Hz, 1H), 5.26 (s, 2H), 6.14 (brt, J=3.7 Hz, 1H), 6.48 (d, J=8.4 Hz, 2H), 6.99 (d, J=8.4 Hz, 2H), 7.02 (s, 1H).

Example 124 trans-4-{4-[5-Chloro-2,7-dimethylimidazo[4,5-b]pyridin-3-ylmethyl]phenylamino}cyclohexanecarboxylic acid ethyl ester (Compound 176)

Compound 176 (0.373 g, 43%) was obtained in a similar manner to Example 116 using Compound P20 (0.650 g, 1.97 mmol) and Compound P38 (0.535 g, 2.95 mmol).

ESI-MS: m/z 441 [M+H]$^+$, 443 [M+2+H]$^+$ $^1$H NMR (CDCl$_3$) δ(ppm): 1.11 (dq, J=3.6, 11.4 Hz, 2H), 1.24 (t, J=7.3 Hz, 3H), 1.54 (dq, J=3.6, 12.6 Hz, 2H), 2.09 (brd, J=13.0 Hz, 2H), 2.15 (brd, J=13.9 Hz, 2H), 2.26 (tt, J=3.6, 12.4 Hz, 1H), 2.52 (s, 3H), 2.60 (s, 3H), 3.19 (tt, J=4.0, 11.4 Hz, 1H), 3.51 (brs, 1H), 4.11 (q, J=7.10 Hz, 2H), 5.26 (s, 2H), 6.47 (d, J=8.6 Hz, 2H), 6.99 (d, J=8.4 Hz, 2H), 7.02 (s, 1H).

INDUSTRIAL APPLICABILITY

The present invention provides a preventive and/or therapeutic agent for neutrophilic inflammatory diseases which comprises, as an active ingredient, bicyclic heterocyclic compound or a pharmaceutically acceptable salt thereof.

The invention claimed is:

1. A bicyclic heterocyclic compound represented by formula (IIIa):

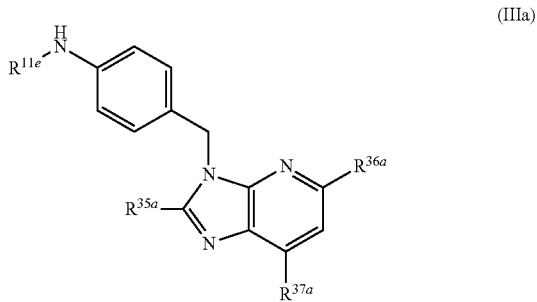

(IIIa)

[wherein R$^{11e}$ represents substituted or unsubstituted lower cycloalkyl, substituted or unsubstituted aryl, a substituted or unsubstituted aliphatic heterocyclic group, substituted or unsubstituted lower cycloalkylcarbonyl, —C(=O)NHR$^{15d}$ (wherein R$^{15d}$ represents substituted or unsubstituted cycloalkyl, or substituted or unsubstituted aryl), or —S(O)$_2$R$^{17a}$ (wherein R$^{17a}$ represents substituted or unsubstituted aryl) and R$^{35a}$, R$^{36a}$, and R$^{37a}$ are the same or different and each represents a hydrogen atom, or substituted or unsubstituted lower alkyl] or a pharmaceutically acceptable salt thereof.

2. The bicyclic heterocyclic compound or the pharmaceutically acceptable salt thereof according to claim 1, wherein R$^{11e}$ is substituted or unsubstituted lower cycloalkyl.

3. The bicyclic heterocyclic compound or the pharmaceutically acceptable salt thereof according to claim 1, wherein R$^{11e}$ is a substituted or unsubstituted aliphatic heterocyclic group.

4. The bicyclic heterocyclic compound or the pharmaceutically acceptable salt thereof according to claim 1, wherein R$^{11e}$ is substituted or unsubstituted cyclohexyl.

5. The bicyclic heterocyclic compound or the pharmaceutically acceptable salt thereof according to claim 4, wherein R$^{35a}$, R$^{36a}$, and R$^{37a}$ are the same or different and each is lower alkyl.

6. The bicyclic heterocyclic compound or the pharmaceutically acceptable salt thereof according to claim 4, wherein R$^{35a}$, R$^{36a}$, and R$^{37a}$ are methyl.

7. The bicyclic heterocyclic compound or the pharmaceutically acceptable salt thereof according to claim 3, wherein R$^{35a}$, R$^{36a}$, and R$^{37a}$ are the same or different and each is lower alkyl.

8. The bicyclic heterocyclic compound or the pharmaceutically acceptable salt thereof according to claim 3, wherein R$^{35a}$, R$^{36a}$, and R$^{37a}$ are methyl.

9. The bicyclic heterocyclic compound or the pharmaceutically acceptable salt thereof according to claim 2, wherein R$^{35a}$, R$^{36a}$, and R$^{37a}$ are the same or different and each is lower alkyl.

10. The bicyclic heterocyclic compound or the pharmaceutically acceptable salt thereof according to claim 2, wherein R$^{35a}$, R$^{36a}$, and R$^{37a}$ are methyl.

11. The bicyclic heterocyclic compound or the pharmaceutically acceptable salt thereof according to claim 1, wherein R$^{35a}$, R$^{36a}$, and R$^{37a}$ are the same or different and each is lower alkyl.

12. The bicyclic heterocyclic compound or the pharmaceutically acceptable salt thereof according to claim 1, wherein R$^{35a}$, R$^{36a}$, and R$^{37a}$ are methyl.

13. A bicyclic heterocyclic compound represented by formula (IIIb):

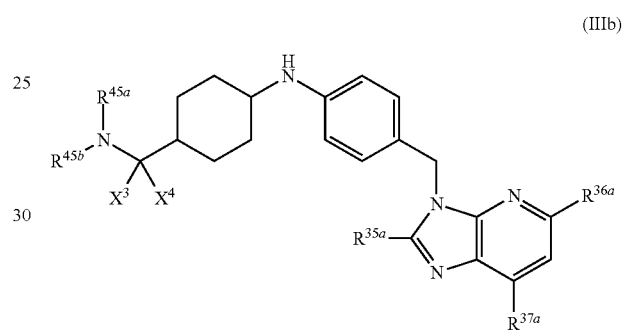

(IIIb)

(wherein X$^3$ and X$^4$ represent hydrogen atoms or X$^3$ and X$^4$ are combined together to represent an oxygen atom, R$^{45a}$ and R$^{45b}$ are the same or different and each represents a hydrogen atom or substituted or unsubstituted lower alkyl, or R$^{45a}$ and R$^{45b}$ are combined together with the adjacent nitrogen atom thereto to form a substituted or unsubstituted aliphatic heterocyclic group, and R$^{35a}$, R$^{36a}$, and R$^{37a}$ are the same or different and each represents lower alkyl) or a pharmaceutically acceptable salt thereof.

14. The bicyclic heterocyclic compound or the pharmaceutically acceptable salt thereof according to claim 13, wherein X$^3$ and X$^4$ are combined together to represent an oxygen atom.

15. The bicyclic heterocyclic compound or the pharmaceutically acceptable salt thereof according to claim 13, wherein X$^3$ and X$^4$ are hydrogen atoms.

16. The bicyclic heterocyclic compound or the pharmaceutically acceptable salt thereof according to claim 13, wherein R$^{45a}$ is a hydrogen atom and R$^{45b}$ is substituted or unsubstituted lower alkyl.

17. The bicyclic heterocyclic compound or the pharmaceutically acceptable salt thereof according to claim 13, wherein R$^{45a}$ is a hydrogen atom and R$^{45b}$ is lower alkyl substituted by aliphatic heterocyclic group.

18. The bicyclic heterocyclic compound or the pharmaceutically acceptable salt thereof according to claim 13, wherein R$^{45a}$ is a hydrogen atom and R$^{45b}$ is ethyl substituted by aliphatic heterocyclic group.

19. The bicyclic heterocyclic compound or the pharmaceutically acceptable salt thereof according to claim 13, wherein $R^{45a}$ and $R^{45b}$ are combined together with the adjacent nitrogen atom thereto to form a substituted or unsubstituted aliphatic heterocyclic group.

* * * * *